US011364241B2

(12) United States Patent
Wang et al.

(10) Patent No.: US 11,364,241 B2
(45) Date of Patent: Jun. 21, 2022

(54) DIHYDROPYRIDOPHTHALAZINONE INHIBITORS OF POLY(ADP-RIBOSE)POLYMERASE (PARP)

(71) Applicant: Medivation Technologies LLC, New York, NY (US)

(72) Inventors: Bing Wang, San Jose, CA (US); Daniel Chu, Santa Clara, CA (US)

(73) Assignee: MEDIVATION TECHNOLOGIES LLC, New York, NY (US)

( * ) Notice: Subject to any disclaimer, the term of this patent is extended or adjusted under 35 U.S.C. 154(b) by 118 days.

(21) Appl. No.: 17/000,271

(22) Filed: Aug. 21, 2020

(65) Prior Publication Data

US 2021/0069191 A1 Mar. 11, 2021

Related U.S. Application Data

(60) Continuation of application No. 16/714,474, filed on Dec. 13, 2019, now Pat. No. 10,780,088, which is a continuation of application No. 15/719,534, filed on Sep. 28, 2017, now Pat. No. 10,543,209, which is a continuation of application No. 14/632,825, filed on Feb. 26, 2015, now Pat. No. 9,820,985, which is a division of application No. 13/787,496, filed on Mar. 6, 2013, now Pat. No. 8,999,987, which is a continuation of application No. 13/077,785, filed on Mar. 31, 2011, now Pat. No. 8,420,650, which is a continuation of application No. 12/510,096, filed on Jul. 27, 2009, now Pat. No. 8,012,976.

(60) Provisional application No. 61/173,088, filed on Apr. 27, 2009, provisional application No. 61/151,036, filed on Feb. 9, 2009, provisional application No. 61/086,687, filed on Aug. 6, 2008.

(51) Int. Cl.
| | |
|---|---|
| *A61K 31/5025* | (2006.01) |
| *A61K 33/243* | (2019.01) |
| *C07D 471/06* | (2006.01) |
| *A61K 31/5377* | (2006.01) |
| *A61K 31/282* | (2006.01) |
| *A61K 31/4745* | (2006.01) |
| *A61K 31/495* | (2006.01) |
| *A61N 5/10* | (2006.01) |

(52) U.S. Cl.
CPC ........ *A61K 31/5025* (2013.01); *A61K 31/282* (2013.01); *A61K 31/4745* (2013.01); *A61K 31/495* (2013.01); *A61K 31/5377* (2013.01); *A61K 33/243* (2019.01); *A61N 5/10* (2013.01); *C07D 471/06* (2013.01); *A61N 2005/1098* (2013.01)

(58) Field of Classification Search
CPC ................................................. A61K 31/5025
See application file for complete search history.

(56) References Cited

U.S. PATENT DOCUMENTS

| | | |
|---|---|---|
| 4,415,504 A | 11/1983 | Chibata et al. |
| 4,526,894 A | 7/1985 | Enomoto et al. |
| 5,328,905 A | 7/1994 | Hamminga et al. |
| 6,903,098 B1 | 6/2005 | Lubisch et al. |
| 7,268,138 B2 | 9/2007 | Kalish et al. |

(Continued)

FOREIGN PATENT DOCUMENTS

| | | |
|---|---|---|
| DE | 19727410 A1 | 1/1999 |
| EP | 0848000 A1 | 6/1998 |

(Continued)

OTHER PUBLICATIONS

Anderson, B.D. et al. (1996). "Preparation of Water-Soluble Compounds through Salt Formation," Chapter 34 in *The Practice of Medicinal Chemistry*, Weymuth, C.G. (ed.), pp. 739-754.

(Continued)

*Primary Examiner* — Paul V Ward
(74) *Attorney, Agent, or Firm* — Pfizer Inc.

(57) ABSTRACT

A compound having the structure set forth in Formula (I) and Formula (II):

Formula (I)

Formula (II)

wherein the substituents Y, Z, A, B, $R_1$, $R_2$, $R_3$, $R_4$ and $R_5$ are as defined herein. Provided herein are inhibitors of poly(ADP-ribose)polymerase activity. Also described herein are pharmaceutical compositions that include at least one compound described herein and the use of a compound or pharmaceutical composition described herein to treat diseases, disorders and conditions that are ameliorated by the inhibition of PARP activity.

16 Claims, No Drawings

(56) References Cited

U.S. PATENT DOCUMENTS

| | | |
|---|---|---|
| 7,429,598 B2 | 9/2008 | Bernardelli et al. |
| 7,446,117 B2 | 11/2008 | Beswick et al. |
| 7,456,178 B2 | 11/2008 | Kalish et al. |
| 7,601,719 B2 | 10/2009 | Kalish et al. |
| 7,750,008 B2 | 7/2010 | Kalish et al. |
| 8,012,976 B2 | 9/2011 | Wang et al. |
| 8,088,760 B2 | 1/2012 | Chu et al. |
| 8,134,007 B2 | 3/2012 | Bagal et al. |
| 8,420,650 B2 | 4/2013 | Wang et al. |
| 8,541,403 B2 | 9/2013 | Chu et al. |
| 8,735,392 B2 | 5/2014 | Wang et al. |
| 8,765,945 B2 | 7/2014 | Wang et al. |
| 8,999,987 B2 | 4/2015 | Wang et al. |
| 9,018,201 B2 | 4/2015 | Chu et al. |
| 9,820,985 B2 | 11/2017 | Wang et al. |
| 9,926,303 B2 | 3/2018 | Wang et al. |
| 10,189,837 B2 | 1/2019 | Wang et al. |
| 2004/0106631 A1 | 6/2004 | Bernardelli et al. |
| 2005/0085476 A1 | 4/2005 | Seko et al. |
| 2006/0004028 A1 | 1/2006 | Shiromizu et al. |
| 2008/0058325 A1 | 3/2008 | Kalish et al. |
| 2009/0088407 A1 | 4/2009 | Kalish et al. |
| 2009/0318436 A1 | 12/2009 | Albrecht et al. |
| 2011/0027226 A1 | 3/2011 | Vennemann et al. |
| 2011/0190266 A1 | 8/2011 | Chu et al. |
| 2011/0196153 A1 | 8/2011 | Wang et al. |
| 2011/0301350 A1 | 12/2011 | Pfrengle et al. |
| 2012/0129865 A1 | 5/2012 | Wang et al. |
| 2013/0053365 A1 | 2/2013 | Wang et al. |
| 2014/0228369 A1 | 8/2014 | Wang et al. |
| 2015/0209363 A1 | 7/2015 | Chu et al. |
| 2016/0280691 A1 | 9/2016 | Henderson et al. |
| 2017/0217921 A1 | 8/2017 | Henderson et al. |
| 2018/0009806 A1 | 1/2018 | Wang et al. |
| 2018/0117045 A1 | 5/2018 | Wang et al. |

FOREIGN PATENT DOCUMENTS

| | | |
|---|---|---|
| EP | 0927718 A1 | 7/1999 |
| EP | 1340819 A1 | 9/2003 |
| EP | 2326650 B1 | 2/2014 |
| JP | 2001302669 A | 10/2001 |
| JP | 2002284699 A | 10/2002 |
| JP | 2007505161 A | 3/2007 |
| JP | 2011530513 A | 12/2011 |
| WO | WO-1996/29327 A1 | 9/1996 |
| WO | WO-1999/011645 A1 | 3/1999 |
| WO | WO-1999/059975 A1 | 11/1999 |
| WO | WO-2002/098424 A1 | 12/2002 |
| WO | WO-2003/002567 A1 | 1/2003 |
| WO | WO-2004/024691 A1 | 3/2004 |
| WO | WO-2004/080976 A1 | 3/2004 |
| WO | WO-2004/105700 A1 | 12/2004 |
| WO | WO-2005/080356 A1 | 9/2005 |
| WO | WO-2008/001134 A1 | 1/2008 |
| WO | WO-2008/135826 A2 | 11/2008 |
| WO | WO-2008/135826 A3 | 11/2008 |
| WO | WO-2010/017055 A1 | 2/2010 |
| WO | WO-2011/097334 A1 | 8/2011 |
| WO | WO-2011/097602 A1 | 8/2011 |
| WO | WO-2011/130661 A1 | 10/2011 |
| WO | WO-2011/140009 A1 | 11/2011 |
| WO | WO-2012/054698 A1 | 4/2012 |
| WO | WO-2012/166151 A1 | 12/2012 |
| WO | WO-2013/028495 A1 | 2/2013 |
| WO | WO-2015/069851 A1 | 5/2015 |
| WO | WO-2016/019125 A1 | 2/2016 |

OTHER PUBLICATIONS

Aveyard et al. (May 1996). "Somatic mutation of PTEN in bladder carcinoma," British Journal of Cancer 80(5-6):904-908.

Bastin, R.J. et al. (Jul. 19, 2000). "Salt Selection and Optimisation Procedures for Pharmaceutical New Chemical Entities," Org. Process Res. Dev. 4(5):427-435.

Bauer, J.F. (2008). "Polymorphism—A Critical Consideration in Pharmaceutical Development, Manufacturing, and Stability," Journal of Validation Technology 14(5):15-23.

Berge, S.M. et al. (Jan. 1977). "Pharmaceutical Salts," J. Pharm. Sci. 66(1):1-19.

Bruni, P. et al. (Jun. 29, 2000). "PTEN expression is reduced in a subset of sporadic thyroid carcinomas: evidence that PTEN-growth suppressing activity in thyroid cancer cells is mediated by p27KIP1," Oncogene 19(28):3146-3155.

Cantley et al. (Apr. 13, 1999). "New Insights into Tumor Suppression: PTEN Suppresses Tumor Formation by Restraining the Phosphoinositide 3-Kinase/AKT Pathway," Proc. Natl. Acad. Sci. 96(8):4240-4245.

CAS Reg. No. 1283718-99-9, Chemical Name "5-Quinolinecarboxylic acid, 1,2,3,4-tetrahydro-4-oxo-2-(trifluoromethyl)-methyl ester," entered on Apr. 21, 2011.

Corrected Notice of Allowability dated Oct. 12, 2017, for U.S. Appl. No. 14/632,825, filed Feb. 26, 2015, 2 pages.

Diaz, J.L. et al. (May 9, 2013, e-pub. Apr. 26, 2013). "Synthesis and Biological Evaluation of a New Series of Hexahydro-2H-pyrano[3,2-c]quinolones as Novel Selective σ1 Receptor Ligands," J. Med. Chem. 56(9):3656-3665.

EPO Extended European Search Report dated Feb. 8, 2012 for EP Pat. Appln. No. 09805360.6 (6 pages).

EPO Extended European Search Report dated Jul. 10, 2014 for EP Appln. No. 14154664.8 (7 pages).

EPO Extended European Search Report dated Jul. 3, 2013 for EP Pat. Appln. No. 11740322.0 (5 pages).

European Extended Search Report dated Sep. 15, 2017, for EP Application No. 17161893.7, filed on Jul. 27, 2009, 10 pages.

European Searching Authority, "Supplementary European Search Report for European Patent Application No. EP 11740513.4" (dated May 29, 2013).

Final Office Action dated Dec. 4, 2015, for U.S. Appl. No. 14/632,825, filed Feb. 26, 2015, 28 pages.

Final Office Action dated Feb. 17, 2017, for U.S. Appl. No. 14/632,825, filed Feb. 26, 2015, 18 pages.

Final Office Action dated Mar. 11, 2016, for U.S. Appl. No. 14/252,668, filed Apr. 14, 2014, 6 pages.

Final Office Action dated May 1, 2017, for U.S. Appl. No. 14/632,825, filed Feb. 26, 2015, 19 pages.

Final Office Action dated Oct. 17, 2013, for U.S. Appl. No. 13/277,607, filed Oct. 20, 2011, 6 pages.

Final Rejection dated Feb. 2, 2017, for U.S. Appl. No. 14/671,944, filed Mar. 27, 2015, 7 pages.

Gaymes, T.J. et al. (Nov. 19, 2010). "Microsatellite Instability (MSI) in High Risk Myelodyplastic Syndrome (MDS) and Acute Myeloid Leukemia (AML) Cells Promotes Frameshift Mutations in DNA Repair Genes: Indications for PARP Inhibitor Therapy," Blood 52nd Annual Meeting of the American Society of Hematology (ASH), (2010), p. 513, vol. 116, No. 21, Abstract 1194, American Society of Hematology, Orlando, FL, USA.

Gaymes, T.J. et al. (May 2009). "Inhibitors of Poly ADP-Ribose Polymerase (PARP) Induce Apoptosis of Myeloid Leukemic Cells: Potential for Therapy of Myeloid Leukemia and Myelodysplastic Syndromes," Haematologica 94(5):638-646.

Ham, M.F. et al. (Mar. 2009). "Impairment of Double-Strand Breaks Repair and Aberrant Splicing of ATM and MRE11 in Leukemia-Lymphoma Cell Lines with Microsatellite Instability," Cancer Science 97(3):226-234.

International Search Report dated Jan. 23, 2015, for PCT Patent Application No. PCT/US2014/064273 filed on Nov. 6, 2014, 4 pages.

International Search Report dated Oct. 20, 2015, for PCT Patent Application No. PCT/US2015/042867 filed on Jul. 30, 2015, 3 pages.

International Searching Authority, PCT International Preliminary Report on Patentability dated Feb. 8, 2011, for International Patent Application No. PCT/US2009/051879, filed on Jul. 27, 2009, 6 pages.

(56) References Cited

OTHER PUBLICATIONS

ISA, International Search Report and Written Opinion dated Apr. 18, 2011 for Intl. Appln. No. PCT/US2011/023965 (6 pages).
ISA, International Search Report and Written Opinion dated Apr. 21, 2011 for Intl. Appln. No. PCT/US2011/023532 (10 pages).
ISA, International Search Report and Written Opinion for Intl. Appln. No. PCT/US2011/032728 dated Jun. 28, 2011 (8 pages).
ISA, International Search Report and Written Opinion for Intl. Appln. No. PCT/US2011/057039 dated Nov. 30, 2011 (9 pages).
ISA, International Search Report and Written Opinion for Intl. Appln. No. for PCT/US2011/039045 dated Apr. 27, 2012 (20 pages).
ISA, International Search Report dated Apr. 6, 2010 for Intl. Appln. No. PCT/US2009/051879 (9 pages).
Ivanova, N. V. et al. (2006). "A Convenient Synthesis of 4,5-Disubstituted 1,2,4-Triazoles Functionalized in Position 3," *Synthesis* 2006(1):156-160.
Karlberg, et al. (Feb. 16, 2010). Crystal Structure of the Catalytic Domain of Human PARP2 in Complex with PARP Inhibitor ABT-888, Biochemistry 49(6):1056-1058.
Kurasawa, Y. et al. (Jun. 2008). "PTEN Expression and Methylation Status in Oral Squamous Cell Carcinoma," Oncology Reports 19(6):1429-1434.
McEllin, B. et al. (Jul. 1, 2010, e-pub. Jun. 8, 2010). "PTEN Loss Compromises Homologous Recombination Repair in Astrocytes: Implications for Gliobastoma Therapy with Temozolomide or Poly (ADP-Ribose) Polymerase Inhibitors," Cancer Res. 70(13):5457-5464.
McMahon, G. (2000). "VEGF Receptor Signaling in Tumor Angiogenesis," The Oncologist 5(Suppl. 1):3-10.
Mendes-Pereira et al., "Synthetic lethal targeting of PTEN mutant cells with PTEN mutant cells with PARP inhibitors," EMBO Mol. Med. (2009), vol. 1, pp. 315-322.
Merchant et al., "Synthesis of Benzoquinolizine Derivatives," Indian Journal of Chemistry, (1987), pp. 471-472, vol. 268.
Mriouah et al., "Celluar response to cetuximab in PTEN-silenced head and neck squamous cell carcinoma cell line", International Journal of Oncology, (2010), pp. 1555-1563, vol. 37.
Non-Final Office Action dated Apr. 17, 2013, for U.S. Appl. No. 13/277,607, filed Oct. 20, 2011, 6 pages.
Non-Final Office Action dated Feb. 16, 2012, for U.S. Appl. No. 13/077,785, filed Mar. 31, 2011, 8 pages.
Non-Final Office Action dated Jan. 16, 2018 for U.S. Appl. No. 14/671,944, filed Mar. 27, 2015, 6 pages.
Non-Final Office Action dated Jul. 30, 2014, for U.S. Appl. No. 13/787,496, filed Mar. 6, 2013, 13 pages.
Non-Final Office Action dated Jun. 14, 2012, for U.S. Appl. No. 13/077,785, filed Mar. 31, 2011, 5 pages.
Non-Final Office Action dated Jun. 22, 2015, for U.S. Appl. No. 14/252,668, filed Apr. 14, 2014, 6 pages.
Non-Final Office Action dated May 11, 2016, for U.S. Appl. No. 14/632,825, filed Feb. 26, 2015, 26 pages.
Non-Final Office Action dated May 5, 2015, for U.S. Appl. No. 14/632,825, filed Feb. 26, 2015, 7 pages.
Non-Final Office Action dated Sep. 6, 2013, for U.S. Appl. No. 13/023,140, filed Feb. 8, 2011, 8 pages.
Non-Final Rejection dated May 20, 2016, for U.S. Appl. No. 14/671,944, filed Mar. 27, 2015, 6 pages.
Notice of Allowance dated Apr. 11, 2011, for U.S. Appl. No. 12/510,096, filed Jul. 27, 2009, 5 pages.
Notice of Allowance dated Apr. 17, 2017, for U.S. Appl. No. 14/252,668, filed Apr. 14, 2014, 5 pages.
Notice of Allowance dated Aug. 25, 2016, for U.S. Appl. No. 14/252,668, filed Apr. 14, 2014, 5 pages.
Notice of Allowance dated Dec. 16, 2016, for U.S. Appl. No. 14/252,668, filed Apr. 14, 2014, 5 pages.
Notice of Allowance dated Dec. 26, 2012, for U.S. Appl. No. 13/077,785, filed Mar. 31, 2011, 6 pages.
Notice of Allowance dated Dec. 28, 2010, for U.S. Appl. No. 12/510,096, filed Jul. 27, 2009, 6 pages.
Notice of Allowance dated Jan. 15, 2014, for U.S. Appl. No. 13/277,607, filed Oct. 20, 2011, 6 pages.
Notice of Allowance dated Nov. 14, 2014, for U.S. Appl. No. 13/787,496, filed Mar. 6, 2013, 5 pages.
Notice of Allowance dated Nov. 17, 2017, for U.S. Appl. No. 14/293,642, filed Jun. 2, 2014, 5 pages.
Pinedo et al. "Translational Research: The Role of VEGF in Tumor Angiogenesis," The Oncologist, (2000), pp. 1-2, vol. 5, No. 1.
Salmena et al. "Tenets of PTEN Tumor Suppression," Cell, (May 2, 2008), pp. 403-414, vol. 133.
Science IP Search dated Jan. 9, 2009, 5 pages.
Shen, Y. et al. (Sep. 15, 2013). "BMN673, a Novel and Highly Potent PARP1/2 Inhibitor for the Treatment of Human Cancers with DNA Repair Deficiency," *Clinical Cancer Research* 19(18):5003-5015.
Stefanska, B. et al. (2005). "2,7-Dihydro-3H-Pyridazino[5,4,3-kl]Acridin-3-One Derivatives, Novel Type of Cytrotoxic Agents Active on Multidrug-Resistant Cell Lines. Synthesis and Biological Evaluation," *Bioorganic & Medicinal Chemistry* 13:1969-1975.
Thomas, et al. "Preclinical selection of a novel poly(ADP-ribose) polymerase inhibitor for clinical trial," Mol. Cancer Ther., (2007), pp. 945-956, vol. 6, No. 3.
Translation of Office Action for Japanese Application No. 2013-535079, including Japanese language copies of cited references (a) Takada, N., "API form screening and selection in drug discovery stage," Pharm. Stage. 2007, 6(1), 20-25; and (b) Kojima, T., "Optimization of Solid Form Selection in Drug Development," J. Pharm. Sci. Technol., 2008, 68(5), 344-349 (20 pages).
United Kingdom Intellectual Property Office, "Patents Act 1977 Combined Search and Examination Report under Section 17 & 18, (3) for Application No. GB 0913474.3," (dated Nov. 12, 2009).
United Kingdom Intellectual Property Office, "Patents Act 1977 Examination Report under 18, (3) for Application No. GB 0913474.3," (dated Sep. 14, 2010).
Zips D. et al. (2005). "New Anticancer Agents: In Vitro and In Vivo Evaluation," In Vivo 19(1):1-7.

DIHYDROPYRIDOPHTHALAZINONE INHIBITORS OF POLY(ADP-RIBOSE)POLYMERASE (PARP)

CROSS-REFERENCE

This application is a continuation of U.S. application Ser. No. 16/714,474, filed Dec. 13, 2019, now U.S. Pat. No. 10,780,088, which is a continuation of U.S. application Ser. No. 15/719,534, filed Sep. 28, 2017, now U.S. Pat. No. 10,534,209, which is a continuation of U.S. application Ser. No. 14/632,825, filed Feb. 26, 2015, now U.S. Pat. No. 9,820,985, which is a divisional of U.S. patent application Ser. No. 13/787,496, filed Mar. 6, 2013, now U.S. Pat. No. 8,999,987, which is a continuation of U.S. patent application Ser. No. 13/077,785, filed Mar. 31, 2011, now U.S. Pat. No. 8,420,650, which is a continuation of U.S. patent application Ser. No. 12/510,096, filed Jul. 27, 2009, now U.S. Pat. No. 8,012,976, which claims the benefit of U.S. provisional applications Nos. 61/173,088, filed Apr. 27, 2009, 61/151,036, filed Feb. 9, 2009, and 61/086,687, filed Aug. 6, 2008, all of which are herein incorporated by reference in their entireties.

FIELD OF THE INVENTION

Described herein are compounds, methods of making such compounds, pharmaceutical compositions and medicaments containing such compounds, and methods of using such compounds to treat or prevent diseases or conditions associated with the enzyme poly(ADP-ribose)polymerase (PARP).

BACKGROUND OF THE INVENTION

The family of poly(ADP-ribose)polymerases (PARP) includes approximately 18 proteins, which all display a certain level of homology in their catalytic domain but differ in their cellular functions (Ame et al., *BioEssays*, 26(8), 882-893 (2004)). PARP-1 and PARP-2 are unique members of the family, in that their catalytic activities are stimulated by the occurrence of DNA strand breaks.

PARP has been implicated in the signaling of DNA damage through its ability to recognize and rapidly bind to DNA single or double strand breaks (D'Amours, et al., *Biochem. J.*, 342, 249-268 (1999)). It participates in a variety of DNA-related functions including gene amplification, cell division, differentiation, apoptosis, DNA base excision repair as well as effects on telomere length and chromosome stability (d'Adda di Fagagna, et al., *Nature Gen.*, 23(1), 76-80 (1999)).

SUMMARY OF THE INVENTION

Provided herein are compounds, compositions and methods for modulating the activity of PARP. Among the compounds that are provided herein, are compounds that are inhibitors of PARP. Also described herein is the use of such compounds, compositions and methods for the treatment of diseases, disorders or conditions associated with the activity of PARP.

In some embodiments, compounds provided herein have the structure of Formula (I) and Formula (II) and pharmaceutically acceptable salts, solvates, esters, acids and prodrugs thereof. In certain embodiments, provided herein are compounds having the structure of Formula (I) and Formula (II) that are inhibitors of the enzyme poly(ADP-ribose) polymerase (PARP).

Described herein are 8-B,Z-2-$R_4$-4-$R_1$-5-$R_2$-6$R_3$-7$R_5$-9-A,Y-8,9-dihydro-2H-pyrido[4,3,2-de]phthalazin-3(7H)-one s, 8-B,Z-5-$R_2$-9-A,Y-8,9-dihydro-2H-pyrido[4,3,2-de] phthalazin-3(7H)-one s, in which A, B, Z, Y, $R_1$, $R_2$, $R_3$, $R_4$ and $R_5$ are further described herein. In certain embodiments, isomers including enantiomers and diastereoisomers, and chemically protected forms of compounds having a structure represented by Formula (I) and Formula (II) are also provided.

Formula (I) is as follows:

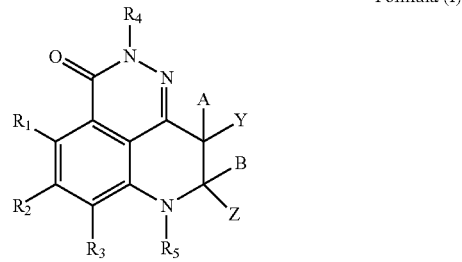

Formula (I)

wherein:

Y and Z are each independently selected from the group consisting of:
a) an aryl group optionally substituted with 1, 2, or 3 $R_6$; wherein each $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;
b) a heteroaryl group optionally substituted with 1, 2, or 3 $R_6$;
c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene;

$R_1$, $R_2$, and $R_3$ are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl;

A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_5$cycloalkyl, wherein B is not OH;

$R_A$, and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with one or more substituents;

$R_4$ and $R_5$ are each independently selected from the group consisting of hydrogen, alkyl, cycloalkyl, alkoxyalkyl, haloalkyl, hydroxyalkylene, and $(NR_AR_B)$alkylene;

and isomers, salts, solvates, chemically protected forms, and prodrugs thereof.

Formula (II) is as follows:

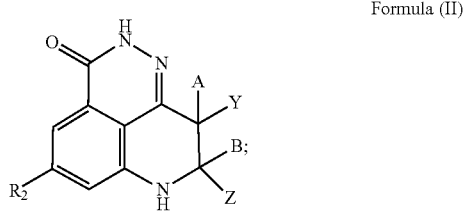

Formula (II)

wherein:
Y is an aryl or heteroaryl group optionally substituted with at least one $R_6$;
Z is an aryl group optionally substituted with at least one $R_6$;
A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH;
$R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;
$R_2$ is selected from hydrogen, Br, Cl, I, or F;
$R_A$, and $R_B$ are independently selected from the group consisting of hydrogen, $C_1$-$C_6$alkyl, $C_3$-$C_8$cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$alkyl)-, —NCO($C_1$-$C_6$alkyl)-, —NCO($C_3$-$C_8$cycloalkyl)-N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$alkyl-)-, —N(substituted-heteroaryl-$C_1$-$C_6$alkyl-)-, and —S— or $S(O)_q$—, wherein q is 1 or 2 and the 3-10 membered heterocycle ring is optionally substituted with one or more substituents; or a pharmaceutically acceptable salt, solvate or prodrug thereof.

In certain embodiments are provided compounds of Formula (I) or a therapeutically acceptable salt thereof wherein $R_1$, $R_2$, $R_3$ are independently selected from a group consisting of hydrogen, alkyl, and halogen; $R_4$ is hydrogen and $R_5$ is selected from the group consisting hydrogen, alkyl, cycloalkyl, alkoxyalkyl, haloalkyl, hydroxyalkylene, and $(NR_AR_B)$alkylene; $R_A$, and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with one or more substituents.

In one embodiment is a compound of Formula (I) wherein Y is an aryl group. In another embodiment the aryl group is a phenyl group. In yet another embodiment the phenyl group is substituted with at least one $R_6$ selected from Br, Cl, F, or I. In one embodiment $R_6$ is F. In one embodiment the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In one embodiment $R_6$ is $(NR_AR_B)C_1$-$C_6$alkylene. In another embodiment $C_1$-$C_6$alkyl is selected from methylene, ethylene, n-propylene, iso-propylene, n-butylene, iso-butylene, and tert-butylene. In yet another embodiment $C_1$-$C_6$alkyl is methylene. In yet a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In one embodiment $C_1$-$C_6$alkyl is methyl. In another embodiment $C_1$-$C_6$alkyl is ethyl. In yet another embodiment $C_3$-$C_8$cycloalkyl is cyclopropyl, cyclobutyl, cyclopentyl, and cyclohexyl. In a further embodiment $C_3$-$C_8$cycloalkyl is cyclopropyl. In yet a further embodiment $R_6$ is hydroxyalkylene. In one embodiment hydroxyalkylene is selected from $CH_2OH$, $CH_2CH_2OH$, $CH_2CH_2CH_2OH$, $CH(OH)CH_3$, $CH(OH)CH_2CH_3$, $CH_2CH(OH)CH_3$, and $CH_2CH_2CH_2CH_2OH$. In another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In yet another embodiment the hetero functionality is —N($C_1$-$C_6$alkyl). In a further embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl. In one embodiment Y is a heteroaryl group optionally substituted with at least one $R_6$. In another embodiment the heteroaryl group is selected from furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In yet another embodiment the heteroaryl group is imidazole. In a further embodiment imidazole is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment the heteroaryl group is furan. In another embodiment the heteroaryl group is thiazole. In yet another the heteroaryl group is 1,3,4-oxadiazole. In a further embodiment heteroaryl group is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment Z is an aryl group. In another embodiment the aryl group is a phenyl group. In yet another embodiment the phenyl group is substituted with at least one $R_6$ selected from Br, Cl, F, or I. In a further embodiment $R_6$ is F. In yet a further embodiment $R_6$ is $C_1$. In one embodiment the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In another embodiment $R_6$ is $(NR_AR_B)C_1$-$C_6$alkylene. In yet another embodiment $C_1$-$C_6$alkyl is selected from methylene, ethylene, n-propylene, iso-propylene, n-butylene, iso-butylene, and tert-butylene. In yet a further embodiment $C_1$-$C_6$alkyl is methylene. In a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In another embodiment $C_1$-$C_6$alkyl is methyl. In yet another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In a further embodiment the hetero functionality is —N($C_1$-$C_6$alkyl). In one embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl. In one embodiment Z is a heteroaryl group optionally substituted with at least one $R_6$. In another embodiment the heteroaryl group is selected from furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In yet another embodiment the heteroaryl group is imidazole. In a further embodiment imidazole is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment the heteroaryl group is furan. In another embodiment the heteroaryl group is thiazole. In yet another embodiment the heteroaryl group is 1,3,4-oxadiazole. In a further embodiment heteroaryl group is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In another embodiment $R_2$ is hydrogen. In yet another embodiment $R_2$ is selected from F, Cl, Br, and I. In a further embodiment $R_2$ is F.

In one embodiment is a compound of Formula (I) wherein A is hydrogen. In another embodiment A is $C_1$-$C_6$alkyl. In a further embodiment, A is selected from methyl, ethyl, n-propyl, iso-propyl, n-butyl, iso-butyl, tert-butyl, n-pentyl, and n-hexyl. In yet another embodiment, methyl, ethyl, n-propyl, iso-propyl, n-butyl, iso-butyl, tert-butyl, n-pentyl, and n-hexyl are optionally substituted with OH, $NO_2$, CN, Br, Cl, F, and I. In a further embodiment A is methyl. In yet another embodiment, A is selected from F, Cl, Br, and I. In another embodiment, A is $C_3$-$C_8$cycloalkyl. In another embodiment, A is cyclopropyl, cyclobutyl, cyclopentyl, or cyclohexyl. In one embodiment, A is substituted with OH, $NO_2$, or CN. In a further embodiment, B is $C_1$-$C_6$alkyl. In a further embodiment, B is selected from methyl, ethyl, n-propyl, iso-propyl, n-butyl, iso-butyl, tert-butyl, n-pentyl, and n-hexyl. In yet another embodiment, methyl, ethyl, n-propyl, iso-propyl, n-butyl, iso-butyl, tert-butyl, n-pentyl, and n-hexyl are optionally substituted with OH, $NO_2$, CN, Br, Cl, F, and I. In one embodiment is a compound of Formula (I) wherein B is hydrogen. In a further embodiment B is methyl. In yet another embodiment, B is selected from F, Cl, Br, and I. In another embodiment, B is $C_3$-$C_8$cycloalkyl. In another embodiment, B is cyclopropyl, cyclobutyl, cyclopentyl, or cyclohexyl. In one embodiment, A is substituted with OH, $NO_2$, or CN. In a further embodiment, is a compound of Formula (I) wherein A is hydrogen and B is selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl. In another embodiment, is a compound of Formula (I) wherein B is hydrogen and A is selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl. In yet another embodiment, both A and B are hydrogen. In a further embodiment, both A and B are selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl.

In one embodiment is a compound of Formula (II) wherein Y is an aryl group. In another embodiment the aryl group is a phenyl group. In yet another embodiment the phenyl group is substituted with at least one $R_6$ selected from Br, Cl, F, or I. In one embodiment $R_6$ is F. In one embodiment the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In one embodiment $R_6$ is $(NR_AR_B)C_1$-$C_6$alkylene. In another embodiment $C_1$-$C_6$alkyl is selected from methylene, ethylene, n-propylene, iso-propylene, n-butylene, iso-butylene, and tert-butylene. In yet another embodiment $C_1$-$C_6$alkylene is methylene. In yet a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In one embodiment $C_1$-$C_6$alkyl is methyl. In another embodiment $C_1$-$C_6$alkyl is ethyl. In yet another embodiment $C_3$-$C_8$cycloalkyl is cyclopropyl, cyclobutyl, cyclopentyl, and cyclohexyl. In a further embodiment $C_3$-$C_8$cycloalkyl is cyclopropyl. In yet a further embodiment $R_6$ is hydroxyalkylene. In one embodiment hydroxyalkylene is selected from $CH_2OH$, $CH_2CH_2OH$, $CH_2CH_2CH_2OH$, $CH(OH)CH_3$, $CH(OH)CH_2CH_3$, $CH_2CH(OH)CH_3$, and $CH_2CH_2CH_2CH_2OH$. In another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In yet another embodiment the hetero functionality is —N($C_1$-$C_6$alkyl). In a further embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl. In one embodiment Y is a heteroaryl group optionally substituted with at least one $R_6$. In another embodiment the heteroaryl group is selected from furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In yet another embodiment the heteroaryl group is imidazole. In a further embodiment imidazole is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment the heteroaryl group is furan. In another embodiment the heteroaryl group is thiazole. In yet another embodiment the heteroaryl group is 1,3,4-oxadiazole. In a further embodiment heteroaryl group is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment Z is an aryl group. In another embodiment the aryl group is a phenyl group. In yet another embodiment the phenyl group is substituted with at least one $R_6$ selected from Br, Cl, F, or I. In a further embodiment $R_6$ is F. In yet a further embodiment $R_6$ is Cl. In one embodiment the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In another embodiment $R_6$ is $(NR_AR_B)C_1$-$C_6$alkylene. In yet another embodiment $C_1$-$C_6$alkylene is selected from methylene, ethylene, n-propylene, iso-propylene, n-butylene, iso-butylene, and tert-butylene. In yet a further embodiment $C_1$-$C_6$alkyl is methylene. In a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In another embodiment $C_1$-$C_6$alkyl is methyl. In yet another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In a further embodiment the hetero functionality is —N($C_1$-$C_6$alkyl). In one embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl. In another embodiment $R_2$ is hydrogen. In yet another embodiment $R_2$ is selected from F, Cl, Br, and I. In a further embodiment $R_2$ is F.

In one embodiment is a compound of Formula (II) wherein A is hydrogen. In another embodiment A is $C_1$-$C_6$alkyl. In a further embodiment, A is selected from methyl, ethyl, n-propyl, iso-propyl, n-butyl, iso-butyl, tert-butyl, n-pentyl, and n-hexyl. In yet another embodiment, methyl, ethyl, n-propyl, iso-propyl, n-butyl, iso-butyl, tert-butyl, n-pentyl, and n-hexyl are optionally substituted with OH, $NO_2$, CN, Br, Cl, F, and I. In a further embodiment A is methyl. In yet another embodiment, A is selected from F, Cl, Br, and I. In another embodiment, A is $C_3$-$C_8$cycloalkyl. In another embodiment, A is cyclopropyl, cyclobutyl, cyclopentyl, or cyclohexyl. In one embodiment, A is substituted with OH, $NO_2$, or CN. In one embodiment is a compound of Formula (II) wherein B is hydrogen. In a further embodiment, B is $C_1$-$C_6$alkyl. In a further embodiment, B is selected from methyl, ethyl, n-propyl, iso-propyl, n-butyl, iso-butyl, tert-butyl, n-pentyl, and n-hexyl. In yet another embodiment, methyl, ethyl, n-propyl, iso-propyl, n-butyl, iso-butyl, tert-butyl, n-pentyl, and n-hexyl are optionally substituted with OH, $NO_2$, CN, Br, Cl, F, and I. In a further embodiment B is methyl. In yet another embodiment, B is selected from F, Cl, Br, and I. In another embodiment, B is $C_3$-$C_8$cycloalkyl. In another embodiment, B is cyclopropyl, cyclobutyl, cyclopentyl, or cyclohexyl. In one embodiment, A is substituted with OH, $NO_2$, or CN. In a further embodiment, is a compound of Formula (II) wherein A is hydrogen and B is selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl. In another embodiment, is a compound of Formula (II) wherein B is hydrogen and A is selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl. In yet another embodiment, both A and B are hydrogen. In a further embodiment, both A and B are selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl.

In yet a further aspect is a compound selected from:

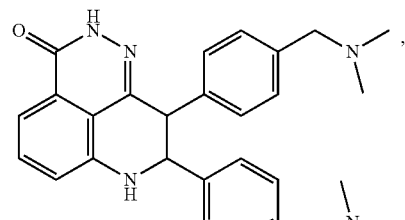

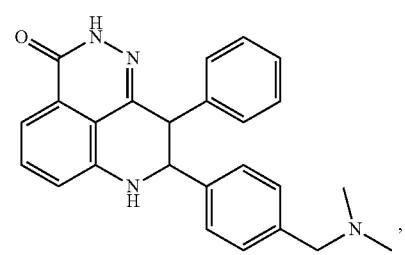

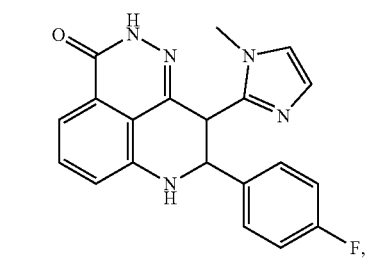

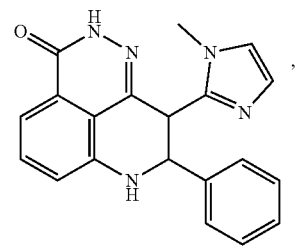

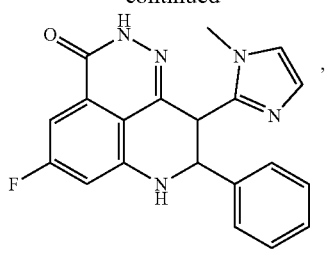
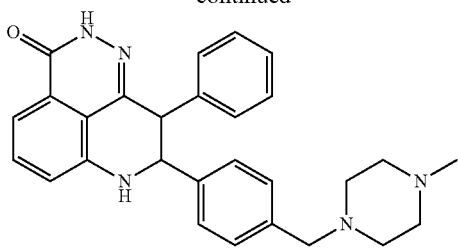
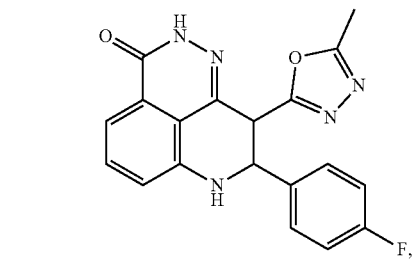
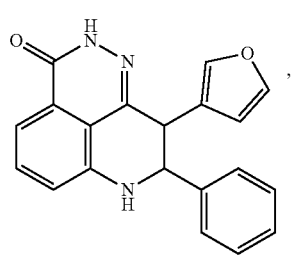
or a pharmaceutically acceptable salt, solvate or prodrug thereof.

In yet another aspect is a compound selected from:
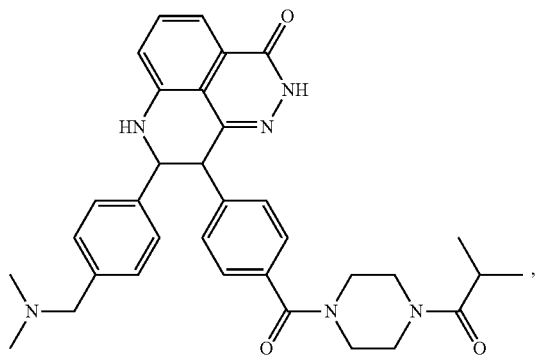
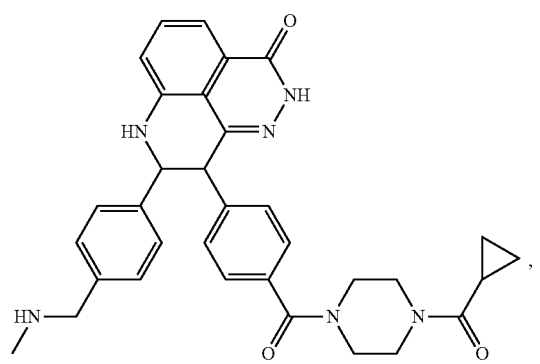
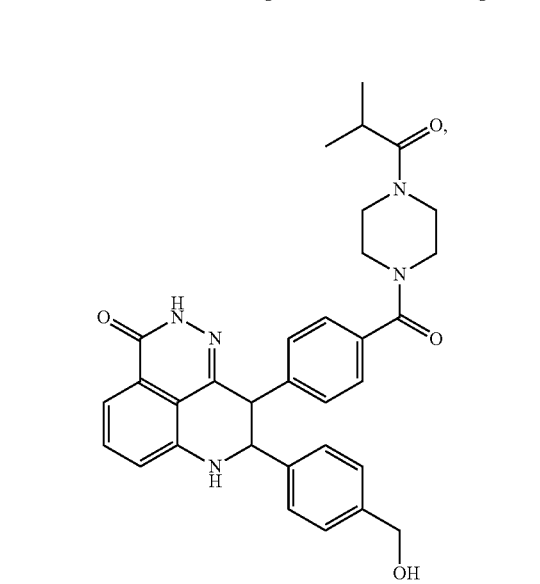
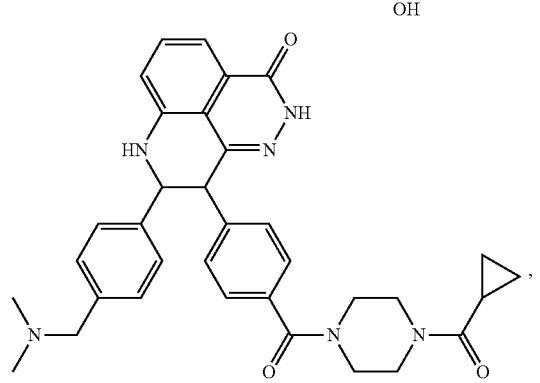
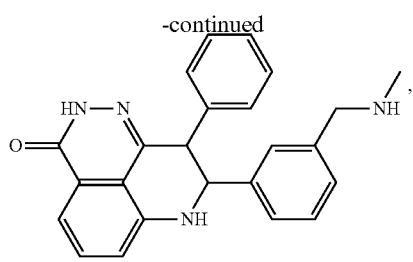
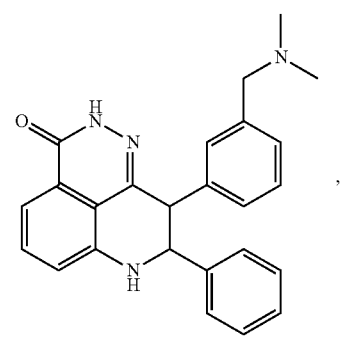
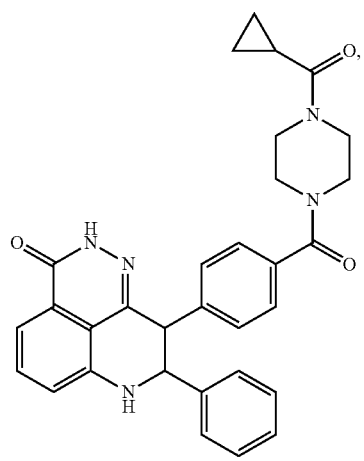
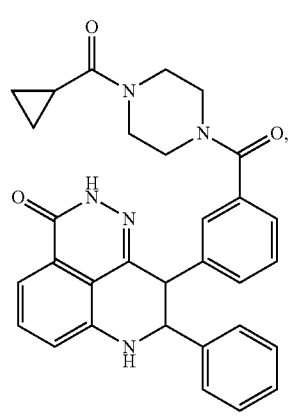

-continued
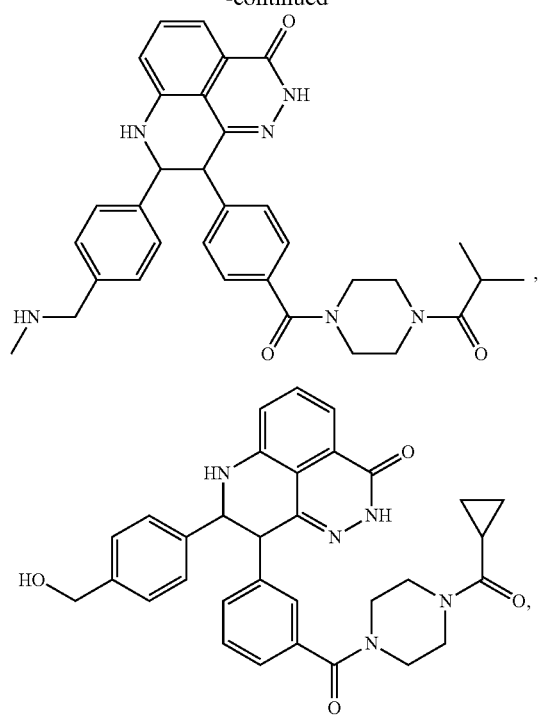
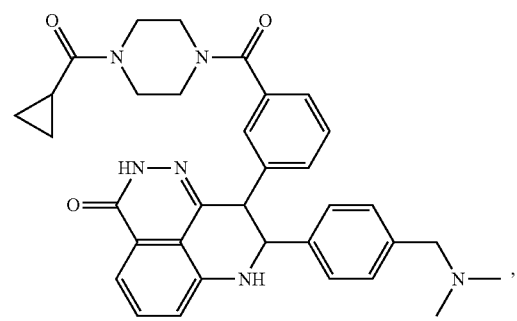
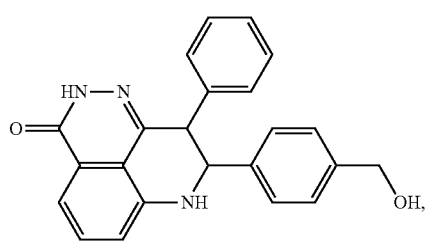
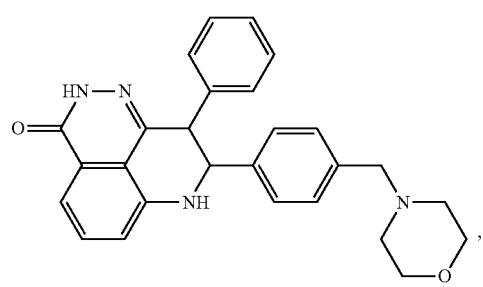
-continued
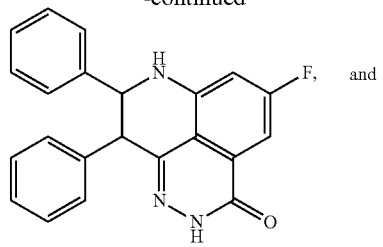
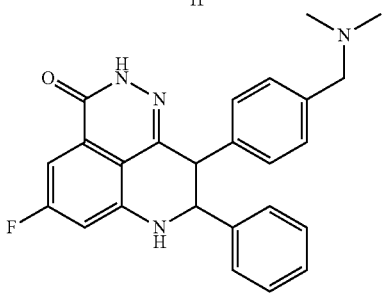
or a pharmaceutically acceptable salt, solvate or prodrug thereof.
In yet another aspect is a compound selected from:
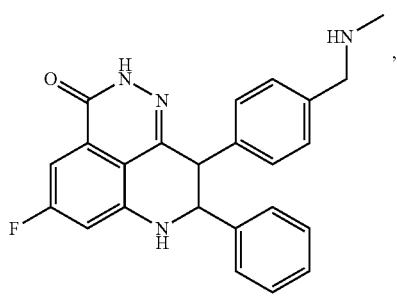
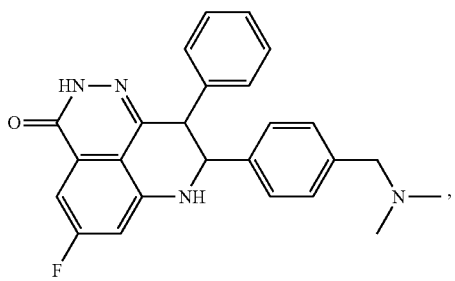
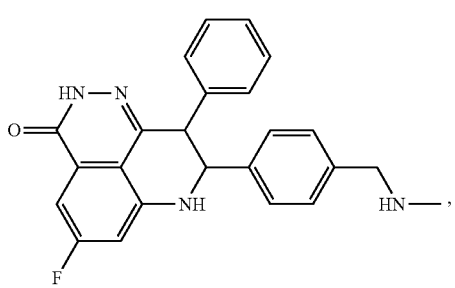

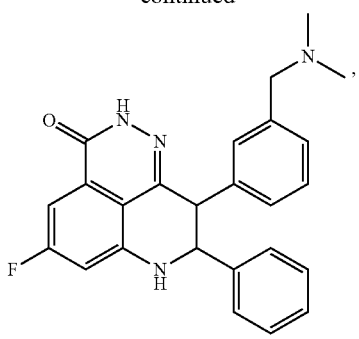
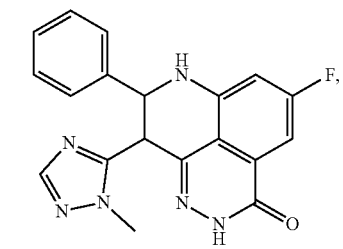
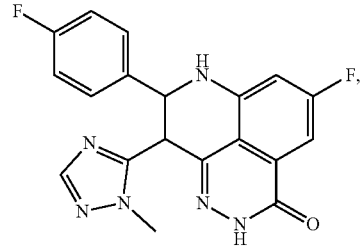
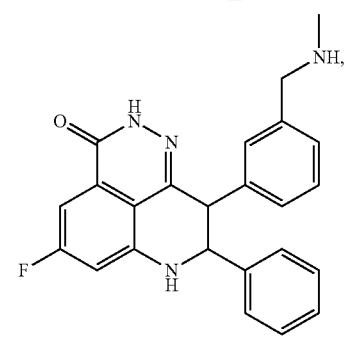
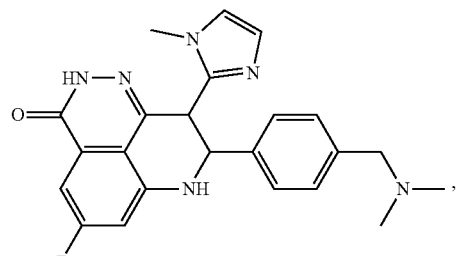
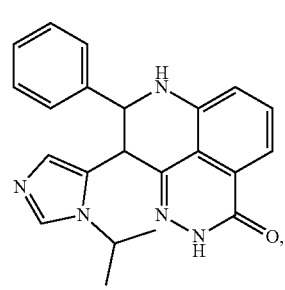
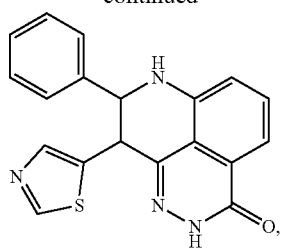
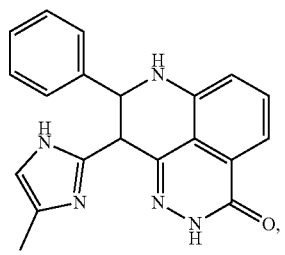
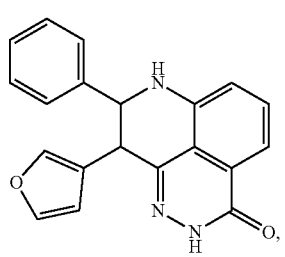
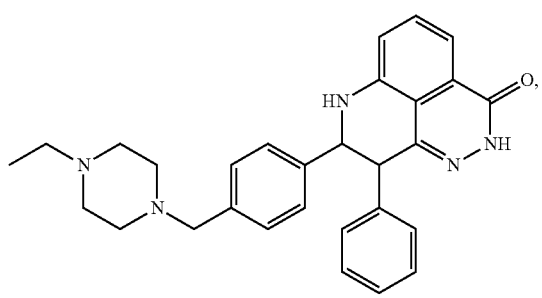
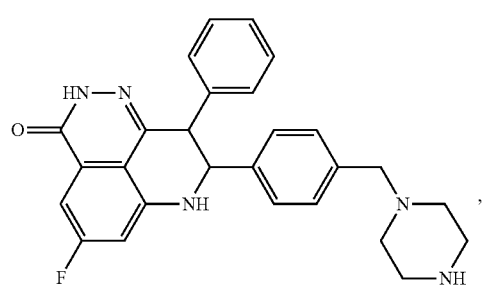
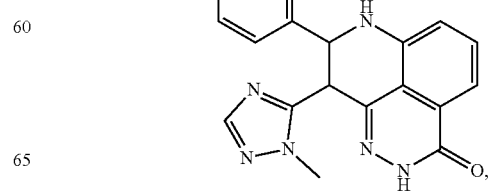

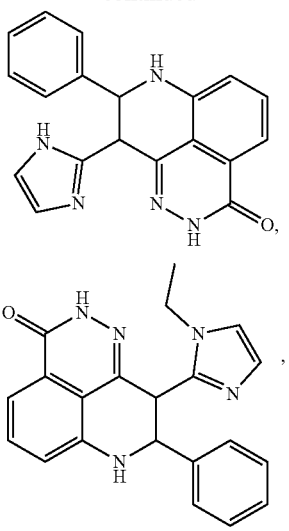
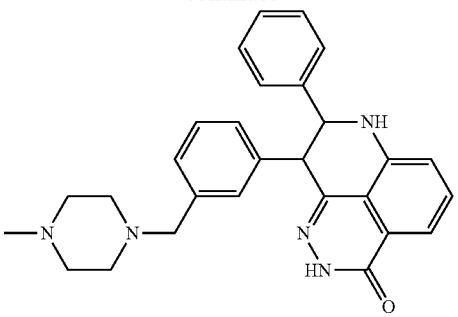
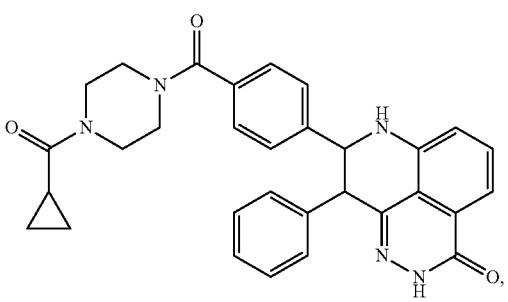
or a pharmaceutically acceptable salt, solvate or prodrug thereof
In yet a further embodiment is a compound selected from:
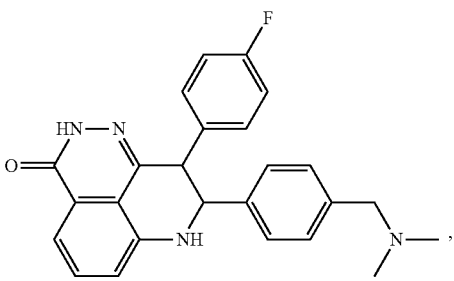
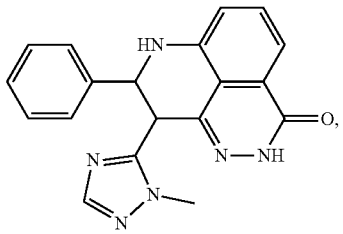
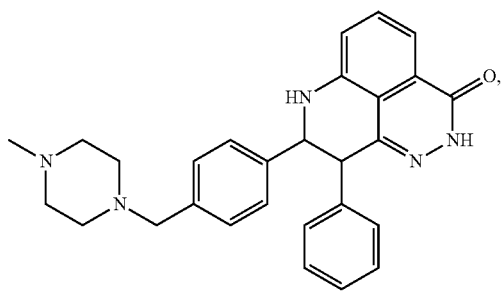
and -continued

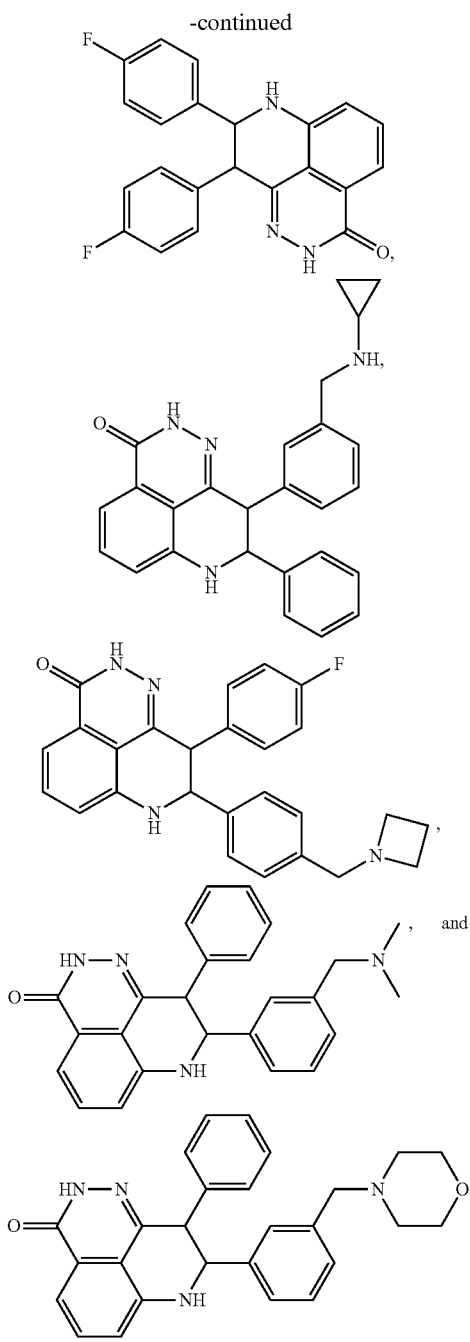

or a pharmaceutically acceptable salt, solvate or prodrug thereof.

In yet a further embodiment is a compound selected from:
(8S,9R)-5-fluoro-9-(1-methyl-1H-imidazol-2-yl)-8-phenyl-8,9-dihydro-2H-pyrido[4,3,2-de]phthalazin-3(7H)-one,
(8R,9S)-5-fluoro-9-(1-methyl-1H-imidazol-2-yl)-8-phenyl-8,9-dihydro-2H-pyrido[4,3,2-de]phthalazin-3(7H)-one,
(8S,9R)-5-fluoro-8-(4-fluorophenyl)-9-(1-methyl-1H-imidazol-2-yl)-8,9-dihydro-2H-pyrido[4,3,2-de]phthalazin-3(7H)-one,
(8R,9S)-5-fluoro-8-(4-fluorophenyl)-9-(1-methyl-1H-imidazol-2-yl)-8,9-dihydro-2H-pyrido[4,3,2-de]phthalazin-3(7H)-one,
(8S,9R)-8-(4-fluorophenyl)-9-(1-methyl-1H-imidazol-2-yl)-8,9-dihydro-2H-pyrido[4,3,2-de]phthalazin-3(7H)-one,
(8R,9S)-8-(4-fluorophenyl)-9-(1-methyl-1H-imidazol-2-yl)-8,9-dihydro-2H-pyrido[4,3,2-de]phthalazin-3(7H)-one,
(8S,9R)-5-fluoro-9-(1-methyl-1H-1,2,4-triazol-5-yl)-8-phenyl-8,9-dihydro-2H-pyrido[4,3,2-de]phthalazin-3(7H)-one,
(8R,9S)-5-fluoro-9-(1-methyl-1H-1,2,4-triazol-5-yl)-8-phenyl-8,9-dihydro-2H-pyrido[4,3,2-de]phthalazin-3(7H)-one,
(8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one,
(8R,9S)-5-fluoro-8-(4-fluorophenyl)-9-(1-methyl-1H-1,2,4-triazol-5-yl)-8,9-dihydro-2H-pyrido[4,3,2-de]phthalazin-3(7H)-one,
(8S,9R)-8-(4-fluorophenyl)-9-(1-methyl-1H-1,2,4-triazol-5-yl)-8,9-dihydro-2H-pyrido[4,3,2-de]phthalazin-3(7H)-one,
(8R,9S)-8-(4-fluorophenyl)-9-(1-methyl-1H-1,2,4-triazol-5-yl)-8,9-dihydro-2H-pyrido[4,3,2-de]phthalazin-3(7H)-one,
(8S,9R)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one, and
(8R,9S)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one,
or a pharmaceutically acceptable salt, solvate or prodrug thereof.

In another aspect is a pharmaceutical composition comprising a compound of Formula (I) and Formula (II) or a pharmaceutically acceptable salt, pharmaceutically acceptable solvate, or pharmaceutically acceptable prodrug and a pharmaceutically acceptable carrier, excipient, binder or diluent thereof.

In one aspect is a method of inhibiting poly(ADP-ribose) polymerase (PARP) in a subject in need of PARP inhibition comprising administering to the subject a therapeutically effective amount of a compound of Formula (I) and Formula (II).

In another aspect is a method of treating a disease ameliorated by the inhibition of PARP comprising administering to a subject in need of treatment a therapeutically effective amount of a compound of Formula (I) and Formula (II).

In one embodiment the disease is selected from the group consisting of: vascular disease; septic shock; ischaemic injury; reperfusion injury; neurotoxicity; hemorrhagic shock; inflammatory diseases; multiple sclerosis; secondary effects of diabetes; and acute treatment of cytoxicity following cardiovascular surgery.

In another aspect is a method of treating cancer, comprising administering to a subject in need of treatment a therapeutically effective amount of a compound of Formula (I) and Formula (II) in combination with ionizing radiation, one or more chemotherapeutic agents, or a combination thereof.

In one embodiment the compound of Formula (I) and Formula (II) is administered simultaneously with ionizing radiation, one or more chemotherapeutic agents, or a combination thereof. In another embodiment the compound of Formula (I) and Formula (II) is administered sequentially with ionizing radiation, one or more chemotherapeutic agents, or a combination thereof.

In yet another aspect is a method of treating a cancer deficient in Homologous Recombination (HR) dependent DNA double strand break (DSB) repair pathway, comprising administering to a subject in need of treatment a therapeutically effective amount of a compound of Formula (I) and Formula (II).

In one embodiment the cancer comprises one or more cancer cells having a reduced or abrogated ability to repair DNA DSB by HR relative to normal cells. In another embodiment the cancer cells have a BRCA1 or BRCA2 deficient phenotype. In yet another embodiment the cancer cells are deficient in BRCA1 or BRCA2. In a further embodiment the subject is heterozygous for a mutation in a gene encoding a component of the HR dependent DNA DSB repair pathway. In yet a further embodiment the subject is heterozygous for a mutation in BRCA1 and/or BRCA2. In one embodiment the cancer is breast, ovarian, pancreatic or prostate cancer. In another embodiment the treatment further comprises administration of ionizing radiation or a chemotherapeutic agent.

In one aspect is the use of a compound of Formula (I) and Formula (II) in the formulation of a medicament for the treatment of a poly(ADP-ribose)polymerase mediated disease or condition.

In another aspect is an article of manufacture, comprising packaging material, a compound of Formula (I) and Formula (II), and a label, wherein the compound is effective for modulating the activity of the enzyme poly(ADP-ribose) polymerase, or for treatment, prevention or amelioration of one or more symptoms of a poly(ADP-ribose)polymerase-dependent or poly(ADP-ribose)polymerase-mediated disease or condition, wherein the compound is packaged within the packaging material, and wherein the label indicates that the compound, or pharmaceutically acceptable salt, pharmaceutically acceptable N-oxide, pharmaceutically active metabolite, pharmaceutically acceptable prodrug, or pharmaceutically acceptable solvate thereof, or a pharmaceutical composition comprising such a compound is used for modulating the activity of poly(ADP-ribose)polymerase, or for treatment, prevention or amelioration of one or more symptoms of a poly(ADP-ribose)polymerase-dependent or poly(ADP-ribose)polymerase-mediated disease or condition.

DETAILED DESCRIPTION OF THE INVENTION

PARP has an essential role in facilitating DNA repair, controlling RNA transcription, mediating cell death, and regulating immune response. PARP inhibitors demonstrate efficacy in numerous models of disease particularly in models of ischemia reperfusion injury, inflammatory disease, degenerative diseases, protection from above adverse effects of cytotoxic compounds, and potentiation of cytotoxic cancer therapy. They are efficacious in the prevention of ischemia reperfusion injury in models of myocardial infarction, stoke, other neural trauma, organ transplantation, as well as reperfusion of the eye, kidney, gut and skeletal muscle. Inhibitors are efficacious in inflammatory diseases such as arthritis, gout, inflammatory bowel disease, CNS inflammation such as MS and allergic encephalitis, sepsis, septic shock, hemorrhagic shock, pulmonary fibrosis, and uveitis. PARP inhibitors also show benefit in several models of degenerative disease including diabetes and Parkinson's disease. PARP inhibitors ameliorate the liver toxicity following acetaminophen overdose, cardiac and kidney toxicities from doxorubicin and platinum based antineoplastic agents, as well as skin damage secondary to sulfur mustards.

In various cancer models, PARP inhibitors are shown to potentiate radiation and chemotherapy by increasing apoptosis of cancer cells, limiting tumor growth, decreasing metastasis, and prolonging the survival of tumor-bearing animals.

In certain embodiments are provided compounds of Formula (I)

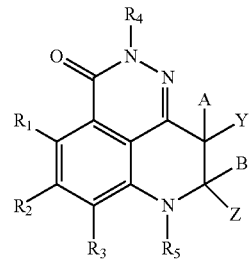

Formula (I)

or a therapeutically acceptable salt thereof wherein $R_1$, $R_2$, and $R_3$ are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl;

$R_A$, and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —N(aryl)-, alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with one or more substituents; $R_4$ and $R_5$ are each independently selected from the group consisting of hydrogen, alkyl, cycloalkyl, alkoxyalkyl, haloalkyl, hydroxyalkylene, and $(NR_AR_B)$alkylene;

A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH;

Y and Z are each independently selected from the group consisting of:

a) an aryl group optionally substituted with 1, 2, or 3 substituents $R_6$; $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;

b) a heteroaryl group optionally substituted with 1, 2, or 3 substituents $R_6$; $R_6$ is previously as defined;

c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene; or a pharmaceutically acceptable salt, solvate or prodrug thereof.

In certain embodiments are provided compounds of Formula (I) or a therapeutically acceptable salt thereof wherein $R_1$, $R_2$, $R_3$ are independently selected from a group consisting of hydrogen, alkyl, and halogen; $R_4$ is hydrogen and $R_5$ is selected from the group consisting hydrogen, alkyl, cycloalkyl, alkoxyalkyl, haloalkyl, hydroxyalkylene, and $(NR_AR_B)$alkylene; $R_A$, and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with one or more substituents; A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH; Y and Z are each independently selected from the group consisting of:
a) an aryl group optionally substituted with 1, 2, or 3 $R_6$; wherein each $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;
b) a heteroaryl group optionally substituted with 1, 2, or 3 $R_6$;
c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene; or a pharmaceutically acceptable salt, solvate or prodrug thereof.

In certain embodiments are provided compounds of Formula (I) or a therapeutically acceptable salt thereof wherein $R_1$, $R_2$, and $R_3$ are independently selected from a group consisting of hydrogen, alkyl, and halogen; $R_4$ and $R_5$ are hydrogen; $R_A$ and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with one or more substituents; A and B are each independently selected from hydrogen, Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl; Y and Z are each independently selected from the group consisting of:

In certain embodiments are provided compounds of Formula (I) or a therapeutically acceptable salt thereof wherein $R_1$, $R_2$, $R_3$, $R_4$ and $R_5$ are hydrogen; $R_A$, and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with one or more substituents; A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH; Y and Z are each independently selected from the group consisting of:

a) an aryl group optionally substituted with 1, 2, or 3 $R_6$; wherein each $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;

b) a heteroaryl group optionally substituted with 1, 2, or 3 $R_6$;

c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene; or a pharmaceutically acceptable salt, solvate or prodrug thereof.

In one embodiment is a compound of Formula (I) wherein $R_1$, $R_2$, $R_3$ are each independently selected from a group consisting of hydrogen, alkyl, and halogen; $R_4$ is hydrogen and $R_5$ is selected from the group consisting hydrogen, alkyl, cycloalkyl, alkoxyalkyl, haloalkyl, hydroxyalkylene, and $(NR_AR_B)$alkylene; and isomers, salts, solvates, chemically protected forms, and prodrugs thereof.

In another embodiment is a compound of Formula (I) wherein $R_1$, $R_2$, $R_3$ are each independently selected from a group consisting of hydrogen, alkyl, and halogen; $R_4$ and $R_5$ are hydrogen; and isomers, salts, solvates, chemically protected forms, and prodrugs thereof.

In a further embodiment is a compound of Formula (I) wherein $R_1$, $R_2$, $R_3$, $R_4$ are each hydrogen and $R_5$ is alkyl.

In yet another embodiment is a compound of Formula (I) wherein $R_1$, $R_2$, $R_3$, $R_4$ are each hydrogen; and $R_5$ is methyl.

In one embodiment is a compound of Formula (I) wherein $R_1$, $R_2$, and $R_3$ are each hydrogen.

In another embodiment is a compound of Formula (I) wherein Y and Z are each independently selected from the group consisting of:
a) a phenyl group optionally substituted with 1, 2, or 3 $R_6$;
b) a pyridyl group optionally substituted with 1, 2, or 3 $R_6$; and
c) a substituent independently selected from the group consisting of hydrogen, alkoxyalkyl, alkoxycarbonylalkyl, alkyl, arylalkyl, cycloalkyl, cycloalkylalkyl, haloalkyl, oxo, heterocycloalkyl, heterocycloalkylalkyl, alkylcarbonyl, arylcarbonyl, heteroarylcarbonyl, $(NR_AR_B)$alkylene, $(NR_AR_B)$carbonyl, and $(NR_AR_B)$carbonylalkylene.

In a further embodiment is a compound of Formula (I) wherein Y and Z are each independently selected from the group consisting of
a) a phenyl group optionally substituted with 1, 2, or 3 $R_6$;
b) a imidazole group optionally substituted with 1, 2, or 3 $R_6$; and
c) a substituent independently selected from the group consisting of hydrogen, alkoxyalkyl, alkoxycarbonylalkyl, alkyl, arylalkyl, cycloalkyl, cycloalkylalkyl, haloalkyl, oxo, heterocycloalkyl, heterocycloalkylalkyl, alkylcarbonyl, arylcarbonyl, heteroarylcarbonyl, $(NR_AR_B)$alkylene $(NR_AR_B)$carbonyl, and $(NR_AR_B)$carbonylalkylene.

In a further embodiment is a compound of Formula (I) wherein Y and Z are each independently selected from the group consisting of
d) a phenyl group optionally substituted with 1, 2, or 3 $R_6$;
e) a triazole group optionally substituted with 1, 2, or 3 $R_6$; and
f) a substituent independently selected from the group consisting of hydrogen, alkoxyalkyl, alkoxycarbonylalkyl, alkyl, arylalkyl, cycloalkyl, cycloalkylalkyl, haloalkyl, oxo, heterocycloalkyl, heterocycloalkylalkyl, alkylcarbonyl, arylcarbonyl, heteroarylcarbonyl, $(NR_AR_B)$alkylene $(NR_AR_B)$carbonyl, and $(NR_AR_B)$carbonylalkylene.

In one embodiment is a compound of Formula (I) wherein $R_5$ is hydrogen or an alkyl group. In another embodiment, $R_5$ is hydrogen. In a further embodiment, $R_5$ is $C_1$-$C_6$ alkyl. In yet a further embodiment, $R_5$ is $CH_3$. In another embodiment, $R_5$ is $CH_2CH_3$.

In another embodiment is a compound of Formula (I) wherein $R_4$ is hydrogen or an alkyl group. In yet another embodiment, $R_4$ is hydrogen.

In one embodiment, $R_2$ is selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl. In a further embodiment $R_2$ is a halogen selected from F, Cl, Br, and I. In yet a further embodiment, $R_2$ is fluorine. In one embodiment, $R_2$ is hydrogen.

In another embodiment, $R_3$ is selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl. In a further embodiment, $R_3$ is hydrogen. In some embodiments, $R_1$ is selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl. In a further embodiment, $R_1$ is hydrogen.

Also disclosed herein are compounds of Formula (I) wherein Z is an aryl group optionally substituted with 1, 2, or 3 $R_6$; wherein each $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In one embodiment is a compound of Formula (I) wherein Z is an optionally substituted phenyl group. In one embodiment, Z is a phenyl group. In another embodiment, the phenyl group is optionally substituted with at least one $R_6$ selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$ carbonyl, $(NR_AR_B)$carbonylalkylene, $(NR_AR_B)$sulfonyl, and $(NR_AR_B)$sulfonylalkylene. In another embodiment, $R_6$ is $(NR_AR_B)$alkylene. In a further embodiment, $R_6$ is $CH_2(NR_AR_B)$. In a further embodiment, $R_6$ is $CH_2(NR_AR_B)$ wherein $NR_AR_B$ is azetidine, pyrrolidine, piperidine or morpholine. In yet a further embodiment, $R_A$ is H or alkyl. In another embodiment, $R_A$ is $C_1$-$C_6$alkyl. In yet another embodiment, $R_A$ is $CH_3$. In another embodiment, $R_B$ is H or alkyl. In one embodiment, $R_B$ is $C_1$-$C_6$alkyl. In yet another embodiment, $R_B$ is $CH_3$. In a further embodiment, $R_6$ is $CH_2NHCH_3$. In yet a further embodiment, $R_6$ is $CH_2NCH_3CH_3$. In one embodiment, $R_6$ is (C=O)heterocycloalkyl(C=O)alkyl. In one embodiment $R_6$ is (C=O) heterocycloalkyl(C=O)alkyl wherein the heterocycloalkyl group has at least one heteroatom selected from O, N, and S. In another embodiment, the heterocycloalkyl group has two N atoms. In a further embodiment, $R_6$ is (C=O) heterocycloalkyl(C=O)alkyl wherein alkyl is selected from methyl, ethyl, n-propyl, iso-propyl, cyclopropyl, n-butyl, iso-butyl, and t-butyl. In one embodiment, the alkyl group is cyclopropyl. In another embodiment, the alkyl group is iso-propyl. In one embodiment, $R_6$ is

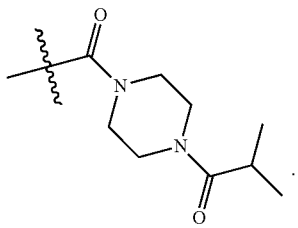 [SMILES: *C(=O)N1CCN(C(=O)C(C)C)CC1]

In another embodiment, $R_6$ is

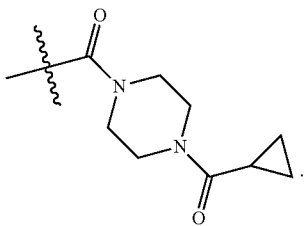 [SMILES: *C(=O)N1CCN(C(=O)C2CC2)CC1]

Presented herein are compounds of Formula (I) wherein Z is an optionally substituted heteroaryl group. In one embodiment, the heteroaryl group is selected from pyridine, pyrimidine, pyrazine, pyrazole, oxazole, thiazole, isoxazole, isothiazole, 1,3,4-oxadiazole, pyridazine, 1,3,5-trazine, 1,2,4-triazine, quinoxaline, benzimidazole, benzotriazole, purine, 1H-[1,2,3]triazolo[4,5-d]pyrimidine, triazole, imidazole, thiophene, furan, isobenzofuran, pyrrole, indolizine, isoindole, indole, indazole, isoquinoline, quinoline, phthalazine, naphthyridine, quinazoline, cinnoline, and pteridine. In one embodiment, Z is pyridine. In another embodiment, Z is optionally substituted pyridine.

Also disclosed herein are compounds of Formula (I) wherein Y is an aryl group optionally substituted with 1, 2, or 3 $R_6$; wherein each $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$ carbonyl, $(NR_AR_B)$carbonylalkylene, $(NR_AR_B)$sulfonyl, and $(NR_AR_B)$sulfonylalkylene. In one embodiment is a compound of Formula (I) wherein Y is an optionally substituted phenyl group. In one embodiment, Y is a phenyl group. In another embodiment, the phenyl group is optionally substituted with at least one $R_6$ selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$ carbonyl, $(NR_AR_B)$carbonylalkylene, $(NR_AR_B)$sulfonyl, and $(NR_AR_B)$sulfonylalkylene. In a further embodiment, $R_6$ is $CH_2(NR_AR_B)$. In yet a further embodiment, $R_A$ is H or alkyl. In another embodiment, $R_A$ is $C_1$-$C_6$alkyl. In yet another embodiment, $R_A$ is $CH_3$. In another embodiment, $R_B$ is H or alkyl. In one embodiment, $R_B$ is $C_1$-$C_6$alkyl. In yet another embodiment, $R_B$ is $CH_3$. In a further embodiment, $R_6$ is $CH_2NHCH_3$. In yet a further embodiment, $R_6$ is $CH_2NCH_3CH_3$. In one embodiment, $R_6$ is (C=O)heterocycloalkyl(C=O)alkyl. In one embodiment $R_6$ is (C=O) heterocycloalkyl(C=O)alkyl wherein the heterocycloalkyl group has at least one heteroatom selected from O, N, and S. In another embodiment, the heterocycloalkyl group has two N atoms. In a further embodiment, $R_6$ is (C=O) heterocycloalkyl(C=O)alkyl wherein alkyl is selected from methyl, ethyl, n-propyl, iso-propyl, cyclopropyl, n-butyl, iso-butyl, and t-butyl. In one embodiment, the alkyl group is cyclopropyl. In another embodiment, the alkyl group is iso-propyl. In one embodiment, $R_6$ is

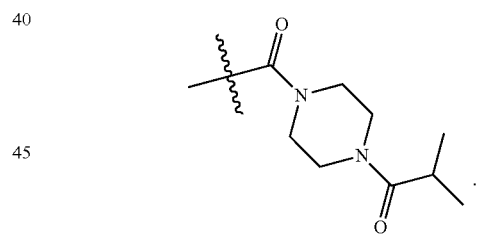

In another embodiment, $R_6$ is

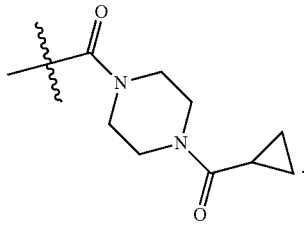 [SMILES: *C(=O)N1CCN(C(=O)C2CC2)CC1]

Presented herein are compounds of Formula (I) wherein Y is an optionally substituted heteroaryl group. In one embodiment, the heteroaryl group is selected from pyridine, pyrimidine, pyrazine, pyrazole, oxazole, thiazole, isoxazole, isothiazole, 1,3,4-oxadiazole, pyridazine, 1,3,5-trazine, 1,2,4- triazine, quinoxaline, benzimidazole, benzotriazole, purine, 1H-[1,2,3]triazolo[4,5-d]pyrimidine, triazole, imidazole, thiophene, furan, isobenzofuran, pyrrole, indolizine, isoindole, indole, indazole, isoquinoline, quinoline, phthalazine, naphthyridine, quinazoline, cinnoline, and pteridine. In one embodiment, Y is pyridine. In another embodiment, Y is optionally substituted pyridine. In one embodiment, Y is imidazole. In another embodiment, Y is optionally substituted imidazole. In one embodiment, Y is triazole. In another embodiment, Y is optionally substituted triazole.

In one embodiment, Y is a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene. In one embodiment, Y is alkyl. In another embodiment, Y is $C_1$-$C_6$ alkyl. In a further embodiment, Y is selected from methyl, ethyl, n-propyl, iso-propyl, n-butyl, iso-butyl or tert-butyl. In another embodiment, Y is iso-propyl.

Also disclosed herein are compounds of Formula (I) wherein Y is an optionally substituted heterocycloalkyl group. In one embodiment, the heterocycloalkyl group is selected from pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. In another embodiment the heterocycloalkyl group is selected from pyrrolidinyl, imidazolidinyl, piperidinyl, piperazinyl, pyrazolidinyl, tetrahydrofuranyl, tetrahydrothiophenyl, 1,3-oxathiolanyl, indolinyl, isoindolinyl, morpholinyl, and pyrazolinyl. In another embodiment, the heterocycloalkyl group is piperidinyl.

In another aspect is a compound of Formula (IA):

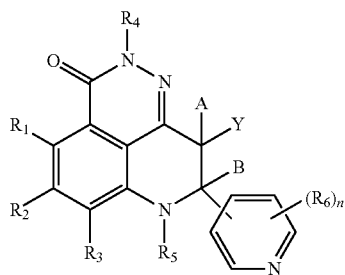

Formula (IA)

or a therapeutically acceptable salt, solvate or prodrug thereof wherein $R_1$, $R_2$, and $R_3$ are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl;

$R_A$ and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with one or more substituents; $R_4$ and $R_5$ are each independently selected from the group consisting of hydrogen, alkyl, cycloalkyl, alkoxyalkyl, haloalkyl, hydroxyalkylene, and $(NR_AR_B)$alkylene;

A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH;

Y is selected from the group consisting of:

a) an aryl group optionally substituted with 1, 2, or 3 substituents $R_6$; $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;

b) a heteroaryl group optionally substituted with 1, 2, or 3 substituents $R_6$; $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkylene, nitro, oxo, heteroaryl, heteroarylalkoxy, heteroaryloxy, heteroarylthio, heteroarylalkylthio, heterocycloalkyl, heterocycloalkoxy, heterocycloalkylthio, heterocyclooxy, heterocyclothio, $NR_AR_B$, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene;

c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene; and n is an integer from 0-4; or a pharmaceutically acceptable salt, solvate or prodrug thereof.

In another embodiment is a compound of Formula (IA) having the structure:

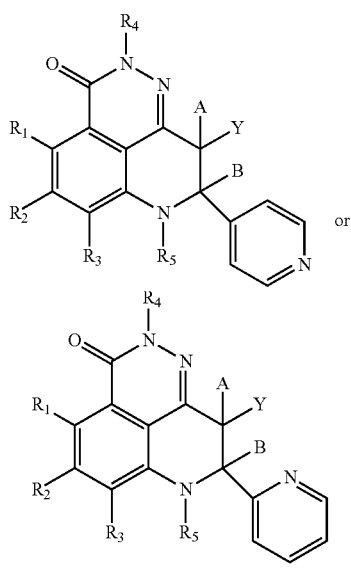

or a pharmaceutically acceptable salt, solvate, or prodrug thereof.

In one embodiment is a compound of Formula (IA) wherein Y is an aryl group. In another embodiment, Y is a heteroaryl group. In a further embodiment, the aryl group is a phenyl group. In yet a further embodiment is a compound of Formula (IA) wherein the phenyl group is substituted with at least one $R_6$. In yet another embodiment the phenyl group is substituted with at least one $R_6$ selected from Br, Cl, F, or I. In one embodiment $R_6$ is F. In one embodiment is a compound of Formula (IA) wherein the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In one embodiment $R_6$ is $(NR_AR_B)C_1$-$C_6$alkylene. In another embodiment $C_1$-$C_6$alkylene is selected from methylene, ethylene, n-propylene, iso-propylene, n-butylene, iso-butylene, and tert-butylene. In yet another embodiment $C_1$-$C_6$alkylene is methylene. In yet a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In one embodiment $C_1$-$C_6$alkyl is methyl. In another embodiment $C_1$-$C_6$alkyl is ethyl. In one embodiment is a compound of Formula (IA) wherein $C_3$-$C_8$cycloalkyl is cyclopropyl, cyclobutyl, cyclopentyl, and cyclohexyl. In a further embodiment $C_3$-$C_8$cycloalkyl is cyclopropyl. In one embodiment is a compound of Formula (IA) wherein $R_6$ is hydroxyalkylene. In one embodiment hydroxyalkylene is selected from $CH_2OH$, $CH_2CH_2OH$, $CH_2CH_2CH_2OH$, $CH(OH)CH_3$, $CH(OH)CH_2CH_3$, $CH_2CH(OH)CH_3$, and $CH_2CH_2CH_2CH_2OH$. In another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In yet another embodiment the hetero functionality is —N($C_1$-$C_6$alkyl). In a further embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl.

In one embodiment is a compound of Formula (IA) wherein Y is a heteroaryl group optionally substituted with at least one $R_6$. In another embodiment the heteroaryl group is selected from furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In yet another embodiment the heteroaryl group is imidazole. In a further embodiment imidazole is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment the heteroaryl group is furan. In another embodiment the heteroaryl group is thiazole. In yet another embodiment the heteroaryl group is 1,3,4-oxadiazole. In a further embodiment heteroaryl group is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl.

In one embodiment is a compound of Formula (IA) wherein A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl and B is not OH.

In yet another embodiment is a compound selected from:

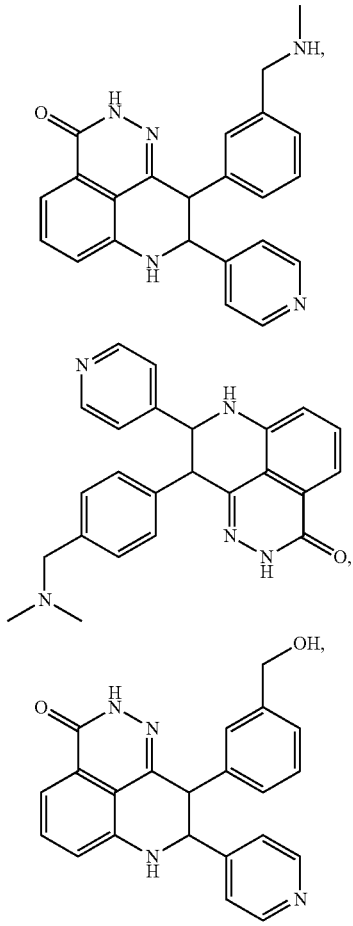

33
-continued
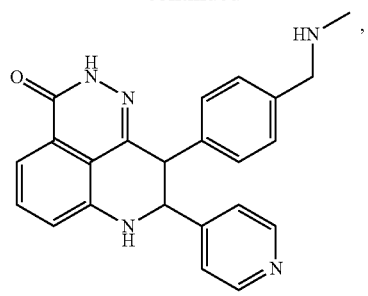
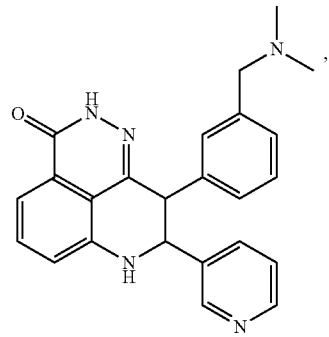
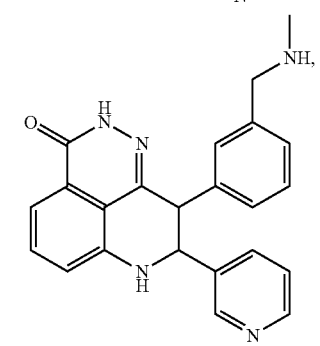
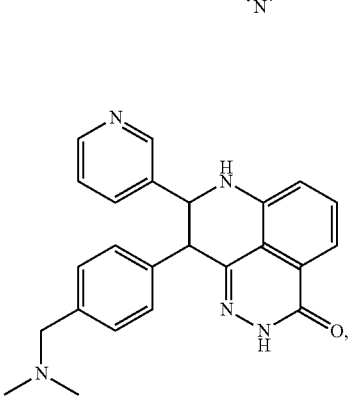
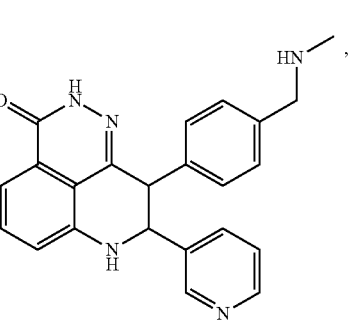
34
-continued
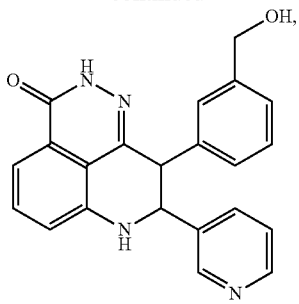
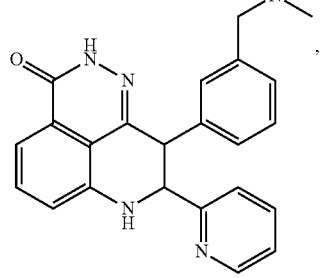
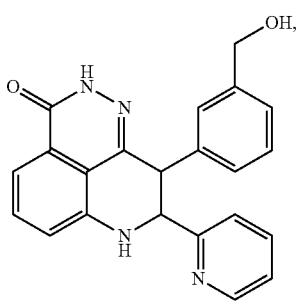
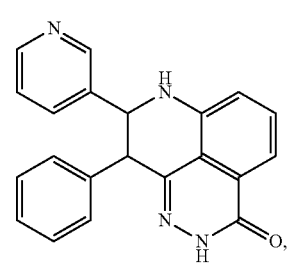
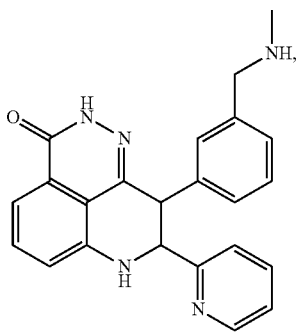

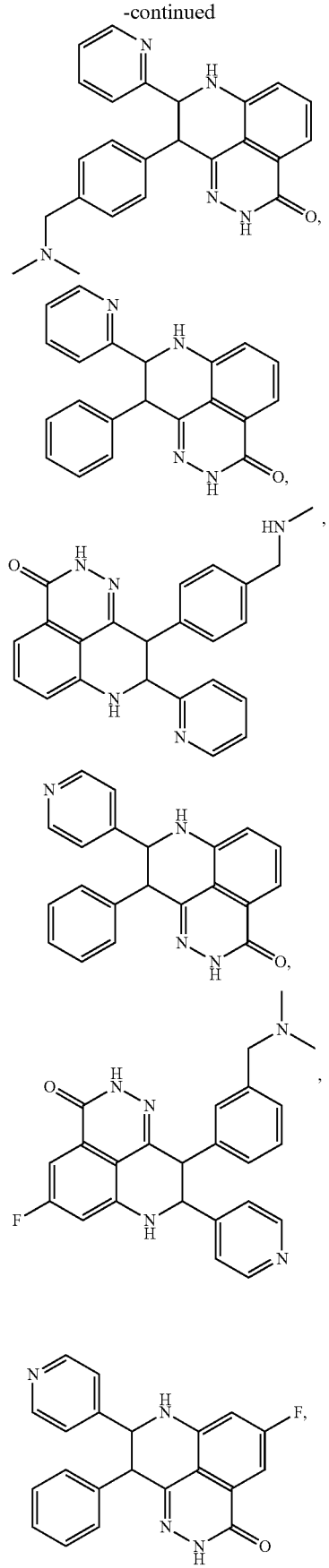
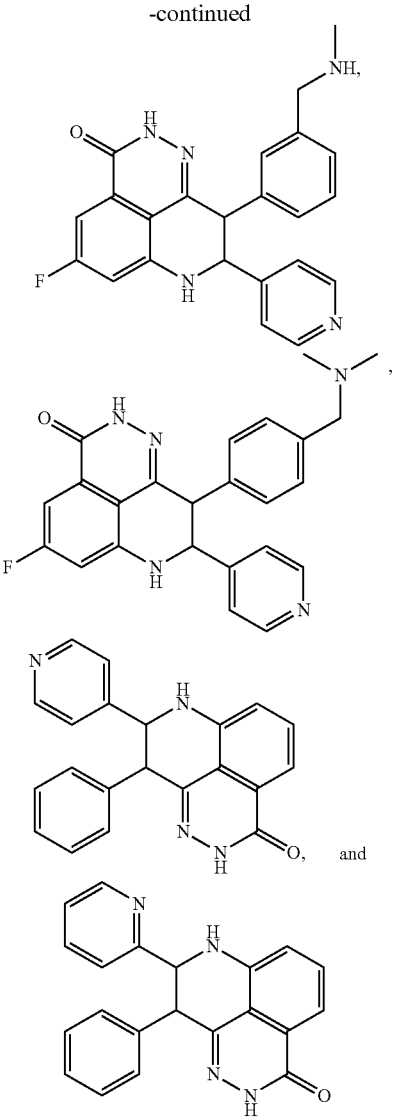

or a pharmaceutically acceptable salt, solvate or prodrug thereof.

In one embodiment is a compound of Formula (I) wherein Y is a heteroaryl group selected from furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In another embodiment, Y is an imidazole group. In yet another embodiment, the imidazole group is substituted with a $C_1$-$C_6$alkyl group. In another embodiment, the $C_1$-$C_6$alkyl group is methyl, ethyl, n-propyl, iso-propyl, n-butyl, iso-butyl, and tert-butyl. In a further embodiment $C_1$-$C_6$alkyl is methyl. In another embodiment is a compound of Formula (I) wherein Y is a substituted imidazole group and Z is selected from an aryl group or a heteroaryl group. In a further embodiment, Z is an aryl group. In yet a further embodiment, the aryl group is a phenyl group. In yet a further embodiment, the aryl group is a phenyl group substituted by a halogen. In yet a further embodiment Z is a heteroaryl group. In another embodiment, the heteroaryl group is furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In a further embodiment, the heteroaryl group is imidazole. In another embodiment, the imidazole group is substituted with a $C_1$-$C_6$alkyl group. In another embodiment, the $C_1$-$C_6$alkyl group is methyl, ethyl, n-propyl, iso-propyl, n-butyl, iso-butyl, and tert-butyl. In a further embodiment $C_1$-$C_6$alkyl is methyl.

In another embodiment is a compound of Formula (I) wherein Y is a triazole group. In yet another embodiment, the triazole group is substituted with a $C_1$-$C_6$alkyl group. In another embodiment, the $C_1$-$C_6$alkyl group is methyl, ethyl, n-propyl, iso-propyl, n-butyl, iso-butyl, and tert-butyl. In a further embodiment $C_1$-$C_6$alkyl is methyl. In another embodiment is a compound of Formula (I) wherein Y is a substituted triazole group and Z is selected from an aryl group or a heteroaryl group. In a further embodiment, Z is an aryl group. In yet further embodiment, the aryl group is a phenyl group. In yet a further embodiment, the aryl group is a phenyl group substituted by a halogen. In yet a further embodiment Z is a heteroaryl group. In another embodiment, the heteroaryl group is furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In a further embodiment, the heteroaryl group is triazole. In another embodiment, the triazole group is substituted with a $C_1$-$C_6$alkyl group. In another embodiment, the $C_1$-$C_6$alkyl group is methyl, ethyl, n-propyl, iso-propyl, n-butyl, iso-butyl, and tert-butyl. In a further embodiment $C_1$-$C_6$alkyl is methyl.

In another embodiment is a compound selected from

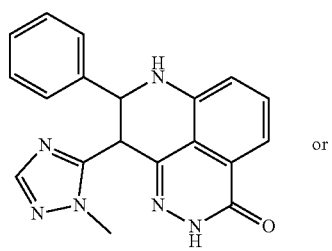

or

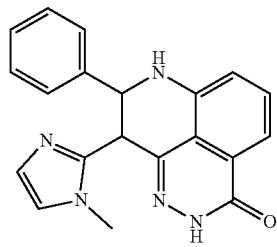

or a pharmaceutically acceptable salt, solvate or prodrug thereof.

In one aspect is a compound of Formula (II):

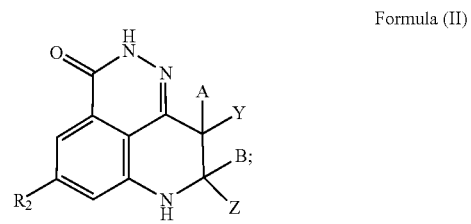

Formula (II)

wherein:
Y is an aryl or heteroaryl group optionally substituted with at least one $R_6$;
Z is an aryl group optionally substituted with at least one $R_6$;
$R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;
$R_2$ is selected from hydrogen, Br, Cl, I, or F;
A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH;
$R_A$, and $R_B$ are independently selected from the group consisting of hydrogen, $C_1$-$C_6$alkyl, $C_3$-$C_8$cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$alkyl)-, —NCO($C_1$-$C_6$alkyl)-, —NCO($C_3$-$C_8$cycloalkyl)-N(aryl)-, —N(aryl-$C_1$-$C_6$alkyl-)-, —N(substituted-aryl-$C_1$-$C_6$alkyl-)-, —N(heteroaryl)-, —N(heteroaryl-$C_1$-$C_6$alkyl-)-, —N(substituted-heteroaryl-$C_1$-$C_6$alkyl-)-, and —S— or S(O)$_q$—, wherein q is 1 or 2 and the 3-10 membered heterocycle ring is optionally substituted with one or more substituents; or a pharmaceutically acceptable salt, solvate or prodrug thereof.

In one embodiment is a compound of Formula (II) wherein Y is an aryl group. In another embodiment the aryl group is a phenyl group. In yet another embodiment the phenyl group is substituted with at least one $R_6$ selected from Br, Cl, F, or I. In one embodiment $R_6$ is F. In one embodiment the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In one embodiment $R_6$ is $(NR_AR_B)C_1$-$C_6$alkylene. In another embodiment $C_1$-$C_6$alkylene is selected from methylene, ethylene, n-propylene, iso-propylene, n-butylene, iso-butylene, and tert-butylene. In yet another embodiment $C_1$-$C_6$alkylene is methylene. In yet a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In one embodiment $C_1$-$C_6$alkyl is methyl. In another embodiment $C_1$-$C_6$alkyl is ethyl. In yet another embodiment $C_3$-$C_8$cycloalkyl is cyclopropyl, cyclobutyl, cyclopentyl, and cyclohexyl. In a further embodiment $C_3$-$C_8$cycloalkyl is cyclopropyl. In yet a further embodiment $R_6$ is hydroxyalkylene. In one embodiment hydroxyalkylene is selected from $CH_2OH$, $CH_2CH_2OH$, $CH_2CH_2CH_2OH$, $CH(OH)CH_3$, $CH(OH)CH_2CH_3$, $CH_2CH(OH)CH_3$, and $CH_2CH_2CH_2CH_2OH$. In another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In yet another embodiment the hetero functionality is —N($C_1$-$C_6$alkyl). In a further embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl.

In one embodiment is a compound of Formula (II) wherein Y is a heteroaryl group optionally substituted with at least one $R_6$. In another embodiment the heteroaryl group is selected from furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In yet another embodiment the heteroaryl group is imidazole. In a further embodiment imidazole is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment the heteroaryl group is furan. In another embodiment the heteroaryl group is thiazole. In yet another embodiment the heteroaryl group is 1,3,4-oxadiazole. In a further embodiment heteroaryl group is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl.

In one embodiment is a compound of Formula (II) wherein Z is an aryl group. In another embodiment the aryl group is a phenyl group. In yet another embodiment the phenyl group is substituted with at least one $R_6$ selected from Br, Cl, F, or I. In a further embodiment $R_6$ is F. In yet a further embodiment $R_6$ is $C_1$. In one embodiment the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In another embodiment $R_6$ is $(NR_AR_B)C_1$-$C_6$alkylene. In yet another embodiment $C_1$-$C_6$alkylene is selected from methylene, ethylene, n-propylene, iso-propylene, n-butylene, iso-butylene, and tert-butylene. In yet a further embodiment $C_1$-$C_6$alkylene is methylene. In a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In another embodiment $C_1$-$C_6$alkyl is methyl. In yet another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In a further embodiment the hetero functionality is —N($C_1$-$C_6$alkyl). In one embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl. In a further embodiment, $R_6$ is $CH_2(NR_AR_B)$ wherein $NR_AR_B$ is azetidine, pyrrolidine, piperidine or morpholine. In another embodiment $R_2$ is hydrogen. In yet another embodiment $R_2$ is selected from F, Cl, Br, and I. In a further embodiment $R_2$ is F.

In one embodiment is a compound of Formula (II) wherein A and B are hydrogen. In another embodiment A and B are independently selected from hydrogen and $C_1$-$C_6$alkyl.

In a further embodiment is a compound of Formula (II) wherein Z is aryl and Y is independently selected from the group consisting of
a) phenyl group optionally substituted with 1, 2, or 3 $R_6$;
b) a imidazole group optionally substituted with 1, 2, or 3 $R_6$;
c) a triazole group optionally substituted with 1, 2, or 3 $R_6$; and
d) a substituent independently selected from the group consisting of hydrogen, alkoxyalkyl, alkoxycarbonylalkyl, alkyl, arylalkyl, cycloalkyl, cycloalkylalkyl, haloalkyl, oxo, heterocycloalkyl, heterocycloalkylalkyl, alkylcarbonyl, arylcarbonyl, heteroarylcarbonyl, $(NR_AR_B)$alkylene $(NR_AR_B)$carbonyl.

In a further embodiment is a compound of Formula (II) wherein Z is phenyl and Y is independently selected from the group consisting of
e) phenyl group optionally substituted with 1, 2, or 3 $R_6$;
f) a imidazole group optionally substituted with 1, 2, or 3 $R_6$;
g) a triazole group optionally substituted with 1, 2, or 3 $R_6$; and
h) a substituent independently selected from the group consisting of hydrogen, alkoxyalkyl, alkoxycarbonylalkyl, alkyl, arylalkyl, cycloalkyl, cycloalkylalkyl, haloalkyl, oxo, heterocycloalkyl, heterocycloalkylalkyl, alkylcarbonyl, arylcarbonyl, heteroarylcarbonyl, $(NR_AR_B)$alkylene $(NR_AR_B)$carbonyl.

In a further embodiment is a compound of Formula (II) wherein Z is phenyl substituted with 1, 2, or 3 $R_6$ and Y is independently selected from the group consisting of
i) phenyl group optionally substituted with 1, 2, or 3 $R_6$;
j) a imidazole group optionally substituted with 1, 2, or 3 $R_6$;
k) a triazole group optionally substituted with 1, 2, or 3 $R_6$; and
l) a substituent independently selected from the group consisting of hydrogen, alkoxyalkyl, alkoxycarbonylalkyl, alkyl, arylalkyl, cycloalkyl, cycloalkylalkyl, haloalkyl, oxo, heterocycloalkyl, heterocycloalkylalkyl, alkylcarbonyl, arylcarbonyl, heteroarylcarbonyl, $(NR_AR_B)$alkylene $(NR_AR_B)$carbonyl.

In a further embodiment, A is selected from methyl, ethyl, n-propyl, iso-propyl, n-butyl, iso-butyl, tert-butyl, n-pentyl, and n-hexyl. In yet another embodiment, methyl, ethyl, n-propyl, iso-propyl, n-butyl, iso-butyl, tert-butyl, n-pentyl, and n-hexyl are optionally substituted with OH, $NO_2$, CN, Br, Cl, F, and I. In a further embodiment A is methyl. In yet another embodiment, A is selected from F, Cl, Br, and I. In another embodiment, A is $C_3$-$C_8$cycloalkyl. In a further embodiment, A is OH. In another embodiment, A is cyclopropyl, cyclobutyl, cyclopentyl, or cyclohexyl. In one embodiment, A is substituted with OH, $NO_2$, or CN. In a further embodiment, A is hydrogen. In a further embodiment, B is hydrogen. In a further embodiment, B is $C_1$-$C_6$alkyl. In a further embodiment, B is selected from methyl, ethyl, n-propyl, iso-propyl, n-butyl, iso-butyl, tert-butyl, n-pentyl, and n-hexyl. In yet another embodiment, methyl, ethyl, n-propyl, iso-propyl, n-butyl, iso-butyl, tert-butyl, n-pentyl, and n-hexyl are optionally substituted with OH, $NO_2$, CN, Br, Cl, F, and I. In a further embodiment B is methyl. In yet another embodiment, B is selected from F, Cl, Br, and I. In another embodiment, B is $C_3$-$C_8$cycloalkyl.

In another embodiment, B is cyclopropyl, cyclobutyl, cyclopentyl, or cyclohexyl. In one embodiment, A is substituted with OH, NO$_2$, or CN. In a further embodiment, is a compound of Formula (II) wherein A is hydrogen and B is selected from Br, Cl, F, I, C$_1$-C$_6$alkyl, C$_3$-C$_8$cycloalkyl, alkoxy, alkoxyalkyl wherein C$_1$-C$_6$alkyl, C$_3$-C$_8$cycloalkyl, alkoxy, alkoxyalkyl are optionally substituted with at least one substituent selected from OH, NO$_2$, CN, Br, Cl, F, I, C$_1$-C$_6$alkyl, and C$_3$-C$_8$cycloalkyl. In another embodiment, is a compound of Formula (II) wherein B is hydrogen and A is selected from Br, Cl, F, I, C$_1$-C$_6$alkyl, C$_3$-C$_8$cycloalkyl, alkoxy, alkoxyalkyl wherein C$_1$-C$_6$alkyl, C$_3$-C$_8$cycloalkyl, alkoxy, alkoxyalkyl are optionally substituted with at least one substituent selected from OH, NO$_2$, CN, Br, Cl, F, I, C$_1$-C$_6$alkyl, and C$_3$-C$_8$cycloalkyl. In yet another embodiment, both A and B are hydrogen. In a further embodiment, both A and B are selected from Br, Cl, F, I, OH, C$_1$-C$_6$alkyl, C$_3$-C$_8$cycloalkyl, alkoxy, alkoxyalkyl wherein C$_1$-C$_6$alkyl, C$_3$-C$_8$cycloalkyl, alkoxy, alkoxyalkyl are optionally substituted with at least one substituent selected from OH, NO$_2$, CN, Br, Cl, F, I, C$_1$-C$_6$alkyl, and C$_3$-C$_8$cycloalkyl wherein B is not OH.

Also described herein are stereoisomers of compounds of Formula (I), (IA), or (II), such as enantiomers, diastereomers, and mixtures of enantiomers or diastereomers. In one embodiment is a stereoisomer of a compound of Formula (II) having the structures:

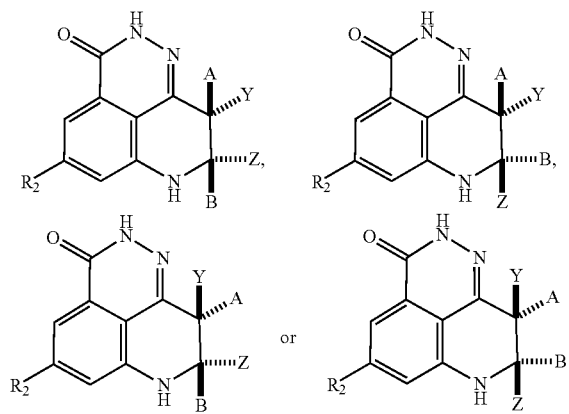

wherein:
Y is an aryl or heteroaryl group optionally substituted with at least one R$_6$;
Z is an aryl group optionally substituted with at least one R$_6$;
A and B are each independently selected from hydrogen, Br, Cl, F, I, OH, C$_1$-C$_6$alkyl, C$_3$-C$_8$cycloalkyl, alkoxy, alkoxyalkyl wherein C$_1$-C$_6$alkyl, C$_3$-C$_8$cycloalkyl, alkoxy, alkoxyalkyl are optionally substituted with at least one substituent selected from OH, NO$_2$, CN, Br, Cl, F, I, C$_1$-C$_6$alkyl, and C$_3$-C$_8$cycloalkyl, wherein B is not OH;
R$_6$ is selected from OH, NO$_2$, CN, Br, Cl, F, I, C$_1$-C$_6$alkyl, C$_3$-C$_8$cycloalkyl, C$_2$-C$_8$heterocycloalkyl; C$_2$-C$_6$alkenyl, alkoxy, alkoxyalkyl, alkoxycarbonyl, alkoxycarbonylalkyl, C$_2$-C$_6$alkynyl, aryl, arylalkyl, C$_3$-C$_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, C$_2$-C$_8$heterocycloalkylthio, heterocyclooxy, heterocyclothio, NR$_A$R$_B$, (NR$_A$R$_B$)C$_1$-C$_6$alkylene, (NR$_A$R$_B$)carbonyl, (NR$_A$R$_B$)carbonylalkylene, (NR$_A$R$_B$)sulfonyl, and (NR$_A$R$_B$)sulfonylalkylene;
R$_2$ is selected from hydrogen, Br, Cl, I, or F;
R$_A$, and R$_B$ are independently selected from the group consisting of hydrogen, C$_1$-C$_6$alkyl, C$_3$-C$_8$cycloalkyl, and alkylcarbonyl; or R$_A$ and R$_B$ taken together with the atom to which they are attached form a 3-10 membered heterocycle ring optionally having one to three heteroatoms or hetero functionalities selected from the group consisting of —O—, —NH, —N(C$_1$-C$_6$alkyl)-, —NCO(C$_1$-C$_6$alkyl)-, —NCO(C$_3$-C$_8$cycloalkyl)-N(aryl)-, —N(aryl-C$_1$-C$_6$alkyl-)-, —N(substituted-aryl-C$_1$-C$_6$alkyl-)-, —N(heteroaryl)-, —N(heteroaryl-C$_1$-C$_6$alkyl-)-, —N(substituted-heteroaryl-C$_1$-C$_6$alkyl-)-, and —S— or S(O)$_q$—, wherein q is 1 or 2 and the 3-10 membered heterocycle ring is optionally substituted with one or more substituents; or a pharmaceutically acceptable salt, solvate or prodrug thereof.

In one embodiment is the stereoisomer of the compound of Formula (II) shown above, having the substituents shown above, wherein R$_2$ is fluorine. In another embodiment is the compound of Formula (II) shown above, having the substituents shown above, wherein Y is an imidazole group. In another embodiment is the compound of Formula (II) shown above, having the substituents shown above, wherein the imidazole group of Y is substituted with a C$_1$-C$_6$alkyl group. In a further embodiment, the C$_1$-C$_6$alkyl is methyl. In yet another embodiment is a compound of Formula (II), shown above, having the substituents shown above, wherein Y is a triazole group. In another embodiment is the compound of Formula (II) shown above, having the substituents shown above, wherein the triazole group of Y is substituted with a C$_1$-C$_6$alkyl group. In a further embodiment, the C$_1$-C$_6$alkyl is methyl. In yet a further embodiment is the compound of Formula (II) shown above, having the substituents above, wherein the Y group is an aryl group. In a further embodiment is the compound of Formula (II) shown above, having the substituents shown above, wherein the aryl group of Y is a phenyl group. In a further embodiment, the phenyl group is substituted with a halogen. In yet a further embodiment, the halogen is F. In yet another embodiment the halogen is selected from Br, Cl, and I. In yet another embodiment, is the compound of Formula (II) shown above, having the substituents shown above, wherein Z is an aryl group. In yet another embodiment is the compound of Formula (II) shown above, having the substituents shown above, wherein the aryl group of Z is a phenyl group. In a further embodiment, the phenyl group of Z is substituted with a halogen, selected from F, Br, Cl, and I. In yet another embodiment, the phenyl group of Z is substituted with F. In yet a further embodiment the phenyl group of Z is substituted with C$_1$-C$_6$alkylene (NR$_A$R$_B$). In yet a further embodiment, the C$_1$-C$_6$alkylene group is methylene. In yet another embodiment NR$_A$R$_B$ is azetidine.

In one embodiment is a compound selected from:
(8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one,
(8R,9S)-5-fluoro-8-(4-fluorophenyl)-9-(1-methyl-1H-1,2,4-triazol-5-yl)-8,9-dihydro-2H-pyrido[4,3,2-de]phthalazin-3(7H)-one,
(8S,9R)-8-(4-fluorophenyl)-9-(1-methyl-1H-imidazol-2-yl)-8,9-dihydro-2H-pyrido[4,3,2-de]phthalazin-3(7H)-one,
(8R,9S)-8-(4-fluorophenyl)-9-(1-methyl-1H-imidazol-2-yl)-8,9-dihydro-2H-pyrido[4,3,2-de]phthalazin-3(7H)-one,
(8S,9R)-8-(4-fluorophenyl)-9-(1-methyl-1H-1,2,4-triazol-5-yl)-8,9-dihydro-2H-pyrido[4,3,2-de]phthalazin-3(7H)-one, (8R,9S)-8-(4-fluorophenyl)-9-(1-methyl-1H-1,2,4-triazol-5-yl)-8,9-dihydro-2H-pyrido[4,3,2-de]phthalazin-3(7H)-one,
(8S,9R)-5-fluoro-8-(4-fluorophenyl)-9-(1-methyl-1H-imidazol-2-yl)-8,9-dihydro-2H-pyrido[4,3,2-de]phthalazin-3(7H)-one,
(8R,9S)-5-fluoro-8-(4-fluorophenyl)-9-(1-methyl-1H-imidazol-2-yl)-8,9-dihydro-2H-pyrido[4,3,2-de]phthalazin-3(7H)-one,
(8S,9R)-5-fluoro-9-(1-methyl-1H-imidazol-2-yl)-8-phenyl-8,9-dihydro-2H-pyrido[4,3,2-de]phthalazin-3(7H)-one,
(8R,9S)-5-fluoro-9-(1-methyl-1H-imidazol-2-yl)-8-phenyl-8,9-dihydro-2H-pyrido[4,3,2-de]phthalazin-3(7H)-one,
(8S,9R)-8-(4-(azetidin-1-ylmethyl)phenyl)-9-(4-fluorophenyl)-8,9-dihydro-2H-pyrido[4,3,2-de]phthalazin-3(7H)-one, and
(8R,9S)-8-(4-(azetidin-1-ylmethyl)phenyl)-9-(4-fluorophenyl)-8,9-dihydro-2H-pyrido[4,3,2-de]phthalazin-3(7H)-one, or a pharmaceutically acceptable salt, solvate or prodrug thereof.

In one aspect is a compound selected from:
9-diphenyl-8,9-dihydro-2H-pyrido[4,3,2-de]phthalazin-3(7H)-one;
8,9-bis(4-(methylamino)methyl)phenyl-8,9-dihydro-2H-pyrido[4,3,2-de]phthalazin-3(7H)-one;
8,9-di(pyridin-4-yl)-8,9-dihydro-2H-pyrido[4,3,2-de]phthalazin-3(7H)-one;
8,9-di(pyridin-3-yl)-8,9-dihydro-2H-pyrido[4,3,2-de]phthalazin-3(7H)-one;
8,9-di(pyridin-2-yl)-8,9-dihydro-2H-pyrido[4,3,2-de]phthalazin-3(7H)-one;
9-isopropyl-8-phenyl-8,9-dihydro-2H-pyrido[4,3,2-de]phthalazin-3(7H)-one;
9-(4-((methylamino)methyl)phenyl)-8-phenyl-8,9-dihydro-2H-pyrido[4,3,2-de]phthalazin-3(7H)-one;
9-(4-((dimethylamino)methyl)phenyl)-8-phenyl-8,9-dihydro-2H-pyrido[4,3,2-de]phthalazin-3(7H)-one;
9-(3-((methylamino)methyl)phenyl)-8-phenyl-8,9-dihydro-2H-pyrido[4,3,2-de]phthalazin-3(7H)-one;
8-(4-((methylamino)methyl)phenyl)-9-phenyl-8,9-dihydro-2H-pyrido[4,3,2-de]phthalazin-3(7H)-one;
8,9-bis(3-((methylamino)methyl)phenyl)-8,9-dihydro-2H-pyrido[4,3,2-de]phthalazin-3(7H)-one;
9-(4-(hydroxymethyl)phenyl)-8-phenyl-8,9-dihydro-2H-pyrido[4,3,2-de]phthalazin-3(7H)-one;
9-(3-(4-isobutyrylpiperazine-1-carbonyl)phenyl)-8-phenyl-8,9-dihydro-2H-pyrido[4,3,2-de]phthalazin-3(7H)-one;
8,9-bis(3-(4-isobutyrylpiperazine-1-carbonyl)phenyl)-8,9-dihydro-2H-pyrido[4,3,2-de]phthalazin-3(7H)-one;
9-(piperidin-3-yl)-8-(pyridin-3-yl)-8,9-dihydro-2H-pyrido[4,3,2-de]phthalazin-3(7H)-one;
9-(piperidin-4-yl)-8-(pyridin-4-yl)-8,9-dihydro-2H-pyrido[4,3,2-de]phthalazin-3(7H)-one;
8,9-bis(4-((dimethylamino)methyl)phenyl)-8,9-dihydro-2H-pyrido[4,3,2-de]phthalazin-3(7H)-one;
9-(4-(4-(cyclopropanecarbonyl)piperazine-1-carbonyl)phenyl)-8-(4((methylamino)methyl)phenyl)-8,9-dihydro-2H-pyrido[4,3,2-de]phthalazin-3(7H)-one;
9-(4-(4-(cyclopropanecarbonyl)piperazine-1-carbonyl)phenyl)-8-(4((dimethylamino)methyl)phenyl)-8,9-dihydro-2H-pyrido[4,3,2-de]phthalazin-3(7H)-one;
8-(4-(hydroxymethyl)phenyl)-9-(4-(4-isobutyrylpiperazine-1-carbonyl)phenyl)-8,9-dihydro-2H-pyrido[4,3,2-de]phthalazin-3(7H)-one;
8-(4-((dimethylamino)methyl)phenyl)-9-(4-(4-isobutyrylpiperazine-1-carbonyl)phenyl)-8,9-dihydro-2H-pyrido[4,3,2-de]phthalazin-3(7H)-one;
9-(4-(4-(cyclopropanecarbonyl)piperazine-1-carbonyl)phenyl)-8-phenyl-8,9-dihydro-2H-pyrido[4,3,2-de]phthalazin-3(7H)-one;
9-(3-(4-(cyclopropanecarbonyl)piperazine-1-carbonyl)phenyl)-8-phenyl-8,9-dihydro-2H-pyrido[4,3,2-de]phthalazin-3(7H)-one;
9-(3-((dimethylamino)methyl)phenyl)-8-phenyl-8,9-dihydro-2H-pyrido[4,3,2-de]phthalazin-3(7H)-one;
8-(3-((methylamino)methyl)phenyl)-9-phenyl-8,9-dihydro-2H-pyrido[4,3,2-de]phthalazin-3(7H)-one;
8-(4-((dimethylamino)methyl)phenyl)-9-phenyl-8,9-dihydro-2H-pyrido[4,3,2-de]phthalazin-3(7H)-one;
8-(4-(morpholinomethyl)phenyl)-9-phenyl-8,9-dihydro-2H-pyrido[4,3,2-de]phthalazin-3(7H)-one;
8-(4-(hydroxymethyl)phenyl)-9-phenyl-8,9-dihydro-2H-pyrido[4,3,2-de]phthalazin-3(7H)-one;
9-(3-(4-(cyclopropanecarbonyl)piperazine-1-carbonyl)phenyl)-8-(4-((dimethylamino)methyl)phenyl)-8,9-dihydro-2H-pyrido[4,3,2-de]phthalazin-3(7H)-one;
9-(3-(4-(cyclopropanecarbonyl)piperazine-1-carbonyl)phenyl)-8-(4-(hydroxymethyl)phenyl)-8,9-dihydro-2H-pyrido[4,3,2-de]phthalazin-3(7H)-one;
9-(4-(4-isobutyrylpiperazine-1-carbonyl)phenyl)-8-(4-((methylamino)methyl)phenyl)-8,9-dihydro-2H-pyrido[4,3,2-de]phthalazin-3(7H)-one;
9-(3-(4-isobutyrylpiperazine-1-carbonyl)phenyl)-8-(pyridin-4-yl)-8,9-dihydro-2H-pyrido[4,3,2-de]phthalazin-3(7H)-one;
9-(3-((dimethylamino)methyl)phenyl)-8-(pyridin-4-yl)-8,9-dihydro-2H-pyrido[4,3,2-de]phthalazin-3(7H)-one;
9-(3-((methylamino)methyl)phenyl)-8-(pyridin-4-yl)-8,9-dihydro-2H-pyrido[4,3,2-de]phthalazin-3(7H)-one;
9-(4-((dimethylamino)methyl)phenyl)-8-(pyridin-4-yl)-8,9-dihydro-2H-pyrido[4,3,2-de]phthalazin-3(7H)-one;
9-(3-(hydroxymethyl)phenyl)-8-(pyridin-4-yl)-8,9-dihydro-2H-pyrido[4,3,2-de]phthalazin-3(7H)-one;
9-(4-((methylamino)methyl)phenyl)-8-(pyridin-4-yl)-8,9-dihydro-2H-pyrido[4,3,2-de]phthalazin-3(7H)-one;
9-(3-((dimethylamino)methyl)phenyl)-8-(pyridin-3-yl)-8,9-dihydro-2H-pyrido[4,3,2-de]phthalazin-3(7H)-one;
9-(3-((methylamino)methyl)phenyl)-8-(pyridin-3-yl)-8,9-dihydro-2H-pyrido[4,3,2-de]phthalazin-3(7H)-one;
9-(4-((dimethylamino)methyl)phenyl)-8-(pyridin-3-yl)-8,9-dihydro-2H-pyrido[4,3,2-de]phthalazin-3(7H)-one;
9-(4-((methylamino)methyl)phenyl)-8-(pyridin-3-yl)-8,9-dihydro-2H-pyrido[4,3,2-de]phthalazin-3(7H)-one;
9-(3-(hydroxymethyl)phenyl)-8-(pyridin-3-yl)-8,9-dihydro-2H-pyrido[4,3,2-de]phthalazin-3(7H)-one;
9-(3-((dimethylamino)methyl)phenyl)-8-(pyridin-2-yl)-8,9-dihydro-2H-pyrido[4,3,2-de]phthalazin-3(7H)-one;
9-(3-((methylamino)methyl)phenyl)-8-(pyridin-2-yl)-8,9-dihydro-2H-pyrido[4,3,2-de]phthalazin-3(7H)-one;
9-(3-(hydroxymethyl)phenyl)-8-(pyridin-2-yl)-8,9-dihydro-2H-pyrido[4,3,2-de]phthalazin-3(7H)-one;
9-(4-((dimethylamino)methyl)phenyl)-8-(pyridin-2-yl)-8,9-dihydro-2H-pyrido[4,3,2-de]phthalazin-3(7H)-one;
9-(4-((methylamino)methyl)phenyl)-8-(pyridin-2-yl)-8,9-dihydro-2H-pyrido[4,3,2-de]phthalazin-3(7H)-one;
9-phenyl-8-(pyridin-2-yl)-8,9-dihydro-2H-pyrido[4,3,2-de]phthalazin-3(7H)-one;
9-phenyl-8-(pyridin-3-yl)-8,9-dihydro-2H-pyrido[4,3,2-de]phthalazin-3(7H)-one;
9-phenyl-8-(pyridin-4-yl)-8,9-dihydro-2H-pyrido[4,3,2-de]phthalazin-3(7H)-one;
5-fluoro-9-phenyl-8-(pyridin-4-yl)-8,9-dihydro-2H-pyrido[4,3,2-de]phthalazin-3(7H)-one;

9-(3-((dimethylamino)methyl)phenyl)-5-fluoro-8-(pyridin-4-yl)-8,9-dihydro-2H-pyrido[4,3,2-de]phthalazin-3(7H)-one;

5-fluoro-9-(3-((methylamino)methyl)phenyl)-8-(pyridin-4-yl)-8,9-dihydro-2H-pyrido[4,3,2-de]phthalazin-3(7H)-one;

9-(4-((dimethylamino)methyl)phenyl)-5-fluoro-8-(pyridin-4-yl)-8,9-dihydro-2H-pyrido[4,3,2-de]phthalazin-3(7H)-one;

5-fluoro-8,9-diphenyl-8,9-dihydro-2H-pyrido[4,3,2-de]phthalazin-3(7H)-one;

9-(4-((dimethylamino)methyl)phenyl)-5-fluoro-8-phenyl-8,9-dihydro-2H-pyrido[4,3,2-de]phthalazin-one;

5-fluoro-9-(4-((methylamino)methyl)phenyl)-8-phenyl-8,9-dihydro-2H-pyrido[4,3,2-de]phthalazin-one;

9-(3-((dimethylamino)methyl)phenyl)-5-fluoro-8-phenyl-8,9-dihydro-2H-pyrido[4,3,2-de]phthalazin-one;

8-(4-((dimethylamino)methyl)phenyl)-5-fluoro-9-phenyl-8,9-dihydro-2H-pyrido[4,3,2-de]phthalazin-one;

5-fluoro-9-(3-((methylamino)methyl)phenyl)-8-phenyl-8,9-dihydro-2H-pyrido[4,3,2-de]phthalazin-one;

5-fluoro-8-(4-((methylamino)methyl)phenyl)-9-phenyl-8,9-dihydro-2H-pyrido[4,3,2-de]phthalazin-one;

7-methyl-8,9-diphenyl-8,9-dihydro-2H-pyrido[4,3,2-de]phthalazin-3(7H)-one;

7-ethyl-8,9-diphenyl-8,9-dihydro-2H-pyrido[4,3,2-de]phthalazin-3(7H)-one;

5-fluoro-9-(1-methyl-1H-imidazol-2-yl)-8-phenyl-8,9-dihydro-2H-pyrido[4,3,2-de]phthalazin-3(7H)-one;

5-fluoro-8-(4-fluorophenyl)-9-(1-methyl-1H-imidazol-2-yl)-8,9-dihydro-2H-pyrido[4,3,2-de]phthalazin-3(7H)-one;

8-(4-((dimethylamino)methyl)phenyl)-9-(1-methyl-1H-imidazol-2-yl)-8,9-dihydro-2H-pyrido[4,3,2-de]phthalazin-3(7H)-one;

9-(1-isopropyl-1H-imidazol-5-yl)-8-phenyl-8,9-dihydro-2H-pyrido[4,3,2-de]phthalazin-3(7H)-one;

9-(4-methyl-1H-imidazol-2-yl)-8-phenyl-8,9-dihydro-2H-pyrido[4,3,2-de]phthalazin-3(7H)-one;

8-phenyl-9-(thiazol-5-yl)-8,9-dihydro-2H-pyrido[4,3,2-de]phthalazin-3(7H)-one;

9-(furan-3-yl)-8-phenyl-8,9-dihydro-2H-pyrido[4,3,2-de]phthalazin-3(7H)-one;

8-(4-((4-ethylpiperazin-1-yl)methyl)phenyl)-9-phenyl-8,9-dihydro-2H-pyrido[4,3,2-de]phthalazin-3(7H)-one;

9-phenyl-8-(4-(piperazin-1-ylmethyl)phenyl)-8,9-dihydro-2H-pyrido[4,3,2-de]phthalazin-3(7H)-one;

8-(1-methyl-1H-imidazol-2-yl)-9-phenyl-8,9-dihydro-2H-pyrido[4,3,2-de]phthalazin-3(7H)-one;

9-(1-methyl-1H-imidazol-2-yl)-8-phenyl-8,9-dihydro-2H-pyrido[4,3,2-de]phthalazin-3(7H)-one;

8,9-bis(1-methyl-1H-imidazol-2-yl)-8,9-dihydro-2H-pyrido[4,3,2-de]phthalazin-3(7H)-one;

9-(1H-imidazol-2-yl)-8-phenyl-8,9-dihydro-2H-pyrido[4,3,2-de]phthalazin-3(7H)-one;

9-(1-ethyl-1H-imidazol-2-yl)-8-phenyl-8,9-dihydro-2H-pyrido[4,3,2-de]phthalazin-3(7H)-one;

8-phenyl-9-(1-propyl-1H-imidazol-2-yl)-8,9-dihydro-2H-pyrido[4,3,2-de]phthalazin-3(7H)-one;

9-(1-methyl-1H-imidazol-5-yl)-8-phenyl-8,9-dihydro-2H-pyrido[4,3,2-de]phthalazin-3(7H)-one;

9-(3-((diethylamino)methyl)phenyl)-8-(4-((diethylamino)methyl)phenyl)-8,9-dihydro-2H-pyrido[4,3,2-de]phthalazin-3(7H)-one;

9-(3-((4-methylpiperazin-1-yl) methyl)phenyl)-8-phenyl-8,9-dihydro-2H-pyrido[4,3,2-de]phthalazin-3(7H)-one;

8-(4-(4-(cyclopropanecarbonyl) piperazine-1-carbonyl)phenyl)-9-phenyl-8,9-dihydro-2H-pyrido[4,3,2-de]phthalazin-3(7H)-one;

9-phenyl-8-(pyridin-4-yl)-8,9-dihydro-2H-pyrido[4,3,2-de]phthalazin-3(7H)-one;

9-phenyl-8-(piperidin-4-yl)-8,9-dihydro-2H-pyrido[4,3,2-de]phthalazin-3(7H)-one;

9-phenyl-8-(pyridin-2-yl)-8,9-dihydro-2H-pyrido[4,3,2-de]phthalazin-3(7H)-one;

8-(4-((4-methylpiperazin-1-yl)methyl)phenyl)-9-phenyl-8,9-dihydro-2H-pyrido[4,3,2-de]phthalazin-3(7H)-one;

8,9-bis(4-fluorophenyl)-8,9-dihydro-2H-pyrido[4,3,2-de]phthalazin-3(7H)-one;

8-(4-((dimethylamino)methyl)phenyl)-9-(4-fluorophenyl)-8,9-dihydro-2H-pyrido[4,3,2-de]phthalazin-3(7H)-one;

8-(4-fluorophenyl)-9-(1-methyl-1H-imidazol-2-yl)-8,9-dihydro-2H-pyrido[4,3,2-de]phthalazin-3(7H)-one;

8,9-bis(3-((dimethylamino)methyl)phenyl)-8,9-dihydro-2H-pyrido[4,3,2-de]phthalazin-3(7H)-one;

9-(3-((cyclopropylamino)methyl)phenyl)-8-phenyl-8,9-dihydro-2H-pyrido[4,3,2-de]phthalazin-3(7H)-one;

8-(3-((dimethylamino)methyl)phenyl)-9-phenyl-8,9-dihydro-2H-pyrido[4,3,2-de]phthalazin-3(7H)-one;

8-(3-(morpholinomethyl)phenyl)-9-phenyl-8,9-dihydro-2H-pyrido[4,3,2-de]phthalazin-3(7H)-one;

8-(4-(azetidin-1-ylmethyl)phenyl)-9-(4-fluorophenyl)-8,9-dihydro-2H-pyrido[4,3,2-de]phthalazin-3(7H)-one;

5-fluoro-8-(4-fluorophenyl)-9-(1-methyl-1H-1,2,4-triazol-5-yl)-8,9-dihydro-2H-pyrido[4,3,2-de]phthalazin-3(7H)-one;

9-(1-methyl-1H-1,2,4-triazol-5-yl)-8-phenyl-8,9-dihydro-2H-pyrido[4,3,2-de]phthalazin-3(7H)-one;

8-(4-((dimethylamino)methyl)phenyl)-9-(1-methyl-1H-1,2,4-triazol-5-yl)-8,9-dihydro-2H-pyrido[4,3,2-de]phthalazin-3(7H)-one;

8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one;

8-(4-fluorophenyl)-9-methyl-9-(1-methyl-1H-1,2,4-triazol-5-yl)-8,9-dihydro-2H-pyrido[4,3,2-de]phthalazin-3(7H)-one;

8-(4-fluorophenyl)-9-(1,4,5-trimethyl-1H-imidazol-2-yl)-8,9-dihydro-2H-pyrido[4,3,2-de]phthalazin-3(7H)-one;

8-(4-fluorophenyl)-9-(1-methyl-1H-1,2,3-triazol-4-yl)-8,9-dihydro-2H-pyrido[4,3,2-de]phthalazin-3(7H)-one;

9-(4,5-dimethyl-4H-1,2,4-triazol-3-yl)-8-phenyl-8,9-dihydro-2H-pyrido[4,3,2-de]phthalazin-3(7H)-one;

9-(4,5-dimethyl-4H-1,2,4-triazol-3-yl)-8-(4-fluorophenyl)-8,9-dihydro-2H-pyrido[4,3,2-de]phthalazin-3(7H)-one;

8-(4-chlorophenyl)-9-(1-methyl-1H-imidazol-2-yl)-8,9-dihydro-2H-pyrido[4,3,2-de]phthalazin-3(7H)-one;

9-(1-methyl-1H-imidazol-2-yl)-8-(4-(trifluoromethyl)phenyl)-8,9-dihydro-2H-pyrido[4,3,2-de]phthalazin-3(7H)-one;

8-(4-fluorophenyl)-9-(thiazol-2-yl)-8,9-dihydro-2H-pyrido[4,3,2-de]phthalazin-3(7H)-one;

9-(1-ethyl-1H-imidazol-2-yl)-8-(4-fluorophenyl)-8,9-dihydro-2H-pyrido[4,3,2-de]phthalazin-3(7H)-one;

8-(4-((4-ethyl-3-methylpiperazin-1-yl)methyl)phenyl)-9-phenyl-8,9-dihydro-2H-pyrido[4,3,2-de]phthalazin-3(7H)-one;

8-(4-((4-ethylpiperazin-1-yl)methyl)phenyl)-9-(4-fluorophenyl)-8,9-dihydro-2H-pyrido[4,3,2-de]phthalazin-3(7H)-one;

9-(4-fluorophenyl)-8-(4-((4-methylpiperazin-1-yl)methyl)phenyl)-8,9-dihydro-2H-pyrido[4,3,2-de]phthalazin-3(7H)-one;

9-(4-fluorophenyl)-8-(4-(piperazin-1-ylmethyl)phenyl)-8,9-dihydro-2H-pyrido[4,3,2-de]phthalazin-3(7H)-one;

9-(4-fluorophenyl)-8-(4-((3-methylpiperazin-1-yl)methyl)phenyl)-8,9-dihydro-2H-pyrido[4,3,2-de]phthalazin-3(7H)-one;

9-(4-fluorophenyl)-8-(4-(pyrrolidin-1-ylmethyl)phenyl)-8,9-dihydro-2H-pyrido[4,3,2-de]phthalazin-3(7H)-one;

9-phenyl-8,9-dihydro-2H-pyrido[4,3,2-de]phthalazin-3(7H)-one;

8-(4-Fluorophenyl)-9-(4-methyl-4H-1,2,4-triazol-3-yl)-8,9-dihydro-2H-pyrido[4,3,2-de]phthalazin-3(7H)-one;

8-(4-fluorophenyl)-9-(1-methyl-1H-1,2,4-triazol-5-yl)-8,9-dihydro-2H-pyrido[4,3,2-de]phthalazin-3(7H)-one;

8-(4-fluorophenyl)-9-(1-methyl-1H-imidazo[4,5-c]pyridin-2-yl)-8,9-dihydro-2H-pyrido[4,3,2-de]phthalazin-3(7H)-one;

5-chloro-9-(1-methyl-1H-imidazol-2-yl)-8-phenyl-8,9-dihydro-2H-pyrido[4,3,2-de]phthalazin-3(7H)-one;

8-(4-((dimethylamino)methyl)phenyl)-5-fluoro-9-(4-fluorophenyl)-8,9-dihydro-2H-pyrido[4,3,2-de]phthalazin-3(7H)-one;

8,9-bis(4-((dimethylamino)methyl)phenyl)-5-fluoro-8,9-dihydro-2H-pyrido[4,3,2-de]phthalazin-3(7H)-one;

8-(4-((dimethylamino)methyl)phenyl)-5-fluoro-9-phenyl-8,9-dihydro-2H-pyrido[4,3,2-de]phthalazin-3(7H)-one;

8-(4-((3,4-dimethylpiperazin-1-yl)methyl)phenyl)-9-(4-fluorophenyl)-8,9-dihydro-2H-pyrido[4,3,2-de]phthalazin-3(7H)-one;

8-(4-((3,5-dimethylpiperazin-1-yl)methyl)phenyl)-9-(4-fluorophenyl)-8,9-dihydro-2H-pyrido[4,3,2-de]phthalazin-3(7H)-one;

9-phenyl-8-(4-(pyrrolidin-1-ylmethyl)phenyl)-8,9-dihydro-2H-pyrido[4,3,2-de]phthalazin-3(7H)-one;

9-phenyl-8-(4-(pyrrolidin-1-ylmethyl)phenyl)-8,9-dihydro-2H-pyrido[4,3,2-de]phthalazin-3(7H)-one;

9-(1-methyl-1H-imidazol-2-yl)-8-(4-(pyrrolidin-1-ylmethyl)phenyl)-8,9-dihydro-2H-pyrido[4,3,2-de]phthalazin-3(7H)-one;

9-(4-fluorophenyl)-8-(1-methyl-1H-imidazol-2-yl)-8,9-dihydro-2H-pyrido[4,3,2-de]phthalazin-3(7H)-one;

9-(4-fluorophenyl)-8-(quinolin-6-yl)-8,9-dihydro-2H-pyrido[4,3,2-de]phthalazin-3(7H)-one;

8-(4-((dimethylamino)methyl)phenyl)-9-p-tolyl-8,9-dihydro-2H-pyrido[4,3,2-de]phthalazin-3(7H)-one;

9-(4-chlorophenyl)-8-(4-((dimethylamino)methyl)phenyl)-8,9-dihydro-2H-pyrido[4,3,2-de]phthalazin-3(7H)-one;

8-(4-((dimethylamino)methyl)phenyl)-9-(4-methoxyphenyl)-8,9-dihydro-2H-pyrido[4,3,2-de]phthalazin-3(7H)-one;

8-(4-((diethylamino)methyl)phenyl)-9-phenyl-8,9-dihydro-2H-pyrido[4,3,2-de]phthalazin-3(7H)-one;

8-(4-((diethylamino)methyl)phenyl)-9-(4-fluorophenyl)-8,9-dihydro-2H-pyrido[4,3,2-de]phthalazin-3(7H)-one;

9-(4-chlorophenyl)-8-(4-((diethylamino)methyl)phenyl)-8,9-dihydro-2H-pyrido[4,3,2-de]phthalazin-3(7H)-one;

(E)-6-fluoro-4-((1-methyl-1H-imidazol-2-yl)methyleneamino)isobenzofuran-1(3H)-one;

5-fluoro-9-(4-fluorophenyl)-8-(1-methyl-1H-imidazol-2-yl)-8,9-dihydro-2H-pyrido[4,3,2-de]phthalazin-3(7H)-one;

8-(4-((dimethylamino)methyl)phenyl)-9-(4-ethylphenyl)-8,9-dihydro-2H-pyrido[4,3,2-de]phthalazin-3(7H)-one;

8-(4-((dimethylamino)methyl)phenyl)-9-(4-isopropylphenyl)-8,9-dihydro-2H-pyrido[4,3,2-de]phthalazin-3(7H)-one;

8-(4-((dimethylamino)methyl)phenyl)-9-(4-(trifluoromethyl)phenyl)-8,9-dihydro-2H-pyrido[4,3,2-de]phthalazin-3(7H)-one;

8-(4-((diethylamino)methyl)phenyl)-9-p-tolyl-8,9-dihydro-2H-pyrido[4,3,2-de]phthalazin-3(7H)-one;

9-(4-fluorophenyl)-8-(4-(1-methylpyrrolidin-2-yl)phenyl)-8,9-dihydro-2H-pyrido[4,3,2-de]phthalazin-3(7H)-one;

9-(4-fluorophenyl)-8-(4-(pyrrolidin-2-yl)phenyl)-8,9-dihydro-2H-pyrido[4,3,2-de]phthalazin-3(7H)-one;

8-(4-fluorophenyl)-9-methyl-9-(1-methyl-1H-imidazol-2-yl)-8,9-dihydro-2H-pyrido[4,3,2-de]phthalazin-3(7H)-one;

9-(4-fluorophenyl)-8-(1H-imidazol-2-yl)-8,9-dihydro-2H-pyrido[4,3,2-de]phthalazin-3(7H)-one;

5-fluoro-9-(1-methyl-1H-1,2,4-triazol-5-yl)-8-phenyl-8,9-dihydro-2H-pyrido[4,3,2-de]phthalazin-3(7H)-one;

9-(4-fluorophenyl)-9-hydroxy-8-(1-methyl-1H-imidazol-2-yl)-8,9-dihydro-2H-pyrido[4,3,2-de]phthalazin-3(7H)-one;

(8S,9R)-5-fluoro-9-(1-methyl-1H-imidazol-2-yl)-8-phenyl-8,9-dihydro-2H-pyrido[4,3,2-de]phthalazin-3(7H)-one;

(8R,9S)-5-fluoro-9-(1-methyl-1H-imidazol-2-yl)-8-phenyl-8,9-dihydro-2H-pyrido[4,3,2-de]phthalazin-3(7H)-one;

(8S,9R)-5-fluoro-8-(4-fluorophenyl)-9-(1-methyl-1H-imidazol-2-yl)-8,9-dihydro-2H-pyrido[4,3,2-de]phthalazin-3(7H)-one;

(8R,9S)-5-fluoro-8-(4-fluorophenyl)-9-(1-methyl-1H-imidazol-2-yl)-8,9-dihydro-2H-pyrido[4,3,2-de]phthalazin-3(7H)-one;

(8S,9R)-8-(4-fluorophenyl)-9-(1-methyl-1H-imidazol-2-yl)-8,9-dihydro-2H-pyrido[4,3,2-de]phthalazin-3(7H)-one;

(8R,9S)-8-(4-fluorophenyl)-9-(1-methyl-1H-imidazol-2-yl)-8,9-dihydro-2H-pyrido[4,3,2-de]phthalazin-3(7H)-one;

(8S,9R)-5-fluoro-9-(1-methyl-1H-1,2,4-triazol-5-yl)-8-phenyl-8,9-dihydro-2H-pyrido[4,3,2-de]phthalazin-3(7H)-one;

(8R,9S)-5-fluoro-9-(1-methyl-1H-1,2,4-triazol-5-yl)-8-phenyl-8,9-dihydro-2H-pyrido[4,3,2-de]phthalazin-3(7H)-one;

(8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one;

(8R,9S)-5-fluoro-8-(4-fluorophenyl)-9-(1-methyl-1H-1,2,4-triazol-5-yl)-8,9-dihydro-2H-pyrido[4,3,2-de]phthalazin-3(7H)-one;

(8S,9R)-8-(4-fluorophenyl)-9-(1-methyl-1H-1,2,4-triazol-5-yl)-8,9-dihydro-2H-pyrido[4,3,2-de]phthalazin-3(7H)-one;

(8R,9S)-8-(4-fluorophenyl)-9-(1-methyl-1H-1,2,4-triazol-5-yl)-8,9-dihydro-2H-pyrido[4,3,2-de]phthalazin-3(7H)-one;

(8S,9R)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one; and (8R,9S)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one;

or a pharmaceutical acceptable salt, solvate or prodrug therefore.

In some embodiments, provided herein is a pharmaceutical composition comprising of a compound of Formula (I), (IA) or (II) or stereoisomers, or a pharmaceutically acceptable salt, a pharmaceutically acceptable solvate, pharmaceutically acceptable prodrug thereof and a pharmaceutically acceptable carrier, excipient, binder or diluent.

Certain embodiments provide a method of inhibiting PARP in a subject in recognized need of such treatment comprising administering to the subject a therapeutically acceptable amount of a compound of Formula (I), (IA) or (II) or a therapeutically acceptable salt thereof.

In one embodiment, provided herein is a method of treating a disease ameliorated by the inhibition of PARP comprising administering to a subject in need of treatment a therapeutically-effective amount of a compound of Formula (I), (IA) or (II). In some embodiments, the disease is selected from the group consisting of: vascular disease; septic shock; ischemic injury; reperfusion injury; neurotoxicity; hemorrhagic shock; inflammatory diseases; multiple sclerosis; secondary effects of diabetes; and acute treatment of cytotoxicity following cardiovascular surgery.

In certain embodiments, provided herein is a method for the treatment of cancer, comprising administering to a subject in need of treatment a therapeutically-effective amount of a compound of Formula (I), (IA) or (II).

Certain embodiments provide a method of potentiation of cytotoxic cancer therapy in a subject in recognized need of such treatment comprising administering to the subject a therapeutically acceptable amount of a compound of Formula (I), (IA) or (II) or a therapeutically acceptable salt thereof.

In some embodiments, provided herein is a method for the treatment of cancer, comprising administering to a subject in need of treatment a therapeutically-effective amount of a compound of Formula (I), (IA) or (II) in combination with ionizing radiation or one or more chemotherapeutic agents. In some embodiments, the compound described herein is administered simultaneously with ionizing radiation or one or more chemotherapeutic agents. In other embodiments, the compound described herein is administered sequentially with ionizing radiation or one or more chemotherapeutic agents.

In certain embodiments, provided herein is a method for the treatment of cancer, which includes administering to a subject in need of treatment a therapeutically-effective amount of a compound of Formula (I), (IA) or (II) in combination with ionizing radiation and one or more chemotherapeutic agents. In some embodiments, the compound described herein is administered simultaneously with ionizing radiation and one or more chemotherapeutic agents. In other embodiments, the compound described herein is administered sequentially with ionizing radiation and one or more chemotherapeutic agents.

Certain embodiments provide a method of treating leukemia, colon cancer, glioblastomas, lymphomas, melanomas, carcinomas of breast, or cervical carcinomas in a subject in recognized need of such treatment comprising administering to the subject a therapeutically acceptable amount of a compound of Formula (I), (IA) or (II) or therapeutically acceptable salt thereof.

In some embodiments, provided herein is a method of treatment of a cancer deficient in Homologous Recombination (HR) dependent DNA double strand break (DSB) repair pathway, which includes administering to a subject in need of treatment a therapeutically-effective amount of a compound of Formula (I), (IA) or (II). In certain embodiments, the cancer includes one or more cancer cells having a reduced or abrogated ability to repair DNA DSB by HR relative to normal cells. In some embodiments, the cancer cells have a BRCA1 or BRCA2 deficient phenotype. In some embodiments, the cancer cells are deficient in BRCA1 or BRCA2. In some embodiments, the methods provided herein involve treatment of an individual who is heterozygous for a mutation in a gene encoding a component of the HR dependent DNA DSB repair pathway. In certain embodiment, the individual is heterozygous for a mutation in BRCA1 and/or BRCA2. In some embodiments, the method of treatment of a cancer includes treatment of breast, ovary, pancreas and/or prostate cancer. In some embodiments, the method of treatment of a cancer further includes administration of ionizing radiation or a chemotherapeutic agent.

The primary function of the DNA mismatch repair (MMR) system is to eliminate single-base mismatches and insertion-deletion loops that may arise during DNA replication. Insertion-deletion loops result from gains or losses of short repeat units within microsatellite sequences, also known as microsatellite instability (MSI). At least six different MMR proteins are required. For mismatch recognition, the MSH2 protein forms a heterodimer with either MSH6 or MSH3 depending on the type of lesion to be repaired (MSH6 is required for the correction of single-base mispairs, whereas both MSH3 and MSH6 may contribute to the correction of insertion-deletion loops). A heterodimer of MLH1 and PMS2 coordinates the interplay between the mismatch recognition complex and other proteins necessary for MMR. These additional proteins may include at least exonuclease 1 (EXO1), possibly helicase(s), proliferating cell nuclear antigen (PCNA), single-stranded DNA-binding protein (RPA), and DNA polymerases $\delta$ and $\epsilon$. In addition to PMS2, MLH1 may heterodimerize with two additional proteins, MLH3 and PMS1. Recent observations indicate that PMS2 is required for the correction of single-base mismatches, and PMS2 and MLH3 both contribute to the correction of insertion-deletion loops. Additional homologs of the human MMR proteins are known that are required for functions other than MMR. These proteins include MSH4 and MSH5 that are necessary for meiotic (and possibly mitotic) recombination but are not presumed to participate in MMR.

Germline mutations of human MMR genes cause susceptibility to hereditary nonpolyposis colon cancer (HNPCC), one of the most common cancer syndromes in humans. An excess of colon cancer and a defined spectrum of extracolonic cancers, diagnosed at an early age and transmitted as an autosomal dominant trait, constitute the clinical definition of the syndrome. MSI, the hallmark of HNPCC, occurs in approximately 15% to 25% of sporadic tumors of the colorectum and other organs as well. According to international criteria, a high degree of MSI (MSI-H) is defined as instability at two or more of five loci or 30% to 40% of all microsatellite loci studied, whereas instability at fewer loci is referred to as MSI-low (MSI-L). MSI occurs in a substantial proportion (2% to 50% of tumors) among non-HNPCC cancers (eg, cancers of the breast, prostate, and lung). On the basis of the proportion of unstable markers, categories MSS, MSI-L, and MSI-H can be distinguished in these cancers in analogy to HNPCC cancers. In one embodiment is a method for treating a cancer deficient in mismatch DNA repair pathway. In another embodiment is a method for treating a cancer demonstrating microsatellite instability due to reduced or impaired DNA repair pathways. In another embodiment is a method for treating a cancer demonstrating genomic instability due to reduced or impaired DNA repair pathways.

Certain embodiments provide a method of treating ischemia reperfusion injury associated with, but not limited to, myocardial infarction, stroke, other neural trauma, and organ transplantation, in a subject in recognized need of such treatment comprising administering to the subject a therapeutically acceptable amount of a compound of Formula (I), (IA) or (II) or a therapeutically acceptable salt thereof.

Certain embodiments provide a method of treating reperfusion including, but not limited to, reperfusion of the eye, kidney, gut, and skeletal muscle, in a subject in recognized need of such treatment comprising administering to the subject a therapeutically acceptable amount of a compound of Formula (I), (IA) or (II) or a therapeutically acceptable salt thereof.

Certain embodiments provide a method of treating inflammatory diseases including, but not limited to, arthritis, gout, inflammatory bowel disease, CNS inflammation, multiple sclerosis, allergic encephalitis, sepsis, septic shock, hemorrhagic shock, pulmonary fibrosis, and uveitis in a subject in recognized need of such treatment comprising administering to the subject a therapeutically acceptable amount of a compound of Formula (I), (IA) or (II) or a therapeutically acceptable salt thereof.

Certain embodiments provide a method of treating immunological diseases or disorders such a rheumatoid arthritis and septic shock in a subject in recognized need of such treatment comprising administering to the subject a therapeutically acceptable amount of a compound of Formula (I), (IA) or (II) or a therapeutically acceptable salt thereof.

Certain embodiments provide a method of treating degenerative diseases including, but not limited to, diabetes and Parkinson's disease in a subject in recognized need of such treatment comprising administering to the subject a therapeutically acceptable amount of a compound of Formula (I), (IA) or (II) or a therapeutically acceptable salt thereof.

Certain embodiments provide a method of treating hypoglycemia in a subject in recognized need of such treatment comprising administering to the subject a therapeutically acceptable amount of a compound of Formula (I), (IA) or (II) or a therapeutically acceptable salt thereof.

Certain embodiments provide a method of treating retroviral infection in a subject in recognized need of such treatment comprising administering to the subject a therapeutically acceptable amount of a compound of Formula (I), (IA) or (II) or a therapeutically acceptable salt thereof.

Certain embodiments provide a method of treating liver toxicity following acetaminophen overdose in a subject in recognized need of such treatment comprising administering to the subject a therapeutically acceptable amount of a compound of Formula (I), (IA) or (II) or a therapeutically acceptable salt thereof.

Certain embodiments provide a method of treating cardiac and kidney toxicities from doxorubicin and platinum based antineoplastic agents in a subject in recognized need of such treatment comprising administering to the subject a therapeutically acceptable amount of a compound of Formula (I), (IA) or (II) or a therapeutically acceptable salt thereof.

Certain embodiments provide a method of treating skin damage secondary to sulfur mustards in a subject in recognized need of such treatment comprising administering to the subject a therapeutically acceptable amount of a compound of Formula (I), (IA) or (II) or a therapeutically acceptable salt thereof.

Certain embodiments provide a use of a compound of Formula (I), (IA) or (II) or a therapeutically acceptable salt thereof, to prepare a medicament for inhibiting the PARP enzyme in a subject in recognized need of such treatment.

Certain embodiments provide a use of a compound of Formula (I), (IA) or (II) or a therapeutically acceptable salt thereof, to prepare a medicament for inhibiting tumor growth in a subject in recognized need of such treatment.

Certain embodiments provide a use of a compound of Formula (I), (IA) or (II) or a therapeutically acceptable salt thereof, to prepare a medicament for treating cancer in a subject in recognized need of such treatment.

Certain embodiments provide a use of a compound of Formula (I), (IA) or (II) or a therapeutically acceptable salt thereof, to prepare a medicament for treating leukemia, colon cancer, glioblastomas, lymphomas in a subject in recognized need of such treatment.

Certain embodiments provide a method of treating degenerative diseases including, but not limited to, diabetes and Parkinson's disease in a subject in recognized need of such treatment comprising administering to the subject a therapeutically acceptable amount of a compound of Formula (I), (IA) or (II) or a therapeutically acceptable salt thereof.

Certain embodiments provide a use of a compound of Formula (I), (IA) or (II) or a therapeutically acceptable salt thereof, to prepare a medicament for potentiation of cytotoxic cancer therapy in a subject in recognized need of such treatment comprising administering to the subject a therapeutically acceptable amount of a compound of Formula (I), (IA) or (II) or a therapeutically acceptable salt thereof.

Certain embodiments provide a use of a compound of Formula (I), (IA) or (II) or a therapeutically acceptable salt thereof, to prepare a medicament for treating ischemia reperfusion injury associated with, but not limited to, myocardial infarction, stroke, other neural trauma, and organ transplantation, in a subject in recognized need of such treatment comprising administering to the subject a therapeutically acceptable amount of a compound of Formula (I), (IA) or (II) or a therapeutically acceptable salt thereof.

Certain embodiments provide a use of a compound of Formula (I), (IA) or (II) or a therapeutically acceptable salt thereof, to prepare a medicament for treating reperfusion including, but not limited to, reperfusion of the eye, kidney, gut and skeletal muscle, in a subject in recognized need of such treatment comprising administering to the subject a therapeutically acceptable amount of a compound of Formula (I), (IA) or (II) or a therapeutically acceptable salt thereof.

Certain embodiments provide a use of a compound of Formula (I), (IA) or (II) or a therapeutically acceptable salt thereof, to prepare a medicament for treating inflammatory diseases including, but not limited to, arthritis, gout, inflammatory bowel disease, CNS inflammation, multiple sclerosis, allergic encephalitis, sepsis, septic shock, hemorrhagic shock, pulmonary fibrosis, and uveitis in a subject in recognized need of such treatment comprising administering to the subject a therapeutically acceptable amount of a compound of Formula (I), (IA) or (II) or a therapeutically acceptable salt thereof.

Certain embodiments provide a use of a compound of Formula (I), (IA) or (II) or a therapeutically acceptable salt thereof, to prepare a medicament for treating immunological diseases or disorders such as rheumatoid arthritis and septic shock in a mammal in recognized need of such treatment comprising administering to the subject a therapeutically acceptable amount of a compound of Formula (I), (IA) or (II) or a therapeutically acceptable salt thereof.

Certain embodiments provide a use of a compound of Formula (I), (IA) or (II) or a therapeutically acceptable salt thereof, to prepare a medicament for treating hypoglycemia in a subject in recognized need of such treatment comprising administering to the subject a therapeutically acceptable amount of a compound of Formula (I), (IA) or (II) or a therapeutically acceptable salt thereof.

Certain embodiments provide a use of a compound of Formula (I), (IA) or (II) or a therapeutically acceptable salt thereof, to prepare a medicament for treating retroviral infection in a subject in recognized need of such treatment comprising administering to the subject a therapeutically acceptable amount of a compound of Formula (I), (IA) or (II) or a therapeutically acceptable salt thereof.

Certain embodiments provide a use of a compound of Formula (I), (IA) or (II) or a therapeutically acceptable salt thereof, to prepare a medicament for treating liver toxicity following acetaminophen overdose in a subject in recognized need of such treatment comprising administering to the subject a therapeutically acceptable amount of a compound of Formula (I), (IA) or (II) or a therapeutically acceptable salt thereof.

Certain embodiments provide a use of a compound of Formula (I), (IA) or (II) or a therapeutically acceptable salt thereof, to prepare a medicament for treating cardiac and kidney toxicities from doxorubicin and platinum based antineoplastic agents in a subject in recognized need of such treatment comprising administering to the mammal a therapeutically acceptable amount of a compound of Formula (I), (IA) or (II) or a therapeutically acceptable salt thereof.

Certain embodiments provide a use of a compound of Formula (I), (IA) or (II) or a therapeutically acceptable salt thereof, to prepare a medicament for treating skin damage secondary to sulfur mustards in a subject in recognized need of such treatment comprising administering to the mammal a therapeutically acceptable amount of a compound of Formula (I), (IA) or (II) or a therapeutically acceptable salt thereof.

Articles of manufacture, comprising packaging material, a compound provided herein that is effective for modulating the activity of the enzyme poly(ADP-ribose)polymerase, or for treatment, prevention or amelioration of one or more symptoms of a poly(ADP-ribose)polymerase-dependent or poly(ADP-ribose)polymerase-mediated disease or condition, within the packaging material, and a label that indicates that the compound or composition, or pharmaceutically acceptable salt, pharmaceutically acceptable N-oxide, pharmaceutically active metabolite, pharmaceutically acceptable prodrug, or pharmaceutically acceptable solvate thereof, is used for modulating the activity of poly(ADP-ribose)polymerase, or for treatment, prevention or amelioration of one or more symptoms of a poly(ADP-ribose)polymerase-dependent or poly(ADP-ribose)polymerase-mediated disease or condition, are provided.

Any combination of the groups described above for the various variables is contemplated herein.

In one embodiment, disclosed herein is a pharmaceutical composition comprising a compound, pharmaceutically acceptable salt, pharmaceutically acceptable N-oxide, pharmaceutically active metabolite, pharmaceutically acceptable prodrug, or pharmaceutically acceptable solvate of any of the compounds disclosed herein. In some embodiments, the pharmaceutical compositions further comprises a pharmaceutically acceptable diluent, excipient or binder. In certain embodiments, the pharmaceutical composition further comprises a second pharmaceutically active ingredient.

In one embodiment, the PARP mediated disease or condition in a patient, or the PARP dependent disease or condition in a patient is cancer or a non-cancerous disorder. In some embodiments, the disease or condition is iatrogenic.

In some embodiments are methods for reducing/inhibiting the activity of PARP in a subject that include administering to the subject at least once an effective amount of a compound described herein.

Certain embodiments provided herein are methods for modulating, including reducing and/or inhibiting the activity of PARP, directly or indirectly, in a subject comprising administering to the subject at least once an effective amount of at least one compound described herein.

In further embodiments are methods for treating PARP mediated conditions or diseases, comprising administering to the subject at least once an effective amount of at least one compound described herein.

Some embodiments include the use of a compound described herein in the manufacture of a medicament for treating a disease or condition in a subject in which the activity of at least one PARP protein contributes to the pathology and/or symptoms of the disease or condition.

In any of the aforementioned embodiments are further embodiments in which administration is enteral, parenteral, or both, and wherein:
(a) the effective amount of the compound is systemically administered to the subject;
(b) the effective amount of the compound is administered orally to the subject;
(c) the effective amount of the compound is intravenously administered to the subject;
(d) the effective amount of the compound administered by inhalation;
(e) the effective amount of the compound is administered by nasal administration;
(f) the effective amount of the compound is administered by injection to the subject;
(g) the effective amount of the compound is administered topically (dermal) to the subject;
(h) the effective amount of the compound is administered by ophthalmic administration; and/or
(i) the effective amount of the compound is administered rectally to the subject.

In any of the aforementioned embodiments are further embodiments that include single administrations of the effective amount of the compound, including further embodiments in which the compound is administered to the subject (i) once; (ii) multiple times over the span of one day; (iii) continually; or (iv) continuously.

In any of the aforementioned embodiments are further embodiments that include multiple administrations of the effective amount of the compound, including further embodiments wherein:
(i) the compound is administered in a single dose;
(ii) the time between multiple administrations is every 6 hours;
(iii) the compound is administered to the subject every 8 hours.

In further or alternative embodiments, the method includes a drug holiday, wherein the administration of the compound is temporarily suspended or the dose of the compound being administered is temporarily reduced; at the end of the drug holiday, dosing of the compound is resumed. In some embodiments, the length of the drug holiday varies from 2 days to 1 year.

In any of the aforementioned embodiments involving the treatment of proliferative disorders, including cancer, are further embodiments that include administering at least one additional agent selected from among alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, paclitaxel, Taxol®, temozolomide, thioguanine, and classes of drugs including hormones (an antiestrogen, an antiandrogen, or gonadotropin releasing hormone analogues, interferons such as, for example, alpha interferon, nitrogen mustards such as, for example, busulfan, melphalan or mechlorethamine, retinoids such as, for example, tretinoin, topoisomerase inhibitors such as, for example, irinotecan or topotecan, tyrosine kinase inhibitors such as, for example, gefinitinib or imatinib, and agents to treat signs or symptoms induced by such therapy including allopurinol, filgrastim, granisetron/ondansetron/palonosetron, and dronabinol.

Other objects, features and advantages of the compounds, methods and compositions described herein will become apparent from the following description. It should be understood, however, that the description and the specific examples, while indicating specific embodiments, are given by way of illustration only, since various changes and modifications within the spirit and scope of the present description will become apparent from this detailed description.

Described herein are compounds, methods of making such compounds, pharmaceutical compositions and medicaments that include such compounds, and methods of using such compounds to treat or prevent diseases or conditions associated with PARP activity.

Described herein are compounds having activity in inhibiting the enzyme poly(ADP-ribose)polymerase (PARP). In some embodiments, the compounds have the structure set forth in Formula (I), (IA) or (II).

The mammalian enzyme PARP-1 is a multidomain protein. PARP-1 is implicated in the signaling of DNA damage through its ability to recognize and rapidly bind to DNA single or double strand breaks. D'Amours, et al., *Biochem. J.*, 342, 249-268 (1999); and Virag et al. *Pharmacological Reviews*, vol. 54, no. 3, 375-429 (2002) are hereby incorporated by reference for such disclosure.

The family of poly(ADP-ribose)polymerases includes approximately 18 proteins, which all display a certain level of homology in their catalytic domain but differ in their cellular functions. PARP-1 and PARP-2 are unique members of the family, in that their catalytic activities are stimulated by the occurrence of DNA strand breaks. Ame et al., *BioEssays.*, 26(8), 882-893 (2004) is hereby incorporated by reference for such disclosure.

PARP-1 participates in a variety of DNA-related functions including gene amplification, cell division, differentiation, apoptosis, DNA base excision repair as well as effects on telomere length and chromosome stability. d'Adda di Fagagna, et al., *Nature Gen.*, 23(1), 76-80 (1999) is hereby incorporated by reference for such disclosure.

Studies on the mechanism by which PARP-1 modulates DNA repair and other processes identifies its importance in the formation of poly(ADP-ribose) chains within the cellular nucleus. The DNA-bound, activated PARP-1 utilizes NAD+ to synthesize poly(ADP-ribose) on a variety of nuclear target proteins, including topoisomerases, histones and PARP itself. Althaus, F. R. and Richter, C., ADP-Ribosylation of Proteins: Enzymology and Biological Significance, Springer-Verlag, Berlin (1987); and Rhun, et al., *Biochem. Biophys. Res. Commun.*, 245, 1-10 (1998) are hereby incorporated by reference for such disclosure.

Poly(ADP-ribosyl)ation is also associated with malignant transformation. For example, PARP-1 activity is higher in the isolated nuclei of SV40-transformed fibroblasts, while both leukemic cells and colon cancer cells show higher enzyme activity than the equivalent normal leukocytes and colon mucosa. Furthermore, malignant prostate tumors have increased levels of active PARP as compared to benign prostate cells, which is associated with higher levels of genetic instability. Miwa, et al., *Arch. Biochem. Biophys.*, 181, 313-321 (1977); Burzio, et al., *Proc. Soc. Exp. Biol. Med.*, 149, 933-938 (1975); Hirai, et al., *Cancer Res.*, 43, 3441-3446 (1983); and Mcnealy, et al., *Anticancer Res.*, 23, 1473-1478 (2003) are hereby incorporated by reference for such disclosure.

In cells treated with alkylating agents, the inhibition of PARP leads to a marked increase in DNA-strand breakage and cell killing. PARP-1 inhibitors also enhance the effects of radiation response by suppressing the repair of potentially lethal damage. PARP inhibitors are also effective in radiosensitizing hypoxic tumor cells. In certain tumor cell lines, chemical inhibition of PARP activity is also associated with marked sensitization to very low doses of radiation.

Furthermore, PARP-1 knockout (PARP-/-) animals exhibit genomic instability in response to alkylating agents and γ-irradiation. Data indicates that PARP-1 and PARP-2 possess both overlapping and non-redundant functions in the maintenance of genomic stability, making them both interesting targets. Wang, et al., *Genes Dev.*, 9, 509-520 (1995); Menissier de Murcia, et al., *Proc. Natl. Acad. Sci. USA*, 94, 7303-7307 (1997); and Menissier de Murcia, et al., *EMBO. J.*, 22(9), 2255-2263 (2003) are hereby incorporated by reference for such disclosure.

There is also a role for PARP-1 in certain vascular diseases, such as, for example, septic shock, ischaemic injury and neurotoxicity. Oxygen radical DNA damage that leads to strand breaks in DNA, which are subsequently recognized by PARP-1, is a major contributing factor to such disease states as shown by PARP-1 inhibitor studies. PARP also plays a role in the pathogenesis of hemorrhagic shock. Cantoni, et al., *Biochim. Biophys. Acta*, 1014, 1-7 (1989); Szabo, et al., *J. Clin. Invest.*, 100, 723-735 (1997); Cosi, et al., *J. Neurosci. Res.*, 39, 3846 (1994); Said, et al., *Proc. Natl. Acad. Sci. USA.*, 93, 4688-4692 (1996); and Liaudet, et al., *Proc. Natl. Acad. Sci. USA.*, 97(3), 10203-10208 (2000) are hereby incorporated by reference for such disclosure.

Furthermore, efficient retroviral infection of mammalian cells is blocked by the inhibition of PARP-1 activity. Such inhibition of recombinant retroviral vector infections occurs in various different cell types. In some embodiments, inhibitors of PARP-1 are used in anti-viral therapies and in cancer treatment. Gaken, et al., *J. Virology*, 70(6), 3992-4000 (1996) is hereby incorporated by reference for such disclosure.

Moreover, in certain embodiments, PARP-1 inhibition delays the onset of aging characteristics in human fibroblasts. While not intending to bound by any theory, this may be related to the role that PARP plays in controlling telomere function. Rattan and Clark, *Biochem. Biophys. Res. Comm.*, 201(2), 665-672 (1994); and d'Adda di Fagagna, et al., *Nature Gen.*, 23(1), 76-80 (1999) are hereby incorporated by reference for such disclosure.

In some embodiments, PARP inhibitors are relevant to the treatment of inflammatory bowel disease, ulcerative colitis and Crohn's disease. Szabo C., Role of Poly(ADP-Ribose) Polymerase Activation in the Pathogenesis of Shock and Inflammation, In PARP as a Therapeutic Target; Ed J. Zhang, 2002 by CRC Press; 169-204; Zingarelli, B, et al., *Immunology*, 113(4), 509-517 (2004); and Jijon, H. B., et al., *Am. J. Physiol. Gastrointest. Liver Physiol.*, 279, G641-G651 (2000) are hereby incorporated by reference for such disclosure.

In certain embodiments, PARP inhibitors, such as those of Formula (I), (IA) or (II), have utility in: (a) preventing or inhibiting poly(ADP-ribose) chain formation by, e.g., inhibiting the activity of cellular PARP (PARP-1 and/or PARP-2);

(b) treating vascular disease; septic shock; ischaemic injury, both cerebral and cardiovascular; reperfusion injury, both cerebral and cardiovascular; neurotoxicity, including acute and chronic treatments for stroke and Parkinson's disease; hemorrhagic shock; inflammatory diseases, such as arthritis, inflammatory bowel disease, ulcerative colitis and Crohn's disease; multiple sclerosis; secondary effects of diabetes; as well as the acute treatment of cytotoxicity following cardiovascular surgery or diseases ameliorated by the inhibition of the activity of PARP; (c) use as an adjunct in cancer therapy or for potentiating tumor cells for treatment with ionizing radiation and/or chemotherapeutic agents.

In specific embodiments, compounds provided herein, such as, for example, Formula (I), (IA) or (II), are used in anti-cancer combination therapies (or as adjuncts) along with alkylating agents, such as methyl methanesulfonate (MMS), temozolomide and dacarbazine (DTIC), also with topoisomerase-1 inhibitors like Topotecan, Irinotecan, Rubitecan, Exatecan, Lurtotecan, Gimetecan, Diflomotecan (homocamptothecins); as well as 7-substituted non-silatecans; the 7-silyl camptothecins, BNP 1350; and non-camptothecin topoisomerase-I inhibitors such as indolocarbazoles also dual topoisomerase-I and II inhibitors like the benzophenazines, XR 11576/MLN 576 and benzopyridoindoles. In certain embodiments, such combinations are given, for example, as intravenous preparations or by oral administration as dependent on the method of administration for the particular agent.

In some embodiments, PARP inhibitors, such as, for example, compounds of Formula (I), (IA) or (II), are used in the treatment of disease ameliorated by the inhibition of PARP, which includes administering to a subject in need of treatment a therapeutically-effective amount of a compound provided herein, and in one embodiment in the form of a pharmaceutical composition. In certain embodiments, PARP inhibitors, such as, for example, compounds of Formula (I), (IA) or (II), are used in the treatment of cancer, which includes administering to a subject in need of treatment a therapeutically-effective amount of a compound provided herein in combination, and in one embodiment in the form of a pharmaceutical composition, simultaneously or sequentially with radiotherapy (ionizing radiation) or chemotherapeutic agents.

In certain embodiments, PARP inhibitors, such as, for example, compounds of Formula (I), (IA) or (II), are used in the preparation of a medicament for the treatment of cancer which is deficient in Homologous Recombination (HR) dependent DNA double strand break (DSB) repair activity, or in the treatment of a patient with a cancer which is deficient in HR dependent DNA DSB repair activity, which includes administering to said patient a therapeutically-effective amount of the compound.

The HR dependent DNA DSB repair pathway repairs double-strand breaks (DSBs) in DNA via homologous mechanisms to reform a continuous DNA helix. The components of the HR dependent DNA DSB repair pathway include, but are not limited to, ATM (NM_000051), RAD51 (NM_002875), RAD51L1 (NM_002877), RAD51C (NM_002876), RAD51L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485). Other proteins involved in the HR dependent DNA DSB repair pathway include regulatory factors such as EMSY. HR components are also described in Wood, et al., *Science*, 291, 1284-1289 (2001), which is hereby incorporated by reference for such disclosure. K. K. Khanna and S. P. Jackson, *Nat. Genet.* 27(3): 247-254 (2001); and Hughes-Davies, et al., *Cell*, 115, pp 523-535 are also incorporated herein by reference for such disclosure.

In some embodiments, a cancer which is deficient in HR dependent DNA DSB repair includes one or more cancer cells which have a reduced or abrogated ability to repair DNA DSBs through that pathway, relative to normal cells, i.e. the activity of the HR dependent DNA DSB repair pathway are reduced or abolished in the one or more cancer cells.

In certain embodiments, the activity of one or more components of the HR dependent DNA DSB repair pathway is abolished in the one or more cancer cells of an individual having a cancer which is deficient in HR dependent DNA DSB repair. Components of the HR dependent DNA DSB repair pathway include the components listed above.

In some embodiments, the cancer cells have a BRCA1 and/or a BRCA2 deficient phenotype, i.e., BRCA1 and/or BRCA2 activity is reduced or abolished in the cancer cells. In certain embodiments, cancer cells with this phenotype are deficient in BRCA1 and/or BRCA2, i.e., expression and/or activity of BRCA1 and/or BRCA2 is reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor or by an epigenetic mechanism such as gene promoter methylation.

BRCA1 and BRCA2 are tumor suppressors whose wild-type alleles are frequently lost in tumors of heterozygous carriers. BRCA1 and/or BRCA2 mutations are associated with breast cancer. Amplification of the EMSY gene, which encodes a BRCA2 binding factor, is associated with breast and ovarian cancer. Jasin M., *Oncogene*, 21(58), 8981-93 (2002); Tutt, et al., *Trends Mol Med.*, 8(12), 571-6, (2002); and Radice, P. J., *Exp Clin Cancer Res.*, 21(3 Suppl), 9-12 (2002) are hereby incorporated by reference for such disclosure.

Carriers of mutations in BRCA1 and/or BRCA2 are also at elevated risk of cancer of the ovary, prostate and pancreas.

In some embodiments, the individual is heterozygous for one or more variations, such as mutations and polymorphisms, in BRCA1 and/or BRCA2 or a regulator thereof. The detection of variation in BRCA1 and BRCA2 is described, for example in EP 699 754, EP 705 903, Neuhausen, S. L. and Ostrander, E. A., *Genet. Test*, 1, 75-83 (1992); Janatova M., et al., *Neoplasma*, 50(4), 246-50 (2003), which is hereby incorporated by reference for such disclosure. Determination of amplification of the BRCA2 binding factor EMSY is described in Hughes-Davies, et al., *Cell*, 115, 523-535).

In certain instances, mutations and polymorphisms associated with cancer are detected at the nucleic acid level by detecting the presence of a variant nucleic acid sequence or at the protein level by detecting the presence of a variant (i.e. a mutant or allelic variant) polypeptide.

Definitions

Unless defined otherwise, all technical and scientific terms used herein have the standard meaning pertaining to the claimed subject matter belongs. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless otherwise indicated, conventional methods of mass spectroscopy, NMR, HPLC, protein chemistry, biochemistry, recombinant DNA techniques and pharmacology are employed. Unless specific definitions are provided, the standard nomenclature employed in connection with, and the standard laboratory procedures and techniques of, analytical chemistry, synthetic organic chemistry, and medicinal and pharmaceutical chemistry are employed. In certain instances, standard techniques are used for chemical syntheses, chemical analyses, pharmaceutical preparation, formulation, and delivery, and treatment of patients. In certain embodiments, standard techniques are used for recombinant DNA, oligonucleotide synthesis, and tissue culture and transformation (e.g., electroporation, lipofection). In some embodiments, reactions and purification techniques are performed e.g., using kits of manufacturer's specifications or as commonly accomplished or as described herein.

As used throughout this application and the appended claims, the following terms have the following meanings:

The term "alkenyl" as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (i.e., an alkenylene group). In some embodiments, alkenyl groups are optionally substituted. Illustrative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-cecenyl.

The term "alkoxy" as used herein, means an alkyl group, as defined herein, appended to the parent molecular moiety through an oxygen atom. Illustrative examples of alkoxy include, but are not limited to, methoxy, ethoxy, propoxy, 2-propoxy, butoxy, tert-butoxy, pentyloxy, and hexyloxy.

The term "alkyl" as used herein, means a straight, branched chain, or cyclic (in this case, it would also be known as "cycloalkyl") hydrocarbon containing from 1-10 carbon atoms. Illustrative examples of alkyl include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

The term "$C_1$-$C_6$-alkyl" as used herein, means a straight, branched chain, or cyclic (in this case, it would also be known as "cycloalkyl") hydrocarbon containing from 1-6 carbon atoms. Representative examples of alkyl include, but are not limited to, methyl, ethyl, n-propyl, iso-propyl, cyclopyl, n-butyl, sec-butyl, tert-butyl, cyclobutyl, n-pentyl, isopentyl, neopentyl, cyclopentyl, and n-hexyl.

The term "cycloalkyl" as used herein, means a monocyclic or polycyclic radical that contains only carbon and hydrogen, and includes those that are saturated, partially unsaturated, or fully unsaturated. Cycloalkyl groups include groups having from 3 to 10 ring atoms. Representative examples of cyclic include but are not limited to, the following moieties:

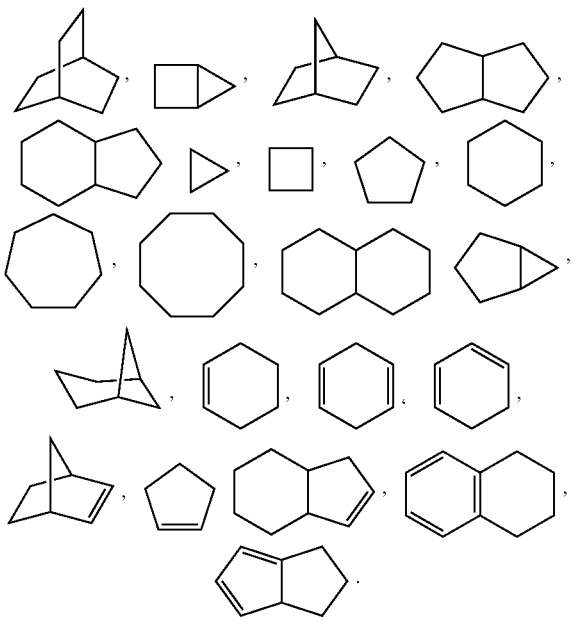

In some embodiments, depending on the structure, a cycloalkyl group is a monoradical or a diradical (e.g., a cycloalkylene group).

The term "cycloalkyl groups" as used herein refers to groups which are optionally substituted with 1, 2, 3, or 4 substituents selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxyl, hydroxyalkylene, mercapto, oxo, —$NR_AR_A$, and ($NR_AR_B$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, 5-cycloheptylbutyl.

The term "carbocyclic" as used herein, refers to a compound which contains one or more covalently closed ring structures, and that the atoms forming the backbone of the ring are all carbon atoms The term "carbocycle" as used herein, refers to a ring, wherein each of the atoms forming the ring is a carbon atom. Carbocylic rings include those formed by three, four, five, six, seven, eight, nine, or more than nine carbon atoms. Carbocycles are optionally substituted.

The term "alkoxyalkyl" as used herein, means at least one alkoxy group, as defined herein, appended to the parent molecular moiety through an alkyl group, as defined herein. Illustrative examples of alkoxyalkyl include, but are not limited to, 2-methoxyethyl, 2-ethoxyethyl, tert-butoxyethyl and methoxymethyl.

The term "alkoxycarbonyl" as used herein, means an alkoxy group, as defined herein, appended to the parent molecular moiety through a carbonyl group, as defined herein. Illustrative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein.

The term "alkylcarbonyl" as used herein, means an alkyl group, as defined herein, appended to the parent molecular moiety through a carbonyl group, as defined herein. Illustrative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Illustrative examples of alkylcarbonyloxy include, but are not limited to, acetyloxy, ethylcarbonyloxy, and tert-butylcarbonyloxy.

The term "alkylthio" or "thioalkoxy" as used herein, means an alkyl group, as defined herein, appended to the parent molecular moiety through a sulfur atom. Illustrative examples of alkylthio include, but are not limited to, methylthio, ethylthio, butylthio, tert-butylthio, and hexylthio.

The term "alkylthioalkyl" as used herein, means an alkylthio group, as defined herein, appended to the parent molecular moiety through an alkyl group, as defined herein. Illustrative examples of alkylthioalkyl include, but are not limited to, methylthiomethyl, 2-(ethylthio)ethyl, butylthiomethyl, and hexylthioethyl.

The term "alkynyl" as used herein, means a straight, branched chain hydrocarbon containing from 2-10 carbons and containing at least one carbon-carbon triple bond. In some embodiments, alkynyl groups are optionally substituted. Illustrative examples of alkynyl include, but are not limited to, acetylenyl, 1-propynyl, 2-propynyl, 3-butynyl, 2-pentynyl, and 1-butynyl.

The term "aromatic" as used herein, refers to a planar ring having a delocalized it-electron system containing $4n+2$ π electrons, where n is an integer. In some embodiments, aromatic rings are formed by five, six, seven, eight, nine, or more than nine atoms. In other embodiments, aromatics are optionally substituted. The term includes monocyclic or fused-ring polycyclic (i.e., rings which share adjacent pairs of carbon atoms) groups.

The term "aryl" as used herein, refers to an aromatic ring wherein each of the atoms forming the ring is a carbon atom. In some embodiments, aryl rings are formed by five, six, seven, eight, nine, or more than nine carbon atoms. Examples of aryl groups include, but are not limited to phenyl, naphthalenyl, phenanthrenyl, anthracenyl, fluorenyl, and indenyl.

In some embodiments, the term "aryl" as used herein means an aryl group that is optionally substituted with one, two, three, four or five substituents independently selected from the group consisting of alkenyl, alkoxy, alkoxyalkyl, alkoxycarbonyl, alkyl, alkylcarbonyl, alkylcarbonyloxy, alkylthio, alkylthioalkyl, alkynyl, carbonyl, cyano, formyl, haloalkoxy, haloalkyl, halogen, hydroxyl, hydroxyalkylene, mercapto, nitro, —$NR_AR_A$, and ($NR_AR_B$)carbonyl.

The term "arylalkyl" as used herein, means an aryl group, as defined herein, appended to the parent molecular moiety through an alkyl group, as defined herein. Illustrative examples of arylalkyl include, but are not limited to benzyl, 2-phenylethyl, -phenylpropyl, 1-methyl-3-phenylpropyl, and 2-naphth-2-ylethyl.

The term "carbonyl" as used herein, means a —C(O)— group.

The term "carboxy" as used herein, means a —COOH group.

The term "cyano" as used herein, means a —CN group.

The term "formyl" as used herein, means a —C(O)H group.

The term "halo" or "halogen" as used herein, means a —Cl, —Br, —I or —F.

The term "mercapto" as used herein, means a —SH group.

The term "nitro" as used herein, means a —$NO_2$ group.

The term "hydroxy" as used herein, means a —OH group.

The term "oxo" as used herein, means a =O group.

The term "bond" or "single bond" as used herein, refers to a chemical bond between two atoms, or two moieties when the atoms joined by the bond are considered to be part of larger substructure.

The terms "haloalkyl," "haloalkenyl," "haloalkynyl" and "haloalkoxy" as used herein, include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

The term "alkylamine" refers to the $N(alkyl)_xH_y$ group, where x and y are selected from among x=1, y=1 and x=2, y=0. In some embodiments, when x=2, the alkyl groups, taken together with the N atom to which they are attached, optionally form a cyclic ring system.

The term "amide" as used herein, is a chemical moiety with the formula —C(O)NHR or —NHC(O)R, where R is selected from among hydrogen, alkyl, cycloalkyl, aryl, heteroaryl (bonded through a ring carbon) and heterocycloalkyl (bonded through a ring carbon). In some embodiments, an amide moiety forms a linkage between an amino acid or a peptide molecule and a compound described herein, thereby forming a prodrug. In some embodiments, any amine, or carboxyl side chain on the compounds described herein is amidified.

The term "ester" refers to a chemical moiety with formula —COOR, where R is selected from among alkyl, cycloalkyl, aryl, heteroaryl (bonded through a ring carbon) and heterocycloalkyl (bonded through a ring carbon). In some embodiments, any hydroxy, or carboxyl side chain on the compounds described herein is esterified.

The terms "heteroalkyl" "heteroalkenyl" and "heteroalkynyl" as used herein, include optionally substituted alkyl, alkenyl and alkynyl radicals in which one or more skeletal chain atoms are selected from an atom other than carbon, e.g., oxygen, nitrogen, sulfur, silicon, phosphorus or combinations thereof.

The term "heteroatom" as used herein refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms are all the same as one another, or some or all of the two or more heteroatoms are each different from the others.

The term "ring" as used herein, refers to any covalently closed structure. Rings include, for example, carbocycles (e.g., aryls and cycloalkyls), heterocycles (e.g., heteroaryls and heterocycloalkyls), aromatics (e.g. aryls and heteroaryls), and non-aromatics (e.g., cycloalkyls and heterocycloalkyls). In some embodiments, rings are optionally substituted. In some embodiments, rings form part of a ring system.

As used herein, the term "ring system" refers to two or more rings, wherein two or more of the rings are fused. The term "fused" refers to structures in which two or more rings share one or more bonds.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In some embodiments, the polycyclic heteroaryl group is fused or non-fused. Illustrative of heteroaryl groups include, but are not limited to, the following moieties:

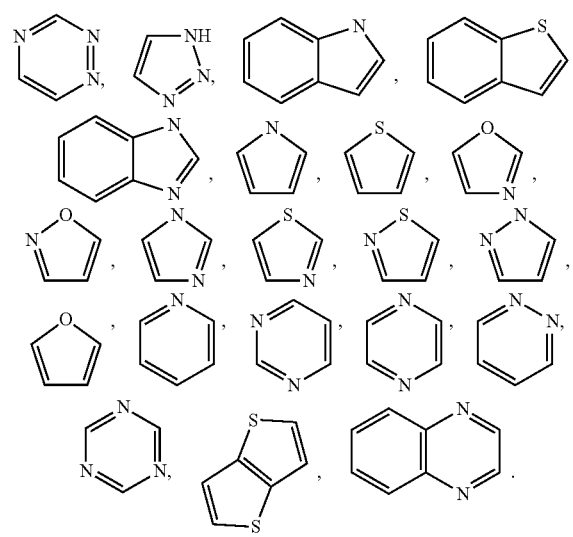

In some embodiments, depending on the structure, a heteroaryl group is a monoradical or a diradical (i.e., a heteroarylene group).

The term "heteroaryl" means heteroaryl groups that are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alynyl, carboxy, cyano, formyl, haloalkoxy, haloalkyl, halogen, hydroxyl, hydroxyalkylene, mercapto, nitro, —$NR_AR_B$, and ($NR_AR_B$)carbonyl.

The term "heteroarylalkyl" as used herein, means a heteroaryl, as defined herein, appended to the parent molecular moiety through an alkyl group, as defined herein. Illustrative examples of heteroarylalkyl include, but are not limited to, pyridinylmethyl.

The term "heterocycloalkyl" or "non-aromatic heterocycle" as used herein, refers to a non-aromatic ring wherein one or more atoms forming the ring is a heteroatom. A "heterocycloalkyl" or "non-aromatic heterocycle" group refers to a cycloalkyl group that includes at least one heteroatom selected from nitrogen, oxygen and sulfur. In some embodiments, the radicals are fused with an aryl or heteroaryl. In some embodiments, heterocycloalkyl rings are formed by three, four, five, six, seven, eight, nine, or more than nine atoms. In some embodiments, heterocycloalkyl rings are optionally substituted. In certain embodiments, heterocycloalkyls contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include, but are not limited to

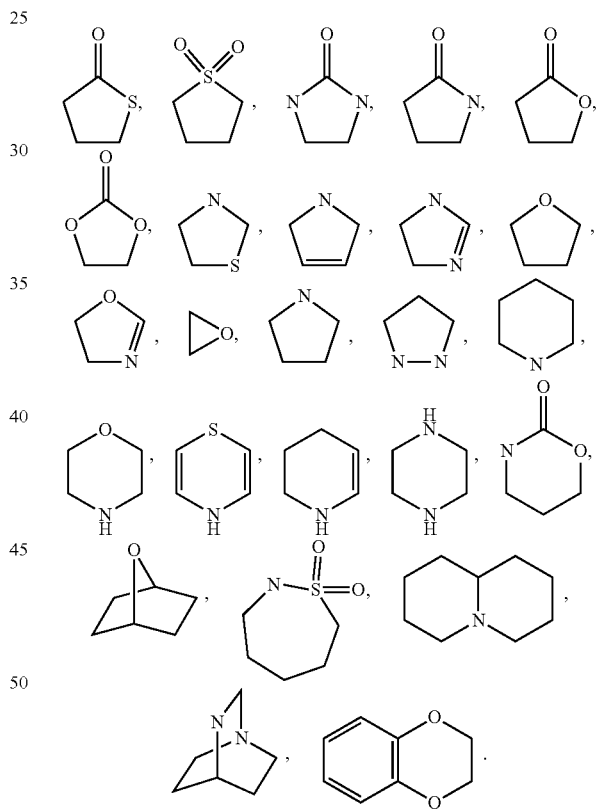

The term heterocycloalkyl also includes all ring forms of the carbohydrates, including but not limited to the monosaccharides, the disaccharides and the oligosaccharides.

The term "heterocycle" refers to heteroaryl and heterocycloalkyl used herein, refers to groups containing one to four heteroatoms each selected from O, S and N, wherein each heterocycle group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom)

must be present in the ring. Designations such as "$C_1$-$C_6$ heterocycle" refer only to the number of carbon atoms in the ring and do not refer to the total number of atoms in the ring. In some embodiments, it is understood that the heterocycle ring has additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In some embodiments, in heterocycles that have two or more heteroatoms, those two or more heteroatoms are the same or different from one another. In some embodiments, heterocycles are optionally substituted. In some embodiments, binding to a heterocycle is at a heteroatom or via a carbon atom. Heterocycloalkyl groups include groups having only 4 atoms in their ring system, but heteroaryl groups must have at least 5 atoms in their ring system. The heterocycle groups include benzo-fused ring systems. An example of a 4-membered heterocycle group is azetidinyl (derived from azetidine). An example of a 5-membered heterocycle group is thiazolyl. An example of a 6-membered heterocycle group is pyridyl, and an example of a 10-membered heterocycle group is quinolinyl. Examples of heterocycloalkyl groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. In some embodiments, the foregoing groups, as derived from the groups listed above, are C-attached or N-attached where such is possible. For instance, in some embodiments, a group derived from pyrrole is pyrrol-1-yl (N-attached) or pyrrol-3-yl (C-attached). Further, in some embodiments, a group derived from imidazole is imidazol-1-yl or imidazol-3-yl (both N-attached) or imidazol-2-yl, imidazol-4-yl or imidazol-5-yl (all C-attached). The heterocycle groups include benzo-fused ring systems and ring systems substituted with one or two oxo (=O) moieties such as pyrrolidin-2-one. In some embodiments, depending on the structure, a heterocycle group is a monoradical or a diradical (i.e., a heterocyclene group).

The heterocycles described herein are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alynyl, carboxy, cyano, formyl, haloalkoxy, haloalkyl, halogen, hydroxyl, hydroxyalkylene, mercapto, nitro, —$NR_AR_B$, and ($NR_AR_B$)carbonyl.

The term "heterocycloalkoxy" refers to a heterocycloalkyl group, as defined herein, appended to the parent molecular moiety through an alkoxy group.

The term "heterocycloalkylthio" refers to a heterocycloalkyl group, as defined herein, appended to the parent molecular moiety through an alkylthio group.

The term "heterocyclooxy" refers to a heterocycloalkyl group, as defined herein, appended to the parent molecular moiety through an oxygen atom.

The term "heterocyclothio" refers to a heterocycloalkyl group, as defined herein, appended to the parent molecular moiety through a sulfur atom.

The term "heteroarylalkoxy" refers to a heteroaryl group, as defined herein, appended to the parent molecular moiety through an alkoxy group.

The term "heteroarylalkylthio" refers to a heteroaryl group, as defined herein, appended to the parent molecular moiety through an alkylthio group.

The term "heteroaryloxy" refers to a heteroaryl group, as defined herein, appended to the parent molecular moiety through an oxygen atom.

The term "heteroarylthio" refers to a heteroaryl group, as defined herein, appended to the parent molecular moiety through a sulfur atom.

In some embodiments, the term "membered ring" embraces any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "non-aromatic 5, 6, 7, 8, 9, 10, 11 or 12-bicyclic heterocycle" as used herein, means a heterocycloalkyl, as defined herein, consisting of two carbocyclic rings, fused together at the same carbon atom (forming a spiro structure) or different carbon atoms (in which two rings share one or more bonds), having 5 to 12 atoms in its overall ring system, wherein one or more atoms forming the ring is a heteroatom. Illustrative examples of non-aromatic 5, 6, 7, 8, 9, 10, 11, or 12-bicyclic heterocycle ring include, but are not limited to, 2-azabicyclo[2.2.1]heptanyl, 7-azabicyclo[2.2.1]heptanyl, 2-azabicyclo[3.2.0]heptanyl, 3-azabicyclo[3.2.0]heptanyl, 4-azaspiro[2.4]heptanyl, 5-azaspiro[2.4]heptanyl, 2-oxa-5-azabicyclo[2.2.1]heptanyl, 4-azaspiro[2.5]octanyl, 5-azaspiro[2.5]octanyl, 5-azaspiro[3.4]octanyl, 6-azaspiro[3.4]octanyl, 4-oxa-7-azaspiro[2.5]octanyl, 2-azabicyclo[2.2.2]octanyl, 1,3-diazabicyclo[2.2.2]octanyl, 5-azaspiro[3.5]nonanyl, 6-azaspiro[3.5]nonanyl, 5-oxo-8-azaspiro[3.5]nonanyl, octahydrocyclopenta[c]pyrrolyl, octahydro-1H-quinolizinyl, 2,3,4,6,7,9a-hexahydro-1H-quinolizinyl, decahydropyrido[1,2-a]azepinyl, decahydro-1H-pyrido[1,2-a]azocinyl, 1-azabicyclo[2.2.1]heptanyl, 1-azabicyclo[3.3.1]nonanyl, quinuclidinyl, and 1-azabicyclo[4.4.0]decanyl.

The term hydroxyalkylene" as used herein, means at least one hydroxyl group, as defined herein, is appended to the parent molecular moiety through an alkylene group, as defined herein. Illustrative examples of hydroxyalkylene include, but not limited to hydroxymethylene, 2-hydroxyethylene, 3-hydroxypropylene and 4-hydroxyheptylene.

The term "$NR_ANR_B$" as used herein, means two group, $R_A$ and $R_B$, which are appended to the parent molecular moiety through a nitrogen atom. $R_A$ and $R_B$ are each independently hydrogen, alkyl, and alkylcarbonyl. Illustrative examples of $NR_AR_B$ include, but are not limited to, amino, methylamino, acetylamino, and acetylmethylamino.

The term "($NR_ANR_B$)carbonyl" as used herein, means a $R_AR_B$, group, as defined herein, appended to the parent molecular moiety through a carbonyl group, as defined herein. Illustrative examples of ($NR_AR_B$)carbonyl include, but are not limited to, aminocarbonyl, (methylamino)carbonyl, (dimethylamino)carbonyl, and (ethylmethylamino)carbonyl.

The term "$NR_CNR_D$" as used herein, means two group, $R_C$ and $R_D$, which are appended to the parent molecular moiety through a nitrogen atom. $R_C$ and $R_D$ are each independently hydrogen, alkyl, and alkylcarbonyl. Illustrative examples of $NR_CR_D$ include, but are not limited to, amino, methylamino, acetylamino, and acetylmethylamino.

The term "($NR_CNR_D$)carbonyl" as used herein, means a $R_CR_D$, group, as defined herein, appended to the parent molecular moiety through a carbonyl group, as defined herein. Illustrative examples of ($NR_CR_D$)carbonyl include, but are not limited to, aminocarbonyl, (methylamino)carbonyl, (dimethylamino)carbonyl, and (ethylmethylamino)carbonyl.

As used herein, the term "mercaptyl" refers to a (alkyl)S— group.

As used herein, the term "moiety" refers to a specific segment or functional group of a molecule. Chemical moieties are often recognized chemical entities embedded in or appended to a molecule.

As used herein, the term "sulfinyl" refers to a —S(=O)—R, where R is selected from the group consisting of alkyl, cycloalkyl, aryl, heteroaryl (bonded through a ring carbon) and heterocycloalkyl (bonded through a ring carbon).

As used herein, the term "sulfonyl" refers to a —S(=O)$_2$—R, where R is selected from the group consisting of alkyl, cycloalkyl, aryl, heteroaryl (bonded through a ring carbon) and heterocycloalkyl (bonded through a ring carbon).

As used herein, the term "O carboxy" refers to a group of formula RC(=O)O—.

As used herein, the term "C carboxy" refers to a group of formula —C(=O)OR.

As used herein, the term "acetyl" refers to a group of formula —C(=O)CH$_3$.

As used herein, the term "trihalomethanesulfonyl" refers to a group of formula $X_3CS(=O)_2$— where X is a halogen.

As used herein, the term "isocyanato" refers to a group of formula —NCO.

As used herein, the term "thiocyanato" refers to a group of formula —CNS.

As used herein, the term "isothiocyanato" refers to a group of formula —NCS.

As used herein, the term "S sulfonamido" refers to a group of formula —S(=O)$_2$NR$_2$.

As used herein, the term "N sulfonamido" refers to a group of formula RS(=O)$_2$NH—.

As used herein, the term "trihalomethanesulfonamido" refers to a group of formula $X_3CS(=O)_2NR$—.

As used herein, the term "O carbamyl" refers to a group of formula —OC(=O)NR$_2$.

As used herein, the term "N carbamyl" refers to a group of formula ROC(=O)NH—.

As used herein, the term "O thiocarbamyl" refers to a group of formula —OC(=S)NR$_2$.

As used herein, the term "N thiocarbamyl" refers to a group of formula ROC(=S)NH—.

As used herein, the term "C amido" refers to a group of formula —C(=O)NR$_2$.

As used herein, the term "N amido" refers to a group of formula RC(=O)NH—.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

The term "substituted" means that the referenced group is optionally substituted (substituted or unsubstituted) with one or more additional group(s) individually and independently selected from alkyl, cycloalkyl, aryl, heteroaryl, heteroalicyclic, hydroxy, alkoxy, aryloxy, mercapto, alkylthio, arylthio, alkylsulfoxide, arylsulfoxide, alkylsulfone, arylsulfone, cyano, halo, carbonyl, thiocarbonyl, isocyanato, thiocyanato, isothiocyanato, nitro, perhaloalkyl, perfluoroalkyl, silyl, and amino, including mono- and di-substituted amino groups, and the protected derivatives thereof. By way of example an optional substituents is $L_sR_s$, wherein each $L_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted $C_1$-$C_6$ alkyl), or -(substituted or unsubstituted $C_2$-$C_6$ alkenyl); and each $R_s$ is independently selected from H, (substituted or unsubstituted lower alkyl), (substituted or unsubstituted lower cycloalkyl), heteroaryl, or heteroalkyl.

The term "protecting group" refers to a removable group which modifies the reactivity of a functional group, for example, a hydroxyl, ketone or amine, against undesirable reaction during synthetic procedures and to be later removed. Examples of hydroxy-protecting groups include, but not limited to, methylthiomethyl, tert-dimethylsilyl, tert-butyldiphenylsilyl, ethers such as methoxymethyl, and esters including acetyl, benzoyl, and the like. Examples of ketone protecting groups include, but not limited to, ketals, oximes, O-substituted oximes for example O-benzyl oxime, O-phenylthiomethyl oxime, 1-isopropoxycyclohexyl oxime, and the like. Examples of amine protecting groups include, but are not limited to, tert-butoxycarbonyl (Boc) and carbobenzyloxy (Cbz).

The term "optionally substituted" as defined herein, means the referenced group is substituted with zero, one or more substituents as defined herein.

The term "protected-hydroxy" refers to a hydroxy group protected with a hydroxy protecting group, as defined above.

In some embodiments, compounds of the described herein exist as stereoisomers, wherein asymmetric or chiral centers are present. Stereoisomers are designated (R) or (S) depending on the configuration of substituents around the chiral carbon atom. The term (R) and (S) used herein are configurations as defined in IUPAC 1974 Recommendations for Section E, Fundamental Stereochemistry, Pure Appl. Chem., (1976), 45:13-30, hereby incorporated by reference. The embodiments described herein specifically includes the various stereoisomers and mixtures thereof. Stereoisomers include enantiomers, diastereomers, and mixtures of enantiomers or diastereomers. In some embodiments, individual stereoisomers of compounds are prepared synthetically from commercially available starting materials which contain asymmetric or chiral centers or by preparation of racemic mixtures followed by resolution. These methods of resolution are exemplified by (1) attachment of a mixture of enantiomers to a chiral axillary, separation of the resulting mixture of diastereomers by recrystallization or chromatography and liberation of the optically pure product from the auxiliary or (2) direct separation of the mixture of optical enantiomers on chiral chromatographic column.

The methods and formulations described herein include the use of N-oxides, crystalline forms (also known as polymorphs), or pharmaceutically acceptable salts of compounds described herein, as well as active metabolites of these compounds having the same type of activity. In some situations, compounds exist as tautomers. All tautomers are included within the scope of the compounds presented herein. In some embodiments, the compounds described herein exist in unsolvated as well as solvated forms with pharmaceutically acceptable solvents such as water, ethanol, and the like. The solvated forms of the compounds presented herein are also considered to be disclosed herein.

Throughout the specification, groups and substituents thereof are chosen, in certain embodiments, to provide stable moieties and compounds.

Preparation of Compounds Described Herein

In certain embodiments, the compounds described herein are synthesized using any synthetic techniques including standard synthetic techniques and the synthetic processes described herein. In specific embodiments, the following synthetic processes are utilized.

Formation of Covalent Linkages by Reaction of an Electrophile with a Nucleophile Selected examples of covalent linkages and precursor functional groups which yield them are given in the Table entitled "Examples of Covalent Linkages and Precursors Thereof." Precursor functional groups are shown as electrophilic groups and nucleophilic groups. In certain embodiments, a functional group on an organic substance is attached directly, or attached via any useful spacer or linker as defined below.

TABLE 1

Examples of Covalent Linkages and Precursors Thereof

| Covalent Linkage Product | Electrophile | Nucleophile |
| --- | --- | --- |
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

In general, carbon electrophiles are susceptible to attack by complementary nucleophiles, including carbon nucleophiles, wherein an attacking nucleophile brings an electron pair to the carbon electrophile in order to form a new bond between the nucleophile and the carbon electrophile.

Suitable carbon nucleophiles include, but are not limited to alkyl, alkenyl, aryl and alkynyl Grignard, organolithium, organozinc, alkyl-, alkenyl, aryl- and alkynyl-tin reagents (organostannanes), alkyl-, alkenyl-, aryl- and alkynyl-borane reagents (organoboranes and organoboronates); these carbon nucleophiles have the advantage of being kinetically stable in water or polar organic solvents. Other carbon nucleophiles include phosphorus ylids, enol and enolate reagents; these carbon nucleophiles have the advantage of being relatively easy to generate from precursors. Carbon nucleophiles, when used in conjunction with carbon electrophiles, engender new carbon-carbon bonds between the carbon nucleophile and carbon electrophile.

Non-carbon nucleophiles suitable for coupling to carbon electrophiles include but are not limited to primary and secondary amines, thiols, thiolates, and thioethers, alcohols, alkoxides, azides, semicarbazides, and the like. These non-carbon nucleophiles, when used in conjunction with carbon electrophiles, typically generate heteroatom linkages (C—X—C), wherein X is a heteroatom, e.g., oxygen or nitrogen.

Use of Protecting Groups

The term "protecting group" refers to chemical moieties that block some or all reactive moieties and prevent such groups from participating in chemical reactions until the protective group is removed. In specific embodiments, more than one protecting group is utilized. In more specific embodiments, each protective group is removable by a different process. Protective groups that are cleaved under totally disparate reaction conditions fulfill the requirement of differential removal. In various embodiments, protective groups are removed by acid, base, or hydrogenolysis. Groups such as trityl, dimethoxytrityl, acetal and t-butyldimethylsilyl are acid labile and are, in some embodiments, used to protect carboxy and hydroxy reactive moieties in the presence of amino groups protected with Cbz groups, which are removable by hydrogenolysis, and Fmoc groups, which are base labile. In some embodiments, carboxylic acid and hydroxy reactive moieties are blocked with base labile groups such as, without limitation, methyl, ethyl, and acetyl in the presence of amines blocked with acid labile groups such as t-butyl carbamate or with carbamates that are both acid and base stable but hydrolytically removable.

In certain embodiments, carboxylic acid and hydroxy reactive moieties are blocked with hydrolytically removable protective groups such as the benzyl group, while, in some embodiments, amine groups capable of hydrogen bonding with acids are blocked with base labile groups such as Fmoc. In various embodiments, carboxylic acid reactive moieties are protected by conversion to simple ester derivatives as exemplified herein, or they are blocked with oxidatively-removable protective groups such as 2,4-dimethoxybenzyl, while, in some embodiments, co-existing amino groups are blocked with fluoride labile silyl carbamates.

In certain instances, allyl blocking groups are useful in the presence of acid- and base-protecting groups since the former are stable. In some embodiments, such groups are subsequently removed by metal or pi-acid catalysts. For example, in some embodiments, an allyl-blocked carboxylic acid is deprotected with a $Pd^0$-catalyzed reaction in the presence of acid labile t-butyl carbamate or base-labile acetate amine protecting groups. In some embodiments, a protecting group is a resin to which a compound or intermediate is attached. As long as the residue is attached to the resin, that functional group is blocked and cannot react. Once released from the resin, the functional group is available to react.

In some embodiments, blocking/protecting groups are selected from, by way of non-limiting example:

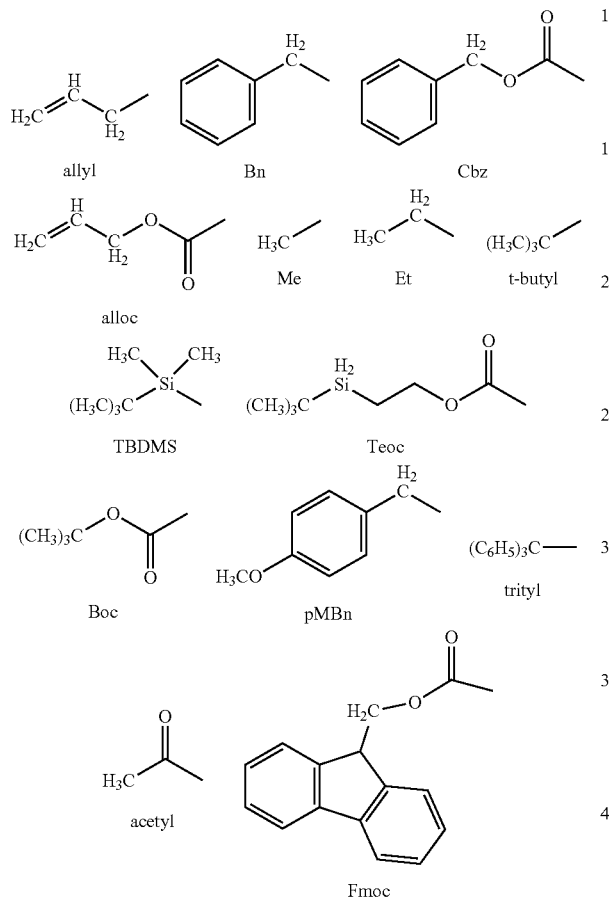

Other protecting groups are described in Greene and Wuts, Protective Groups in Organic Synthesis, 3rd Ed., John Wiley & Sons, New York, N.Y., 1999.

Compounds of Formula (I)

In certain embodiments, compounds of Formula (I), composing of Ia to If, are prepared in various ways, as outlined in Synthetic Schemes 1 and 2. In each scheme, the variables (e.g., $R_1$, $R_2$, $R_3$, $R_4$, $R_5$, Y, and Z) correspond to the same definitions as those recited above while R is alkyl and Y' is the same or different group defined by Y and Z' is the same or different group defined by Z. In some embodiments, compounds are synthesized using methodologies analogous to those described below by the use of appropriate alternative starting materials.

In certain embodiments, compounds of Formula (Ia, and Ib) wherein Y is identical to Z are synthesized according to Synthetic Scheme 1. Thus, the preparation of the intermediate 3 wherein $R_5$ is hydrogen is achieved by condensation of 4-aminoisobenzofuran-1(3H)-one 1 with an aldehyde 2 in the presence of a base preferably alkaline alkoxides in appropriate solvents such as ethyl acetate or ethyl propionate at either ambient or elevated temperature. Compounds of Formula Ia wherein $R_5$ is hydrogen is prepared by treating the intermediate 3 with hydrazine hydrate at ambient or elevated temperature. Compounds of Formula Ia wherein $R_5$ is alkyl or substituted alkyl is prepared from compound of Formula Ia wherein $R_5$ is hydrogen by reductive amination reaction with $R_7$—CHO wherein $R_7$ is alkyl, substituted alkyl. In some embodiments, the preparation of the compounds in Formula Ib is accomplished by further modification of Ia. Through appropriate functional group transformations on the moiety of Y and Z, one affords the compounds of Formula Ib with different entities of Y' and Z' at 2- or 3-positions.

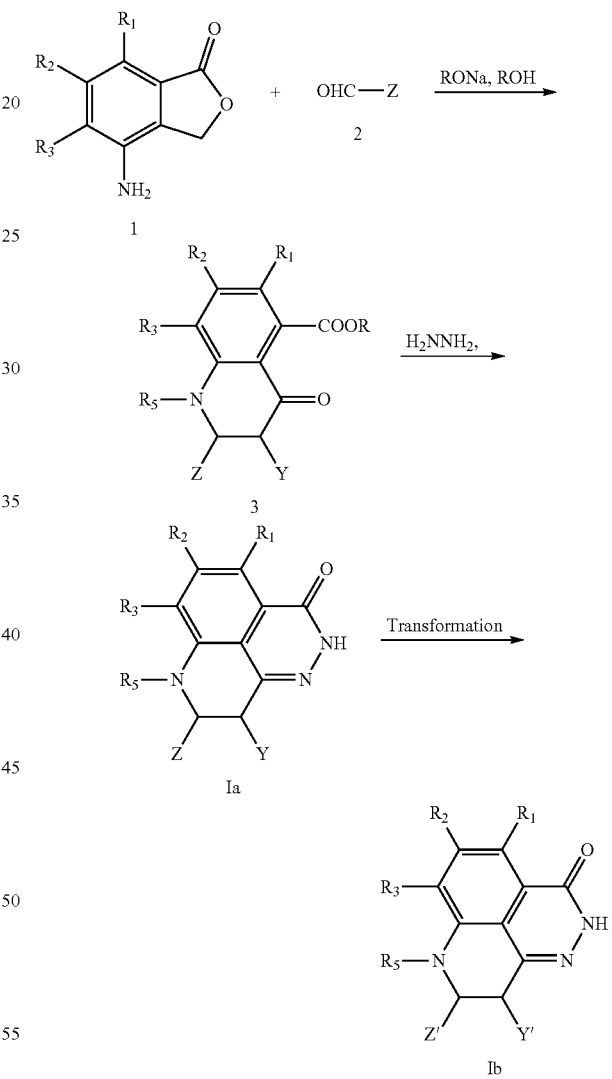

In certain embodiments, compounds of Formula (Ic, and Id) are synthesized according to Synthetic Scheme 2. For example, the intermediate 5 is prepared by condensation of the reagent 1 with an aldehyde 4 in the presence of water absorbent such sodium sulfate or magnesium sulfate at elevated temperature. A subsequent condensation reaction of this intermediate with another aldehyde in the presence of a base preferably alkaline alkoxides in appropriate solvents such as ethyl acetate or ethyl propionate at either ambient or elevated temperature gives the intermediate 6 wherein $R_5$ is hydrogen. Compounds of Formula Ic wherein $R_5$ is hydrogen is prepared by treating the intermediate 6 with hydrazine hydrate at ambient or elevated temperature. Compounds of Formula Ic wherein $R_5$ is alkyl, substituted alkyl are prepared from compounds of Formula Ic wherein $R_5$ is hydrogen by reductive amination reaction with $R_7$—CHO wherein $R_7$ is alkyl, or substituted alkyl. In some embodiments, the preparation of compounds of Formula Id are accomplished by further modification of Ic. Through appropriate functional group transformations on the moiety of Y and Z, one could afford the compounds of Formula Ic with different entities of Y' and Z' at 2- or 3-positions.

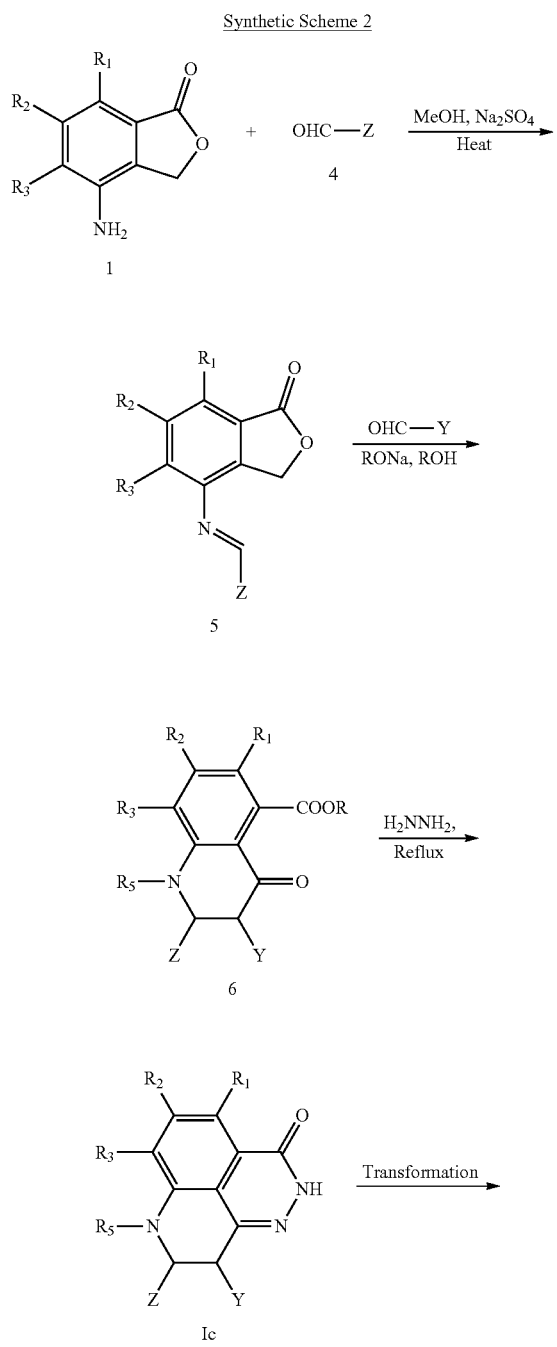

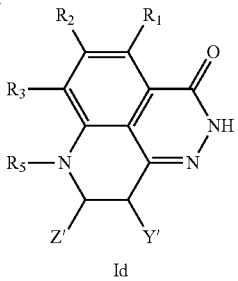

Certain Pharmaceutical Terminology

The term "acceptable" with respect to a formulation, composition or ingredient, as used herein, means having no persistent detrimental effect on the general health of the subject being treated.

As used herein, the term "selective binding compound" refers to a compound that selectively binds to any portion of one or more target proteins.

As used herein, the term "selectively binds" refers to the ability of a selective binding compound to bind to a target protein, such as, for example, PARP, with greater affinity than it binds to a non-target protein. In certain embodiments, specific binding refers to binding to a target with an affinity that is at least about 10, about 50, about 100, about 250, about 500, about 1000 or more times greater than the affinity for a non-target.

As used herein, the term "target protein" refers to a molecule or a portion of a protein capable of being bound by a selective binding compound. In certain embodiments, a target protein is the enzyme poly(ADP-ribose)polymerase (PARP).

As used herein, the terms "treating" or "treatment" encompass either or both responsive and prophylaxis measures, e.g., designed to inhibit, slow or delay the onset of a symptom of a disease or disorder, achieve a full or partial reduction of a symptom or disease state, and/or to alleviate, ameliorate, lessen, or cure a disease or disorder and/or its symptoms.

As used herein, amelioration of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

As used herein, the term "modulator" refers to a compound that alters an activity of a molecule. For example, a modulator includes a compound that causes an increase or a decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

As used herein, the term "selective modulator" refers to a compound that selectively modulates a target activity.

As used herein, the term "PARP" refers to the family of the enzyme poly(ADP-ribose)polymerase which includes approximately 18 proteins, particularly poly(ADP-ribose)polymerase-1 (PARP-1) and poly(ADP-ribose)polymerase-2 (PARP-2).

As used herein, the term "selective PARP modulator" refers to a compound that selectively modulates at least one activity associated with the enzyme poly(ADP-ribose)polymerase (PARP). In various embodiments, the selective modulator selectively modulates the activity of PARP-1, PARP-2, both PARP-1 and PARP-2 or several members of the family of the enzyme poly(ADP-ribose)polymerase (PARP).

As used herein, the term "method of inhibiting PARP" refers to a method of inhibiting the activity of either one or more of the family of enzyme poly(ADP-ribose)polymerase (PARP). As used herein, the term "inhibition of PARP" refers to inhibition of the activity of either one or more of the family of enzyme poly(ADP-ribose)polymerase (PARP).

As used herein, the term "modulating the activity of the enzyme poly(ADP-ribose)polymerase" refers to a modulating the activity of either one or more of the family of enzyme poly(ADP-ribose)polymerase (PARP).

As used herein, the term "selectively modulates" refers to the ability of a selective modulator to modulate a target activity to a greater extent than it modulates a non-target activity. In certain embodiments the target activity is selectively modulated by, for example about 2 fold up to more that about 500 fold, in some embodiments, about 2, 5, 10, 50, 100, 150, 200, 250, 300, 350, 400, 450 or more than 500 fold.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "agonist" refers to a compound, the presence of which results in a biological activity of a protein that is the same as the biological activity resulting from the presence of a naturally occurring ligand for the protein, such as, for example, PARP.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" or "inhibitor" refers to a compound, the presence of which results in a decrease in the magnitude of a biological activity of a protein. In certain embodiments, the presence of an antagonist results in complete inhibition of a biological activity of a protein, such as, for example, the enzyme poly(ADP-ribose)polymerase (PARP).

As used herein, the $IC_{50}$ refers to an amount, concentration or dosage of a particular test compound that achieves a 50% inhibition of a maximal response, such as modulation of PARP, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

The term "cancer", as used herein refers to an abnormal growth of cells which tend to proliferate in an uncontrolled way and, in some cases, to metastasize (spread). The types of cancer include, but are not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents include chemicals used to stabilize compounds because they provide a more stable environment. Salts dissolved in buffered solutions (which also can provide pH control or maintenance) are utilized as diluents in certain embodiments, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "enzymatically cleavable linker," as used herein refers to unstable or degradable linkages which are degraded by one or more enzymes.

The term "inflammatory disorders" refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arteritis); joints (arthritis: crystalline, osteo-, psoriatic, reactive, rheumatoid, Reiter's);

gastrointestinal tract (Chrohn's Disease, ulcerative colitis); skin (dermatitis); or multiple organs and tissues (systemic lupus erythematosus).

The term "PARP-mediated", as used herein, refers to conditions or disorders that are ameliorated by the one or more of the family of enzyme poly(ADP-ribose)polymerase (PARP).

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, in certain instances, enzymes produce specific structural alterations to a compound. In some embodiments, metabolites of the compounds disclosed herein are identified either by administration of compounds to a host and analysis of tissue samples from the host, or by incubation of compounds with hepatic cells in vitro and analysis of the resulting compounds.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

By "pharmaceutically acceptable" or "therapeutically acceptable", as used herein, refers a material, such as a carrier or diluent, which does not abrogate the biological activity or properties of the compound, and is relatively nontoxic. In certain instances, nontoxic and non-abrogative materials includes materials that when administered to an individual do not cause substantial, undesirable biological effects and/or do not interact in a deleterious manner with any of the components of the composition in which it is contained.

The term "pharmaceutically acceptable salt" or "therapeutically acceptable salt", refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

A "prodrug" refers to an agent that is converted into the parent drug in vivo. Prodrugs are often useful because, in some situations, they are easier to administer than the parent drug. In certain instances, a prodrug is bioavailable by oral administration whereas the parent is not. In some instances, a prodrug has improved solubility in pharmaceutical compositions over the parent drug. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid or amino group where the peptide is metabolized to reveal the active moiety. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In some embodiments, the prodrug is designed to alter the metabolic stability or the transport characteristics of a drug, to mask side effects or toxicity, to improve the flavor of a drug or to alter other characteristics or properties of a drug.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Composition/Formulation

In certain embodiments, pharmaceutical compositions are formulated in any manner, including using one or more physiologically acceptable carriers comprising excipients and/or auxiliaries which facilitate processing of the active compounds into pharmaceutical preparations. In some embodiments, proper formulation is dependent upon the route of administration chosen. In various embodiments, any techniques, carriers, and excipients are used as suitable.

Provided herein are pharmaceutical compositions that include a compound described herein and a pharmaceutically acceptable diluent(s), excipient(s), and/or carrier(s). In addition, in some embodiments, the compounds described herein are administered as pharmaceutical compositions in which compounds described herein are mixed with other active ingredients, as in combination therapy.

A pharmaceutical composition, as used herein, refers to a mixture of a compound described herein with other chemical components, such as carriers, stabilizers, diluents, dispersing agents, suspending agents, thickening agents, and/or excipients. In certain embodiments, a pharmaceutical composition facilitates administration of the compound to an organism. In some embodiments, practicing the methods of treatment or use provided herein, includes administering or using a pharmaceutical composition comprising a therapeutically effective amount of a compound provided herein. In specific embodiments, the methods of treatment provided for herein include administering such a pharmaceutical composition to a mammal having a disease or condition to be treated. In one embodiment, the mammal is a human. In some embodiments, the therapeutically effective amount varies widely depending on the severity of the disease, the age and relative health of the subject, the potency of the compound used and other factors. In various embodiments, the compounds described herein are used singly or in combination with one or more therapeutic agents as components of mixtures.

In certain embodiments, the pharmaceutical compositions provided herein are formulated for intravenous injections. In certain aspects, the intravenous injection formulations provided herein are formulated as aqueous solutions, and, in some embodiments, in physiologically compatible buffers such as Hank's solution, Ringer's solution, or physiological saline buffer. In certain embodiments, the pharmaceutical compositions provided herein are formulated for transmucosal administration. In some aspects, transmucosal formulations include penetrants appropriate to the barrier to be permeated. In certain embodiments, the pharmaceutical compositions provided herein are formulated for other parenteral injections, appropriate formulations include aqueous or nonaqueous solutions, and in one embodiment, with physiologically compatible buffers or excipients.

In certain embodiments, the pharmaceutical compositions provided herein are formulated for oral administration. In certain aspects, the oral formulations provided herein comprise compounds described herein that are formulated with pharmaceutically acceptable carriers or excipients. Such carriers enable the compounds described herein to be formulated as tablets, powders, pills, dragees, capsules, liquids, gels, syrups, elixirs, slurries, suspensions and the like, for oral ingestion by a patient to be treated.

In some embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are optionally added, such as the cross-linked croscarmellose sodium, polyvinylpyrrolidone, agar, or alginic acid or a salt thereof such as sodium alginate.

In certain embodiments, provided herein is a pharmaceutical composition formulated as dragee cores with suitable coatings. In certain embodiments, concentrated sugar solutions are used in forming the suitable coating, and optionally contain gum arabic, talc, polyvinylpyrrolidone, carbopol gel, polyethylene glycol, and/or titanium dioxide, lacquer solutions, and suitable organic solvents or solvent mixtures. In some embodiments, dyestuffs and/or pigments are added to tablets, dragees and/or the coatings thereof for, e.g., identification or to characterize different combinations of active compound doses.

In certain embodiments, pharmaceutical preparations which are used include orally include push-fit capsules made of gelatin, as well as soft, sealed capsules made of gelatin and a plasticizer, such as glycerol or sorbitol. In some embodiments, the push-fit capsules contain the active ingredients in admixture with filler such as lactose, binders such as starches, and/or lubricants such as talc or magnesium stearate and, optionally, stabilizers. In certain embodiments, in soft capsules, the active compounds are dissolved or suspended in suitable liquids, such as fatty oils, liquid paraffin, or liquid polyethylene glycols. In addition, stabilizers are optionally added. In certain embodiments, the formulations for oral administration are in dosages suitable for such administration.

In certain embodiments, the pharmaceutical compositions provided herein are formulated for buccal or sublingual administration. In certain embodiments, buccal or sublingual compositions take the form of tablets, lozenges, or gels formulated in a conventional manner. In certain embodiments, parenteral injections involve bolus injection or continuous infusion. In some embodiments, formulations for injection are presented in unit dosage form, e.g., in ampoules or in multi-dose containers, with an added preservative. In some embodiments, the pharmaceutical composition described herein is in a form suitable for parenteral injection as a sterile suspensions, solutions or emulsions in oily or aqueous vehicles, and optionally contains formulatory agents such as suspending, stabilizing and/or dispersing agents. Pharmaceutical formulations for parenteral administration include aqueous solutions of the active compounds in water-soluble form. In some embodiments, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes. In certain embodiments, aqueous injection suspensions contain substances which increase the viscosity of the suspension, such as sodium carboxymethyl cellulose, sorbitol, or dextran. Optionally, the suspensions also contain suitable stabilizers or agents which increase the solubility of the compounds to allow for the preparation of highly concentrated solutions. In alternative embodiments, the active ingredient is in powder form for constitution with a suitable vehicle, e.g., sterile pyrogen-free water, before use.

In some embodiments, the compounds described herein are administered topically. In specific embodiments, the compounds described herein are formulated into a variety of topically administrable compositions, such as solutions, suspensions, lotions, gels, pastes, medicated sticks, balms, creams or ointments. Such pharmaceutical compounds optionally contain solubilizers, stabilizers, tonicity enhancing agents, buffers and/or preservatives.

In certain embodiments, the pharmaceutical compositions provided herein are formulated for transdermal administration of compounds described herein. In some embodiments, administration of such compositions employs transdermal delivery devices and transdermal delivery patches. In certain embodiments, the compositions are lipophilic emulsions or buffered, aqueous solutions, dissolved and/or dispersed in a polymer or an adhesive. Such patches include those constructed for continuous, pulsatile, or on demand delivery of pharmaceutical agents. In some embodiments, transdermal delivery of the compounds described herein is accomplished by use of iontophoretic patches and the like. In certain embodiments, transdermal patches provide controlled delivery of the compounds provided herein, such as, for example, compounds of Formula (I), (IA) or (II). In certain embodiments, the rate of absorption is slowed by using rate-controlling membranes or by trapping the compound within a polymer matrix or gel. Conversely, absorption enhancers are optionally used to increase absorption. Absorption enhancer and carrier include absorbable pharmaceutically acceptable solvents that assist in passage of the compound through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In certain embodiments, the pharmaceutical compositions provided herein are formulated for administration by inhalation. In certain embodiments, in such pharmaceutical compositions formulated for inhalation, the compounds described herein are in a form as an aerosol, a mist or a powder. In some embodiments, pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In certain aspects of a pressurized aerosol, the dosage unit is determined by providing a valve to deliver a metered amount. In certain embodiments, capsules and cartridges of, such as, by way of example only, gelatin for use in an inhaler or insufflator is formulated containing a powder mix of the compound described herein and a suitable powder base such as lactose or starch.

In some embodiments, the compounds described herein are formulated in rectal compositions such as enemas, rectal gels, rectal foams, rectal aerosols, suppositories, jelly suppositories, or retention enemas. In certain embodiments, rectal compositions optionally contain conventional suppository bases such as cocoa butter or other glycerides, as well as synthetic polymers such as polyvinylpyrrolidone, PEG, and the like. In certain suppository forms of the compositions, a low-melting wax such as, but not limited to, a mixture of fatty acid glycerides, optionally in combination with cocoa butter is first melted.

In various embodiments provided herein, the pharmaceutical compositions are formulated in a conventional manner using one or more physiologically acceptable carriers comprising excipients and auxiliaries which facilitate processing of the active compounds into pharmaceutically acceptable preparations. In certain embodiments, proper formulation is dependent upon the route of administration chosen. In various embodiments, any of the techniques, carriers, and excipients is used as suitable. In some embodiments, pharmaceutical compositions comprising a compound described herein are manufactured in a conventional manner, such as, by way of example only, by means of conventional mixing, dissolving, granulating, dragee-making, levigating, emulsifying, encapsulating, entrapping or compression processes.

In certain embodiments, the pharmaceutical compositions include at least one pharmaceutically acceptable carrier, diluent or excipient and a compound described herein described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds described herein exist as tautomers. All tautomers are included within the scope of the compounds presented herein. Additionally, included herein are the solvated and unsolvated forms of the compounds described herein. Solvated compounds include those that are solvated with pharmaceutically acceptable solvents such as water, ethanol, and the like. The solvated forms of the compounds presented herein are also considered to be disclosed herein. In some embodiments, the pharmaceutical compositions described herein include other medicinal or pharmaceutical agents, carriers, adjuvants, such as preserving, stabilizing, wetting or emulsifying agents, solution promoters, salts for regulating the osmotic pressure, and/or buffers. In additional embodiments, the pharmaceutical compositions described herein also contain other therapeutically valuable substances.

Methods for the preparation of compositions containing the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. In various embodiments, the compositions are in liquid solutions or suspensions, solid forms suitable for solution or suspension in a liquid prior to use, or as emulsions. These compositions optionally contain minor amounts of nontoxic, auxiliary substances, such as wetting or emulsifying agents, pH buffering agents, and so forth.

In some embodiments, a composition comprising a compound described herein takes the form of a liquid where the agents are present in solution, in suspension or both. In some embodiments, when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

Useful aqueous suspension optionally contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions optionally comprise an mucoadhesive polymer, selected for example from carboxymethylcellulose, carbomer (acrylic acid polymer), poly (methylmethacrylate), polyacrylamide, polycarbophil, acrylic acid/butyl acrylate copolymer, sodium alginate and dextran.

Useful compositions optionally include solubilizing agents to aid in the solubility of a compound described herein. The term "solubilizing agent" generally includes agents that result in formation of a micellar solution or a true solution of the agent. Solubilizing agents include certain acceptable nonionic surfactants, for example polysorbate 80, and ophthalmically acceptable glycols, polyglycols, e.g., polyethylene glycol 400, and glycol ethers.

Useful compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Useful compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Certain useful compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Some useful compositions optionally include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Certain useful compositions optionally one or more antioxidants to enhance chemical stability where required. Suitable antioxidants include, by way of example only, ascorbic acid and sodium metabisulfite.

In some embodiments, aqueous suspension compositions are packaged in single-dose non-reclosable containers. In alternative embodiments, multiple-dose reclosable containers are used, in which case it is typical to include a preservative in the composition.

In various embodiments, any delivery system for hydrophobic pharmaceutical compounds is employed. Liposomes and emulsions are examples of delivery vehicles or carriers for hydrophobic drugs. In certain embodiments, certain organic solvents such as N-methylpyrrolidone are employed. In some embodiments, the compounds are delivered using a sustained-release system, such as semipermeable matrices of solid hydrophobic polymers containing the therapeutic agent. Various sustained-release materials are utilized in the embodiments herein. In certain embodiments, sustained-release capsules release the compounds for a few weeks up to over 100 days. In some embodiments, depending on the chemical nature and the biological stability of the therapeutic reagent, additional strategies for protein stabilization are employed.

In certain embodiments, the formulations or compositions described herein benefit from and/or optionally comprise antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Methods of Dosing and Treatment Regimens

In certain embodiments, the compounds described herein are used in the preparation or manufacture of medicaments for the treatment of diseases or conditions that are mediated by the enzyme poly(ADP-ribose)polymerase (PARP) or in which inhibition of the enzyme poly(ADP-ribose)polymerase (PARP) ameliorates the disease or condition. In some embodiments, a method for treating any of the diseases or conditions described herein in a subject in need of such treatment, involves administration of pharmaceutical compositions containing at least one compound described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. In some embodiments, amounts effective for this use will depend on the severity and course of the disease or condition, previous therapy, the patient's health status, weight, and response to the drugs, and the judgment of the treating physician. In certain instances, it is considered appropriate for the caregiver to determine such therapeutically effective amounts by routine experimentation (including, but not limited to, a dose escalation clinical trial).

In certain prophylactic applications, compositions containing the compounds described herein are administered to a patient susceptible to or otherwise at risk of a particular disease, disorder or condition. In some embodiments, the amount administere is defined to be a "prophylactically effective amount or dose." In certain embodiments of this use, the precise amounts of compound administered depend on the patient's state of health, weight, and the like. In some embodiments, it is considered appropriate for the caregiver to determine such prophylactically effective amounts by routine experimentation (e.g., a dose escalation clinical trial). In certain embodiments, when used in a patient, effective amounts for this use will depend on the severity and course of the disease, disorder or condition, previous therapy, the patient's health status and response to the drugs, and the judgment of the treating physician.

In certain instances, a patient's condition does not improve or does not significantly improve following administration of a compound or composition described herein and, upon the doctor's discretion the administration of the compounds is optionally administered chronically, that is, for an extended period of time, including throughout the duration of the patient's life in order to ameliorate or otherwise control or limit the symptoms of the patient's disease or condition.

In certain cases wherein the patient's status does improve or does not substantially improve, upon the doctor's discretion the administration of the compounds are optionally given continuously; alternatively, the dose of drug being administered is optionally temporarily reduced or temporarily suspended for a certain length of time (i.e., a "drug holiday"). In certain embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes a reduction from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In certain embodiments, once improvement of the patient's conditions has occurred, a maintenance dose is administered if necessary. In some embodiments, the dosage, e.g., of the maintenance dose, or the frequency of administration, or both, are reduced as a function of the symptoms, to a level at which the improved disease, disorder or condition is retained. In certain embodiments, however, patients are optionally given intermittent treatment on a long-term basis upon any recurrence of symptoms.

In certain embodiments, the amount of a given agent that corresponds to an effective amount varies depending upon factors such as the particular compound, disease or condition and its severity, the identity (e.g., weight) of the subject or host in need of treatment. In some embodiments, the effective amount is, nevertheless, determined according to the particular circumstances surrounding the case, including, e.g., the specific agent that is administered, the route of administration, the condition being treated, and the subject or host being treated. In certain embodiments, however, doses employed for adult human treatment is in the range of about 0.02 to about 5000 mg per day, in a specific embodiment about 1 to about 1500 mg per day. In various embodiments, the desired dose is conveniently presented in a single dose or as divided doses administered simultaneously (or over a short period of time) or at appropriate intervals, for example as two, three, four or more sub-doses per day.

In some embodiments, the pharmaceutical compositions described herein are in a unit dosage form suitable for single administration of precise dosages. In some instances, in unit dosage form, the formulation is divided into unit doses containing appropriate quantities of one or more compound. In certain embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. In alternative embodiments, multiple-dose reclosable containers are used, in which case it is typical to include a preservative in the composition. By way of example only, formulations for parenteral injection are, in some embodiments, presented in unit dosage form, which include, but are not limited to ampoules, or in multi-dose containers, with an added preservative.

In certain embodiments, the daily dosages appropriate for the compounds described herein described herein are from about 0.01 to about 2.5 mg/kg per body weight. In some embodiments, an indicated daily dosage in the larger subject, including, but not limited to, humans, is in the range from about 0.5 mg to about 100 mg, conveniently administered in divided doses, including, but not limited to, up to four times a day or in extended release form. In certain embodiments, suitable unit dosage forms for oral administration comprise from about 1 to about 50 mg active ingredient. The foregoing ranges are merely suggestive, as the number of variables in regard to an individual treatment regime is large, and considerable excursions from these recommended values are not uncommon. In certain embodiments, the dosages are altered depending on a number of variables, not limited to the activity of the compound used, the disease or condition to be treated, the mode of administration, the requirements of the individual subject, the severity of the disease or condition being treated, and the judgment of the practitioner.

In certain embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. In certain embodiments, compounds exhibiting high therapeutic indices are preferred. In some embodiments, the data obtained from cell culture assays and animal studies is used in formulating a range of dosage for use in human. In specific embodiments, the dosage of such compounds lies within a range of circulating concentrations that include the $ED_{50}$ with minimal toxicity. In certain embodiments, the dosage varies within this range depending upon the dosage form employed and the route of administration utilized.

Combination Treatments

In certain instances, it is appropriate to administer at least one compound described herein in combination with another therapeutic agent. By way of example only, if one of the side effects experienced by a patient upon receiving one of the compounds herein is inflammation, then, in some embodiments, it is appropriate to administer an anti-inflammatory agent in combination with the initial therapeutic agent. In some embodiments, the therapeutic effectiveness of one of the compounds described herein is enhanced by administration of an adjuvant (i.e., in some embodiments, by itself the adjuvant has minimal therapeutic benefit, but in combination with another therapeutic agent, the overall therapeutic benefit to the patient is enhanced). In certain embodiments, the benefit experienced by a patient is increased by administering one of the compounds described herein with another therapeutic agent (which also includes a therapeutic regimen) that also has therapeutic benefit. In some embodiments, regardless of the disease, disorder or condition being treated, the overall benefit experienced by the patient as a result of a combination treatment is additive or synergistic.

In certain embodiments, therapeutically-effective dosages vary when the drugs are used in treatment combinations. In some embodiments, therapeutically-effective dosages of drugs and other agents for use in combination treatment regimens is determined in any suitable manner, e.g., through the use of metronomic dosing, i.e., providing more frequent, lower doses in order to minimize toxic side effects. In some embodiments, combination treatment regimen described herein encompass treatment regimens in which administration of a PARP inhibitor described herein is initiated prior to, during, or after treatment with a second agent described above, and continues until any time during treatment with the second agent or after termination of treatment with the second agent. It also includes treatments in which a PARP inhibitor described herein and the second agent being used in combination are administered simultaneously or at different times and/or at decreasing or increasing intervals during the treatment period. Combination treatment further includes periodic treatments that start and stop at various times to assist with the clinical management of the patient. For example, in some embodiments, a PARP inhibitor described herein in the combination treatment is administered weekly at the onset of treatment, decreasing to biweekly, and decreasing further as appropriate.

In certain embodiments, compositions and methods for combination therapy are provided herein. In accordance with one aspect, the pharmaceutical compositions disclosed herein are used to in a method of treating a PARP mediated disease or condition or a disease or condition that is ameliorated by inhibition of PARP. In accordance with certain aspects, the pharmaceutical compositions disclosed herein are used to treat vascular disease; septic shock; ischaemic injury; reperfusion injury; neurotoxicity; hemorrhagic shock; inflammatory diseases; multiple sclerosis; secondary effects of diabetes; and acute treatment of cytotoxicity following cardiovascular surgery. In a certain aspect, the pharmaceutical compositions disclosed herein are used in combination, either simultaneously or sequentially, with ionizing radiation or one or more chemotherapeutic agents.

In certain embodiments, combination therapies described herein are used as part of a specific treatment regimen intended to provide a beneficial effect from the co-action of a PARP inhibitor described herein and a concurrent treatment. It is understood that the dosage regimen to treat, prevent, or ameliorate the condition(s) for which relief is sought, is optionally modified in accordance with a variety of factors.

In certain combination therapies described herein, dosages of the co-administered compounds vary depending on the type of co-drug employed, on the specific drug employed, on the disease or condition being treated and so forth. In some embodiments, when co-administered with one or more biologically active agents, the compound provided herein is administered either simultaneously with the biologically active agent(s), or sequentially. In certain aspects wherein the agents are administered sequentially, the attending physician will decide on the appropriate sequence of administering protein in combination with the biologically active agent(s).

In various embodiments, the multiple therapeutic agents (one of which is one of the compounds described herein) are administered in any order or even simultaneously. In certain instances, administration is simultaneous and the multiple therapeutic agents are, optionally, provided in a single, unified form, or in multiple forms (by way of example only, either as a single pill or as two separate pills). In some embodiments, one of the therapeutic agents is given in multiple doses, or both are given as multiple doses. In some instances, administration is not simultaneous and the timing between the multiple doses varies, by way of non-limiting example, from more than zero weeks to less than four weeks. In addition, the combination methods, compositions and formulations are not to be limited to the use of only two agents; the use of multiple therapeutic combinations are also envisioned.

In additional embodiments, the compounds described herein are used in combination with procedures that provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

In certain embodiments, the compounds described herein and combination therapies are administered before, during or after the occurrence of a disease or condition. In certain embodiments, the timing of administering the composition containing a compound varies. Thus, for example, in some embodiments, the compounds are used as a prophylactic and are administered continuously to subjects with a propensity to develop conditions or diseases in order to prevent the occurrence of the disease or condition. In some embodiments, the compounds and compositions are administered to a subject during or as soon as possible after the onset of the symptoms. In certain embodiments, the administration of the compounds is initiated within the first 48 hours of the onset of the symptoms, within the first 6 hours of the onset of the symptoms, or within 3 hours of the onset of the symptoms. The initial administration is achieved via any route practical, such as, for example, an intravenous injection, a bolus injection, infusion over 5 minutes to about 5 hours, a pill, a capsule, transdermal patch, buccal delivery, and the like, or combination thereof. In some embodiments, a compound is administered as soon as is practicable after the onset of a disease or condition is detected or suspected, and for a length of time necessary for the treatment of the disease, such as, from about 1 month to about 3 months. In certain embodiments, the length of treatment varies for each subject, and the length is determined using any criteria. In exemplary embodiments, a compound or a formulation containing the compound is administered for at least 2 weeks, for about 1 month to about 5 years, or for about 1 month to about 3 years.

Other Combination Therapies

In certain embodiments described herein, methods for treatment of PARP mediated conditions or diseases, such as proliferative disorders, including cancer, include administration to a patient compounds, pharmaceutical compositions, or medicaments described herein in combination with at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, and dronabinol.

Kits/Articles of Manufacture

For use in the therapeutic applications described herein, kits and articles of manufacture are also described herein. In various embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In some embodiments, the containers are formed from a variety of materials such as glass or plastic.

In some embodiments, the articles of manufacture provided herein contain packaging materials. Packaging materials for use in packaging pharmaceutical products include, but are not limited to, blister packs, bottles, tubes, inhalers, pumps, bags, vials, containers, syringes, bottles, and any packaging material suitable for a selected formulation and intended mode of administration and treatment.

In some embodiments, the container(s) described herein comprise one or more compounds described herein, optionally in a composition or in combination with another agent as disclosed herein. The container(s) optionally have a sterile access port (for example in some embodiments the container is an intravenous solution bag or a vial having a stopper pierceable by a hypodermic injection needle). Such kits optionally comprise a compound with an identifying description or label or instructions relating to its use in the methods described herein.

In some embodiments, a kit will comprises one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions is optionally included.

In certain embodiments, a label is on or associated with the container. In some embodiments, a label is on a container when letters, numbers or other characters forming the label are attached, molded or etched into the container itself; a label is associated with a container when it is present within a receptacle or carrier that also holds the container, e.g., as a package insert. In certain embodiments, a label indicates that the contents are to be used for a specific therapeutic application. In some embodiments, the label indicates directions for use of the contents, such as in the methods described herein.

In certain embodiments, the pharmaceutical compositions are presented in a pack or dispenser device which contains one or more unit dosage forms containing a compound provided herein. In some embodiments, the pack contains a metal or plastic foil, such as a blister pack. The pack or dispenser device is optionally accompanied by instructions for administration. In some embodiments, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. In certain embodiments, such notice is, for example, the labeling approved by the U.S. Food and Drug Administration for prescription drugs, or the approved product insert. In some embodiments, compositions containing a compound provided herein are formulated in a compatible pharmaceutical carrier and are placed in an appropriate container labeled for treatment of an indicated condition.

EXAMPLES

The following Examples are intended as an illustration of the various embodiments as defined in the appended claims. In some embodiments, the compounds are prepared by a variety of synthetic routes. All publications, patents, and patent applications cited herein are hereby incorporated by reference for all purposes.

Example 1

Example 1a: Parenteral Composition

To prepare a parenteral pharmaceutical composition suitable for administration by injection, 100 mg of a water-soluble salt of a compound described herein is dissolved in DMSO and then mixed with 10 mL of 0.9% sterile saline. The mixture is incorporated into a dosage unit form suitable for administration by injection.

Example 1b: Oral Composition

To prepare a pharmaceutical composition for oral delivery, 100 mg of a compound described herein is mixed with 750 mg of starch. The mixture is incorporated into an oral dosage unit for, such as a hard gelatin capsule, which is suitable for oral administration.

Example 1c: Sublingual (Hard Lozenge) Composition

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 1d: Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

Example 1e: Rectal Gel Composition

To prepare a pharmaceutical composition for rectal delivery, 100 mg of a compound described herein is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 1f: Topical Gel Composition

To prepare a pharmaceutical topical gel composition, 100 mg of a compound described herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 1g: Ophthalmic Solution Composition

To prepare a pharmaceutical ophthalmic solution composition, 100 mg of a compound described herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 2

8,9-Diphenyl-8,9-dihydro-2H-pyrido[4,3,2-de]phthalazin-3(7H)-one

Example 2A

4-Nitroisobenzofuran-1(3H)-one

A suspension of sodium borohydride (0.757 g, 20 mmol) in anhydrous tetrahydrofuran (120 mL) was cooled to 0° C. A solution of 4-nitrobenzofuran-1,3-dione (6.18 g, 32 mmol) in anhydrous tetrahydrofuran (30 mL) was then added dropwise to the suspension. After the addition, the mixture was allowed to stir at this temperature for 3 hr. The reaction was quenched with 3N hydrochloric acid (to pH=1). Water (40 mL) was added to the mixture and stirred for 1 hr. Tetrahydrofuran was removed under reduced pressure. The residue was partioned between water (150 mL) and ethyl acetate (150 mL×3). The combined organic layers were washed with brine, dried over anhydrous sodium sulfate, concentrated to give crude product. The crude product was purified by chromatography (silica gel, petroleum ether/ethyl acetate=20:1 to 2:1) to give 4-nitroisobenzofuran-1(3H)-one (4.2 g, yield 73%) as a white solid. MS (ESI) m/z: 180 (M+1)$^+$. $^1$H-NMR (400 MHz, CDCl$_3$) δ □5.77 (s, 3H), 7.32-7.34 (d, J=8.4 Hz, 1H), 7.81-7.85 (t, J=8.0 Hz, 1H), 8.29 (d, J=8.0 Hz, 1H), 8.55 (d, J=8.0 Hz, 1H).

Example 2B

4-Aminoisobenzofuran-1(3H)-one

A suspension of 4-nitroisobenzofuran-1(3H)-one (1.0 g, 5.58 mmol) and 10% Pd/C (0.1 g) in ethyl acetate (30 mL) was purged in 1 atm hydrogen and stirred at 25° C. for 3 hr. The mixture was filtered, and the filtrate was concentrated to give 4-aminoisobenzofuran-1(3H)-one (0.8 g, yield 96%) as a off-white solid. MS (ESI) m/z: 150 (M+1)$^+$. $^1$H-NMR (400 MHz, CDCl$_3$) □□δ 3.82 (s, br 1H), 5.19 (s, 3H), 6.91-6.95 (m, 1H), 7.32-7.36 (m, 2H).

Example 2C

Methyl 4-oxo-2,3-diphenyl-1,2,3,4-tetrahydroquinoline-5-carboxylate and ethyl 4-oxo-2,3-diphenyl-1,2,3,4-tetrahydroquinoline-5-carboxylate A mixture of 4-aminoisobenzofuran-1(3H)-one (0.4 g, 2.68 mmol) and benzaldehyde (0.72 g, 6.7 mmol) in ethyl propionate (20 mL) was cooled to 0° C. Then a solution of sodium methoxide in methanol [sodium (248 mg, 10.72 mmol) in methanol (20 mL)] was added dropwise. After the addition, the mixture was heated at reflux for 16 hr. The mixture was quenched with water (10 mL) and solvent was removed in vacuum. The residue was dissolved in water, acidified with 1N hydrochloric acid to pH=6, then extracted with ethyl acetate (50 mL×3). The combined organic layers were washed with brine, dried over anhydrous sodium sulfate, and concentrated to give crude product. The crude product was purified by prep-HPLC to give methyl 4-oxo-2,3-diphenyl-1,2,3,4-tetrahydroquinoline-5-carboxylate (256 mg, yield 27%) and ethyl 4-oxo-2,3-diphenyl-1,2,3,4-tetrahydroquinoline-5-carboxylate (140 mg, yield 14%) as a light yellow solid. Methyl 4-oxo-2,3-diphenyl-1,2,3,4-tetrahydroquinoline-5-carboxylate: MS (ESI) m/z: 358 (M+1)$^+$. $^1$H-NMR (400 MHz, CDCl$_3$) □□δ 3.86 (s, 3H), 3.95-3.98 (d, J=16.4 Hz, 1H), 4.81-4.84 (d, J=12.8 Hz, 1H), 4.89 (s, br 1H), 6.72-6.77 (m, 2H), 6.90-6.93 (m, 2H), 7.11-7.21 (m, 8H), 7.34-7.36 (t, J=7.8 Hz, 1H).

Example 2D 8,9-Diphenyl-8,9-dihydro-2H-pyrido[4,3,2-de]phthalazin-3(7H)-one

A mixture of methyl 4-oxo-2,3-diphenyl-1,2,3,4-tetrahydroquinoline-5-carboxylate (100 mg, mmol) in hydrazine monohydrate (25 mL) was heated to reflux for 20 hr. The mixture was diluted with water (30 mL), extracted with ethyl acetate (30 mL×3). The combined organic layers were washed with brine, dried over anhydrous sodium sulfate, and concentrated to give crude product. The crude product was purified by chromatography (silica gel, petroleum ether/ethyl acetate=20:1 to 8:1) to give 8,9-diphenyl-8,9-dihydro-2H-pyrido[4,3,2-de]phthalazin-3(7H)-one (15.6 mg, yield 16%) as a white solid. MS (ESI) m/z: 340 (M+1)$^+$. $^1$H-NMR (400 MHz, CDCl$_3$) δ □4.22-4.25 (d, J=9.6 Hz, 1H), 4.66-4.69 (d, J=9.6 Hz, 1H), 7.02-7.06 (m, 3H), 7.16-7.26 (m, 8H), 7.57-7.61 (t, J=7.8 Hz, 1H), 7.74-7.76 (d, J=7.6 Hz, 1H), 9.82 (s, 1H).

Example 3

8,9-Bis(4-(methylamino)methyl)phenyl-8,9-dihydro-2H-pyrido[4,3,2-de]phthalazin-3(7H)-one Example 3A Methyl 2,3-bis(4-(diethoxymethyl)phenyl)-4-oxo-1,2,3,4-tetrahydroquinoline-5-carboxylate and ethyl 2,3-bis(4-(diethoxymethyl)phenyl)-4-oxo-1,2,3,4-tetrahydroquinoline-5-carboxylate A mixture of 4-aminoisobenzofuran-1(3H)-one (298 mg, 2 mmol) and 4-(diethoxymethyl)benzaldehyde (1.04 g, 5 mmol) in ethyl propionate (15 mL) was cooled to 0° C. A solution of sodium methoxide in methanol [sodium (184 mg, 8 mmol) in methanol (15 mL)] was then added dropwise. After the addition, the mixture was stirred at 25° C. for 16 hr. The mixture was quenched with water (10 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by chromatography (silica gel, petroleum ether/ethyl acetate=100:1 to 10:1) to give methyl 2,3-bis(4-(-(diethoxymethyl)phenyl)-4- oxo-1,2,3,4-tetrahydroquinoline-5-carboxylate and ethyl 2,3-bis(4-(-(diethoxymethyl)phenyl)-4-oxo-1,2,3,4-tetrahydroquinoline-5-carboxylate (240 mg together, yield 21%) as a light yellow solid. LC-MS (ESI) m/z: 562 (M+1)+ (methyl 2,3-bis(4-(-(diethoxymethyl)phenyl)-4-oxo-1,2,3,4-tetrahydroquinoline-5-carboxylate); 576 (M+1)+ (ethyl 2,3-bis(4-(-(diethoxymethyl)phenyl)-4-oxo-1,2,3,4-tetrahydroquinoline-5-carboxylate).

Example 3B 8,9-Bis(4-(diethoxymethyl)phenyl-8,9-dihydro-2H-pyrido[4,3,2-de]phthalazin-3(7H)-one A mixture of methyl 2,3-bis(4-(diethoxymethyl)phenyl)-4-oxo-1,2,3,4-tetrahydroquinoline-5-carboxylate and ethyl 2,3-bis(4-(diethoxymethyl)phenyl)-4-oxo-1,2,3,4-tetrahydroquinoline-5-carboxylate (240 mg, 0.43 mmol) in hydrazine monohydrate (5 mL) and methanol (5 mL) was stirred at 40° C. for 2 hr. The mixture was cooled to room temperature and filtered to give the 8,9-bis(4-(diethoxymethyl)phenyl)-8,9-dihydro-2H-pyrido[4,3,2-de]phthalazin-3(7H)-one (120 mg, yield 52%) as a light yellow solid. LC-MS (ESI) m/z: 544 (M+1)+. MS (ESI) m/e 381 [M+H]+.

Example 3C 4,4'-(3-Oxo-3,7,8,9-tetrahydro-2H-pyrido[4,3,2-de]phthalazine-8,9-diyl)dibenzaldehyde A mixture of 8,9-bis(4-(diethoxymethyl)phenyl)-8,9-dihydro-2H-pyrido[4,3,2-de]phthalazin-3(7H)-one (120 mg, 0.22 mmol) in 3N hydrochloric acid (5 mL) was stirred at room temperature for 3 hr. Then the mixture was neutralized (basified) with potassium carbonate to pH=8. The resulting suspension was filtered to give 4,4'-(3-oxo-3,7,8,9-tetrahydro-2H-pyrido[4,3,2-de]phthalazine-8,9-diyl)dibenzaldehyde (80 mg, yield 97%) as a light yellow solid. LC-MS (ESI) m/z: 396 (M+1)+.

Example 3D

Bis(4-(methylamino)methyl)phenyl-8,9-dihydro-2H-pyrido[4,3,2-de]phthalazin-3(7H)-one A mixture of 4,4'-(3-oxo-3,7,8,9-tetrahydro-2H-pyrido[4,3,2-de]phthalazine-8,9-diyl)dibenzaldehyde (80 mg, 0.21 mmol) and 27% methylamine alcohol solution (94 mg, 0.82 mmol) in methanol (10 mL) was stirred at room temperature for 40 min. The mixture was then cooled to 0° C. Sodium borohydride (24 mg, 0.64 mmol) was added. After the addition, the mixture was stirred at room temperature for 4 hr. Methanol was removed under reduced pressure. The residue was washed with ethyl acetate and filtered. The filtrate was concentrated to give 8,9-bis(4-(methylamino)methyl)phenyl-8,9-dihydro-2H-pyrido[4,3,2-de]phthalazin-3(7H)-one (29.5 mg, yield 33%) as a light yellow solid. $^1$H-NMR (400 MHz, DMSO-$d_6$) δ □2.20 (d, J=8.8 Hz, 6H), 3.52-3.53 (d, J=2.4 Hz, 4H), 4.31-4.33 (d, J=6.4 Hz, 1H), 4.76-4.77 (d, J=6.4 Hz, 1H), 7.06-7.08 (d, J=6.4 Hz, 2H), 7.12-7.17 (m, 5H), 7.35-7.38 (t, J=6.4 Hz, 2H), 7.49-7.57 (t, J=10.0 Hz, 1H); LC-MS (ESI) m/z: 426 (M+1)+.

Example 4

8,9-Di(pyridin-4-yl)-8,9-dihydro-2H-pyrido[4,3,2-de]phthalazin-3(7H)-one

Example 4A

Methyl 4-oxo-2,3-di(pyridin-4-yl)-1,2,3,4-tetrahydroquinoline-5-carboxylate and ethyl 4-oxo-2,3-di(pyridin-4-yl)-1,2,3,4-tetrahydroquinoline-5-carboxylate A mixture of 4-aminoisobenzofuran-1(3H)-one (149 mg, 1 mmol) and nicotinaldehyde (268 mg, 2.5 mmol) in ethyl propionate (10 mL) was cooled to 0° C. Then a solution of sodium methoxide in methanol [sodium (93 mg, 4 mmol) in methanol (3 mL)] was added dropwise. After the addition, the mixture was stirred at 25° C. for 16 hr. The mixture was quenched with water (5 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by prep-HPLC to give methyl 4-oxo-2,3-di(pyridin-4-yl)-1,2,3,4-tetrahydroquinoline-5-carboxylate (60 mg, yield 17%) and ethyl 4-oxo-2,3-di(pyridin-4-yl)-1,2,3,4-tetrahydroquinoline-5-carboxylate (4 mg, yield 1%) as a light yellow solid. LC-MS (ESI) m/z: 360 (M+1)+(methyl 4-oxo-2,3-di(pyridin-4-yl)-1,2,3,4-tetrahydroquinoline-5-carboxylate), 374 (M+1)+ (ethyl 4-oxo-2,3-di(pyridin-4-yl)-1,2,3,4-tetrahydroquinoline-5-carboxylate).

Example 4B 8,9-Di(pyridin-4-yl)-8,9-dihydro-2H-pyrido[4,3,2-de]phthalazin-3(7H)-one A mixture of methyl 4-oxo-2,3-di(pyridin-4-yl)-1,2,3,4-tetrahydroquinoline-5-carboxylate and ethyl 4-oxo-2,3-di(pyridin-4-yl)-1,2,3,4-tetrahydroquinoline-5-carboxylate (60 mg, 0.17 mmol) in hydrazine monohydrate (7 mL) was heated to reflux for 4 hr. Then the mixture was cooled to room temperature and solvent was removed in vacuum to give crude product. The crude product was purified by pre-HPLC to give 8,9-di(pyridin-4-yl)-8,9-dihydro-2H-pyrido[4,3,2-de]phthalazin-3(7H)-one (15 mg, yield 68%) as a light yellow solid. $^1$H-NMR (400 MHz, DMSO) δ □4.46-4.48 (d, J=8.4 Hz, 1H), 4.90-4.92 (d, J=8.4 Hz, 1H), 7.16-7.20 (m, 3H), 7.32-7.34 (d, J=5.2 Hz, 2H), 7.40-7.42 (d, J=8.4 Hz, 1H), 7.55 (s, 1H), 7.59-7.63 (t, J=8.0 Hz, 1H), 8.40-8.40 (d, J=5.2 Hz, 2H), 8.44-8.45 (d, J=5.2 Hz, 2H). LC-MS (ESI) m/z: 342 (M+1)+.

Example 5

8,9-Di(pyridin-3-yl)-8,9-dihydro-2H-pyrido[4,3,2-de]phthalazin-3(7H)-one

Example 5A methyl 4-oxo-2,3-di(pyridin-3-yl)-1,2,3,4-tetrahydroquinoline-5-carboxylate and ethyl 4-oxo-2,3-di(pyridin-3-yl)-1,2,3,4-tetrahydroquinoline-5-carboxylate A mixture of 4-aminoisobenzofuran-1(3H)-one (298 mg, 2 mmol) and nicotinaldehyde (535 mg, 5 mmol) in ethyl propionate (15 mL) was cooled to 0° C. A solution of sodium methoxide in methanol [sodium (184 mg, 8 mmol) in methanol (15 mL)] was then added dropwise. After the addition, the mixture was stirred at 25° C. for 16 hr. The mixture was quenched with water (10 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by chromatography (silica gel, petroleum ether/ethyl acetate=100:1 to 10:1) to give methyl 4-oxo-2,3-di(pyridin-3-yl)-1,2,3,4-tetrahydroquinoline-5-carboxylate and ethyl 4-oxo-2,3-di(pyridin-3-yl)-1,2,3,4-tetrahydroquinoline-5-carboxylate (480 mg together, yield 67%) as a light yellow solid. LC-MS (ESI) m/z: 360 (M+1)$^+$(methyl 4-oxo-2,3-di(pyridin-3-yl)-1,2,3,4-tetrahydroquinoline-5-carboxylate); 374 (M+1)$^+$ (ethyl 4-oxo-2,3-di(pyridin-3-yl)-1,2,3,4-tetrahydroquinoline-5-carboxylate).

Example 5B 8,9-Di(pyridin-3-yl)-8,9-dihydro-2H-pyrido[4,3,2-de]phthalazin-3(7H)-one A mixture of methyl 4-oxo-2,3-di(pyridin-3-yl)-1,2,3,4-tetrahydroquinoline-5-carboxylate and ethyl 4-oxo-2,3-di(pyridin-3-yl)-1,2,3,4-tetrahydroquinoline-5-carboxylate (480 mg, 1.34 mmol) in hydrazine monohydrate (20 mL) and methanol (5 mL) was heated to reflux for 2 hr. The mixture was then cooled to room temperature and filtered to give 8,9-di(pyridin-3-yl)-8,9-dihydro-2H-pyrido[4,3,2-de]phthalazin-3(7H)-one (320 mg, yield 68%) as a light yellow solid. $^1$H-NMR (400 MHz, DMSO-d$_6$) δ □4.51-4.53 (d, J=8.4 Hz, 1H), 4.89-4.91 (d, J=8.4 Hz, 1H), 7.18-7.20 (m, 1H), 7.24-7.27 (m, 1H), 7.31-7.33 (m, 1H), 7.43-7.44 (m, 1H), 7.60 (s, 1H), 7.58-7.63 (m, 2H), 7.79-7.81 (m, 1H), 8.32-8.34 (m, 2H), 8.41-8.43 (m, 1H), 8.45-8.46 (d, J=1.6 Hz, 1H); LC-MS (ESI) m/z: 342 (M+1)$^+$.

Example 6

8,9-Di(pyridin-2-yl)-8,9-dihydro-2H-pyrido[4,3,2-de]phthalazin-3(7H)-one

Example 6A methyl 4-oxo-2,3-di(pyridin-2-yl)-1,2,3,4-tetrahydroquinoline-5-carboxylate and ethyl 4-oxo-2,3-di(pyridin-2-yl)-1,2,3,4-tetrahydroquinoline-5-carboxylate A mixture of 4-aminoisobenzofuran-1(3H)-one (149 mg, 1 mmol) and nicotinaldehyde (268 mg, 2.5 mmol) in ethyl propionate (10 mL) was cooled to 0° C. A solution of sodium methoxide in methanol [sodium (93 mg, 4 mmol) in methanol (3 mL)] was then added dropwise. After the addition, the mixture was stirred at 25° C. for 16 hr. The mixture was quenched with water (5 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by prep-HPLC to give methyl 4-oxo-2,3-di(pyridin-2-yl)-1,2,3,4-tetrahydroquinoline-5-carboxylate (72 mg, yield 20%) and ethyl 4-oxo-2,3-di(pyridin-2-yl)-1,2,3,4-tetrahydroquinoline-5-carboxylate (14 mg, yield 3%) as a light yellow solid. LC-MS (ESI) m/z: 360 (M+1)$^+$(methyl 4-oxo-2,3-di(pyridin-2-yl)-1,2,3,4-tetrahydroquinoline-5-carboxylate); 374 (M+1)$^+$ (ethyl 4-oxo-2,3-di(pyridin-2-yl)-1,2,3,4-tetrahydroquinoline-5-carboxylate).

Example 6B 8,9-Di(pyridin-2-yl)-8,9-dihydro-2H-pyrido[4,3,2-de]phthalazin-3(7H)-one A mixture of methyl 4-oxo-2,3-di(pyridin-2-yl)-1,2,3,4-tetrahydroquinoline-5-carboxylate and ethyl 4-oxo-2,3-di(pyridin-2-yl)-1,2,3,4-tetrahydroquinoline-5-carboxylate (68 mg, 0.19 mmol) in hydrazine monohydrate (7 mL) was heated to reflux for 4 hr. Then the mixture was cooled to room temperature and solvent was removed in vacuum to give crude product. The crude product was purified by pre-HPLC to give 8,9-di(pyridin-2-yl)-8,9-dihydro-2H-pyrido[4,3,2-de]phthalazin-3(7H)-one (24 mg, yield 37%) as a light yellow solid. $^1$H-NMR (400 MHz, DMSO) δ □5.42-5.43 (d, J=5.2 Hz, 1H), 5.56-5.57 (d, J=5.2 Hz, 1H), 7.30-7.32 (d, J=8.0 Hz, 1H), 7.37-7.39 (d, J=8.0 Hz, 1H), 7.63-7.66 (t, J=6.6 Hz, 1H), 7.68-7.70 (m, 2H), 7.78-7.80 (d, J=7.2 Hz, 1H), 7.87-7.89 (d, J=8.0 Hz, 1H), 8.11-8.16 (m, 2H), 8.66-8.67 (d, J=4.8 Hz, 1H), 8.74-8.76 (d, J=5.6 Hz, 1H); LC-MS (ESI) m/z: 342 (M+1)$^+$.

Example 7

9-Isopropyl-8-phenyl-8,9-dihydro-2H-pyrido[4,3,2-de]phthalazin-3(7H)-one

Example 7A (E)-4-(Benzylideneamino)isobenzofuran-1(3H)-one 4-aminoisobenzofuran-1(3H)-one (600 mg, 4 mmol), benzaldehyde (427 mg, 4 mmol) were added to methanol (20 mL) and stirred under reflux overnight, then the mixture was evaporated under reduced pressure and the residue was dried in vacuum. 600 mg of crude product (E)-4-(benzylideneamino)isobenzofuran-1(3H)-one was obtained which was used for the next synthetic step without further purification.

Example 7B

Methyl 3-isopropyl-4-oxo-2-phenyl-1,2,3,4-tetrahydroquinoline-5-carboxylate 4-(benzylideneamino)isobenzofuran-1(3H)-one (237 mg, 1 mmol), isobutyraldehyde (216 mg, 3 mmol), sodium methanolate (162 mg, 3 mmol) and ethyl propionate (20 mL) were added and the mixture was stirred at room temperature overnight. Then the resulting mixture was evaporated under reduced pressure and extracted with ethyl acetate (100 mL×4) and concentrated. The crude product was purified by column chromatography (silica gel, petroleum ether/ethyl acetate=20:1 to 5:1). 35 mg of solid methyl-3-isopropyl-4-oxo-2-phenyl-1,2,3,4-tetrahydroquinoline-5-carboxylate was obtained. (yield: 11%). LC-MS (ESI) m/z: 308 (M+1)$^+$.

Example 7C

9-Isopropyl-8-phenyl-8,9-dihydro-2H-pyrido[4,3,2-de]phthalazin-3(7H)-one

Methyl 3-isopropyl-4-oxo-2-phenyl-1,2,3,4-tetrahydroquinoline-5-carboxylate (35 mg, 1 mmol) and hydrazine monohydrate (20 mL) were added and the mixture was stirred under 40° C. for 3 h. The resulting mixture was extracted with ethyl acetate (100 mL×4) and concentrated, purified with prep-HPLC. 7 mg of solid 9-isopropyl-8-phenyl-8,9-dihydro-2H-pyrido[4,3,2-de]phthalazin-3(7H)-one was obtained (yield: 15%). $^1$H-NMR (400 MHz, DMSO-d$_6$): δ 0.82-0.83 (d, J=5.2 Hz, 3H), 1.15-1.17 (d, J=5.2 Hz, 3H), 1.89-1.93 (m, 1H), 2.71-2.73 (d, J=6.0 Hz, 1H), 4.83 (s, 1H), 7.11-7.26 (m, 7H), 7.51-7.54 (m, 2H), 12.11 (s, 1H). LC-MS (ESI) m/z: 306 (M+1)$^+$.

Example 8

9-(4-((Methylamino)methyl)phenyl)-8-phenyl-8,9-dihydro-2H-pyrido[4,3,2-de]phthalazin-3(7H)-one and 9-(4-((dimethylamino)methyl)phenyl)-8-phenyl-8,9-dihydro-2H-pyrido[4,3,2-de]phthalazin-3(7H)-one Example 8A 1-(4-(Diethoxymethyl)phenyl)-N-methylmethanamine A mixture of 4-(diethoxymethyl)benzaldehyde (1.04 g, 5 mmol) and methylamine (27~32% solution in methanol, 2.3 g, 20 mmol) in methanol (20 mL) was stirred at room temperature for 40 mins. The mixture was cooled to 0° C., sodium borohydride (0.284 g, 7.5 mmol) was added portionwise. After the addition, the mixture was stirred at room temperature for 4 hr. Methanol was removed under reduced pressure. The residue was partitioned between water (50 mL) and ethyl acetate (50 mL). The organic layer was separated. The aqueous layer was extracted with ethyl acetate (50 mL×3). The combined organic layers were washed with brine, dried over anhydrous sodium sulfate, and concentrated to give crude 1-(4-(diethoxymethyl)phenyl)-N-methylmethanamine (1.1 g) as a light yellow oil which was used in the next step without further purification. LC-MS (ESI) m/z: 224 (M+1)$^+$.

Example 8B

Benzyl 4-(diethoxymethyl)benzyl(methyl)carbamate

To a stirred solution of 1-(4-(diethoxymethyl)phenyl)-N-methylmethanamine (1.1 g, 4.9 mmol) and triethylamine (0.75 g, 7.35 mmol) in anhydrous dichloromethane (10 mL) was added benzyl carbonochloridate (1.0 g, 5.88 mmol) at 0° C. After the addition, the mixture was allowed to stir at room temperature overnight. The mixture was diluted with dichloromethane (50 mL), washed with water (50 mL×3), brine (50 mL), dried over anhydrous sodium sulfate, and concentrated to give crude product which was purified by chromatography (silica gel, petroleum ether/ethyl acetate=100:1 to 20:1) to give benzyl 4-(diethoxymethyl)benzyl(methyl)carbamate (1.0 g, yield 57% for two steps) as a light yellow oil. $^1$H-NMR (400 MHz, CDCl$_3$) □□δ: 3.82 (s, br 1H), 5.19 (s, 3H), 6.91-6.95 (m, 1H), 7.32-7.36 (m, 2H); LC-MS (ESI) m/z: 358 (M+1)$^+$.

Example 8C

Benzyl 4-formylbenzyl(methyl)carbamate

The mixture of benzyl 4-(diethoxymethyl)benzyl(methyl) carbamate (1.0 g, 2.8 mmol) in 3N hydrochloric acid (50 ml) was stirring at room temperature for 1 h. Then the mixture was neutralized with Potassium carbonate. The resulting mixture was extracted with ethyl acetate (100 mL×4), the organic phase was washed with water and saturated sodium bicarbonate, dried with anhydrous sodium sulfate and concentrated to give benzyl 4-formylbenzyl(methyl)carbamate (730 mg, 92%). $^1$H-NMR (400 MHz, CDCl$_3$) □□δ: 2.94 (d, 3H), 4.572 (d, 2H), 5.18 (d, 2H), 7.32-7.39 (m, 7H), 7.84 (m, 2H), 10.00 (s, 1H); LC-MS (ESI) m/z: 284 (M+1)$^+$.

Example 8D

Methyl 3-(4-4(benzyloxycarbonyl)(methyl)amino) methyl)phenyl)-4-oxo-2-phenyl-1,2,3,4-tetrahydro-quinoline-5-carboxylate A mixture of benzyl 4-formylbenzyl(methyl)carbamate (566 mg, 2 mmol) and 4-(benzylideneamino) isobenzofuran-1-one (474 mg, 2 mmol) in ethyl propionate (15 mL) was cooled to 0° C. A solution of sodium methoxide in methanol [sodium (184 mg, 8 mmol) in methanol (15 mL)] was then added dropwise. After the addition, the mixture was stirred at 25° C. for 18 hr. The mixture was quenched with water (10 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by chromatography (silica gel, petroleum ether/ethyl acetate=100:1 to 10:1) to give a mixture of methyl 3-(4-(((benzyloxycarbonyl)(methyl)amino)methyl)-phenyl)-4-oxo-2-phenyl-1,2,3,4-tetrahydroquinoline-5-carboxylate and ethyl 3-(4-(((benzyloxycarbonyl)(methyl)amino) methyl)-phenyl)-4-oxo-2-phenyl-1,2,3,4-tetrahydroquino-line-5-carboxylate (220 mg, yield 20%) as a light yellow solid. LC-MS (ESI) m/z: 535 (M+1)$^+$ and 549 (M+1)$^+$.

Example 8E

Benzyl methyl(4-(3-oxo-8-phenyl-3,7,8,9-tetra-hydro-2H-pyrido[4,3,2-de]phthalazin-9-yl)benzyl) carbamate A mixture of methyl 3-(4-4(benzyloxycarbonyl)(methyl) amino)methyl)phenyl)-4-oxo-2-phenyl-1,2,3,4-tetrahydro-quinoline-5-carboxylate (220 mg, 0.94 mmol) in hydrazine monohydrate (50 mL) and methanol (5 mL) was stirred at 40° C. for 24 hr. The mixture was cooled to room temperature and filtered to give the crude product. The crude product was purified by chromatography (silica gel, petroleum ether/ ethyl acetate=3:1) to give benzyl methyl(4-(3-oxo-8-phenyl-3,7,8,9-tetrahydro-2H-pyrido[4,3,2-de]phthalazin-9-yl)ben-zyl)carbamate (80 mg, yield 16%). LC-MS (ESI) m/z: 517 (M+1)$^+$.

Example 8F 9-(4-((Methylamino)methyl)phenyl)-8-phenyl-8,9-dihydro-2H-pyrido[4,3,2-de]phthalazin-3(7H)-one and 9-(4-((dimethylamino)methyl)phenyl)-8-phenyl-8,9-dihydro-2H-pyrido[4,3,2-de]phthalazin-3(7H)-one A mixture of benzyl methyl(4-(3-oxo-8-phenyl-3,7,8,9-tetrahydro-2H-pyrido[4,3,2-de]phthalazin-9-yl)benzyl)car-bamate (80 mg, 0.26 mmol), 10% Pd/C (20 mg) of methanol (50 ml) was stirring at room temperature for 4 h. The mixture solution was then filtered and evaporated under reduced pressure. The residue was purified by prep-HPLC. 3 mg of 9-(4-((methylamino)methyl)phenyl)-8-phenyl-8,9-dihydro-2H-pyrido[4,3,2-de]phthalazin-3(7H)-one and 6 mg of 9-(4-((dimethylamino)methyl)phenyl)-8-phenyl-8,9-dihydro-2H-pyrido[4,3,2-de]phthalazin-3(7H)-one were obtained, yield 9%. For 9-(4-((methylamino)methyl)-phenyl)-8-phenyl-8,9-dihydro-2H-pyrido[4,3,2-de]phthalazin-3(7H)-one: $^1$H-NMR (400 MHz, CD$_3$OD) δ: 2.50 (s, 3H), 3.87 (s, 2H), 4.38 (d, 1H), 4.75 (d, 1H), 7.15-7.17 (m, 2H), 7.19-7.25 (m, 5H), 7.27-7.28 (m, 3H), 7.57 (d, 1H), 7.65 (t, 1H). LC-MS (ESI) m/z: 383 (M+1)$^+$. For 9-(4-((dimethylamino)methyl)phenyl)-8-phenyl-8,9-dihydro-2H-pyrido[4,3,2-de]phthalazin-3(7H)-one: $^1$H-NMR (400 MHz, CD$_3$OD) δ: 2.31 (s, 6H), 3.57 (s, 2H), 4.33 (d, 1H), 4.73 (d, 1H), 7.10-7.12 (m, 2H), 7.19-7.21 (m, 6H), 7.26-7.27 (m, 2H), 7.58 (d, 1H), 7.64 (t, 1H). LC-MS (ESI) m/z: 397 (M+1)$^+$.

Example 9

9-(3-((Methylamino)methyl)phenyl)-8-phenyl-8,9-dihydro-2H-pyrido[4,3,2-de]phthalazin-3(7H)-one Example 9A Methyl 3-(3-(diethoxymethyl)phenyl)-4-oxo-2-phenyl-1,2,3,4-tetrahydroquinoline-5-carboxylate A mixture of (E)-4-(benzylideneamino)isobenzofuran-1(3H)-one (474 mg, 2 mmol) and 3-(diethoxymethyl)benzaldehyde (418 mg, 2 mmol) in ethyl propionate (20 mL) was cooled to 0° C. Sodium methoxide in methanol solution [sodium (148 mg, 8 mmol) in methanol (2 mL)] was then added dropwise and the mixture was stirred at room temperature overnight. The resulting mixture was evaporated under reduced pressure. The residue was extracted with ethyl acetate (100 mL×3) and the combined organic layers were washed with brine, dried over anhydrous sodium sulfate and concentrated to give crude product. The crude product was purified by column chromatography (silica gel, petroleum ether/ethyl acetate=50:1 to 5:1) to give methyl 3-(3-(diethoxymethyl)phenyl)-4-oxo-2-phenyl-1,2,3,4-tetrahydroquinoline-5-carboxylate (230 mg, yield 25%) as a yellow solid.

Example 9B 9-(3-(Diethoxymethyl)phenyl)-8-phenyl-8,9-dihydro-2H-pyrido[4,3,2-de]phthalazin-3(7H)-one Methyl 3-(3-(diethoxymethyl)phenyl)-4-oxo-2-phenyl-1,2,3,4-tetrahydroquinoline-5-carboxylate (300 mg, 0.65 mmol) in hydrazine monohydrate (20 mL) was stirred at 45° C. for 4 h. The resulting mixture was filtered to give 9-(3-(diethoxymethyl)phenyl)-8-phenyl-8,9-dihydro-2H-pyrido[4,3,2-de]phthalazin-3(7H)-one (95 mg, yield 33%) as a white solid. $^1$H-NMR (400 MHz, DMSO-d6) δ: □1.04-1.08 (t, J=7.0 Hz, 6H), 3.27-3.31 (q, 4H), 4.34-4.36 (d, J=8.8 Hz, 1H), 4.74-4.76 (d, J=8.8 Hz, 1H), 5.34 (s, 1H), 7.08 (s, 1H), 7.14-7.24 (m, 7H), 7.27-7.29 (m, 2H), 7.37-7.39 (d, J=7.2 Hz, 1H), 7.43 (s, 1H), 7.56-7.60 (t, J=8.0 Hz, 1H), 12.15 (s, 1H); LC-MS (ESI) m/z: 442 (M+1)$^+$.

Example 9C 3-(3-Oxo-8-phenyl-3,7,8,9-tetrahydro-2H-pyrido[4,3,2-de]phthalazin-9-yl)benzaldehyde A mixture of 9-(3-(diethoxymethyl)phenyl)-8-phenyl-8,9-dihydro-2H-pyrido[4,3,2-de]phthalazin-3(7H)-one (90 mg, 0.20 mmol) in 3N hydrochloric acid (12 mL) was stirred at room temperature for 20 hr. Then the mixture was adjusted to pH=8 with potassium carbonate. The resulting suspension was extracted with ethyl acetate to give 3-(3-oxo-8-phenyl-3,7,8,9-tetrahydro-2H-pyrido[4,3,2-de]phthalazin-9-yl)benzaldehyde (66 mg, yield 88%) as a light yellow solid. LC-MS (ESI) m/z: 368 (M+1)$^+$.

Example 9D 9-(3-((Methylamino)methyl)phenyl)-8-phenyl-8,9-dihydro-2H-pyrido[4,3,2-de]phthalazin-3(7H)-one A mixture of 3-(3-oxo-8-phenyl-3,7,8,9-tetrahydro-2H-pyrido[4,3,2-de]phthalazin-9-yl)benzaldehyde (66 mg, 0.18 mmol) and 27% methylamine alcohol solution (83 mg, 0.72 mmol) in methanol (15 mL) was stirred at room temperature for 1 h. The mixture was then cooled to 0° C. and sodium borohydride (11 mg, 0.27 mmol) was added. After the addition, the mixture was stirred at room temperature for 4 hr. Methanol was removed under reduced pressure. The residue was purified by prep-HPLC to give 9-(3-((methylamino)methyl)phenyl)-8-phenyl-8,9-dihydro-2H-pyrido[4,3,2-de]phthalazin-3(7H)-one (34 mg, yield 49%) as a light yellow solid. $^1$H-NMR (400 MHz, MeOD-d4) δ: □2.55 (s, 3H), 4.04-4.13 (q, 2H), 4.36-4.38 (d, J=9.6 Hz, 1H), 4.74-4.76 (d, J=8.8 Hz, 1H), 7.18-7.24 (m, 6H), 7.25-7.35 (m, 4H), 7.56-7.58 (d, J=7.6 Hz, 1H), 7.62-7.66 (t, J=8 Hz, 1H); LC-MS (ESI) m/z: 383 (M+1)$^+$.

Example 10

8-(4-((Methylamino)methyl)phenyl)-9-phenyl-8,9-dihydro-2H-pyrido[4,3,2-de]phthalazin-3(7H)-one Example 10A (E)-4-(4-(diethoxymethyl)benzylideneamino)isobenzofuran-1(3H)-one 4-Aminoisobenzofuran-1(3H)-one (600 mg, 4 mmol), 4-(ethoxy(methoxy)methyl) benzaldehyde (1.6 g, 8 mmol) and 1 g of magnesium sulfate were added into 40 mL of dichloromethane and stirred under reflux overnight, then the mixture was evaporated under reduced pressure and the residue was dried in vacuum to give 600 mg of crude product (E)-4-(4-(diethoxymethyl)benzylideneamino) isobenzofuran-1(3H)-one which without further purification was used in next step.

Example 10B

Methyl 2-(4-(dimethoxymethyl)phenyl)-4-oxo-3-phenyl-1,2,3,4-tetrahydroquinoline-5-carboxylate (E)-4-(4-(diethoxymethyl)benzylideneamino)isobenzofuran-1(3H)-one (600 mg, 1 mmol), benzaldehyde (616 mg, 3 mmol), sodium methanolate (414 mg, 7.6 mmol) and ethyl propionate (20 ml) were added and the mixture was stirred at room temperature overnight. The resulting mixture was then evaporated under reduced pressure and extracted with ethyl acetate (100 mL×4) and concentrated. The crude product was purified by column chromatography (silica gel, petroleum ether:ethyl acetate=20:1 to 5:1) to yield 120 mg of solid of methyl 2-(4-(dimethoxymethyl)phenyl)-4-oxo-3- phenyl-1,2,3,4-tetrahydroquinoline-5-carboxylate (yield: 22%). LC-MS (ESI) m/z: 432 (M+1)+.

Example 10C 8-(4-(Dimethoxymethyl)phenyl)-9-phenyl-8,9-dihydro-2H-pyrido[4,3,2-de]phthalazin-3(7H)-one To methyl 2-(4-(dimethoxymethyl)phenyl)-4-oxo-3-phenyl-1,2,3,4-tetrahydroquinoline-5-carboxylate (120 mg, 0.28 mmol) was added hydrazine monohydrate (20 mL) and the mixture was stirred under 40° C. for 3 h. The resulting mixture was evaporated under reduced pressure to 10 ml and then filtered, 89 mg of solid of 8-(4-(dimethoxymethyl)phenyl)-9-phenyl-8,9-dihydro-2H-pyrido[4,3,2-de]phthalazin-3(7H)-one was obtained (yield: 78%). LC-MS (ESI) m/z: 414 (M+1)+.

Example 10D 4-(3-Oxo-9-phenyl-3,7,8,9-tetrahydro-2H-pyrido[4,3,2-de]phthalazin-8-yl)benzaldehyde To 8-(4-(dimethoxymethyl)phenyl)-9-phenyl-8,9-dihydro-2H-pyrido[4,3,2-de]phthalazin-3(7H)-one (89 mg, 0.22 mmol) was added 20 ml of hydrochloric acid (3 mol/L) and the mixture was stirred at room temperature for 2 h. The resulting mixture was evaporated under reduced pressure to 10 ml and then filtered, 59 mg of solid of 4-(3-oxo-9-phenyl-3,7,8,9-tetrahydro-2H-pyrido[4,3,2-de]phthalazin-8-yl)benzaldehyde was obtained; yield: 73%. LC-MS (ESI) m/z: 368 (M+1)+.

Example 10E 8-(4-((Methylamino)methyl)phenyl)-9-phenyl-8,9-dihydro-2H-pyrido[4,3,2-de]phthalazin-3(7H)-one To 4-(3-oxo-9-phenyl-3,7,8,9-tetrahydro-2H-pyrido[4,3,2-de]phthalazin-8-yl)benzaldehyde (59 mg, 0.16 mmol) was added methanamine (20 ml) and the mixture was stirred at room temperature for 2 h. Then 30 mg of sodium borohydride was added and stirred for another 2 h. The resulting mixture was evaporated under reduced pressure and purified by prep-HPLC. 11.5 mg of 8-(4-((methylamino)methyl)phenyl)-9-phenyl-8,9-dihydro-2H-pyrido[4,3,2-de]phthalazin-3(7H)-one was obtained (yield: 19%). $^1$H-NMR (400 MHz, CD$_3$OD) δ: 2.66 (s, 3H), 4.33-4.35 (d, J=8 Hz, 1H), 4.83-4.85 (d, J=7.6 Hz, 1H), 7.10-7.12 (m, 2H), 7.15-7.22 (m, 4H), 7.34-7.42 (m, 4H), 7.55-7.57 (m, 1H), 7.63-7.67 (m, 1H). LC-MS (ESI) m/z: 383 (M+1)+.

Example 11

8,9-Bis(3-((methylamino)methyl)phenyl)-8,9-dihydro-2H-pyrido[4,3,2-de]phthalazin-3(7H)-one

Example 11A

Methyl 2,3-bis(3-(diethoxymethyl)phenyl)-4-oxo-1,2,3,4-tetrahydroquinoline-5-carboxylate and ethyl 2,3-bis(3-(diethoxymethyl)phenyl)-4-oxo-1,2,3,4-tetrahydroquinoline-5-carboxylate A mixture of 4-aminoisobenzofuran-1(3H)-one (298 mg, 2 mmol) and 3-(diethoxymethyl)benzaldehyde (0.83 g, 4 mmol) in ethyl propionate (15 mL) was cooled to 0° C. Then a solution of sodium methoxide in methanol [sodium (184 mg, 8 mmol) in methanol (15 mL)] was added dropwise. After the addition, the mixture was stirred at 25° C. for 18 hr. The mixture was quenched with water (10 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by chromatography (silica gel, petroleum ether/ethyl acetate=100:1 to 10:1) to give a mixture of methyl 2,3-bis(3-(diethoxymethyl)phenyl)-4-oxo-1,2,3,4-tetrahydroquinoline-5-carboxylate and ethyl 2,3-bis(3-(diethoxymethyl)phenyl)-4-oxo-1,2,3,4-tetrahydroquinoline-5-carboxylate (370 mg; yield 33%) as a light yellow solid. LC-MS (ESI) m/z: 562 (M+1)+, and 576 (M+1)+.

Example 11B 8,9-Bis(3-(diethoxymethyl)phenyl)-8,9-dihydro-2H-pyrido[4,3,2-de]phthalazin-3(7H)-one A mixture of methyl 2,3-bis(3-(diethoxymethyl)phenyl)-4-oxo-1,2,3,4-tetrahydroquinoline-5-carboxylate and ethyl 2,3-bis(3-(diethoxymethyl)phenyl)-4-oxo-1,2,3,4-tetrahydroquinoline-5-carboxylate (370 mg, 0.59 mmol) in hydrazine monohydrate (5 mL) and methanol (5 mL) was stirred at 40° C. for 2 hr. The mixture was cooled to room temperature and filtered to give 8,9-bis(3-(diethoxymethyl)phenyl)-8,9-dihydro-2H-pyrido[4,3,2-de]phthalazin-3(7H)-one (250 mg, yield 77%) as a light yellow solid. LC-MS (ESI) m/z: 544 (M+1)+.

Example 11C 3,3'-(3-Oxo-3,7,8,9-tetrahydro-2H-pyrido[4,3,2-de]phthalazin-8,9-diyl)dibenzaldehyde A mixture of 8,9-bis(3-(diethoxymethyl)phenyl)-8,9-dihydro-2H-pyrido[4,3,2-de]phthalazin-3(7H)-one (120 mg, 0.46 mmol) in 3N hydrochloric acid (5 mL) was stirred at room temperature for 3 hr. The mixture was then adjusted to pH=8 with potassium carbonate. The resulting suspension was filtered to give 3,3'-(3-oxo-3,7,8,9-tetrahydro-2H-pyrido[4,3,2-de]phthalazin-8,9-diyl)dibenzaldehyde (160 mg, yield 88%) as a light yellow solid. LC-MS (ESI) m/z: 396 (M+1)+.

Example 11D 8,9-Bis(3-((methylamino)methyl)phenyl)-8,9-dihydro-2H-pyrido[4,3,2-de]phthalazin-3(7H)-one A mixture of 3,3'-(3-oxo-3,7,8,9-tetrahydro-2H-pyrido[4,3,2-de]phthalazin-8,9-diyl)dibenzaldehyde (100 mg, 0.25 mmol) and 27% methylamine alcohol solution (122 mg, 1.07 mmol) in methanol (15 mL) was stirred at room temperature for 40 min. The mixture was then cooled to 0° C. Sodium borohydride (31 mg, 1.00 mmol) was added. After the addition, the mixture was stirred at room temperature for 4 hr. Methanol was removed under reduced pressure. The residue was washed with ethyl acetate and filtered. The filtrate was concentrated to give 8,9-bis(3-((methylamino)methyl)phenyl)-8,9-dihydro-2H-pyrido[4,3,2-de]phthalazin-3(7H)-one (20 mg, yield 19%) as a light yellow solid. $^1$H-NMR (400 MHz, CD$_3$OD) ≡: □2.62-2.63 (d, J=4.0 Hz, 6H), 4.12-4.13 (d, J=10.8 Hz, 4H), 4.42-4.44 (d, J=8.4 Hz, 1H), 4.84-4.86 (d, J=8.4 Hz, 1H), 7.20-7.24 (m, 2H), 7.29-7.33 (m, 6H), 7.52 (s, 1H), 7.57-7.60 (dd, J$_1$=8.0 Hz, J$_2$=1.2 Hz, 1H), 7.65-7.69 (t, J=7.6 Hz, 1H); LC-MS (ESI) m/z: 426 (M+1)$^+$.

Example 12

9-(4-(Hydroxymethyl)phenyl)-8-phenyl-8,9-dihydro-2H-pyrido[4,3,2-de]phthalazin-3(7H)-one Example 12A methyl 3-(4-(diethoxymethyl)phenyl)-4-oxo-2-phenyl-1,2,3,4-tetrahydroquinoline-5-carboxylate and ethyl 3-(4-(Diethoxymethyl)phenyl)-4-oxo-2-phenyl-1,2,3,4-tetrahydroquinoline-5-carboxylate A mixture of (E)-4-(benzylideneamino)isobenzofuran-1 (3H)-one (474 mg, 2 mmol) and 4-(diethoxymethyl)benzaldehyde (0.40 g, 2.4 mmol) in ethyl propionate (15 mL) was cooled to 0° C. A solution of sodium methoxide in methanol [sodium (184 mg, 8 mmol) in methanol (15 mL)] was then added dropwise. After the addition, the mixture was stirred at 25° C. for 18 hr. The mixture was quenched with water (10 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by chromatography (silica gel, petroleum ether/ethyl acetate=100:1 to 10:1) to give methyl 3-(4-(diethoxymethyl) phenyl)-4-oxo-2-phenyl-1,2,3,4-tetrahydroquinoline-5-carboxylate and ethyl 3-(4-(diethoxymethyl)phenyl)-4-oxo-2-phenyl-1,2,3,4-tetrahydroquinoline-5-carboxylate (430 mg, yield: 47%) as a light yellow solid. LC-MS (ESI) m/z: 460 (M+1)$^+$ and 474 (M+1)$^+$.

Example 12B 9-(4-(Diethoxymethyl)phenyl)-8-phenyl-8,9-dihydro-2H-pyrido[4,3,2-de]phthalazin-3(7H)-one A mixture of methyl 3-(4-(diethoxymethyl)phenyl)-4-oxo-2-phenyl-1,2,3,4-tetrahydroquinoline-5-carboxylate and ethyl 3-(4-(diethoxymethyl)phenyl)-4-oxo-2-phenyl-1,2,3,4-tetrahydroquinoline-5-carboxylate (430 mg, 0.94 mmol) in hydrazine monohydrate (10 mL) and methanol (5 mL) was stirred at 40° C. for 24 hr. The mixture was cooled to room temperature and filtered to give the 9-(4-(diethoxymethyl)phenyl)-8-phenyl-8,9-dihydro-2H-pyrido[4,3,2-de]phthalazin-3(7H)-one (270 mg, yield: 65%) as a light yellow solid. LC-MS (ESI) m/z: 442 (M+1)$^+$.

Example 12C 4-(3-Oxo-8-phenyl-3,7,8,9-tetrahydro-2H-pyrido[4,3,2-de]phthalazin-9-yl)benzaldehyde A mixture of 9-(4-(diethoxymethyl)phenyl)-8-phenyl-8,9-dihydro-2H-pyrido[4,3,2-de]phthalazin-3(7H)-one (270 mg, 0.61 mmol) in 3N hydrochloric acid (10 mL) was stirred at room temperature for 3 hr. The mixture was then adjusted to pH=8 with potassium carbonate. The resulting suspension was filtered to give 4-(3-oxo-8-phenyl-3,7,8,9-tetrahydro-2H-pyrido[4,3,2-de]phthalazin-9-yl)benzaldehyde (140 mg, yield: 69%) as a light yellow solid.

Example 12D 9-(4-(Hydroxymethyl)phenyl)-8-phenyl-8,9-dihydro-2H-pyrido[4,3,2-de]phthalazin-3(7H)-one A mixture of 4-(3-oxo-8-phenyl-3,7,8,9-tetrahydro-2H-pyrido[4,3,2-de]phthalazin-9-yl)benzaldehyde (140 mg, 0.42 mmol) and 27% methylamine alcohol solution (194 mg, 1.69 mmol) in methanol (15 mL) was stirred at room temperature for 40 min. Then the mixture was cooled to 0° C. Sodium borohydride (48 mg, 1.26 mmol) was added. After the addition, the mixture was stirred at room temperature for 4 hr. TLC (petroleum ether/ethyl acetate=2:1) show the reaction was complete. Methanol was removed under reduced pressure. The residue was washed with ethyl acetate and filtered. The filtrate was concentrated to give 9-(4-(hydroxymethyl)phenyl)-8-phenyl-8,9-dihydro-2H-pyrido [4,3,2-de]phthalazin-3(7H)-one (20 mg, yield: 13%) as a light yellow solid. $^1$H-NMR (400 MHz, CD$_3$OD) δ: 4.33-4.35 (d, J=8.0 Hz, 1H), 4.53 (s, 2H), 4.74-4.76 (d, J=8.0 Hz, 1H), 7.08-7.10 (d, J=8.0 Hz, 2H), 7.18-7.24 (m, 6H), 7.27-7.29 (d, J=6.8 Hz, 2H), 7.54-7.56 (d, J=7.6 Hz, 1H), 7.62-7.66 (t, J=8.0 Hz, 1H); LC-MS (ESI) m/z: 370 (M+1)$^+$.

Example 13

9-(3-(4-isobutyrylpiperazine-1-carbonyl)phenyl)-8-phenyl-8,9-dihydro-2H-pyrido[4,3,2-de]phthalazin-3 (7H)-one and 8,9-bis(3-(4-isobutyrylpiperazine-1-carbonyl)phenyl)-8,9-dihydro-2H-pyrido[4,3,2-de] phthalazin-3(7H)-one Example 13A tert-Butyl 4-isobutyrylpiperazine-1-carboxylate To a solution of isobutyric acid (6.608 g, 75 mmol) in anhydrous dichloromethane (130 mL) was added triethylamine (8.33 g, 82.5 mmol), 1-hydroxybenzotriazole (10.125 g, 75 mmol), followed by 1-ethyl-3-(3-dimethylaminopropyl)carbodiimide hydrochloride (14.25 g, 75 mmol). After the addition, the mixture was stirred at room temperature for 40 mins. The mixture was then cooled to 0° C., compound 1 (13.97 g, 75 mmol) was added portionwise. After the addition, the mixture was stirred at room temperature overnight. The mixture was diluted with dichloromethane (200 mL), washed with saturated sodium bicarbonate (150 mL×2), 10% citric acid (150 mL), brine (100 mL), dried over anhydrous sodium sulfate, and concentrated to give tert-butyl 4-isobutyrylpiperazine-1-carboxylate (15 g, yield: 78%) as a white solid. LC-MS (ESI) m/z: 257 (M+1)$^+$.

Example 13B

2-Methyl-1-(piperazin-1-yl)propan-1-one

To a stirred mixture of tert-butyl 4-isobutyrylpiperazine-1-carboxylate (6.8 g, 26.5 mmol) in methanol (15 mL) was added hydrochloride/methanol (30 mL, 3M)) at 0° C. After the addition, the mixture was allowed to stir at room temperature overnight. The mixture was concentrated to give 2-methyl-1-(piperazin-1-yl)propan-1-one (5.5 g, yield: 100%) as an off-white solid. $^1$H-NMR (400 MHz, CDCl$_3$) δ: 3.82 (brs, 1H), 5.19 (s, 3H), 6.91-6.95 (m, 1H), 7.32-7.36 (m, 2H); LC-MS (ESI) m/z: 157 (M+1)$^+$.

Example 13C 3-(4-Isobutyrylpiperazine-1-carbonyl)benzaldehyde

To a solution of 3-formylbenzoic acid (750 mg, 5 mmol) in anhydrous dichloromethane (15 mL) was added triethylamine (1.263 g, 12.5 mmol), 1-hydroxybenzotriazole (0.743 g, 5.5 mmol), followed by 1-ethyl-3-(3-dimethylaminopropyl)carbodiimide hydrochloride (1.05 g, 5.5 mmol). After the addition, the mixture was stirred at room temperature for 40 mins. Then the mixture was cooled to 0° C., and 2-methyl-1-(piperazin-1-yl)propan-1-one (1.06 g, 5.5 mmol) was added portionwise. After the addition, the mixture was stirred at room temperature overnight. The mixture was diluted with dichloromethane (50 mL), washed with saturated sodium bicarbonate (50 mL×2), 10% citric acid (50 mL), brine (30 mL), dried over anhydrous sodium sulfate, and concentrated to give 3-(4-isobutyrylpiperazine-1-carbonyl)benzaldehyde (1.44 g, yield: 95%) as a gum. LC-MS (ESI) m/z: 289 $(M+1)^+$.

Example 13D

Methyl 3-(3-(4-isobutyrylpiperazine-1-carbonyl) phenyl)-4-oxo-2-phenyl-1,2,3,4-tetrahydroquinoline-5-carboxylate and methyl 2,3-bis(3-(4-isobutyrylpiperazine-1-carbonyl)phenyl)-4-oxo-1,2,3,4-tetrahydroquinoline-5-carboxylate A mixture of 3-(4-isobutyrylpiperazine-1-carbonyl)benzaldehyde (288 mg, 1 mmol) and 4-(benzylideneamino)isobenzofuran-1(3H)-one (237 mg, 1 mmol) in ethyl propionate (7.5 mL) was cooled to 0° C. Then a solution of sodium methoxide in methanol [sodium (92 mg, 4 mmol) in methanol (7.5 mL)] was added dropwise. After the addition, the mixture was stirred at 25° C. for 18 hr. The mixture was quenched with water (10 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by chromatography (silica gel, petroleum ether/ethyl acetate=10:1 to 1:10) to give methyl 3-(3-(4-isobutyrylpiperazine-1-carbonyl)phenyl)-4-oxo-2-phenyl-1,2,3,4-tetrahydroquinoline-5-carboxylate (110 mg, yield 20%) and methyl 2,3-bis(3-(4-isobutyrylpiperazine-1-carbonyl)phenyl)-4-oxo-1,2,3,4-tetrahydroquinoline-5-carboxylate (90 mg, yield 12%) as light yellow solids. LC-MS (ESI) m/z: 540 $(M+1)^+$ and 722 $(M+1)^+$.

Example 13E 9-(3-(4-Isobutyrylpiperazine-1-carbonyl)phenyl)-8-phenyl-8,9-dihydro-2H-pyrido[4,3,2-de]phthalazin-3(7H)-one A mixture of methyl 3-(3-(4-isobutyrylpiperazine-1-carbonyl)phenyl)-4-oxo-2-phenyl-1,2,3,4-tetrahydroquinoline-5-carboxylate (110 mg, 0.20 mmol) in hydrazine monohydrate (5 mL) and methanol (2 mL) was stirred at 25° C. for 4 hr. The mixture was extracted with ethyl acetate (50 mL×3). The combined organic layers were washed with brine, dried over anhydrous sodium sulfate, and concentrated to give crude product. The crude product was purified by prep-HPLC to give 9-(3-(4-isobutyrylpiperazine-1-carbonyl)phenyl)-8-phenyl-8,9-dihydro-2H-pyrido[4,3,2-de]phthalazin-3(7H)-one (12 mg, yield: 11%) as a white solid. $^1$H-NMR (400 MHz, CD$_3$OD) δ: □0.96-0.98 (d, J=6.8 Hz, 6H), 2.68-2.95 (m, 2H), 3.28-3.55 (m, 7H), 4.19-4.22 (d, J=10.0 Hz, 1H), 4.54-4.57 (d, J=10.4 Hz, 1H), 7.03-7.20 (m, 10H), 7.40-7.50 (m, 2H); LC-MS (ESI) m/z: 522 $(M+1)^+$.

Example 13F 8,9-Bis(3-(4-isobutyrylpiperazine-1-carbonyl)phenyl)-8,9-dihydro-2H-pyrido[4,3,2-de]phthalazin-3(7H)-one A mixture of methyl 2,3-bis(3-(4-isobutyrylpiperazine-1-carbonyl)phenyl)-4-oxo-1,2,3,4-tetrahydroquinoline-5-carboxylate (90 mg, 0.12 mmol) in hydrazine monohydrate (5 mL) and methanol (2 mL) was stirred at 25° C. for 4 hr. The mixture was extracted with ethyl acetate (50 mL×3). The combined organic layers were washed with brine, dried over anhydrous sodium sulfate, and concentrated to give crude product. The crude product was purified by prep-HPLC to give 8,9-bis(3-(4-isobutyrylpiperazine-1-carbonyl)phenyl)-8,9-dihydro-2H-pyrido[4,3,2-de]phthalazin-3(7H)-one (3.2 mg, yield: 4%) as a white solid. $^1$H-NMR (400 MHz, CD$_3$OD) δ: □0.95-0.97 (q, 12H), 2.80-2.88 (m, 2H), 2.98-3.08 (m, 3H), 3.33-3.53 (m, 13H), 4.23-4.26 (d, J=10.4 Hz, 1H), 4.62-4.64 (d, J=10.0 Hz, 1H), 7.02-7.46 (m, 11H); LC-MS (ESI) m/z: 704 $(M+1)^+$.

Example 14

9-(Piperidin-3-yl)-8-(pyridin-3-yl)-8,9-dihydro-2H-pyrido[4,3,2-de]phthalazin-3(7H)-one A suspension of 8,9-di(pyridin-3-yl)-8,9-dihydro-2H-pyrido[4,3,2-de]phthalazin-3(7H)-one (120 mg, 0.35 mmol) and platinum (IV) oxide (60 mg) in methanol (20 mL) was purged in 20 atm hydrogen and stirred at 50° C. for 24 hr. The mixture was filtered and the filtrate was concentrated to give the crude product. The crude product was purified by prep-HPLC to give 9-(piperidin-3-yl)-8-(pyridin-3-yl)-8,9-dihydro-2H-pyrido[4,3,2-de]phthalazin-3(7H)-one (4 mg, yield: 4%) as a light yellow solid. $^1$H-NMR (400 MHz, CD$_3$OD) δ □1.19-1.32 (m, 2H), 1.60-1.65 (m, 2H), 1.94-1.97 (d, J=10.0 Hz, 1H), 2.31-2.43 (m, 2H), 2.82-2.85 (d, J=12.4 Hz, 1H), 3.02-3.05 (d, J=12 Hz, 1H), 3.29-3.32 (dd, $J_1$=2.8 Hz, $J_2$=8.4 Hz, 1H), 4.25-4.26 (d, J=2.8 Hz, 1H), 7.02-7.05 (dd, $J_1$=0.8 Hz, $J_2$=8.8 Hz, 1H), 7.22-7.25 (m, 1H), 7.40-7.53 (m, 3H), 8.25-8.29 (m, 2H); LC-MS (ESI) m/z: 348 $(M+1)^+$.

Example 15

9-(Piperidin-4-yl)-8-(pyridin-4-yl)-8,9-dihydro-2H-pyrido[4,3,2-de]phthalazin-3(7H)-one A mixture of 8,9-di(pyridin-4-yl)-8,9-dihydro-2H-pyrido[4,3,2-de]phthalazin-3(7H)-one (120 mg, 0.35 mmol), platinum (IV) oxide (60 mg) and concentrate hydrochloric acid (0.3 mL) in methanol (20 mL) was stirred at 50° C. under 20 atm of hydrogen. The mixture was filtered out and the filtrate was concentrated to give crude product. The crude product was purified by prep-HPLC to give 9-(piperidin-4-yl)-8-(pyridin-4-yl)-8,9-dihydro-2H-pyrido[4,3,2-de]phthalazin-3(7H)-one (17.6 mg, yield: 16%) as a light yellow solid. $^1$H-NMR (400 MHz, CD$_3$OD) δ □1.25-1.39 (m, 1H), 1.40-1.52 (m, 1H), 1.60-1.70 (m, 1H), 1.75-1.84 (m, 1H), 1.89-1.98 (m, 1H), 2.50-2.57 (m, 1H), 2.60-2.66 (m, 1H), 3.09-3.21 (m, 2H), 3.34-3.37 (dd, $J_1$=8 Hz, $J_2$=2.4 Hz, 1H), 4.24

(d, J=2 Hz, 1H), 7.02-7.04 (dd, $J_1$=8 Hz, $J_2$=0.8 Hz, 1H), 7.09-7.11 (dd, $J_1$=4.8 Hz, $J_2$=1.2 Hz, 2H), 7.41-7.43 (dd, $J_1$=7.6 Hz, $J_2$=0.8 Hz, 1H), 7.50-7.54 (t, J=8 Hz, 1H), 8.30-8.32 (dd, $J_1$=4.4 Hz, $J_2$=1.6 Hz, 2H); LC-MS (ESI) m/z: 348 $(M+1)^+$.

Example 16

8,9-Bis(4-((dimethylamino)methyl)phenyl)-8,9-dihydro-2H-pyrido[4,3,2-de]phthalazin-3(7H)-one

Example 16A 1-(4-(Diethoxymethyl)phenyl)-N,N,-dimethylmethanamine

A mixture of 1-(4-(diethoxymethyl)benzaldehyde (2.08 g, 10 mmol) and dimethylamine (33% aqueous solution, 2.74 g, 20 mmol) in methanol (20 mL) was stirred at room temperature for 40 mins. The mixture was cooled to 0° C., sodium borohydride (0.57 g, 15 mmol) was added portionwise. After the addition, the mixture was stirred at room temperature for 4 hr. Methanol was removed under reduced pressure. The residue was partitioned between water (50 mL) and ethyl acetate (50 mL). The organic layer was separated. The aqueous layer was extracted with ethyl acetate (50 mL×3). The combined organic layers were washed with brine, dried over anhydrous sodium sulfate, and concentrated to give 1-(4-(diethoxymethyl)phenyl)-N,N,-dimethylmethanamine (1.8 g) as a light yellow oil which was used in the next step without further purification. MS (ESI) m/z: 237 $(M+1)^+$.

Example 16B 4-((Dimethylamino)methyl)benzaldehyde

To a solution of 1-(4-(diethoxymethyl)phenyl)-N,N,-dimethylmethanamine (1.0 g, 4 mmol) in methanol (5 mL), a hydrochloric acid methanol solution (10 mL) was added dropwise at 0° C. The reaction solution was stirred at room temperature overnight. Then methanol was removed in vacuo to give 4-((dimethylamino)methyl)benzaldehyde (0.68 g, yield 99%) as a light yellow oil. $^1$H-NMR (400 MHz, CDCl$_3$): δ 2.26 (s, 6H), 3.50 (s, 2H), 7.49 (d, J=6.4 Hz, 2H), 7.84 (d, J=6.4 Hz 2H), 10 (s, 1H). LC-MS (ESI) m/z: 164 $(M+1)^+$.

Example 16C

Methyl 2,3-bis(4-((dimethylamino)methyl)phenyl)-4-oxo-1,2,3,4-tetrahydroquinoline-5-carboxylate and ethyl 2,3-Bis(4-((dimethylamino)methyl)phenyl)-4-oxo-1,2,3,4-tetrahydroquinoline-5-carboxylate A mixture of 4-((dimethylamino)methyl)benzaldehyde (539 mg, 3.3 mmol) and 4-aminoisobenzofuran-1(3H)-one (223 mg, 1.5 mmol) in ethyl propionate (14 mL) was cooled to 0° C. A solution of sodium methoxide in methanol [sodium (138 mg, 6 mmol) in methanol (4 mL)] was then added dropwise. After the addition, the mixture was stirred at room temperature for 20 hr. The mixture was quenched with water (10 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by chromatography (silica gel, petroleum ether/ethyl acetate=100:1 to 10:1) to give a mixture of methyl 2,3-bis(4-((dimethylamino)methyl)phenyl)-4-oxo-1,2,3,4-tetrahydroquinoline-5-carboxylate and ethyl 2,3-bis(4-((dimethylamino)methyl)phenyl)-4-oxo-1,2,3,4-tetrahydroquinoline-5-carboxylate (165 mg) as a light yellow solid.

Example 16D 8,9-Bis(4-((dimethylamino)methyl)phenyl)-8,9-dihydro-2H-pyrido[4,3,2-de]phthalazin-3(7H)-one A mixture of methyl 2,3-bis(4-((dimethylamino)methyl)phenyl)-4-oxo-1,2,3,4-tetrahydroquinoline-5-carboxylate and ethyl 2,3-bis(4-((dimethylamino)methyl)phenyl)-4-oxo-1,2,3,4-tetrahydroquinoline-5-carboxylate (165 mg, 0.34 mmol) in hydrazine monohydrate (12 mL) and methanol (5 mL) was stirred at 40° C. for 6 hrs. The mixture was filtered to give crude product. The crude product was purified by prep-HPLC to give 8,9-bis(4-((dimethylamino)methyl)phenyl)-8,9-dihydro-2H-pyrido[4,3,2-de]phthalazin-3(7H)-one (33.7 mg, yield: 22%) as a light yellow solid. $^1$H-NMR (400 MHz, CD$_3$OD) δ: □2.04 (s, 6H), 2.05 (s, 6H), 3.19-3.20 (m, 2H), 3.24-3.26 (m, 2H), 4.09-4.11 (d, J=8.8 Hz, 1H), 4.52-4.54 (d, J=8.8 Hz, 1H), 6.88-6.90 (m, 2H), 6.99-7.07 (m, 7H), 7.42-7.46 (m, 2H). LC-MS (ESI) m/z: 454 $(M+1)^+$.

Example 17

9-(4-(4-(Cyclopropanecarbonyl)piperazine-1-carbonyl)phenyl)-8-(4((methylamino)methyl)phenyl)-8,9-dihydro-2H-pyrido[4,3,2-de]phthalazin-3(7H)-one

Example 17A tert-Butyl 4-(cyclopropanecarbonyl)piperazine-1-carboxylate

A mixture of compound tert-butyl piperazine-1carboxylate (3.725 g, 20 mmol) and potassium carbonate (5.53 g, 40 mmol) in anhydrous dichloromethane (30 mL) was cooled to 0° C., cyclopropanecarbonyl chloride (2.30 g, 22 mmol) was then added dropwise. After the addition, the mixture was stirred at room temperature overnight. The mixture was diluted with dichloromethane (100 mL), washed with 10% citric acid (50 mL), followed by saturated sodium bicarbonate (50 mL), brine (100 mL), dried over anhydrous sodium sulfate, and concentrated to give tert-butyl 4-(cyclopropanecarbonyl)piperazine-1-carboxylate (3.7 g, yield 73%) as a white solid. $^1$H-NMR (400 MHz, CDCl$_3$) δ (ppm): 0.76-0.81 (m, 2H), 0.98-1.03 (m, 2H), 1.49 (s, 9H), 1.69-1.75 (m, 1H), 3.46-3.48 (m, 4H), 3.63-3.65 (m, 4H); LC-MS (ESI) m/z: 255 $(M+1)^+$.

Example 17B

Cyclopropyl(piperazin-1-yl)methanone Hydrochloride

To a stirred mixture of compound tert-butyl 4-(cyclopropanecarbonyl)piperazine-1-carboxylate (3.7 g, 14.5 mmol) in methanol (15 mL) was added hydrochloride/methanol (15 mL, 3M)) at 0° C. After the addition, the mixture was allowed to stir at room temperature overnight. The mixture was concentrated to give cyclopropyl(piperazin-1-yl)methanone hydrochloride (2.74 g, yield 100%) as an off-white solid. $^1$H-NMR (400 MHz, DMSO-d6) δ (ppm): 0.71-0.76

(m, 4H), 1.96-2.03 (m, 1H), 3.04-3.16 (m, 4H), 3.69-4.08 (m, 4H), 9.58 (s, 2H); LC-MS (ESI) m/z: 155 (M+1)$^+$.

Example 17C 4-(4-(Cyclopropanecarbonyl)piperazine-1-carbonyl) benzaldehyde

To a stirred mixture of 4-formylbenzoic acid (900 mg, 6 mmol) in anhydrous dichloromethane (30 mL) was added triethylamine (1.52 mg, 15 mmol), 1-hydroxybenzotriazole (891 mg, 6.6 mmol), followed by 1-ethyl-3-(3-dimethyl-amino propyl) carbodiimide hydrochloride (1.254 g, 6.6 mmol). After the addition, the mixture was stirred at room temperature for 40 mins. Then the mixture was cooled to 0° C. and cyclopropyl(piperazin-1-yl)methanone hydrochloride (1.259 g, 6.6 mmol) was added in portion-wise. After the addition, the mixture was allowed to stir at room temperature overnight. The mixture was diluted with dichloromethane (50 mL), washed with saturated citric acid (100 mL×2), followed by saturated sodium bicarbonate (100 mL×2), brine (50 mL), dried over anhydrous sodium sulfate, and concentrated to give 4-(4-(cyclopropanecarbonyl)piperazine-1-carbonyl)benzaldehyde (810 mg, yield 80%) as a light yellow oil. $^1$H-NMR (400 MHz, CDCl$_3$) δ (ppm): 0.79-0.85 (m, 2H), 1.00-1.04 (m, 2H), 1.72-1.80 (m, 1H), 3.41-3.81 (m, 8H), 7.58-7.60 (d, J=8.0 Hz, 1H), 7.95-7.97 (d, J=8.0 Hz, 1H), 10.07 (s, 1H); LC-MS (ESI) m/z: 287 (M+1)$^+$.

Example 17D 4-(4-(Diethoxymethyl)benzylideneamino)isobenzofuran-1(3H)-one

To a stirred mixture of 4-(diethoxymethyl)benzaldehyde (3.75 g, 18 mmol) and anhydrous sodium sulfate (21.3 g, 150 mmol) in anhydrous dichloromethane (300 mL) was added 4-aminoisobenzofuran-1(3H)-one (2.24 g, 15 mmol) at 0° C. After the addition, the mixture was stirred at room temperature for 6 days. The mixture was filtered and the cake was washed with dichloromethane (50 mL×3). The filtrate was concentrated to give crude product. The crude product was washed with petroleum ether to give 4-(4-(diethoxymethyl)benzylideneamino)isobenzofuran-1(3H)-one (4.3 g, yield 84%) as a light yellow solid. LC-MS (ESI) m/z: 340 (M+1)$^+$.

Example 17E

Methyl 3-(4-(4-(cyclopropanecarbonyl)piperazine-1-carbonyl)phenyl)-2-(4-(diethoxymethyl)phenyl)-4-oxo-1,2,3,4-tetrahydroquinoline-5-carboxylate A mixture of 4-(4-(cyclopropanecarbonyl)piperazine-1-carbonyl)benzaldehyde (859 mg, 3 mmol) and 4-(4-(diethoxymethyl)benzylideneamino)isobenzofuran-1(3H)-one (1.018 g, 3 mmol) in ethyl propionate (40 mL) was cooled to 0° C. Then a solution of sodium methoxide in methanol [sodium (276 mg, 12 mmol) in methanol (8 mL)] was added dropwise. After the addition, the mixture was stirred at room temperature for 20 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=10:1 to 1:10) to give methyl 3-(4-(4-(cyclopropanecarbonyl)piperazine-1-carbonyl)phenyl)-2-(4-(diethoxymethyl)phenyl)-4-oxo-1,2,3,4-tetrahydroquinoline-5-carboxylate (500 mg, yield 26%). LC-MS (ESI) m/z: 640 (M+1)$^+$.

Example 17F 9-(4-(4-(Cyclopropanecarbonyl)piperazine-1-carbonyl)phenyl)-8-(4-(diethoxymethyl)phenyl)-8,9-dihydro-2H-pyrido[4,3,2-de]phthalazin-3(7H)-one A mixture of methyl 3-(4-(4-(cyclopropanecarbonyl)piperazine-1-carbonyl)phenyl)-2-(4-(diethoxymethyl)phenyl)-4-oxo-1,2,3,4-tetrahydroquinoline-5-carboxylate (526 mg, 0.82 mmol) in 85% hydrazine monohydrate (4 mL) and methanol (3 mL) was stirred at 25° C. for 2 hr. The mixture was extracted with ethyl acetate (50 mL×3). The combined organic layers were washed with brine, dried over anhydrous sodium sulfate, and concentrated to give 9-(4-(4-(cyclopropanecarbonyl)piperazine-1-carbonyl)phenyl)-8-(4-(diethoxymethyl)phenyl)-8,9-dihydro-2H-pyrido[4,3,2-de]phthalazin-3(7H)-one (330 mg, yield 65%) as a yellow solid. $^1$H-NMR (400 MHz, DMSO-d6) δ (ppm): 0.72-0.76 (m, 4H), 1.09-1.12 (m, 6H), 1.99 (s, 1H), 3.39-3.73 (m, 12H), 4.70 (s, 1H), 5.40 (s, 1H), 5.99 (s, 1H), 6.68-7.31 (m, 9H), 7.41-7.61 (m, 3H), 12.19 (s, 1H); LC-MS (ESI) m/z: 622 (M+1)$^+$.

Example 17G 4-(9-(4-(4-(Cyclopropanecarbonyl)piperazine-1-carbonyl)phenyl)-3-oxo-3,7,8,9-tetrahydro-2H-pyrido[4,3,2-de]phthalazin-8-yl)benzaldehyde A mixture of 9-(4-(4-(cyclopropanecarbonyl)piperazine-1-carbonyl)phenyl)-8-(4-(diethoxymethyl)phenyl)-8,9-dihydro-2H-pyrido[4,3,2-de]phthalazin-3(7H)-one (280 mg, 0.45 mmol) in 3N hydrochloric acid (10 mL) was stirred at room temperature for 3 hr. Then the mixture was neutralized with potassium carbonate. The resulting suspension was filtered to give 4-(9-(4-(4-(cyclopropanecarbonyl)piperazine-1-carbonyl)phenyl)-3-oxo-3,7,8,9-tetrahydro-2H-pyrido[4,3,2-de]phthalazin-8-yl)benzaldehyde (220 mg, yield 89%) as a light yellow solid. LC-MS (ESI) m/z: 548 (M+1)$^+$.

Example 17H 9-(4-(4-(Cyclopropanecarbonyl)piperazine-1-carbonyl)phenyl)-8-(4((methylamino)methyl)phenyl)-8,9-dihydro-2H-pyrido[4,3,2-de]phthalazin-3(7H)-one A mixture of 4-(9-(4-(4-(cyclopropanecarbonyl)piperazine-1-carbonyl)phenyl)-3-oxo-3,7,8,9-tetrahydro-2H-pyrido[4,3,2-de]phthalazin-8-yl)benzaldehyde (80 mg, 0.15 mmol) and 27% methylamine alcohol solution (50 mg, 0.44 mmol) in methanol (10 mL) was stirred at room temperature for 40 min. Then the mixture was cooled to 0° C. Sodium borohydride (8.3 mg, 0.23 mmol) was added. After the addition, the mixture was stirred at this temperature for 2 hr. Methanol was removed under reduced pressure. The residue was washed with ethyl acetate/methanol (10/1) and filtered. The filtrate was concentrated to give the crude product. The crude product was purified by prep-HPLC to give 9-(4-(4-(cyclopropanecarbonyl)piperazine-1-carbonyl)phenyl)-8-(4

((methylamino)methyl)phenyl)-8,9-dihydro-2H-pyrido[4,3,2-de]phthalazin-3(7H)-one (6.4 mg, yield 7%) as a light yellow solid. $^1$H-NMR (400 MHz, CD$_3$OD) δ (ppm): 0.83-0.91 (m, 4H), 1.94-2.03 (m, 1H), 2.66-2.68 (d, J=6.0 Hz, 3H), 3.35-3.79 (m, 8H), 4.11 (s, 2H), 4.42-4.44 (d, J=7.6 Hz, 1H), 4.88-4.90 (d, J=7.2 Hz, 1H), 7.21-7.26 (m, 3H), 7.29-7.36 (m, 4H), 7.41-7.43 (d, J=8.4 Hz, 2H), 7.55-7.57 (d, J=7.2 Hz, 1H), 7.63-7.67 (t, J=8.0 Hz, 1H); LC-MS (ESI) m/z: 563 (M+1)$^+$.

Example 18

9-(4-(4-(Cyclopropanecarbonyl)piperazine-1-carbonyl)phenyl)-8-(4((dimethylamino)methyl)phenyl)-8,9-dihydro-2H-pyrido[4,3,2-de]phthalazin-3(7H)-one A mixture of 4-(9-(4-(4-(cyclopropanecarbonyl)piperazine-1-carbonyl)phenyl)-3-oxo-3,7,8,9-tetrahydro-2H-pyrido[4,3,2-de]phthalazin-8-yl)benzaldehyde (80 mg, 0.15 mmol) and 27% dimethylamine solution (62 mg, 0.44 mmol) in methanol (10 mL) was stirred at room temperature for 40 min. Then the mixture was cooled to 0° C. Sodium borohydride (8.3 mg, 0.22 mmol) was added. After the addition, the mixture was stirred at this temperature for 2 hr. Methanol was removed under reduced pressure. The residue was washed with ethyl acetate/methanol (10/1) and filtered. The filtrate was concentrated to give the crude product. The crude product was purified by prep-HPLC to give 9-(4-(4-(cyclopropanecarbonyl)piperazine-1-carbonyl)phenyl)-8-(4((dimethylamino)methyl)phenyl)-8,9-dihydro-2H-pyrido[4,3,2-de]phthalazin-3(7H)-one (4.2 mg, yield 5%) as a light yellow solid. $^1$H-NMR (400 MHz, CD$_3$OD) δ (ppm): 0.73-0.79 (m, 4H), 1.84 (m, 1H), 2.69 (s, 6H), 3.47-3.72 (m, 8H), 4.14 (s, 2H), 4.31-4.33 (d, J=8.0 Hz, 1H), 7.12-7.35 (m, 9H), 7.47-7.58 (m, 2H); LC-MS (ESI) m/z: 577 (M+1)$^+$.

Example 19

8-(4-(Hydroxymethyl)phenyl)-9-(4-(4-isobutyrylpiperazine-1-carbonyl)phenyl)-8,9-dihydro-2H-pyrido[4,3,2-de]phthalazin-3(7H)-one Example 20

8-(4-((Dimethylamino)methyl)phenyl)-9-(4-(4-isobutyrylpiperazine-1-carbonyl)phenyl)-8,9-dihydro-2H-pyrido[4,3,2-de]phthalazin-3(7H)-one Example 19A tert-Butyl 4-isobutyrylpiperazine-1-carboxylate To a solution of isobutyric acid (6.608 g, 75 mmol) in anhydrous dichloromethane (130 mL) was added triethylamine (8.33 g, 82.5 mmol), 1-hydroxybenzotriazole (10.125 g, 75 mmol), followed by 1-ethyl-3-(3-dimethylaminopropyl)carbodiimide hydrochloride (14.25 g, 75 mmol). After the addition, the mixture was stirred at room temperature for 40 mins. Then the mixture was cooled to 0° C., and tert-butyl piperazine-1-carboxylate (13.97 g, 75 mmol) was added portion-wise. After the addition, the mixture was stirred at room temperature overnight. The mixture was diluted with dichloromethane (200 mL), washed with saturated sodium bicarbonate (150 mL×2), 10% citric acid (150 mL), brine (100 mL), dried over anhydrous sodium sulfate, and concentrated to give tert-butyl 4-isobutyrylpiperazine-1-carboxylate (15 g, yield 78%) as a white solid. $^1$H-NMR (400 MHz, CDCl$_3$) δ (ppm): 1.13-1.14 (d, J=6.8 Hz, 6H), 1.47 (s, 9H), 2.75-2.82 (m, 1H), 3.43-3.58 (m, 4H); LC-MS (ESI) m/z: 257 (M+1)$^+$.

Example 19B

2-Methyl-1-(piperazin-1-yl)propan-1-one

To a stirred mixture of tert-butyl 4-isobutyrylpiperazine-1-carboxylate (6.8 g, 26.5 mmol) in methanol (15 mL) was added hydrochloride/methanol (30 mL, 3M) at 0° C. After the addition, the mixture was allowed to stir at room temperature overnight. The mixture was concentrated to give 2-methyl-1-(piperazin-1-yl)propan-1-one (5.5 g, yield 100%) as an off-white solid. $^1$H-NMR (400 MHz, DMSO-d6) δ (ppm): 0.99-1.00 (d, J=6.4 Hz, 6H), 2.84-2.89 (m, 1H), 3.03-3.07 (d, 4H), 3.68-3.74 (d, 4H), 9.58 (s, 2H); LC-MS (ESI) m/z: 157 (M+1)$^+$.

Example 19C 4-(4-Isobutyrylpiperazine-1-carbonyl)benzaldehyde

To a stirred mixture of 4-formylbenzoic acid (1.5 g, 10 mmol) in anhydrous dichloromethane (30 mL) was added triethylamine (2.52 g, 25 mmol), 1-hydroxybenzotriazole (1.5 g, 11 mmol), followed by 1-ethyl-3-(3-dimethylamino propyl) carbodiimide hydrochloride (2.1 g, 11 mmol). After the addition, the mixture was stirred at room temperature for 40 mins. Then the mixture was cooled to 0° C. and 2-methyl-1-(piperazin-1-yl)propan-1-one (2.12 g, 11 mmol) was added in portion-wise. After the addition, the mixture was allowed to stir at room temperature overnight. The mixture was diluted with dichloromethane (50 mL), washed with saturated citric acid (100 mL×2), followed by saturated sodium bicarbonate (100 mL×2), brine (50 mL), dried over anhydrous sodium sulfate, and concentrated to give 4-(4-isobutyrylpiperazine-1-carbonyl)benzaldehyde (2 g, yield 70%) as a light yellow oil. $^1$H-NMR (400 MHz, CDCl$_3$) δ (ppm): 1.15 (d, 6H), 2.80 (brs, 1H), 3.39-3.80 (m, 8H), 7.58 (d, J=8.0 Hz, 1H), 7.95 (d, J=8.0 Hz, 1H), 10.07 (s, 1H); LC-MS (ESI) m/z: 289 (M+1)$^+$.

Example 19D

Methyl 2-(4-(diethoxymethyl)phenyl)-3-(4-(4-isobutyrylpiperazine-1-carbonyl)phenyl)-4-oxo-1,2,3,4-tetrahydroquinoline-5-carboxylate A mixture of 4-(4-isobutyrylpiperazine-1-carbonyl)benzaldehyde (950 mg, 3.3 mmol) and (E)-4-(4-(diethoxymethyl) benzylideneamino)isobenzofuran-1(3H)-one (1.018 g, 3 mmol) in ethyl propionate (40 mL) was cooled to 0° C. Then a solution of sodium methoxide in methanol [sodium (345 mg, 12 mmol) in methanol (8 mL)] was added dropwise. After the addition, the mixture was stirred at room temperature for 24 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=10:1 to 1:10) to give methyl 2-(4-(diethoxymethyl)phenyl)-3-(4-(4-isobutyrylpiperazine-1-carbonyl)phenyl)-4-oxo-1,2,3,4-tetrahydroquinoline-5-carboxylate (491 mg, yield 25%).

Example 19E 8-(4-(Diethoxymethyl)phenyl)-9-(4-(4-isobutyrylpiperazine-1-carbonyl)phenyl)-8,9-dihydro-2H-pyrido[4,3,2-de]phthalazin-3(7H)-one A mixture of methyl 2-(4-(diethoxymethyl)phenyl)-3-(4-(4-isobutyrylpiperazine-1-carbonyl)phenyl)-4-oxo-1,2,3,4-tetrahydroquinoline-5-carboxylate (491 mg, 0.77 mmol) in 85% hydrazine monohydrate (4 mL) and methanol (3 mL) was stirred at 25° C. for overnight. The mixture was extracted with ethyl acetate (50 mL×3). The combined organic layers were washed with brine, dried over anhydrous sodium sulfate, and concentrated to give 8-(4-(diethoxymethyl)phenyl)-9-(4-(4-isobutyrylpiperazine-1-carbonyl)phenyl)-8,9-dihydro-2H-pyrido[4,3,2-de]phthalazin-3(7H)-one (365 mg, yield 77%) as a yellow solid.

Example 19F 4-(9-(4-(4-(Isobutyrylpiperazine-1-carbonyl)phenyl)-3-oxo-3,7,8,9-tetrahydro-2H-pyrido[4,3,2-de]phthalazin-8-yl)benzaldehyde A mixture of 8-(4-(diethoxymethyl)phenyl)-9-(4-(4-isobutyrylpiperazine-1-carbonyl)phenyl)-8,9-dihydro-2H-pyrido[4,3,2-de]phthalazin-3(7H)-one (365 mg, 0.59 mmol) in 3N hydrochloric acid (10 mL) was stirred at room temperature for 3 hr. Then the mixture was neutralized with potassium carbonate. The resulting suspension was filtered to give crude. The crude product was purified by prep-HPLC to give the 4-(9-(4-(4-(isobutyrylpiperazine-1-carbonyl)phenyl)-3-oxo-3,7,8,9-tetrahydro-2H-pyrido[4,3,2-de]phthalazin-8-yl)benzaldehyde (80 mg, yield 28%) as a light yellow solid. $^1$H-NMR (400 MHz, CD$_3$OD) δ (ppm): 1.11-1.13 (d, J=6.8 Hz, 6H), □ 2.95-3.14 (brs, 1H), 3.38-3.80 (m, 8H), 4.37-4.40 (d, J=7.2 Hz, 1H), 4.75-4.77 (d, J=7.6 Hz, 1H), 7.20-7.33 (m, 9H), 7.57-7.59 (d, J=7.6 Hz, 1H), 7.60-7.76 (t, J=8.0 Hz, 1H), 9.92 (s, 1H); LC-MS (ESI) m/z: 550 (M+1)$^+$.

Examples 19G & 20

8-(4-(Hydroxymethyl)phenyl)-9-(4-(4-isobutyrylpiperazine-1-carbonyl)phenyl)-8,9-dihydro-2H-pyrido[4,3,2-de]phthalazin-3(7H)-one & 8-(4-((dimethylamino)methyl)phenyl)-9-(4-(4-isobutyrylpiperazine-1-carbonyl)phenyl)-8,9-dihydro-2H-pyrido[4,3,2-de]phthalazin-3(7H)-one A mixture of compound 7 (50 mg, 0.09 mmol) and 33% dimethylamine aq solution (25 mg, 0.18 mmol) in methanol (10 mL) was stirred at room temperature for 40 min. Then the mixture was cooled to 0° C. Sodium borohydride (5 mg, 0.13 mmol) was added. After the addition, the mixture was stirred at this temperature for 2 hr. TLC (petroleum ether/ethyl acetate=2:1) show the reaction was complete. Methanol was removed under reduced pressure. The residue was washed with ethyl acetate/methanol (10/1) and filtered. The filtrate was concentrated to give the crude product. The crude product was purified by prep-HPLC to give 8-(4-((dimethylamino)methyl)phenyl)-9-(4-(4-isobutyrylpiperazine-1-carbonyl)phenyl)-8,9-dihydro-2H-pyrido[4,3,2-de]phthalazin-3(7H)-one (4 mg, yield 9%) and 8-(4-(hydroxymethyl)phenyl)-9-(4-(4-isobutyrylpiperazine-1-carbonyl)phenyl)-8,9-dihydro-2H-pyrido[4,3,2-de]phthalazin-3(7H)-one (16 mg, yield 36%) as light yellow solids. 8-(4-((dimethylamino)methyl)phenyl)-9-(4-(4-isobutyrylpiperazine-1-carbonyl)phenyl)-8,9-dihydro-2H-pyrido[4,3,2-de]phthalazin-3(7H)-one: $^1$H-NMR (400 MHz, CD$_3$OD) δ (ppm): 1.10-1.12 (d, J=6.8 Hz, 6H), 2.80 (s, 6H), 2.96-3.00 (brs, 1H), 3.33-3.70 (m, 8H), 4.12 (s, 2H), 4.43-4.44 (d, J=7.6 Hz, 1H), 4.89-4.91 (d, J=7.6 Hz, 1H), 7.22-7.27 (m, 3H), 7.31-7.37 (m, 4H), 7.42-7.44 (d, J=8.0 Hz, 2H), 7.56-7.58 (d, J=7.2 Hz, 1H), 7.64-7.68 (t, J=8.0 Hz 1H); LC-MS (ESI) m/z: 579 (M+1)$^+$. 8-(4-(hydroxymethyl)phenyl)-9-(4-(4-isobutyrylpiperazine-1-carbonyl)phenyl)-8,9-dihydro-2H-pyrido[4,3,2-de]phthalazin-3(7H)-one: $^1$H-NMR (400 MHz, CD$_3$OD) δ (ppm): 1.10-1.12 (d, J=6.4 Hz, 6H), 2.95 (brs, 1H), 3.33-3.81 (m, 8H), 4.39-4.41 (d, J=8.2 Hz, 1H), 4.53 (s, 2H), 4.77-4.79 (d, J=7.6 Hz 1H), 7.20-7.30 (m, 9H), 7.55-7.57 (dd, J$_1$=8.0 Hz, J$_2$=1.0 Hz, 1H), 7.63-7.67 (t, J=8.0 Hz, 1H); LC-MS (ESI) m/z: 552 (M+1)$^+$.

Example 21

9-(4-(4-(Cyclopropanecarbonyl)piperazine-1-carbonyl)phenyl)-8-phenyl-8,9-dihydro-2H-pyrido[4,3,2-de]phthalazin-3(7H)-one

Example 21A (E)-4-(benzylideneamino)isobenzofuran-1(3H)-one

To a stirred mixture of benzaldehyde (1.91 g, 18 mmol) and anhydrous sodium sulfate (21.3 g, 150 mmol) in anhydrous dichloromethane (100 mL) was added 4-aminoisobenzofuran-1(3H)-one (2.24 g, 15 mmol) at 0° C. After the addition, the mixture was stirred at room temperature for 6 days. The mixture was filtered and the cake was washed with dichloromethane (50 mL×3). The filtrate was concentrated to give crude product. The crude product was washed with petroleum ether to give (E)-4-(benzylideneamino)isobenzofuran-1(3H)-one (3.38 g, yield 95%) as a white solid. $^1$H-NMR (400 MHz, CDCl$_3$) δ (ppm): 5.41 (s, 2H), 7.36-7.37 (d, J=7.6 Hz, 1H), 7.49-7.59 (m, 4H), 7.77-7.78 (d, J=7.6 Hz, 1H), 7.92-7.94 (d, J=8.0 Hz, 2H), 8.55 (s, 1H), LC-MS (ESI) m/z: 238 (M+1)$^+$.

Example 21B

Methyl 3-(4-(4-(cyclopropanecarbonyl)piperazine-1-carbonyl)phenyl)-4-oxo-2-phenyl-1,2,3,4-tetrahydroquinoline-5-carboxylate A mixture of compound 4-(4-(cyclopropanecarbonyl)piperazine-1-carbonyl) benzaldehyde (429 mg, 1.5 mmol) and (E)-4-(benzylideneamino)isobenzofuran-1(3H)-one ((355.5 mg, 1.5 mmol) in ethyl propionate (12 mL) was cooled to 0° C. Then a solution of sodium methoxide in methanol [sodium (138 mg, 6 mmol) in methanol (12 mL)] was added dropwise. After the addition, the mixture was stirred at 25° C. for 18 hr. The mixture was quenched with water (10 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by chromatography (silica gel, petroleum ether/ethyl acetate=10:1 to 1:10) to give methyl 3-(4-(4-(cyclopropanecarbonyl)piperazine-1-carbonyl)phenyl)-4-oxo-2-phenyl- 1,2,3,4-tetrahydroquinoline-5-carboxylate (90 mg, yield 11%). LC-MS (ESI) m/z: 538 (M+1)$^+$.

Example 21C 9-(4-(4-(Cyclopropanecarbonyl)piperazine-1-carbonyl)phenyl)-8-phenyl-8,9-dihydro-2H-pyrido[4,3,2-de]phthalazin-3(7H)-one-3(7H)-one A mixture of methyl 3-(4-(4-(cyclopropanecarbonyl)piperazine-1-carbonyl)phenyl)-4-oxo-2-phenyl-1,2,3,4-tetrahydroquinoline-5-carboxylate (90 mg, 0.16 mmol) in 85% hydrazine monohydrate (5 mL) and methanol (2 mL) was stirred at 25° C. for 4 hr. The mixture was extracted with ethyl acetate (50 mL×3). The combined organic layers were washed with brine, dried over anhydrous sodium sulfate, and concentrated to give crude product. The crude product was purified by prep-HPLC to give 9-(4-(4-(cyclopropanecarbonyl)piperazine-1-carbonyl)phenyl)-8-phenyl-8,9-dihydro-2H-pyrido[4,3,2-de]phthalazin-3(7H)-one (18 mg, yield 22%) as a white solid. $^1$H-NMR (400 MHz, CD$_3$OD) δ (ppm): 0.86-0.94 (m, 4H), 2.00 (s, 1H), 3.33-3.82 (m, 8H), 4.41-4.43 (d, J=8.4 Hz, 1H), 4.78-4.80 (d, J=8.4 Hz, 1H), 7.21-7.27 (m, 6H), 7.30-7.35 (m, 4H), 7.58-7.60 (m, 1H), 7.65-7.69 (t, J=8.0 Hz, 4H); LC-MS (ESI) m/z: 520 (M+1)$^+$.

Example 22

9-(3-(4-(Cyclopropanecarbonyl)piperazine-1-carbonyl)phenyl)-8-phenyl-8,9-dihydro-2H-pyrido[4,3,2-de]phthalazin-3(7H)-one Example 22A Methyl 3-(3-(4-(cyclopropanecarbonyl)piperazine-1-carbonyl)phenyl)-4-oxo-2-phenyl-1,2,3,4-tetrahydroquinoline-5-carboxylate A mixture of 3-(4-(cyclopropanecarbonyl)piperazine-1-carbonyl) benzaldehyde (286 mg, 1 mmol) and (E)-4-(benzylideneamino)isobenzofuran-1(3H)-one (237 mg, 1 mmol) in ethyl propionate (7.5 mL) was cooled to 0° C. Then a solution of sodium methoxide in methanol [sodium (92 mg, 4 mmol) in methanol (7.5 mL)] was added dropwise. After the addition, the mixture was stirred at 25° C. for 18 hr. The mixture was quenched with water (10 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by chromatography (silica gel, petroleum ether/ethyl acetate=10:1 to 1:10) to give methyl 3-(3-(4-(cyclopropanecarbonyl)piperazine-1-carbonyl)phenyl)-4-oxo-2-phenyl-1,2,3,4-tetrahydroquinoline-5-carboxylate (64 mg, yield 12%). LC-MS (ESI) m/z: 538 (M+1)$^+$.

Example 22B 9-(3-(4-(Cyclopropanecarbonyl)piperazine-1-carbonyl)phenyl)-8-phenyl-8,9-dihydro-2H-pyrido[4,3,2-de]phthalazin-3(7H)-one A mixture of methyl 3-(3-(4-(cyclopropanecarbonyl)piperazine-1-carbonyl)phenyl)-4-oxo-2-phenyl-1,2,3,4-tetrahydroquinoline-5-carboxylate (64 mg, 0.12 mmol) in 85% hydrazine monohydrate (5 mL) and methanol (2 mL) was stirred at 25° C. for 4 hr. The mixture was extracted with ethyl acetate (50 mL×3). The combined organic layers were washed with brine, dried over anhydrous sodium sulfate, and concentrated to give crude product. The crude product was purified by prep-HPLC to give 9-(3-(4-(cyclopropanecarbonyl)piperazine-1-carbonyl)phenyl)-8-phenyl-8,9-dihydro-2H-pyrido[4,3,2-de]phthalazin-3(7H)-one (8 mg, yield 13%) as a light yellow solid. $^1$H-NMR (400 MHz, CD$_3$OD) δ (ppm): 0.73-0.81 (m, 4H), 1.18-1.19 (m, 1H), 3.20-3.71 (m, 8H), 4.23-4.25 (d, J=10.0 Hz, 1H), 4.59-4.61 (d, J=8.4 Hz, 1H), 7.08-7.26 (m, 10H), 7.45-7.54 (m, 2H); LC-MS (ESI) m/z: 520 (M+1)$^+$.

Example 23

9-(3-((Dimethylamino)methyl)phenyl)-8-phenyl-8,9-dihydro-2H-pyrido[4,3,2-de]phthalazin-3(7H)-one A mixture of 3-(3-oxo-8-phenyl-3,7,8,9-tetrahydro-2H-pyrido[4,3,2-de]phthalazin-9-yl)benzaldehyde (45 mg, 0.12 mmol) and 33% dimethylamine solution (50.2 mg, 0.366 mmol) in methanol (5 mL) was stirred at room temperature for 1 h. Then the mixture was cooled to 0° C., sodium borohydride (6.95 mg, 0.184 mmol) was added portionwise. After the addition, the mixture was stirred at this temperature for 2 hr. Methanol was removed under reduced pressure. The residue was purified by prep-HPLC to give 9-(3-((dimethylamino)methyl)phenyl)-8-phenyl-8,9-dihydro-2H-pyrido[4,3,2-de]phthalazin-3(7H)-one (21 mg, yield 44%) as a light yellow solid. $^1$H-NMR (400 MHz, CD$_3$OD) δ (ppm): 2.59 (s, 3H), 2.75 (s, 3H), 4.11-4.27 (q, 2H), 4.31-4.34 (d, J=10.4 Hz, 1H), 4.68-4.71 (d, J=10.4 Hz, 1H), 7.17-7.30 (m, 9H), 7.33-7.37 (t, J=7.6 Hz, 1H), 7.56-7.58 (d, J=7.6 Hz, 1H), 7.60-7.64 (t, J=8.0 Hz, 1H); LC-MS (ESI) m/z: 396 (M+1)$^+$.

Example 24

8-(3-((Methylamino)methyl)phenyl)-9-phenyl-8,9-dihydro-2H-pyrido[4,3,2-de]phthalazin-3(7H)-one Example 24A (E)-4-(3-(Diethoxymethyl)benzylideneamino) isobenzofuran-1(3H)-one To a stirred mixture of 3-(diethoxymethyl)benzaldehyde (3.75 g, 18 mmol) and anhydrous sodium sulfate (21.3 g, 150 mmol) in anhydrous dichloromethane (300 mL) was added 4-aminoisobenzofuran-1(3H)-one (2.24 g, 15 mmol) at 0° C. After the addition, the mixture was stirred at room temperature for 6 days. The mixture was filtered and the cake was washed with dichloromethane (50 mL×3). The filtrate was concentrated to give crude product. The crude product was washed with petroleum ether to give (E)-4-(3-(diethoxymethyl)benzylideneamino)isobenzofuran-1(3H)-one (3.1 g, yield 61%) as a white solid. LC-MS (ESI) m/z: 340 (M+1)$^+$.

Example 24B

Methyl 2-(3-(diethoxymethyl)phenyl)-4-oxo-3-phenyl-1,2,3,4-tetrahydroquinoline-5-carboxylate and ethyl 2-(3-(diethoxymethyl)phenyl)-4-oxo-3-phenyl-1,2,3,4-tetrahydroquinoline-5-carboxylate 3(7H)-one A mixture of (E)-4-(3-(diethoxymethyl)benzylideneamino)isobenzofuran-1(3H)-one (678 mg, 2 mmol) and benzaldehyde (212 mg, 2.2 mmol) in ethyl propionate (20 mL) was cooled to 0° C. Then a solution of sodium methoxide in methanol [sodium (183 mg, 8 mmol) in methanol (10 mL)] was added dropwise. After the addition, the mixture was stirred at room temperature for 24 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=10:1 to 1:10) to give a mixture of methyl 2-(3-(diethoxymethyl)phenyl)-4-oxo-3-phenyl-1,2,3,4-tetrahydroquinoline-5-carboxylate and ethyl 2-(3-(diethoxymethyl)phenyl)-4-oxo-3-phenyl-1,2,3,4-tetrahydroquinoline-5-carboxylate (160 mg, yield 17%).

Example 24C 8-(3-(Diethoxymethyl)phenyl)-9-phenyl-8,9-dihydro-2H-pyrido[4,3,2-de]phthalazin-3(7H)-one A mixture of methyl 2-(3-(diethoxymethyl)phenyl)-4-oxo-3-phenyl-1,2,3,4-tetrahydroquinoline-5-carboxylate and ethyl 2-(3-(diethoxymethyl)phenyl)-4-oxo-3-phenyl-1,2,3,4-tetrahydroquinoline-5-carboxylate (160 mg, 0.36 mmol) in 85% hydrazine monohydrate (4 mL) and methanol (3 mL) was stirred at 25° C. for overnight. The mixture was extracted with ethyl acetate (50 mL×3). The combined organic layers were washed with brine, dried over anhydrous sodium sulfate, and concentrated to give the 8-(3-(diethoxymethyl)phenyl)-9-phenyl-8,9-dihydro-2H-pyrido[4,3,2-de]phthalazin-3(7H)-one (90 mg, yield 58%) as a yellow solid. LC-MS (ESI) m/z: 442 (M+1)$^+$.

Example 24D 3-(3-Oxo-9-phenyl-3,7,8,9-tetrahydro-2H-pyrido[4,3,2-de]phthalazin-8-yl)benzaldehyde A mixture of 8-(3-(diethoxymethyl)phenyl)-9-phenyl-8,9-dihydro-2H-pyrido[4,3,2-de]phthalazin-3(7H)-one (90 mg, 0.21 mmol) in 3N hydrochloric acid (10 mL) was stirred at room temperature for 3 hr. Then the mixture was neutralized with potassium carbonate. The resulting suspension was filtered to give 3-(3-oxo-9-phenyl-3,7,8,9-tetrahydro-2H-pyrido[4,3,2-de]phthalazin-8-yl)benzaldehyde (40 mg, yield 50%) as a light yellow solid. $^1$H-NMR (400 MHz, CDCl$_3$) δ (ppm): 4.24 (d, J=7.6 Hz, 1H), 4.77 (d, J=7.6 Hz, 1H), 4.85 (brs, 1H), 7.01-7.03 (m, 2H), 7.08-7.10 (m, 1H), 7.21-7.24 (m, 3H), 7.37-7.39 (m, 2H), 7.61-7.65 (m, 1H), 7.74-7.75 (m, 2H), 7.79-7.81 (m, 1H), 9.59 (brs, 1H), 9.92 (s, 1H). LC-MS (ESI) m/z: 368 (M+1)$^+$.

Example 24E 8-(3-((Methylamino)methyl)phenyl)-9-phenyl-8,9-dihydro-2H-pyrido[4,3,2-de]phthalazin-3(7H)-one A mixture of 3-(3-oxo-9-phenyl-3,7,8,9-tetrahydro-2H-pyrido[4,3,2-de]phthalazin-8-yl)benzaldehyde (40 mg, 0.11 mmol) and 27% methylamine alcohol solution (28 mg, 0.23 mmol) in methanol (10 mL) was stirred at room temperature for 40 min. Then the mixture was cooled to 0° C. Sodium borohydride (7 mg, 0.18 mmol) was added. After the addition, the mixture was stirred at this temperature for 2 hr. Methanol was removed under reduced pressure. The residue was washed with ethyl acetate/methanol (10/1) and filtered. The filtrate was concentrated to give the crude product. The crude product was purified by prep-HPLC to give 8-(3-((methylamino)methyl)phenyl)-9-phenyl-8,9-dihydro-2H-pyrido[4,3,2-de]phthalazin-3(7H)-one (4 mg, yield 10%) as a light yellow solid. $^1$H-NMR (400 MHz, CD$_3$OD) δ (ppm): 2.44 (s, 6H), 3.99 (m, 2H), 4.21 (m, 1H), 4.69 (m, 1H), 6.98-7.00 (d, J=7.2 Hz, 1H), 7.05-7.10 (m, 4H), 7.21-7.23 (m, 3H), 7.31 (s, 1H), 7.46-7.48 (d, J=8.0 Hz, 1H), 7.51-7.53 (m, 1H). LC-MS (ESI) m/z: 383 (M+1)$^+$.

Example 25

8-(4-((Dimethylamino)methyl)phenyl)-9-phenyl-8,9-dihydro-2H-pyrido[4,3,2-de]phthalazin-3(7H)-one Example 25A Methyl 2-(4-(dimethoxymethyl)phenyl)-4-oxo-3-phenyl-1,2,3,4-tetrahydroquinoline-5-carboxylate To a solution of (E)-4-(4-(dimethoxymethyl)benzylideneamino)isobenzofuran-1(3H)-one (600 mg, 1 mmol) and benzaldehyde (616 mg, 3 mmol) in ethyl propionate (20 mL), sodium methanolate (414 mg, 7.6 mmol) were added and the mixture was stirred at room temperature overnight. Then the resulting mixture was evaporated under reduced pressure and extracted with ethyl acetate (100 mL×4) and concentrated. The crude product was purified by column chromatography (silica gel, petroleum ether:ethyl acetate 20:1 to 5:1) to obtain a white solid of methyl 2-(4-(dimethoxymethyl)phenyl)-4-oxo-3-phenyl-1,2,3,4-tetrahydroquinoline-5-carboxylate (120 mg, yield 22%). LC-MS (ESI) m/z: 432 (M+1)$^+$.

Example 25B 8-(4-(Dimethoxymethyl)phenyl)-9-phenyl-8,9-dihydro-2H-pyrido[4,3,2-de]phthalazin-3(7H)-one Methyl 2-(4-(dimethoxymethyl)phenyl)-4-oxo-3-phenyl-1,2,3,4-tetrahydroquinoline-5-carboxylate (120 mg, 0.28 mmol) and 85% hydrazine monohydrate (20 mL) were added and the mixture was stirred under 40° C. for 3 h. The resulting mixture was evaporated under reduced pressure to 10 mL and then filtered to give 8-(4-(dimethoxymethyl)phenyl)-9-phenyl-8,9-dihydro-2H-pyrido[4,3,2-de]phthalazin-3(7H)-one (89 mg, yield 78%). LC-MS (ESI) m/z: 414 (M+1)$^+$.

Example 25C 4-(3-Oxo-9-phenyl-3,7,8,9-tetrahydro-2H-pyrido[4,3,2-de]phthalazin-8-yl)benzaldehyde 8-(4-(Dimethoxymethyl)phenyl)-9-phenyl-8,9-dihydro-2H-pyrido[4,3,2-de]phthalazin-3(7H)-one (89 mg, 0.22 mmol) and 20 ml of 3 N hydrochloric acid were added and the mixture was stirred at room temperature for 2 h. The resulting mixture was neutralized with potassium carbonate and then filtered to give 4-(3-oxo-9-phenyl-3,7,8,9-tetrahydro-2H-pyrido[4,3,2-de]phthalazin-8-yl)benzaldehyde (59, yield 73%). LC-MS (ESI) m/z: 368.

Example 25D 8-(4-((Dimethylamino)methyl)phenyl)-9-phenyl-8,9-dihydro-2H-pyrido[4,3,2-de]phthalazin-3(7H)-one 4-(3-Oxo-9-phenyl-3,7,8,9-tetrahydro-2H-pyrido[4,3,2-de]phthalazin-8-yl)benzaldehyde (59 mg, 0.16 mmol) and dimethylamine (5 mL) were added and the mixture was stirred at room temperature for 2 h. Then 20 mg of sodium borohydride was added and stirred for another 2 h. The resulting mixture was evaporated under reduced pressure and purified by prep-HPLC to give 8-(4-((dimethylamino)methyl)phenyl)-9-phenyl-8,9-dihydro-2H-pyrido[4,3,2-de]phthalazin-3(7H)-one (20 mg, yield 32%). $^1$H-NMR (400 MHz, DMSO-d6) δ (ppm): 2.18 (s, 6H), 4.28-4.30 (d, J=8 Hz, 1H), 4.72-4.74 (d, J=8 Hz, 1H), 7.06-7.08 (m, 2H), 7.13-7.20 (m, 6H), 7.23-7.25 (m, 2H), 7.54-7.65 (m, 2H). LC-MS (ESI) m/z: 397 (M+1)$^+$.

Example 26 & 27

8-(4-(Morpholinomethyl)phenyl)-9-phenyl-8,9-dihydro-2H-pyrido[4,3,2-de]phthalazin-3(7H)-one and 8-(4-(Hydroxymethyl)phenyl)-9-phenyl-8,9-dihydro-2H-pyrido[4,3,2-de]phthalazin-3(7H)-one 4-(3-Oxo-9-phenyl-3,7,8,9-tetrahydro-2H-pyrido[4,3,2-de]phthalazin-8-yl)benzaldehyde (59 mg, 0.16 mmol) and morpholine (42 mg) were added and the mixture was stirred at room temperature for 2 h. Then 20 mg of sodium borohydride was added and stirred for another 2 h. The resulting mixture was evaporated under reduced pressure and purified by prep-HPLC to give 8-(4-(morpholinomethyl)phenyl)-9-phenyl-8,9-dihydro-2H-pyrido[4,3,2-de]phthalazin-3(7H)-one (8 mg, yield 11%) and 8-(4-(hydroxymethyl)phenyl)-9-phenyl-8,9-dihydro-2H-pyrido[4,3,2-de]phthalazin-3(7H)-one (7 mg, yield 12%). 8-(4-(morpholinomethyl)phenyl)-9-phenyl-8,9-dihydro-2H-pyrido[4,3,2-de]phthalazin-3(7H)-one: $^1$H-NMR (400 MHz, DMSO-d6) δ (ppm): 2.31 (s, 4H), 3.36 (s, 4H), 3.61-3.63 (m, 4H), 4.15-4.17 (d, J=10 Hz, 1H), 4.58-4.61 (d, J=10 Hz, 1H), 4.79 (s, 1H), 6.94-7.19 (m, 10H), 7.51-7.55 (m, 1H), 7.68-7.70 (m, 1H), 7.63 (s, 1H). LC-MS (ESI) m/z: 439 (M+1)$^+$. 8-(4-(hydroxymethyl)phenyl)-9-phenyl-8,9-dihydro-2H-pyrido[4,3,2-de]phthalazin-3(7H)-one: $^1$H-NMR (400 MHz, DMSO-d6) δ (ppm): 4.21-4.25 (m, 1H), 4.63-4.70 (m, 1H), 4.86 (s, 1H), 6.97-7.06 (m, 3H), 7.11-7.26 (m, 7H), 7.58-7.62 (m, 1H), 7.75-7.77 (m, 1H). LC-MS (ESI) m/z: 370 (M+1)$^+$.

Examples 28 & 29

9-(3-(4-(Cyclopropanecarbonyl)piperazine-1-carbonyl)phenyl)-8-(4-((dimethylamino)methyl)phenyl)-8,9-dihydro-2H-pyrido[4,3,2-de]phthalazin-3(7H)-one and 9-(3-(4-(cyclopropanecarbonyl)piperazine-1-carbonyl)phenyl)-8-(4-(hydroxymethyl)phenyl)-8,9-dihydro-2H-pyrido[4,3,2-de]phthalazin-3(7H)-one

Example 28A 3-(4-(Cyclopropanecarbonyl)piperazine-1-carbonyl)benzaldehyde

To a stirred mixture of 3-formylbenzoic acid (450 mg, 3 mmol) in anhydrous dichloromethane (20 mL) was added triethylamine (758 mg, 7.5 mmol), 1-hydroxybenzotriazole (466 mg, 3.45 mmol), followed by 1-ethyl-3-(3-dimethylamino propyl) carbodiimide hydrochloride (629 mg, 3.45 mmol). After the addition, the mixture was stirred at room temperature for 40 mins. Then the mixture was cooled to 0° C. and cyclopropyl(piperazin-1-yl)methanone hydrochloride (629 mg, 3.3 mmol) was added in portion-wise. After the addition, the mixture was allowed to stir at room temperature overnight. The mixture was diluted with dichloromethane (50 mL), washed with saturated citric acid (100 mL×2), followed by saturated sodium bicarbonate (100 mL×2), brine (50 mL), dried over anhydrous sodium sulfate, and concentrated to give 3-(4-(cyclopropanecarbonyl)piperazine-1-carbonyl) benzaldehyde (810 mg, yield 94%) as a light yellow oil. $^1$H-NMR (400 MHz, CDCl$_3$) δ (ppm): 0.79-0.85 (m, 2H), 1.00-1.04 (m, 2H), 1.73-1.76 (m, 1H), 3.47-3.77 (m, 8H), 7.62-7.66 (t, J=7.6 Hz, 1H), 7.70-7.72 (d, J=7.6 Hz, 1H), 7.95-7.98 (m, 2H), 10.1 (s, 1H); LC-MS (ESI) m/z: 287 (M+1)$^+$.

Example 28B

Methyl 3-(3-(4-(cyclopropanecarbonyl)piperazine-1-carbonyl)phenyl)-2-(4-(diethoxymethyl)phenyl)-4-oxo-1,2,3,4-tetrahydroquinoline-5-carboxylate A mixture of 3-(4-(cyclopropanecarbonyl)piperazine-1-carbonyl) benzaldehyde (940 mg, 3.3 mmol) and (E)-4-(4-(diethoxymethyl) benzylideneamino)isobenzofuran-1(3H)-one (1.018 g, 3 mmol) in ethyl propionate (40 mL) was cooled to 0° C. Then a solution of sodium methoxide in methanol [sodium (345 mg, 15 mmol) in methanol (8 mL)] was added drop-wise. After the addition, the mixture was stirred at room temperature for 24 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=10:1 to 1:10) to give methyl 3-(3-(4-(cyclopropanecarbonyl)piperazine-1-carbonyl)phenyl)-2-(4-(diethoxymethyl)phenyl)-4-oxo-1,2,3,4-tetrahydroquinoline-5-carboxylate (425 mg, yield 22%).

Example 28C 9-(3-(4-(Cyclopropanecarbonyl)piperazine-1-carbonyl)phenyl)-8-(4-(diethoxymethyl)phenyl)-8,9-dihydro-2H-pyrido[4,3,2-de]phthalazin-3(7H)-one A mixture of methyl 3-(3-(4-(cyclopropanecarbonyl)piperazine-1-carbonyl)phenyl)-2-(4-(diethoxymethyl)phenyl)-4-oxo-1,2,3,4-tetrahydroquinoline-5-(425 mg, 0.67 mmol) in 85% hydrazine monohydrate (4 mL) and methanol (3 mL) was stirred at 25° C. for overnight. The mixture was extracted with ethyl acetate (50 mL×3). The combined organic layers were washed with brine, dried over anhydrous sodium sulfate, and concentrated to give the 9-(3-(4-(cyclopropanecarbonyl)piperazine-1-carbonyl)phenyl)-8-(4-(diethoxymethyl)phenyl)-8,9-dihydro-2H-pyrido[4,3,2-de]phthalazin-3(7H)-one (290 mg, yield 70%) as a yellow solid.

Example 28D 4-(9-(3-(4-(Cyclopropanecarbonyl)piperazine-1-carbonyl)phenyl)-3-oxo-3,7,8,9-tetrahydro-2H-pyrido[4,3,2-de]phthalazin-8-yl)benzaldehyde A mixture of 9-(3-(4-(cyclopropanecarbonyl)piperazine-1-carbonyl)phenyl)-8-(4-(diethoxymethyl)phenyl)-8,9-dihydro-2H-pyrido[4,3,2-de]phthalazin-3(7H)-one (290 mg, 0.48 mmol) in 3N hydrochloric acid (10 mL) was stirred at room temperature overnight. Then the mixture was neutralized with potassium carbonate. The resulting suspension was filtered to give crude. The crude product was purified by prep-HPLC to give the 4-(9-(3-(4-(cyclopropanecarbonyl)piperazine-1-carbonyl)phenyl)-3-oxo-3,7,8,9-tetrahydro-2H-pyrido[4,3,2-de]phthalazin-8-yl)benzaldehyde (20 mg, yield 8%) as a light yellow solid. $^1$H-NMR (400 MHz, CD$_3$OD) δ (ppm): 0.83-0.91 (m, 4H), 1.94-2.03 (m, 1H), 3.18-3.23 (m, 1H), 3.46-3.82 (m, 7H), 4.42 (d, J=7.6 Hz, 1H), 4.87 (d, J=7.4 Hz, 1H), 7.22-7.41 (m, 7H), 7.52-7.54 (d, J=8.0 Hz, 2H), 7.60 (d, 1H), 9.94 (s, 1H); LC-MS (ESI) m/z: 548 (M+1)$^+$.

Examples 28E & 29E 9-(3-(4-(Cyclopropanecarbonyl)piperazine-1-carbonyl)phenyl)-8-(4-((dimethylamino)methyl)phenyl)-8,9-dihydro-2H-pyrido[4,3,2-de]phthalazin-3(7H)-one and 9-(3-(4-(cyclopropanecarbonyl)piperazine-1-carbonyl)phenyl)-8-(4-(hydroxymethyl)phenyl)-8,9-dihydro-2H-pyrido[4,3,2-de]phthalazin-3(7H)-one A mixture of 4-(9-(3-(4-(cyclopropanecarbonyl)piperazine-1-carbonyl)phenyl)-3-oxo-3,7,8,9-tetrahydro-2H-pyrido[4,3,2-de]phthalazin-8-yl)benzaldehyde (20 mg, 0.04 mmol) and 33% dimethylamine aq solution (10 mg, 0.07 mmol) in methanol (10 mL) was stirred at room temperature for 40 min. Then the mixture was cooled to 0° C. Sodium borohydride (2 mg, 0.06 mmol) was added. After the addition, the mixture was stirred at this temperature for 2 hr. Methanol was removed under reduced pressure. The residue was washed with ethyl acetate/methanol (10/1) and filtered. The filtrate was concentrated to give the crude product. The crude product was purified by prep-HPLC to give the compound 9-(3-(4-(cyclopropanecarbonyl)piperazine-1-carbonyl)phenyl)-8-(4-((dimethylamino)methyl)phenyl)-8,9-dihydro-2H-pyrido[4,3,2-de]phthalazin-3(7H)-one (4 mg, yield 19%) and 9-(3-(4-(cyclopropanecarbonyl)piperazine-1-carbonyl)phenyl)-8-(4-(hydroxymethyl)phenyl)-8,9-dihydro-2H-pyrido[4,3,2-de]phthalazin-3(7H)-one (2 mg, yield 9%) as light yellow solids. 9-(3-(4-(cyclopropanecarbonyl)piperazine-1-carbonyl)phenyl)-8-(4-((dimethylamino)methyl)phenyl)-8,9-dihydro-2H-pyrido[4,3,2-de]phthalazin-3(7H)-one: $^1$H-NMR (400 MHz, CD$_3$OD) δ (ppm): 0.83-0.91 (m, 4H), 1.94-2.03 (m, 1H), 2.81 (s, 6H), 3.18-3.23 (m, 1H), 3.35-3.79 (m, 7H), 4.26 (s, 2H), 4.38 (d, J=7.6 Hz, 1H), 4.82 (d, J=7.2 Hz, 1H), 7.22-7.29 (m, 4H), 7.31-7.33 (m, 1H), 7.37-7.45 (m, 4H), 7.58-7.60 (d, J=8.0 Hz, 1H), 7.64-7.68 (t, J=8.0 Hz, 1H); LC-MS (ESI) m/z: 577 (M+1)$^+$. 9-(3-(4-(cyclopropanecarbonyl)piperazine-1-carbonyl)phenyl)-8-(4-(hydroxymethyl)phenyl)-8,9-dihydro-2H-pyrido[4,3,2-de]phthalazin-3(7H)-one: $^1$H-NMR (400 MHz, CD$_3$OD) δ (ppm): 0.83-0.91 (m, 4H), 1.94-2.01 (m, 1H), 3.11-3.14 (m, 1H), 3.35-3.79 (m, 7H), 4.37-4.40 (d, J=10.0 Hz, 1H), 4.55 (s, 2H), 4.38 (d, J=7.6 Hz, 1H), 4.73-4.76 (d, J=9.6 Hz, 1H), 7.12 (s, 1H), 7.20-7.30 (m, 7H), 7.34-7.38 (t, J=8.0 Hz, 1H), 7.56-7.58 (d, J=7.6 Hz, 1H), 7.62-7.66 (t, J=8.0 Hz, 1H); LC-MS (ESI) m/z: 550 (M+1)$^+$.

Example 30

9-(4-(4-Isobutyrylpiperazine-1-carbonyl)phenyl)-8-(4-((methylamino)methyl)phenyl)-8,9-dihydro-2H-pyrido[4,3,2-de]phthalazin-3(7H)-one A mixture of 4-(9-(4-(4-isobutyrylpiperazine-1-carbonyl)phenyl)-3-oxo-3,7,8,9-tetrahydro-2H-pyrido[4,3,2-de]phthalazin-8-yl)benzaldehyde (40 mg, 0.07 mmol) and 33% dimethylamine aq solution (17 mg, 0.14 mmol) in methanol (10 mL) was stirred at room temperature for 40 min. Then the mixture was cooled to 0° C. Sodium borohydride (4 mg, 0.11 mmol) was added. After the addition, the mixture was stirred at this temperature for 2 hr. Methanol was removed under reduced pressure. The residue was washed with ethyl acetate/methanol (10/1) and filtered. The filtrate was concentrated to give the crude product. The crude product was purified by prep-HPLC to give the compound 9-(4-(4-isobutyrylpiperazine-1-carbonyl)phenyl)-8-(4-((methylamino)methyl)phenyl)-8,9-dihydro-2H-pyrido[4,3,2-de]phthalazin-3(7H)-one (18 mg, yield 49%) as a light yellow solid. $^1$H-NMR (400 MHz, CD$_3$OD) δ (ppm): 1.10-1.12 (d, J=6.8 Hz, 6H), 2.67 (s, 3H), 2.81 (brs 1H), 3.33-3.70 (m, 8H), 4.12 (s, 2H), 4.43-4.75 (d, J=7.6 Hz, 1H), 4.88 (d, J=7.4 Hz, 1H), 7.22-7.27 (m, 3H), 7.31-7.37 (m, 4H), 7.42-7.44 (d, J=8.0 Hz, 2H), 7.56-7.58 (d, J=7.2 Hz, 1H), 7.64-7.68 (t, J=8.0 Hz, 1H); LC-MS (ESI) m/z: 579 (M+1)$^+$.

Example 31

9-(3-(4-Isobutyrylpiperazine-1-carbonyl)phenyl)-8-(pyridin-4-yl)-8,9-dihydro-2H-pyrido[4,3,2-de]phthalazin-3(7H)-one Example 31A 3-(4-Isobutyrylpiperazine-1-carbonyl)benzaldehyde To a solution of 3-formylbenzoic acid (750 mg, 5 mmol) in anhydrous dichloromethane (15 mL) was added triethylamine (1.263 g, 12.5 mmol), 1-hydroxybenzotriazole (0.743 g, 5.5 mmol), followed by 1-ethyl-3-(3-dimethylamino propyl)carbodiimide hydrochloride (1.05 g, 5.5 mmol). After the addition, the mixture was stirred at room temperature for 40 mins. Then the mixture was cooled to 0° C. and 2-methyl-1-(piperazin-1-yl)propan-1-one hydrochloride (1.06 g, 5.5 mmol) was added portionwise. After the addition, the mixture was stirred at room temperature overnight. The mixture was diluted with dichloromethane (50 mL), washed with saturated sodium bicarbonate (50 mL×2), 10% citric acid (50 mL), brine (30 mL), dried over anhydrous sodium sulfate, and concentrated to give 3-(4-isobutyrylpiperazine-1-carbonyl)benzaldehyde (1.44 g, yield 95%) as a gum. $^1$H-NMR (400 MHz, CDCl$_3$) δ (ppm): 1.13-1.14 (d, J=6.8 Hz 6H), 2.80 (s, 1H), 3.46-3.80 (m, 8H), 7.62-7.66 (t, J=7.6 Hz, 1H), 7.69-7.71 (d, J=7.6 Hz, 1H), 7.94 (s, 1H), 7.96-7.99 (dd, J$_1$=7.6 Hz, J$_2$=1.2 Hz, 1H), 10.06 (s, 1H); LC-MS (ESI) m/z: 289 (M+1)$^+$.

Example 31B (E)-4-(Pyridin-4-ylmethyleneamino)isobenzofuran-1(3H)-one

A mixture of 4-aminoisobenzofuran-1(3H)-one (894 mg, 6 mmol), isonicotinaldehyde (2.568 g, 24 mmol) and anhydrous sodium sulfate (3.6 g) in anhydrous ethanol (70 mL) was heated to reflux for two days. The mixture was cooled to room temperature and filtered. The filtrate was concentrated to give the crude product. The crude product was washed with petroleum ether to give (E)-4-(pyridin-4-ylmethyleneamino)isobenzofuran-1(3H)-one (1.1 g, yield 77%) as a white solid. $^1$H-NMR (400 MHz, CDCl$_3$) δ (ppm): 5.44 (s, 1H), 7.40-7.42 (d, J=7.6 Hz, 1H), 7.59-7.63 (t, J=7.6 Hz, 1H), 7.77-7.79 (d, J=5.6 Hz, 2H), 7.84-7.86 (d, J=7.6 Hz, 1H), 8.54 (s, 1H), 8.81-8.82 (d, J=4.8 Hz, 1H); LC-MS (ESI) m/z: 239 (M+1)+.

Example 31C

Methyl 3-(3-(4-isobutyryl piperazine-1-carbonyl) phenyl)-4-oxo-2-(pyridin-4-yl)-1,2,3,4-tetrahydroquinoline-5-carboxylate A mixture of 3-(4-isobutyrylpiperazine-1-carbonyl)benzaldehyde (288 mg, 1 mmol) and (E)-4-(pyridin-4-ylmethyleneamino)-isobenzofuran-1(3H)-one (238 mg, 1 mmol) in ethyl propionate (7.5 mL) was cooled to 0° C. Then a solution of sodium methoxide in methanol [sodium (92 mg, 4 mmol) in methanol (7.5 mL)] was added drop-wise. After the addition, the mixture was stirred at 25° C. for 18 hr. The mixture was quenched with water (10 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by chromatography (silica gel, petroleum ether/ethyl acetate=10:1 to 1:10) to give methyl 3-(3-(4-isobutyryl piperazine-1-carbonyl)phenyl)-4-oxo-2-(pyridin-4-yl)-1,2,3,4-tetrahydroquinoline-5-carboxylate (140 mg, yield 26%). LC-MS (ESI) m/z: 541 (M+1)+.

Example 31D 9-(3-(4-Isobutyrylpiperazine-1-carbonyl)phenyl)-8-(pyridin-4-yl)-8,9-dihydro-2H-pyrido[4,3,2-de]phthalazin-3(7H)-one A mixture of methyl 3-(3-(4-isobutyryl piperazine-1-carbonyl)phenyl)-4-oxo-2-(pyridin-4-yl)-1,2,3,4-tetrahydroquinoline-5-carboxylate (140 mg, 0.26 mmol) in 85% hydrazine monohydrate (10 mL) and methanol (3 mL) was stirred at 25° C. for 4 hr. The mixture was extracted with ethyl acetate (50 mL×3). The combined organic layers were washed with brine, dried over anhydrous sodium sulfate, and concentrated to give crude product. The crude product was purified by prep-HPLC to give compound 9-(3-(4-isobutyrylpiperazine-1-carbonyl)phenyl)-8-(pyridin-4-yl)-8,9-dihydro-2H-pyrido[4,3,2-de]phthalazin-3(7H)-one (11 mg, yield 8%) as a white solid. $^1$H-NMR (400 MHz, CD$_3$OD) δ (ppm): 1.11-1.13 (m, 6H), 2.95-2.98 (m, 1H), 3.26-3.68 (m, 8H), 4.40-4.42 (d, J=8.4 Hz, 1H), 4.82-4.84 (d, J=8.4 Hz, 1H), 7.19-7.32 (m, 4H), 7.36-7.39 (m, 3H), 7.59-7.68 (m, 2H), 8.41-8.42 (d, J=6.0 Hz, 2H); LC-MS (ESI) m/z: 523 (M+1)+.

Following the synthetic strategy outlined in Synthetic Scheme I and Synthetic Scheme II and the appropriate experimental procedure as described in Examples 2 to Example 31 and using different aldehydes 2 and appropriate 4-aminoisobenzofuran-1(3H)-one 1, the following compounds are made.

Example 32

9-(3-((Dimethylamino)methyl)phenyl)-8-(pyridin-4-yl)-8,9-dihydro-2H-pyrido[4,3,2-de]phthalazin-3(7H)-one Example 33

9-(3-((Methylamino)methyl)phenyl)-8-(pyridin-4-yl)-8,9-dihydro-2H-pyrido[4,3,2-de]phthalazin-3(7H)-one Example 34

9-(4-((Dimethylamino)methyl)phenyl)-8-(pyridin-4-yl)-8,9-dihydro-2H-pyrido[4,3,2-de]phthalazin-3(7H)-one Example 35

9-(3-(Hydroxymethyl)phenyl)-8-(pyridin-4-yl)-8,9-dihydro-2H-pyrido[4,3,2-de]phthalazin-3(7H)-one Example 36

9-(4-((Methylamino)methyl)phenyl)-8-(pyridin-4-yl)-8,9-dihydro-2H-pyrido[4,3,2-de]phthalazin-3(7H)-one Example 37

9-(3-((Dimethylamino)methyl)phenyl)-8-(pyridin-3-yl)-8,9-dihydro-2H-pyrido[4,3,2-de]phthalazin-3(7H)-one Example 38

9-(3-((Methylamino)methyl)phenyl)-8-(pyridin-3-yl)-8,9-dihydro-2H-pyrido[4,3,2-de]phthalazin-3(7H)-one Example 39

9-(4-((Dimethylamino)methyl)phenyl)-8-(pyridin-3-yl)-8,9-dihydro-2H-pyrido[4,3,2-de]phthalazin-3(7H)-one Example 40

9-(4-((Methylamino)methyl)phenyl)-8-(pyridin-3-yl)-8,9-dihydro-2H-pyrido[4,3,2-de]phthalazin-3(7H)-one Example 41

9-(3-(Hydroxymethyl)phenyl)-8-(pyridin-3-yl)-8,9-dihydro-2H-pyrido[4,3,2-de]phthalazin-3(7H)-one Example 42

9-(3-((Dimethylamino)methyl)phenyl)-8-(pyridin-2-yl)-8,9-dihydro-2H-pyrido[4,3,2-de]phthalazin-3(7H)-one

Example 43

9-(3-((Methylamino)methyl)phenyl)-8-(pyridin-2-yl)-8,9-dihydro-2H-pyrido[4,3,2-de]phthalazin-3(7H)-one

Example 44

9-(3-(Hydroxymethyl)phenyl)-8-(pyridin-2-yl)-8,9-dihydro-2H-pyrido[4,3,2-de]phthalazin-3(7H)-one

Example 45

9-(4-((Dimethylamino)methyl)phenyl)-8-(pyridin-2-yl)-8,9-dihydro-2H-pyrido[4,3,2-de]phthalazin-3(7H)-one

Example 46

9-(4-((Methylamino)methyl)phenyl)-8-(pyridin-2-yl)-8,9-dihydro-2H-pyrido[4,3,2-de]phthalazin-3(7H)-one

Example 47

9-Phenyl-8-(pyridin-2-yl)-8,9-dihydro-2H-pyrido[4,3,2-de]phthalazin-3(7H)-one

Example 48

9-Phenyl-8-(pyridin-3-yl)-8,9-dihydro-2H-pyrido[4,3,2-de]phthalazin-3(7H)-one

Example 49

9-Phenyl-8-(pyridin-4-yl)-8,9-dihydro-2H-pyrido[4,3,2-de]phthalazin-3(7H)-one

Example 50

5-Fluoro-9-phenyl-8-(pyridin-4-yl)-8,9-dihydro-2H-pyrido[4,3,2-de]phthalazin-3(7H)-one

Example 51

9-(3-((Dimethylamino)methyl)phenyl)-5-fluoro-8-(pyridin-4-yl)-8,9-dihydro-2H-pyrido[4,3,2-de]phthalazin-3(7H)-one

Example 52

5-Fluoro-9-(3-((methylamino)methyl)phenyl)-8-(pyridin-4-yl)-8,9-dihydro-2H-pyrido[4,3,2-de]phthalazin-3(7H)-one

Example 53

9-(4-((Dimethylamino)methyl)phenyl)-5-fluoro-8-(pyridin-4-yl)-8,9-dihydro-2H-pyrido[4,3,2-de]phthalazin-3(7H)-one

Example 54

5-Fluoro-8,9-diphenyl-8,9-dihydro-2H-pyrido[4,3,2-de]phthalazin-3(7H)-one

Example 55

9-(4-((Dimethylamino)methyl)phenyl)-5-fluoro-8-phenyl-8,9-dihydro-2H-pyrido[4,3,2-de]phthalazin-one

Example 56

5-Fluoro-9-(4-((methylamino)methyl)phenyl)-8-phenyl-8,9-dihydro-2H-pyrido[4,3,2-de]phthalazin-one

Example 57

9-(3-((Dimethylamino)methyl)phenyl)-5-fluoro-8-phenyl-8,9-dihydro-2H-pyrido[4,3,2-de]phthalazin-one

Example 58

8-(4-((Dimethylamino)methyl)phenyl)-5-fluoro-9-phenyl-8,9-dihydro-2H-pyrido[4,3,2-de]phthalazin-one

Example 59

5-Fluoro-9-(3-((methylamino)methyl)phenyl)-8-phenyl-8,9-dihydro-2H-pyrido[4,3,2-de]phthalazin-one

Example 60

5-Fluoro-8-(4-((methylamino)methyl)phenyl)-9-phenyl-8,9-dihydro-2H-pyrido[4,3,2-de]phthalazin-one

Example 61

7-Methyl-8,9-diphenyl-8,9-dihydro-2H-pyrido[4,3,2-de]phthalazin-3(7H)-one

A solution of 8,9-diphenyl-8,9-dihydro-2H-pyrido[4,3,2-de]phthalazin-3(7H)-one (1.04 mmol) in methanol (20 mL) is treated with formaldehyde (37 wt % in water, 270 μL, 3.61 mmol) at room temperature for overnight. Sodium cyanoborohydride (228 mg, 3.61 mmol) is added and the solution is stirred at room temperature for 3 h. After concentration under reduced pressure, the residue is dissolved in a mixture of trifluoroacetic acid and water and is purified by HPLC giving the 7-methyl-8,9-diphenyl-8,9-dihydro-2H-pyrido[4,3,2-de]phthalazin-3(7H)-one in good yield.

Example 62

7-Ethyl-8,9-diphenyl-8,9-dihydro-2H-pyrido[4,3,2-de]phthalazin-3(7H)-one

Following the experimental conditions outlined in Example 61, replacing the formaldehyde with acetaldehyde, the title compound 7-ethyl-8,9-diphenyl-8,9-dihydro-2H-pyrido[4,3,2-de]phthalazin-3(7H)-one is made.

Example 63

5-Fluoro-9-(1-methyl-1H-imidazol-2-yl)-8-phenyl-8,9-dihydro-2H-pyrido[4,3,2-de]phthalazin-3(7H)-one Example 63A Methyl 5-fluoro-2-methyl-3-nitrobenzoate To a solution of conc. $H_2SO_4$ (700 mL) was added portion-wise 5-fluoro-2-methylbenzoic acid (80 g, 520 mmol) at −5~0° C. Then a mixture of conc. $HNO_3$ (60.4 g, 624 mmol) in conc. $H_2SO_4$ (60 mL) was added drop-wise at −5~0° C. in a period of about 1.5 hrs. After the addition, the mixture was stirred at this temperature for 2 hrs. TLC (petroleum ether/EtOAc=1:1) showed the reaction was complete. The mixture was poured into crash ice with vigorous stirring and the precipitate was collected by filtration. The precipitate was dissolved in EtOAc, washed with brine, dried over anhydrous $Na_2SO_4$, concentrated to give crude 5-fluoro-2-methyl-3-nitrobenzoic acid (54 g). A solution of this crude 5-fluoro-2-methyl-3-nitrobenzoic acid (54 g) in dry methanol (500 mL) was cooled to 0° C., $SOCl_2$ (64.52 g, 542.3 mmol) was added drop-wise. After the addition, the mixture was heated to reflux for 16 hrs. TLC (petroleum ether/EtOAc=1:1) showed the reaction was complete. Solvent was removed under reduced pressure to give crude product. The crude product was purified by silica gel chromatography (petroleum ether to petroleum ether/EtOAc=50:1) to give methyl 5-fluoro-2-methyl-3-nitrobenzoate (28 g, yield 25% for two steps) as a white solid. $^1$H-NMR (400 MHz, $CDCl_3$) □□δ (ppm): 2.59 (s, 3H), 3.95 (s, 3H), 7.60-7.63 (dd, 1H), 7.74-7.77 (dd, 1H); LC-MS (ESI) m/z: 214 $(M+1)^+$, 216 $(M+3)^+$.

Example 63B

6-Fluoro-4-nitroisobenzofuran-1(3H)-one

A mixture of methyl 5-fluoro-2-methyl-3-nitrobenzoate (28 g, 130.5 mmol), NBS (27.8 g, 156.6 mmol) and BPO (3.13 g, 13.1 mmol) in $CCl_4$ (400 mL) was heated to reflux overnight. TLC (petroleum ether/EtOAc=15:1) showed the starting material was consumed completely. Water (200 mL) was added and $CCl_4$ was removed under reduced pressure. The residue was extracted with DCM (200 mL×3). The combined organic layers were washed with brine, dried over $Na_2SO_4$, concentrated to give crude methyl 2-(bromomethyl)-5-fluoro-2-methyl-3-nitrobenzoate (36 g, yield 94%) as a brown oil. A mixture of methyl 2-(bromomethyl)-5-fluoro-2-methyl-3-nitrobenzoate (36 g, 123 mmol) in 1,4-dioxane (250 mL) and water (62.5 mL) was heated to reflux for 4 days. TLC (petroleum ether/EtOAc=15:1) showed the starting material was consumed completely. Dioxane was removed under reduced pressure. The residue was extracted with EtOAc (300 mL×4). The combined organic layers were washed with brine, dried over $Na_2SO_4$, concentrated to give crude product. The crude product was purified by gel chromatography (petroleum ether to petroleum ether/EtOAc=5:1) to give 6-fluoro-4-nitroisobenzofuran-1(3H)-one (19.2 g, yield 79%) as a white solid. $^1$H-NMR (400 MHz, $CDCl_3$) □□δ (ppm): 5.74 (s, 2H), 7.97-7.98 (dd, 1H), 8.24-8.27 (dd, 1H); LC-MS (ESI) m/z: 198 $(M+1)^+$.

Example 63C

4-Amino-6-fluoroisobenzofuran-1(3H)-one

A suspension of 6-fluoro-4-nitroisobenzofuran-1(3H)-one (9.6 g, 48.7 mmol) and Pd/C (10%, 1 g) in EtOAc (300 mL) was stirred at 25° C. under 1 atmosphere of hydrogen for 12 hr. TLC (petroleum ether/EtOAc=2:1) showed the reaction was complete. The mixture was filtered, and the cake was washed with EtOAc (100 mL×3). The filtrate was concentrated to give 4-amino-6-fluoroisobenzofuran-1(3H)-one (7.5 g, yield 92%) as a white solid. $^1$H-NMR (400 MHz, $CDCl_3$) □□ δ (ppm): 3.85 (br s, 2H), 5.14-5.15 (d, 2H), 6.62-6.65 (dd, 1H), 6.98-7.00 (dd, 1H); LC-MS (ESI) m/z: 168 $(M+1)^+$.

Example 63D (E)-4-(Benzylideneamino)-6-fluoroisobenzofuran-1(3H)-one

To a stirred mixture of benzaldehyde (4.125 g, 29.9 mmol) and anhydrous magnesium sulfate (36 g, 299 mmol) in anhydrous acetonitrile (200 mL) was added 4-amino-6-fluoroisobenzofuran-1(3H)-one (5 g, 29.9 mmol) at 0° C. After the addition, the mixture was stirred at room temperature for 6 days. The mixture was filtered and the cake was washed with ethyl acetate (50 mL×3). The filtrate was concentrated to give crude product. The crude product was washed with petroleum ether to give (E)-4-(benzylideneamino)-6-fluoroisobenzofuran-1(3H)-one (5 g, yield: 66%). $^1$H-NMR (400 MHz, $CDCl_3$) δ (ppm): 5.40 (s, 2); 7.11-7.14 (dd, 1H), 7.44-7.46 (dd, 2H), 7.53-7.59 (m, 3H), 7.93-7.95 (m, 2H), 8.54 (s, 1H); LC-MS (ESI) m/z: 256 $(M+1)^+$.

Example 63E

Ethyl 7-fluoro-3-(1-methyl-1H-imidazol-2-yl)-4-oxo-2-phenyl-1,2,3,4-tetrahydroquinoline-5-carboxylate A mixture of (E)-4-(benzylideneamino)-6-fluoroisobenzofuran-1(3H)-one (2 g, 7.8 mmol) and 1-methyl-1H-imidazole-2-carbaldehyde (0.949 g, 8.63 mmol) in ethyl propionate (50 mL) was cooled to 0° C. Then a solution of sodium ethoxide in ethanol [sodium (722 mg, 31.37 mmol) in ethanol (30 mL)] was added drop-wise. After the addition, the mixture was stirred at room temperature for 2 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=10:1 to 1:10) to give the ethyl 7-fluoro-3-(1-methyl-1H-imidazol-2-yl)-4-oxo-2-phenyl-1,2,3,4-tetrahydroquinoline-5-carboxylate (141 mg). $^1$H-NMR (400 MHz, DMSO-d6) □□δ (ppm): 1.18-1.22 (t, 3H), 3.31 (s, 3H), 4.17-4.21 (q, 2H), 4.621-4.65 (d, 2H), 5.17-5.20 (d, 1H), 6.48-6.51 (dd, 1H), 6.70-6.73 (m, 2H), 6.86 (s, 1H), 7.24-7.30 (m, 3H), 7.42-7.44 (t, 2H), 7.76 (s, 1H); LC-MS (ESI) m/z: 394 (M+1)⁺.

Example 63F

5-Fluoro-9-(1-methyl-1H-imidazol-2-yl)-8-phenyl-8, 9-dihydro-2H-pyrido[4,3,2-de]phthalazin-3(7H)-one A mixture of ethyl 7-fluoro-3-(1-methyl-1H-imidazol-2-yl)-4-oxo-2-phenyl-1,2,3,4-tetrahydroquinoline-5-carboxylate (141 mg) in 85% hydrazine monohydrate (10 mL) and methanol (10 mL) was stirred at 45° C. for overnight. Methanol was removed under reduced pressure. The mixture was filtered and washed with water to give 5-fluoro-9-(1-methyl-1H-imidazol-2-yl)-8-phenyl-8,9-dihydro-2H-pyrido[4,3,2-de]phthalazin-3(7H)-one (11 mg, yield: 9%). ¹H-NMR (400 MHz, CD₃OD) □□δ (ppm): 3.34 (s, 3H), 4.65 (d, J=8.0 Hz, 1H), 4.94 (d, J=8.0 Hz, 1H), 6.81 (s, 1H), 6.88-7.02 (m, 2H), 7.18 (dd, 1H), 7.28-7.29 (m, 3H), 7.34-7.36 (m, 2H); ¹⁹F-NMR (400 MHz, CD₃OD) δ: −105.70 (s); LC-MS (ESI) m/z: 362 (M+1)⁺.

Example 64

5-Fluoro-8-(4-fluorophenyl)-9-(1-methyl-1H-imidazol-2-yl)-8,9-dihydro-2H-pyrido[4,3,2-de]phthalazin-3(7H)-one Example 64A (E)-6-Fluoro-4-(4-fluorobenzylideneamino)isobenzofuran-1(3H)-one 4-amino-6-fluoroisobenzofuran-1(3H)-one (1.5 g, 8.98 mmol), 4-fluorobenzaldehyde (1.67 g, 13.47 mmol) and 12.75 g of MgSO₄ were added into 40 ml of DCM and stirred under reflux overnight, then the mixture was evaporated under reduced pressure and the residues was dried in vacuum. 850 mg of (E)-6-fluoro-4-(4-fluorobenzylideneamino)isobenzofuran-1(3H)-one was obtained. ¹H-NMR (400 MHz, CDCl₃) δ (ppm): 5.37 (s, 2); 7.09-7.12 (dd, 1H), 7.19-7.23 (t, 2H), 7.43-7.45 (dd, 1H), 7.92-7.95 (m, 2H), 8.49 (s, 1H); LC-MS (ESI) m/z: 274 (M+1)⁺.

Example 64B

Methyl 7-fluoro-2-(4-fluorophenyl)-3-(1-methyl-1H-imidazol-2-yl)-4-oxo-1,2,3,4-tetrahydroquinoline-5-carboxylate (E)-6-Fluoro-4-(4-fluorobenzylideneamino)isobenzofuran-1(3H)-one (850 mg, 3.13 mmol), 1-methyl-1H-imidazole-2-carbaldehyde (342 mg, 3.13 mmol), sodium methanolate (851 mg, 12.52 mmol) and ethyl propionate (50 ml) were added and the mixture was stirred at room temperature overnight. Then the resulting mixture was evaporated under reduced pressure and extracted with EtOAc (4×100 ml) and concentrated. The crude product was purified by column chromatography (silica gel, petroleum ether:EtOAc 20:1 to 5:1). 20 mg of methyl 7-fluoro-2-(4-fluorophenyl)-3-(1-methyl-1H-imidazol-2-yl)-4-oxo-1,2,3,4-tetrahydroquinoline-5-carboxylate was obtained. LC-MS (ESI) m/z: 412 (M+1)⁺.

Example 64C

5-Fluoro-8-(4-fluorophenyl)-9-(1-methyl-1H-imidazol-2-yl)-8,9-dihydro-2H-pyrido[4,3,2-de]phthalazin-3(7H)-one Methyl 7-fluoro-2-(4-fluorophenyl)-3-(1-methyl-1H-imidazol-2-yl)-4-oxo-1,2,3,4-tetrahydroquinoline-5-carboxylate (20 mg, 0.048 mmol) and hydrazine (3 ml) were added MeOH (20 ml) and the mixture was stirred room temperature for 3 h. The resulting mixture was evaporated under reduced pressure to 5 ml and then filtered; 5.6 mg of 5-fluoro-8-(4-fluorophenyl)-9-(1-methyl-1H-imidazol-2-yl)-8,9-dihydro-2H-pyrido[4,3,2-de]phthalazin-3(7H)-one was obtained. ¹H-NMR (400 MHz, CD₃OD) δ (ppm): 3.35 (s, 3H), 4.65 (d, 1H), 4.95 (d, 1H), 6.84 (s, 1H), 6.87-6.91 (m, 2H), 7.02 (t, 2H), 7.17-7.20 (m, 1H), 7.37-7.40 (m, 1H). LC-MS (ESI) m/z: 380 (M+1)⁺.

Example 65

8-(4-((Dimethylamino)methyl)phenyl)-9-(1-methyl-1H-imidazol-2-yl)-8,9-dihydro-2H-pyrido[4,3,2-de]phthalazin-3(7H)-one Example 65A Ethyl 2-(4-(diethoxymethyl)phenyl)-3-(1-methyl-1H-imidazol-2-yl)-4-oxo-1,2,3,4-tetrahydroquinoline-5-carboxylate A mixture of (E)-4-(4-(diethoxymethyl)benzylideneamino)isobenzofuran-1(3H)-one (678 mg, 2 mmol), 1-methyl-1H-imidazole-2-carbaldehyde (242 mg, 2.2 mmol), sodium ethanolate (544 mg, 8.0 mmol), and ethyl propionate (50 ml) was stirred at room temperature for 3 hr. Then the resulting mixture was evaporated under reduced pressure and extracted with ethyl acetate (100 mL×4) and concentrated. The crude product was purified by column chromatography (silica gel, petroleum ether:ethyl acetate=20:1 to 1.5:1) to give ethyl 2-(4-(diethoxymethyl)phenyl)-3-(1-methyl-1H-imidazol-2-yl)-4-oxo-1,2,3,4-tetrahydroquinoline-5-carboxylate as solid (50 mg, yield 5%). LC-MS (ESI) m/z: 478 (M+1)⁺.

Example 65B 8-(4-(Diethoxymethyl)phenyl)-9-(1-methyl-1H-imidazol-2-yl)-8,9-dihydro-2H-pyrido[4,3,2-de]phthalazin-3(7H)-one A mixture of ethyl 2-(4-(diethoxymethyl)phenyl)-3-(1-methyl-1H-imidazol-2-yl)-4-oxo-1,2,3,4-tetrahydroquinoline-5-carboxylate (490 mg, 1.03 mmol), methanol (20 mL) and hydrazine monohydrate (2 mL) was stirred under 25° C. for 3 hr. The resulting mixture was evaporated under reduced pressure to 10 ml and then filtered, 250 mg of 8-(4-(diethoxymethyl)phenyl)-9-(1-methyl-1H-imidazol-2-yl)-8,9-dihydro-2H-pyrido[4,3,2-de]phthalazin-3(7H)-one as a solid was obtained, yield 55%. LC-MS (ESI) m/z: 446 (M+1)⁺.

Example 65C 4-(9-(1-Methyl-1H-imidazol-2-yl)-3-oxo-3,7,8,9-tetrahydro-2H-pyrido[4,3,2-de]phthalazin-8-yl)benzaldehyde A mixture of 8-(4-(Diethoxymethyl)phenyl)-9-(1-methyl-1H-imidazol-2-yl)-8,9-dihydro-2H-pyrido[4,3,2-de]phthalazin-3(7H)-one (50 mg, 0.11 mmol) and 2 ml of hydrochloric acid (3 N) was stirred at room temperature for 2 hr. The reaction mixture was neutralized by K$_2$CO$_3$ to pH=7 and then filtered, 29 mg of 4-(9-(1-methyl-1H-imidazol-2-yl)-3-oxo-3,7,8,9-tetrahydro-2H-pyrido[4,3,2-de]phthalazin-8-yl)benzaldehyde was obtained, yield 70%. LC-MS (ESI) m/z: 372 (M+1)$^+$.

Example 65D 8-(4-((dimethylamino)methyl)phenyl)-9-(1-methyl-1H-imidazol-2-yl)-8,9-dihydro-2H-pyrido[4,3,2-de]phthalazin-3(7H)-one A mixture of 4-(9-(1-methyl-1H-imidazol-2-yl)-3-oxo-3,7,8,9-tetrahydro-2H-pyrido[4,3,2-de]phthalazin-8-yl)benzaldehyde (80 mg, 0.22 mmol), acetic acid (60 uL) and 27% dimethylamine alcohol solution (2.5 mL, 15 mmol) in acetonitrile (7 mL) was stirred at room temperature for 4h. Then the mixture was cooled to 0° C. NaBH$_3$CN (36 mg, 0.67 mmol) was added. After the addition, the mixture was stirred at room temperature for 4 hr. Methanol was removed under reduced pressure. The residue was washed with ethyl acetate and filtered. The filtrate was concentrated to give 8-(4-((dimethylamino)methyl)phenyl)-9-(1-methyl-1H-imidazol-2-yl)-8,9-dihydro-2H-pyrido[4,3,2-de]phthalazin-3(7H)-one (30 mg, yield 34%) as a white solid. $^1$H-NMR: (400 MHz, DMSO-d$_6$) δ (ppm): 2.11 (s, 6H), 3.36 (s, 2H), 3.37 (s, 3H), 4.65 (d, J=10.4 Hz, 1H), 4.92 (d, J=10.4 Hz, 1H), 6.76 (s, 1H), 6.89 (s, 1H), 7.20 (d, J=7.6 Hz, 3H), 7.35 (d, J=8.0 Hz, 2H), 7.43 (d, J=6.8 Hz, 1H), 7.62 (t, J=7.8 Hz, 1H); LC-MS (ESI) m/z: 401 (M+1)$^+$.

Example 66

9-(1-isopropyl-1H-imidazol-5-yl)-8-phenyl-8,9-dihydro-2H-pyrido[4,3,2-de]phthalazin-3(7H)-one

Example 66A

Ethyl 3-(1-isopropyl-1H-imidazol-5-yl)-4-oxo-2-phenyl-1,2,3,4-tetrahydroquinoline-5-carboxylate A mixture of 1H-imidazole-5-carbaldehyde (800 mg, 8.3 mmol), 2-iodopropane (1.7 g, 10 mmol) and potassium carbonate (1.4 g) in DMF (30 mL) was heated to 50° C. overnight. The mixture was evaporated under reduced pressure, and then extracted with ethyl acetate (100 mL×4). The combined organic layers were dried over anhydrous sodium sulfate, concentrated to give 1-isopropyl-1H-imidazole-5-carbaldehyde (1.1 g), LC-MS (ESI) m/z: 139 (M+1)$^+$. This compound (1.1 g, 8.0 mmol) and (E)-4-(benzylideneamino)isobenzofuran-1(3H)-one (1.7 g, 7.2 mmol) were added in ethyl propionate (50 mL) then sodium ethoxide was added under 0° C. The mixture was stirred overnight at room temperature. The mixture was concentrated and the residue was extracted with ethyl acetate (100 mL×4). The organic layer dried over anhydrous sodium sulfate, purified by chromatography (silica gel, petroleum ether/ethyl acetate=10:1 to 1:1) to give ethyl 3-(1-isopropyl-1H-imidazol-5-yl)-4-oxo-2-phenyl-1,2,3,4-tetrahydroquinoline-5-carboxylate (770 mg, yield 30%). LC-MS (ESI) m/z: 404 (M+1)$^+$.

Example 66B 9-(1-isopropyl-1H-imidazol-5-yl)-8-phenyl-8,9-dihydro-2H-pyrido[4,3,2-de]phthalazin-3(7H)-one A suspension of ethyl 3-(1-isopropyl-1H-imidazol-5-yl)-4-oxo-2-phenyl-1,2,3,4-tetrahydroquinoline-5-carboxylate (770 mg, 1.9 mmol) and hydrazine monohydrate (6 ml, 85%) were added in methanol (10 mL) and stirred at 50° C. overnight. The mixture was filtered, and the white solid was washed with methanol and dried to give 9-(1-isopropyl-1H-imidazol-5-yl)-8-phenyl-8,9-dihydro-2H-pyrido[4,3,2-de]phthalazin-3(7H)-one (90 mg, yield 13%). $^1$H-NMR (400 MHz, DMSO-d6) δ (ppm): 0.82-0.84 (d, J=6.8 Hz, 3H), 1.27-1.29 (d, J=6.4 Hz, 3H), 3.30-3.33 (t, J=6.6 Hz, 1H), 4.67-4.70 (d, J=11.2 Hz, 1H), 4.92-4.95 (d, J=11.2 Hz, 1H), 6.80 (s, 1H), 7.01 (s, 1H), 7.16-7.18 (s, 1H), 7.24-7.28 (m, 3H), 7.31 (s, 1H), 7.36-7.39 (m, 3H), 7.55-7.59 (m, 1H); LC-MS (ESI) m/z: 372 (M+1)$^+$.

Example 67

9-(4-Methyl-1H-imidazol-2-yl)-8-phenyl-8,9-dihydro-2H-pyrido[4,3,2-de]phthalazin-3(7H)-one

Example 67A

1-Benzyl-4-methyl-1H-imidazole-2-carbaldehyde

To a solution of 4-methyl-1H-imidazole (1 g, 5.8 mmol) in 6 mL THF cooled to −50° C. was added n-BuLi (2.9 mL, 625 mmol). The mixture was stirred at −50° C. 40° C. for 2h. Then cooled to −78° C. and added in DMF (0.87 mL) drop-wise. After addition the ice bath was removed, and the mixture was stirred at room temperature 30 min. The resulting mixture was evaporated under reduced pressure to 10 mL and then filtered; the crude product was purified by column chromatography to obtain 1-benzyl-4-methyl-1H-imidazole-2-carbaldehyde (450 mg, yield 38%). LC-MS (ESI) m/z: 201 (M+1)$^+$.

Example 67B

Methyl 3-(1-benzyl-4-methyl-1H-imidazol-2-yl)-4-oxo-2-phenyl-1,2,3,4-tetrahydroquinoline-5-carboxylate A mixture of 1-benzyl-4-methyl-1H-imidazole-2-carbaldehyde (450 mg, 2.25 mmol), (E)-4-(benzylideneamino)isobenzofuran-1(3H)-one (640 mg, 2.7 mmol), sodium methanolate (207 mg, 9 mmol) and ethyl propionate (25 mL) were stirred at room temperature overnight. Then the resulting mixture was evaporated under reduced pressure and extracted with ethyl acetate (4×100 mL) and concentrated to give methyl 3-(1-benzyl-4-methyl-1H-imidazol-2-yl)-4-oxo-2-phenyl-1,2,3,4-tetrahydroquinoline-5-carboxylate (250 mg, yield 25%). LC-MS (ESI) m/z: 438 (M+1)$^+$.

Example 67C 9-(1-Benzyl-4-methyl-1H-imidazol-2-yl)-8-phenyl-8,9-dihydro-2H-pyrido[4,3,2-de]phthalazin-3(7H)-one A mixture of methyl 3-(1-benzyl-4-methyl-1H-imidazol-2-yl)-4-oxo-2-phenyl-1,2,3,4-tetrahydroquinoline-5-carboxylate (250 mg, 0.57 mmol) and hydrazine monohydrate (3 mL) was stirred room temperature for 5 h. The resulting mixture was evaporated under reduced pressure to 15 ml and then filtered; the filtrate was concentrated to give 9-(1-benzyl-4-methyl-1H-imidazol-2-yl)-8-phenyl-8,9-dihydro-2H-pyrido[4,3,2-de]phthalazin-3(7H)-one as a white solid (40 mg, yield 16%). LC-MS (ESI) m/z: 434 (M+1)$^+$.

Example 67D 9-(4-Methyl-1H-imidazol-2-yl)-8-phenyl-8,9-dihydro-2H-pyrido[4,3,2-de]phthalazin-3(7H)-one A mixture of 9-(1-benzyl-4-methyl-1H-imidazol-2-yl)-8-phenyl-8,9-dihydro-2H-pyrido[4,3,2-de]phthalazin-3(7H)-one (40 mg, 0.09 mmol) and palladium hydroxide on carbon catalyst (40 mg, 20% wt) in anhydrous methanol (15 mL) was purged with hydrogen (1 bar) at room temperature for 12 hr. The mixture was filtered and the filtrate was concentrated to give crude product, which was purified by pre-HPLC to give 9-(4-methyl-1H-imidazol-2-yl)-8-phenyl-8,9-dihydro-2H-pyrido[4,3,2-de]phthalazin-3(7H)-one (27 mg, yield 87%). $^1$H-NMR (400 MHz, CD$_3$OD) δ (ppm): 2.22 (dd, 3H), 4.77-4.86 (m, 2H), 7.06 (s, 1H), 7.20 (d, 1H), 7.36 (t, 5H), 7.55 (d, 1H), 7.62 (t, 1H); LC-MS (ESI) m/z: 344 (M+1)$^+$.

Example 68

8-Phenyl-9-(thiazol-5-yl)-8,9-dihydro-2H-pyrido[4,3,2-de]phthalazin-3(7H)-one

Example 68A

Methyl 4-oxo-2-phenyl-3-(thiazol-5-yl)-1,2,3,4-tetrahydroquinoline-5-carboxylate A mixture of thiazole-5-carbaldehyde (500 mg, 4 mmol), (E)-4-(benzylideneamino)isobenzofuran-1(3H)-one (960 mg, 4 mmol), sodium methanolate (375 mg, 16.1 mmol) and ethyl propionate (30 mL) were stirred at room temperature overnight. Then the resulting mixture was evaporated under reduced pressure and extracted with ethyl acetate (4×100 mL) and concentrated. The crude product was purified by column chromatography (silica gel, petroleum ether:ethyl acetate 10:1 to 1:1) to give methyl 4-oxo-2-phenyl-3-(thiazol-5-yl)-1,2,3,4-tetrahydroquinoline-5-carboxylate (110 mg, yield 7%). LC-MS (ESI) m/z: 379 (M+1)$^+$.

Example 68B

8-Phenyl-9-(thiazol-5-yl)-8,9-dihydro-2H-pyrido[4,3,2-de]phthalazin-3(7H)-one

Methyl 4-oxo-2-phenyl-3-(thiazol-5-yl)-1,2,3,4-tetrahydroquinoline-5-carboxylate (110 mg, 0.29 mmol) and hydrazine monohydrate (2 mL) were added to methanol (10 mL) and the mixture was stirred room temperature for 4 h. The resulting mixture was evaporated under reduced pressure to 10 mL and then filtered; the filtrate was concentrated to give 8-phenyl-9-(thiazol-5-yl)-8,9-dihydro-2H-pyrido[4,3,2-de]phthalazin-3(7H)-one (13 mg, yield 13%) as a white solid. $^1$H-NMR (400 MHz, CD$_3$OD) δ (ppm): 4.67 (d, 1H), 4.78 (d, 1H), 7.10-7.19 (m, 4H), 7.24 (t, 2H), 7.45-7.56 (m, 2H), 8.76 (s, 1H); LC-MS (ESI) m/z: 347 (M+1)$^+$.

Example 69

9-(Furan-3-yl)-8-phenyl-8,9-dihydro-2H-pyrido[4,3,2-de]phthalazin-3(7H)-one

Example 69A

Ethyl 3-(furan-3-yl)-4-oxo-2-phenyl-1,2,3,4-tetrahydroquinoline-5-carboxylate

A mixture of (E)-4-(benzylideneamino)isobenzofuran-1(3H)-one (948 mg, 4 mmol) and furan-3-carbaldehyde (422 mg, 4.4 mmol) in ethyl propionate (30 mL) was cooled to 0° C. Then a solution of sodium ethanoxide in ethanol [sodium (368 mg, 16 mmol) in ethanol (20 mL)] was added dropwise. After the addition, the mixture was stirred at room temperature for 2 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=10:1 to 1:1) to give ethyl 3-(furan-3-yl)-4-oxo-2-phenyl-1,2,3,4-tetrahydroquinoline-5-carboxylate (80 mg, yield: 5%). LC-MS (ESI) m/z: 362 (M+1)$^+$.

Example 69B 9-(Furan-3-yl)-8-phenyl-8,9-dihydro-2H-pyrido[4,3,2-de]phthalazin-3(7H)-one A mixture of ethyl 3-(furan-3-yl)-4-oxo-2-phenyl-1,2,3,4-tetrahydroquinoline-5-carboxylate (80 mg) in 85% hydrazine monohydrate (10 mL) and methanol (10 mL) was stirred at 45° C. overnight. Methanol was removed under reduced pressure. The crude product was purified by prep-HPLC to give 9-(furan-3-yl)-8-phenyl-8,9-dihydro-2H-pyrido[4,3,2-de]phthalazin-3(7H)-one (5 mg, yield 7%). $^1$H-NMR (400 MHz, CD$_3$OD) □□ δ (ppm): 4.19 (d, J=8.0 Hz, 1H), 4.67 (d, J=8.0 Hz, 1H), 6.26 (s, 1H), 7.07-7.21 (m, 7H), 7.30 (s, 1H), 7.27 (m, 1H), 7.41 (d, 1H), 7.51 (m, 1H); LC-MS (ESI) m/z: 330 (M+1)$^+$.

Example 70

8-(4-((4-Ethylpiperazin-1-yl)methyl)phenyl)-9-phenyl-8,9-dihydro-2H-pyrido[4,3,2-de]phthalazin-3(7H)-one To a stirred solution of 4-(3-oxo-9-phenyl-3,7,8,9-tetrahydro-2H-pyrido[4,3,2-de]phthalazin-8-yl)benzaldehyde (200 mg, 0.54 mmol) in dichloromethane (30 mL) was added acetic acid (1 mL) followed by the addition of 1-ethylpiperazine (121 mg, 1.63 mmol). After the addition, the mixture was stirred at room temperature overnight. Then the mixture was cooled to 0° C. NaBH(OAc)$_3$ (173 mg, 0.81 mmol) was added. After the addition, the mixture was stirred at this temperature for 12 hr. dichloromethane was removed under reduced pressure. The residue was washed with ethyl acetate/methanol (10/1) and filtered. The filtrate was concentrated to give the crude product. The crude product was purified by prep-HPLC to give 8-(4-((4-ethylpiperazin-1-yl)methyl)phenyl)-9-phenyl-8,9-dihydro-2H-pyrido[4,3,2-de]

phthalazin-3(7H)-one (135 mg, yield 47%) as white solid. $^1$H-NMR (400 MHz, DMSO-d6) δ (ppm): 1.22 (t, 3H), 2.36-2.44 (m, 1H), 2.74-3.11 (m, 8H), 4.01-4.10 (m, 3H), 4.33 (dd, 1H), 4.78 (dd, 1H), 7.13-7.31 (m, 10H), 7.37 (d, 1H), 7.47 (s, 1H), 7.58 (t, 3H); LC-MS (ESI) m/z: 452 (M+1)$^+$.

Example 71

9-Phenyl-8-(4-(piperazin-1-ylmethyl)phenyl)-8,9-dihydro-2H-pyrido[4,3,2-de]phthalazin-3(7H)-one A solution of 4-(3-oxo-9-phenyl-3,7,8,9-tetrahydro-2H-pyrido[4,3,2-de]phthalazin-8-yl)benzaldehyde (200 mg, 0.54 mmol) in dichloromethane (30 mL) was added acetic acid (196 mg, 3.24 mmol) and tert-butyl piperazine-1-carboxylate (304 mg, 1.63 mmol) at room temperature and stirred overnight. Then NaBH(OAc)$_3$ (173 mg, 0.81 mmol) was added to the mixture at 0° C., stirred for one day. The reaction mixture was quenched with aqueous sodium bicarbonate, extracted with dichloromethane. The combined organic layer was washed by brine, dried over anhydrous sodium sulfate, concentrated to give the crude product which was purified by flash chromatography to obtain a solution. To the solution obtained (concentrated to about 50 mL) was added conc. HCl (10 mL) at room temperature and stirred overnight. The mixture was extracted with ethyl acetate for three times, the aqueous phase was concentrated to give 9-phenyl-8-(4-(piperazin-1-ylmethyl)phenyl)-8,9-dihydro-2H-pyrido[4,3,2-de]phthalazin-3(7H)-one (127 mg, yield 46%). $^1$H NMR (400 MHz, DMSO-d6) δ (ppm): 3.47 (br s, 7H), 3.60 (m, 1H), 4.32 (s, 2H), 4.38 (d, 1H), 4.83 (d, 1H), 5.41 (br s, 2H), 7.19 (m, 6H), 7.24 (m, 3H), 7.55 (m, 4H), 9.87 (br s, 2H), 12.20 (s, 1H); LC-MS (ESI) m/z: 438 (M+1)$^+$.

Example 72

8-(1-Methyl-1H-imidazol-2-yl)-9-phenyl-8,9-dihydro-2H-pyrido[4,3,2-de]phthalazin-3(7H)-one Example 72A (E)-4-((l-Methyl-1H-imidazol-2-yl)methyleneamino)benzofuran-1(3H)-one To a stirred mixture of 1-methyl-1H-imidazole-2-carbaldehyde (2.5 g, 23 mmol) and anhydrous sodium sulfate (26.9 g, 190 mmol) in anhydrous dichloromethane (500 mL) was added 4-aminoisobenzofuran-1(3H)-one (2.8 g, 19 mmol) at 0° C. After the addition, the mixture was stirred at room temperature for 6 days. The mixture was filtered and the cake was washed with dichloromethane (50 mL×3). The filtrate was concentrated to give crude product. The crude product was washed with petroleum ether to give (E)-4-((1-methyl-1H-imidazol-2-yl)methyleneamino)benzofuran-1(3H)-one (5 g, yield 98%) as a white solid. LC-MS (ESI) m/z: 242 (M+1)$^+$.

Example 72B

Methyl 2-(1-methyl-1H-imidazol-2-yl)-4-oxo-3-phenyl-1,2,3,4-tetrahydroquinoline-5-carboxylate and ethyl 2-(1-methyl-1H-imidazol-2-yl)-4-oxo-3-phenyl-1,2,3,4-tetrahydroquinoline-5-carboxylate A mixture of (E)-4-((l-methyl-1H-imidazol-2-yl)methyleneamino)benzofuran-1(3H)-one (241 mg, 1 mmol) and benzaldehyde (116 mg, 1.1 mmol) in ethyl propionate (10 mL) was cooled to 0° C. Then a solution of sodium methoxide in methanol [sodium (92 mg, 4 mmol) in methanol (5 mL)] was added drop-wise. After the addition, the mixture was stirred at room temperature for 2 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give a crude product. The crude product was purified by chromatography (silica gel, petroleum ether/ethyl acetate=10:1 to 1:10) to give a mixture of methyl 2-(1-methyl-1H-imidazol-2-yl)-4-oxo-3-phenyl-1,2,3,4-tetrahydroquinoline-5-carboxylate and ethyl 2-(1-methyl-1H-imidazol-2-yl)-4-oxo-3-phenyl-1,2,3,4-tetrahydroquinoline-5-carboxylate (87 mg, yield: 24%). LC-MS (ESI) m/z: 362 (M+1)$^+$, 376 (M+1)$^+$.

Example 72C 8-(1-Methyl-1H-imidazol-2-yl)-9-phenyl-8,9-dihydro-2H-pyrido[4,3,2-de]phthalazin-3(7H)-one A mixture of methyl 2-(1-methyl-1H-imidazol-2-yl)-4-oxo-3-phenyl-1,2,3,4-tetrahydroquinoline-5-carboxylate and ethyl 2-(1-methyl-1H-imidazol-2-yl)-4-oxo-3-phenyl-1,2,3,4-tetrahydroquinoline-5-carboxylate (87 mg) in 85% hydrazine monohydrate (4 mL) and methanol (10 mL) was stirred at room temperature for overnight. The mixture was extracted with ethyl acetate (50 mL×3). The combined organic layers were washed with brine, dried over anhydrous sodium sulfate, and concentrated to give the crude. The crude product was purified by pre-HPLC to give 8-(1-methyl-1H-imidazol-2-yl)-9-phenyl-8,9-dihydro-2H-pyrido[4,3,2-de]phthalazin-3(7H)-one (34 mg, yield 42%) as a yellow solid. $^1$H-NMR (400 MHz, CD$_3$OD) δ (ppm): 3.41 (s, 3H), 4.49 (d, 1H), 5.35 (d, 1H), 7.18-7.20 (m, 2H), 7.26-7.29 (m, 1H), 7.33-7.35 (m, 3H), 7.40 (d, 1H), 7.61 (d, 1H), 7.71-7.75 (m, 2H); LC-MS (ESI) m/z: 344 (M+1)$^+$.

Example 73

9-(1-Methyl-1H-imidazol-2-yl)-8-phenyl-8,9-dihydro-2H-pyrido[4,3,2-de]phthalazin-3(7H)-one Example 73A Ethyl 3-(1-methyl-1H-imidazol-2-yl)-4-oxo-2-phenyl-1,2,3,4-tetrahydroquinoline-5-carboxylate A mixture of (E)-4-(benzylideneamino)isobenzofuran-1(3H)-one (500 mg, 2.1 mmol) and 1-methyl-1H-imidazole-2-carbaldehyde (255 mg, 2.3 mmol) in ethyl propionate (20 mL) was cooled to 0° C. Then a solution of sodium ethoxide in ethanol [sodium (194 mg, 8.4 mmol) in ethanol (10 mL)] was added drop-wise. After the addition, the mixture was stirred at room temperature for 2.5 hr. The mixture was quenched with water (20 mL) and solvent was removed in vacuum. The residue was dissolved in water, and filtered; the cake was washed by water, then ethyl acetate to obtain ethyl 3-(1-methyl-1H-imidazol-2-yl)-4-oxo-2-phenyl-1,2,3,4-tetrahydroquinoline-5-carboxylate as a yellow solid. The solid was dried in vacuum at 50° C. (140 mg, yield 18%). $^1$H-NMR (400 MHz, DMSO-d6) δ (ppm): 1.18-1.21 (t, J=7.2 Hz, 3H), 3.31 (s, 3H), 4.16-4.19 (m, 2H), 4.56-4.59 (d, J=13.2 Hz, 1H), 5.14-5.17 (d, J=13.2 Hz, 1H), 6.54-6.56 (d, J=7.2 Hz, 1H), 6.72 (s, 1H), 6.86 (s, 1H), 6.98-6.99 (d, J=4.8

Hz, 1H), 7.24-7.29 (m, 3H), 7.34-7.38 (t, J=8.0 Hz, 1H), 7.42-7.44 (d, J=7.2 Hz, 2H), 7.49 (s, 1H); LC-MS (ESI) m/z: 376 (M+1)$^+$.

Example 73B 9-(1-Methyl-1H-imidazol-2-yl)-8-phenyl-8,9-dihydro-2H-pyrido[4,3,2-de]phthalazin-3(7H)-one A mixture of ethyl 3-(1-methyl-1H-imidazol-2-yl)-4-oxo-2-phenyl-1,2,3,4-tetrahydroquinoline-5-carboxylate (140 mg) in 85% hydrazine monohydrate (3 mL) and methanol (5 mL) was stirred at room temperature for 2 days. The resulting mixture was filtered and the residue was washed with water (20 mL) and methanol (5 mL) to obtain a white solid. The solid was dried in vacuum at 50° C. to obtain 9-(1-methyl-1H-imidazol-2-yl)-8-phenyl-8,9-dihydro-2H-pyrido[4,3,2-de]phthalazin-3(7H)-one (95 mg, yield 74%). $^1$H-NMR (400 MHz, DMSO-d6) □δ (ppm): 3.40 (s, 3H), 4.64-4.67 (d, J=10.8 Hz, 1H), 4.92-4.94 (d, J=10.4 Hz, 1H), 6.72 (s, 1H), 6.87 (s, 1H), 7.15-7.17 (d, J=8.4 Hz, 2H), 7.26-7.30 (m, 3H), 7.38 (s, 3H), 7.55-7.59 (t, J=7.6 Hz, 1H), 12.15 (s, 1H); LC-MS (ESI) m/z: 344 (M+1)$^+$.

Example 74

8,9-Bis(1-methyl-1H-imidazol-2-yl)-8,9-dihydro-2H-pyrido[4,3,2-de]phthalazin-3(7H)-one Example 74A Ethyl 2,3-bis(1-methyl-1H-imidazol-2-yl)-4-oxo-1,2,3,4-tetrahydroquinoline-5-carboxylate A mixture of 4-aminoisobenzofuran-1(3H)-one (298 mg, 2 mmol) and 1-methyl-1H-imidazole-2-carbaldehyde (440 mg, 4 mmol) in ethyl propionate (20 mL) was cooled to 0° C. Then a solution of sodium ethoxide in ethanol [sodium (184 mg, 8 mmol) in ethanol (10 mL)] was added drop-wise. After the addition, the mixture was stirred at room temperature for 3 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=5:1 to 1, ethyl acetate:methanol=50:1 to 25:1, ammonia hydrate 1 mL) to give ethyl 2,3-bis(1-methyl-1H-imidazol-2-yl)-4-oxo-1,2,3,4-tetrahydroquinoline-5-carboxylate (120 mg, yield 16%). LC-MS (ESI) m/z: 380 (M+1)$^+$.

Example 74B 8,9-bis(1-methyl-1H-imidazol-2-yl)-8,9-dihydro-2H-pyrido[4,3,2-de]phthalazin-3(7H)-one A mixture of ethyl 2,3-bis(1-methyl-1H-imidazol-2-yl)-4-oxo-1,2,3,4-tetrahydroquinoline-5-carboxylate (120 mg) in 85% hydrazine monohydrate (2 mL) and methanol (3 mL) was stirred at room temperature for 3.5 h. Evaporated the solvent and methanol (1 mL) was added, filtered and washed the cake by methanol (2 mL) to obtain a white solid. The solid was dried in vacuum at 50° C. to obtain 8,9-bis(1-methyl-1H-imidazol-2-yl)-8,9-dihydro-2H-pyrido[4,3,2-de]phthalazin-3(7H)-one (45 mg, yield 41%). $^1$H-NMR (400 MHz, CD$_3$OD) δ (ppm): 3.46 (s, 3H), 3.49 (s, 3H), 4.78-4.81 (d, J=12.0 Hz, 1H), 5.08-5.11 (d, J=12.0 Hz, 1H), 6.69 (s, 1H), 6.76-6.79 (m, 3H), 6.99-7.02 (d, J=7.6 Hz, 1H), 7.42-7.49 (m, 2H); LC-MS (ESI) m/z: 348 (M+1)$^+$.

Example 75

9-(1H-imidazol-2-yl)-8-phenyl-8,9-dihydro-2H-pyrido[4,3,2-de]phthalazin-3(7H)-one Example 75A 9-(1-Benzyl-1H-imidazol-2-yl)-8-phenyl-8,9-dihydro-2H-pyrido[4,3,2-de]phthalazin-3(7H)-one Methyl 3-(1-benzyl-1H-imidazol-2-yl)-4-oxo-2-phenyl-1,2,3,4-tetrahydroquinoline-5-carboxylate (3.7 g, 8.46 mmol) in hydrazine monohydrate (25 mL) and methanol (100 mL) was stirred at room temperature for 5 h. The resulting mixture was filtered to give 9-(1-benzyl-1H-imidazol-2-yl)-8-phenyl-8,9-dihydro-2H-pyrido[4,3,2-de]phthalazin-3(7H)-one as a white solid (950 mg, yield 27%). $^1$H-NMR (400 MHz, DMSO-d6) δ (ppm): 4.61-4.64 (d, J=11.2 Hz, 1H), 4.99-5.12 (m, 1H), 6.83-6.89 (m, 4H), 7.14-7.28 (m, 11H), 7.36-7.38 (d, J=7.6 Hz, 1H), 7.54-7.58 (t, J=8.0 Hz, 7H), 12.20 (s, 1H). LC-MS (ESI) m/z: 420 (M+1)$^+$.

Example 75B 9-(1H-imidazol-2-yl)-8-phenyl-8,9-dihydro-2H-pyrido[4,3,2-de]phthalazin-3(7H)-one A mixture of 9-(1-benzyl-1H-imidazol-2-yl)-8-phenyl-8,9-dihydro-2H-pyrido[4,3,2-de]phthalazin-3(7H)-one (200 mg, 0.48 mmol), 20% Pd(OH)$_2$/C catalyst (100 mg) in methanol (15 mL) was purged with 1 atm hydrogen and stirred at 40° C. over overnight. Then the mixture solution was filtered and the filtrate was evaporated under reduced pressure. The residue was washed with methanol to obtain 9-(1H-imidazol-2-yl)-8-phenyl-8,9-dihydro-2H-pyrido[4,3,2-de]phthalazin-3(7H)-one as a light yellow solid (114 mg, yield 72%). $^1$H-NMR (400 MHz, DMSO-d6) δ: 4.41-4.43 (d, J=8.0 Hz, 1H), 4.98-5.00 (d, J=8.8 Hz, 1H), 6.68-6.73 (m, 1H), 6.86-6.97 (m, 1H), 7.12-7.14 (d, J=8.0 Hz, 1H), 7.20-7.37 (m, 7H), 7.54-7.58 (t, J=8.0 Hz, 1H), 11.77 (s, 1H), 12.19 (s, 1H); LC-MS (ESI) m/z: 330 (M+1)$^+$.

Example 76

9-(1-Ethyl-1H-imidazol-2-yl)-8-phenyl-8,9-dihydro-2H-pyrido[4,3,2-de]phthalazin-3(7H)-one Example 76A 1-Ethyl-1H-imidazole-2-carbaldehyde To a suspension of 1H-imidazole-2-carbaldehyde (480 mg, 5 mmol) and potassium carbonate (936 mg, 6 mmol) in N,N-dimethylformamide (7 mL) was added iodoethane (829 mg, 6 mmol) and the mixture was heated at 50° C. for 5 hrs. Solvent was removed under reduced pressure. The residue was partitioned between water (30 mL) and ethyl acetate (30 mL). The aqueous layer was extracted with ethyl acetate (20 mL×3). The combined organic layers were washed with brine, dried over anhydrous sodium sulfate, and concentrated to give 1-ethyl-1H-imidazole-2-carbaldehyde as light yellow oil (520 mg, yield 84%). ¹HNMR (400 MHz, CDCl₃) δ (ppm): 1.42-1.46 (t, J=7.2 Hz, 3H), 4.42-4.47 (q, 2H), 7.19 (s, 1H), 7.29 (s, 1H), 9.82 (s, 1H). LC-MS (ESI) m/z: 125 (M+1)⁺.

Example 76B

Methyl 3-(1-ethyl-1H-imidazol-2-yl)-4-oxo-2-phenyl-1,2,3,4-tetrahydroquinoline-5-carboxylate To 1-ethyl-1H-imidazole-2-carbaldehyde (520 mg, 4.19 mmol), (E)-4-(benzylideneamino) isobenzofuran-1(3H)-one (994 mg, 4.19 mmol), sodium methanolate (385 mg, 16.8 mmol) and ethyl propionate (15 mL) were added and the mixture was stirred at room temperature overnight. Then the resulting mixture was evaporated under reduced pressure and extracted with ethyl acetate (100 mL×4) and concentrated. The crude product was purified by column chromatography (silica gel, petroleum ether/ethyl acetate=20:1 to 5:1). 190 mg of methyl 3-(1-ethyl-1H-imidazol-2-yl)-4-oxo-2-phenyl-1,2,3,4-tetrahydroquinoline-5-carboxylate was obtained. LC-MS (ESI) m/z: 390 (M+1)⁺.

Example 76C 9-(1-Ethyl-1H-imidazol-2-yl)-8-phenyl-8,9-dihydro-2H-pyrido[4,3,2-de]phthalazin-3(7H)-one Methyl 3-(1-ethyl-1H-imidazol-2-yl)-4-oxo-2-phenyl-1,2,3,4-tetrahydroquinoline-5-carboxylate (190 mg, 0.49 mmol) and hydrazine monohydrate (2 mL) were added to methanol (15 mL) and the mixture was stirred room temperature for 3 hrs. Methanol was evaporated and then filtered. The filtrate was concentrated to give 9-(1-ethyl-1H-imidazol-2-yl)-8-phenyl-8,9-dihydro-2H-pyrido[4,3,2-de]phthalazin-3(7H)-one as a white solid (50 mg, yield 28%). ¹H-NMR (400 MHz, DMSO-d6) δ (ppm): ☐0.96 (t, 3H), 3.74-3.79 (m, 2H), 4.61 (d, 1H), 4.95 (d, 1H), 6.78 (dd, 1H), 6.91 (dd, 1H), 7.16 (d, 1H), 7.23-7.31 (m, 4H), 7.37 (s, 3H), 7.57 (t, 1H). LC-MS (ESI) m/z: 358 (M+1)⁺.

Example 77

8-Phenyl-9-(1-propyl-1H-imidazol-2-yl)-8,9-dihydro-2H-pyrido[4,3,2-de]phthalazin-3(7H)-one Example 77A 1-propyl-1H-imidazole-2-carbaldehyde 1H-imidazole-2-carbaldehyde (800 mg, 8.3 mmol), 1-iodopropane (1.7 g, 10 mmol) and potassium carbonate (1.4 g) were added in DMF (30 mL) and the mixture was heated to 50° C. overnight. Then the mixture was evaporated under reduced pressure, and extracted with ethyl acetate (100 mL×4). The combined organic layers were dried over anhydrous sodium sulfate, concentrated to give 1-propyl-1H-imidazole-2-carbaldehyde (1.1 g). LC-MS (ESI) m/z 139 (M+1)⁺.

Example 77B

Ethyl 4-oxo-2-phenyl-3-(1-propyl-1H-imidazol-2-yl)-1,2,3,4-tetrahydroquinoline-5-carboxylate To the mixture of 1-propyl-1H-imidazole-2-carbaldehyde (1.1 g, 8.0 mmol) and (E)-4-(benzylideneamino) isobenzofuran-1(3H)-one (1.7 g, 7.2 mmol) were added in ethyl propionate (50 mL) and then sodium methoxide was added under 0° C. The mixture was stirred overnight at room temperature. The mixture was concentrated and the residue was extracted with ethyl acetate (100 mL×4). The organic layer dried over anhydrous sodium sulfate, purified by chromatography (silica gel, petroleum ether/ethyl acetate=10:1 to 1:1) to give ethyl 4-oxo-2-phenyl-3-(1-propyl-1H-imidazol-2-yl)-1,2,3,4-tetrahydroquinoline-5-carboxylate (770 mg, yield 30%). LC-MS (ESI) m/z: 404 (M+1)⁺.

Example 77C

8-Phenyl-9-(1-propyl-1H-imidazol-2-yl)-8,9-dihydro-2H-pyrido[4,3,2-de]phthalazin-3(7H)-one A suspension of ethyl 4-oxo-2-phenyl-3-(1-propyl-1H-imidazol-2-yl)-1,2,3,4-tetrahydroquinoline-5-carboxylate (770 mg, 1.9 mmol) and hydrazine monohydrate (6 mL, 85%) were added in methanol (10 mL) and stirred at 50° C. overnight. The mixture was filtered, and the white solid was washed with methanol and dried in vacuum to obtain 8-phenyl-9-(1-propyl-1H-imidazol-2-yl)-8,9-dihydro-2H-pyrido[4,3,2-de]phthalazin-3(7H)-one (260 mg, yield 37%). ¹H-NMR (400 MHz, DMSO-d6) ☐☐δ (ppm): 0.59-0.62 (t, J=7.4 Hz, 1H), 1.23-1.40 (m, 2H), 3.62-3.72 (m, 2H), 4.58-4.61 (d, J=11.2 Hz, 1H), 4.97-4.99 (d, J=11.2 Hz, 1H), 6.79 (s, 1H), 6.89 (s, 1H), 7.16-7.59 (m, 8H), 12.15 (s, 1H); LC-MS (ESI) m/z: 372 (M+1)⁺.

Example 78

9-(1-Methyl-1H-imidazol-5-yl)-8-phenyl-8,9-dihydro-2H-pyrido[4,3,2-de]phthalazin-3(7H)-one Example 78A Ethyl 3-(1-methyl-1H-imidazol-5-yl)-4-oxo-2-phenyl-1,2,3,4-tetrahydroquinoline-5-carboxylate A mixture of (E)-4-(benzylideneamino) isobenzofuran-1(3H)-one (474 mg, 2 mmol) and 1-methyl-1H-imidazole-5-carbaldehyde (220 mg, 2 mmol) in ethyl propionate (20 mL) was cooled to 0° C. Then a solution of sodium ethoxide in ethanol [sodium (184 mg, 8 mmol) in ethanol (10 mL)] was added dropwise. After the addition, the mixture was stirred at room temperature for 3 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=5:1 to 3:7) to give ethyl 3-(1-methyl-1H-imidazol-5-yl)-4-oxo-2-phenyl-1,2,3,4-tetrahydroquinoline-5-carboxylate (170 mg, yield 23%). LC-MS (ESI) m/z: 376 (M+1)⁺.

Example 78B 9-(1-Methyl-1H-imidazol-5-yl)-8-phenyl-8,9-dihydro-2H-pyrido[4,3,2-de]phthalazin-3(7H)-one A mixture of ethyl 3-(1-methyl-1H-imidazol-5-yl)-4-oxo-2-phenyl-1,2,3,4-tetrahydroquinoline-5-carboxylate (170 mg) in 85% hydrazine monohydrate (3 mL) and methanol (3 mL) was stirred at room temperature for 5 h. Filtered and washed the cake by methanol (2 mL) to obtain a white solid. The solid was dried in vacuum at 50° C. to obtain 9-(1-methyl-1H-imidazol-5-yl)-8-phenyl-8,9-dihydro-2H-pyrido[4,3,2-de]phthalazin-3(7H)-one (70 mg, yield 46%). $^1$H-NMR (400 MHz, DMSO-d6) δ (ppm): 3.50 (s, 3H), 4.52-4.54 (d, J=9.2 Hz, 1H), 4.83-4.85 (d, J=9.2 Hz, 1H), 6.66 (s, 1H), 7.17-7.19 (d, J=7.6 Hz, 1H), 7.25-7.32 (m, 3H), 7.36-7.44 (m, 5H), 7.56-7.60 (t, J=8.0 Hz, 1H); LC-MS (ESI) m/z: 348 (M+1)$^+$.

Example 79

9-(3-((Diethylamino)methyl)phenyl)-8-(4-((diethylamino)methyl)phenyl)-8,9-dihydro-2H-pyrido[4,3,2-de]phthalazin-3(7H)-one A mixture of 4,4'-(3-oxo-3,7,8,9-tetrahydro-2H-pyrido[4,3,2-de]phthalazin-8,9-diyl)dibenzaldehyde (200 mg, 0.5 mmol) and diethylamine (146 mg, 2.0 mmol) in methanol (10 mL) was stirred at room temperature for 40 min. Then the mixture was cooled to 0° C. Sodium borohydride (56 mg, 1.5 mmol) was added. After the addition, the mixture was stirred at room temperature for 2 hr. Methanol was removed under reduced pressure. The residue was washed with ethyl acetate and filtered. The filtrate was concentrated to give the crude product. The crude product was purified by prep-HPLC to give 9-(3-((diethylamino)methyl)phenyl)-8-(4-((diethylamino)methyl)phenyl)-8,9-dihydro-2H-pyrido[4,3,2-de]phthalazin-3(7H)-one as a white solid (76 mg, yield 29%). $^1$H-NMR (400 MHz, CD$_3$OD) δ (ppm): 1.28-1.33 (m, 12H), 3.13-3.19 (m, 8H), 4.27 (s, 4H), 4.40-4.42 (d, J=7.6 Hz, 1H), 4.84-4.86 (d, J=7.6 Hz, 1H), 7.22-7.27 (m, 3H), 7.38-7.41 (m, 6H), 7.56-7.65 (m, 2H); LC-MS (ESI) m/z: 510 (M+1)$^+$.

Example 80

9-(3-((Methylpiperazin-1-yl) methyl)phenyl)-8-phenyl-8,9-dihydro-2H-pyrido[4,3,2-de]phthalazin-3(7H)-one To a stirred solution of 3-(3-oxo-8-phenyl-3,7,8,9-tetrahydro-2H-pyrido[4,3,2-de]phthalazin-9-yl)benzaldehyde (150 mg, 0.4 mmol) in dryness dichloromethane (10 mL) was added acetic acid followed by 1-methylpiperazine (121 mg, 1.2 mmol). After the addition, the mixture was stirred at room temperature for 1 h, Then the mixture was cooled to 0° C. Sodium borohydride (130 mg, 0.2 mmol) was added. After the addition, the mixture was stirred at this temperature for 3 hr. Dichloromethane was removed under reduced pressure. The residue was washed with ethyl acetate/methanol (10/1) and filtered. The filtrate was concentrated to give the crude product. The crude product was purified by pre-HPLC to give 9-(3-((4-methylpiperazin-1-yl) methyl) phenyl)-8-phenyl-8,9-dihydro-2H-pyrido[4,3,2-de]phthalazin-3(7H)-one as white solid (22 mg, yield 12%). $^1$H-NMR (400 MHz, CD$_3$OD) δ (ppm): 2.31 (s, 3H), 2.36-2.48 (m, 8H), 3.37-3.48 (dd, 2H), 4.30 (dd, 1H), 4.71 (dd, 1H), 7.01 (s, 1H), 7.05 (dd, 1H), 7.17-7.23 (m, 5H), 7.25-7.28 (m, 2H), 7.56 (dd, 1H), 7.61-7.65 (t, 1H); LC-MS (ESI) m/z: 452 (M+1)$^+$.

Example 81

8-(4-(4-(Cyclopropanecarbonyl) piperazine-1-carbonyl)phenyl)-9-phenyl-8,9-dihydro-2H-pyrido[4,3,2-de]phthalazin-3(7H)-one Example 81A Methyl 2-(4-(4-(cyclopropanecarbonyl) piperazine-1-carbonyl)phenyl)-4-oxo-3-phenyl-1,2,3,4-tetrahydroquinoline-5-carboxylate 4-Aminoisobenzofuran-1(3H)-one (372.5 mg, 2.5 mmol), 4-(4-(cyclopropanecarbonyl) piperazine-1-carbonyl) benzaldehyde (645 mg, 2.5 mmol) and 1 g of MgSO$_4$ were added into 40 mL of dichloromethane and stirred under reflux overnight, then the mixture was evaporated under reduced pressure and the residues was dried in vacuum. 385 mg of (E)-4-(4-(4-(cyclopropanecarbonyl) piperazine-1-carbonyl) benzylideneamino)isobenzofuran-1(3H)-one. A mixture of (E)-4-(4-(4-(cyclopropanecarbonyl) piperazine-1-carbonyl) benzylideneamino)isobenzofuran-1(3H)-one (385 mg, 0.92 mmol), benzaldehyde (97.9 mg, 0.97 mmol), sodium methanolate (199 mg, 3.68 mmol) and ethyl propionate (10 mL) was stirred at room temperature overnight. Then the resulting mixture was evaporated under reduced pressure and extracted with ethyl acetate (100 mL×4) and concentrated. The crude product was purified by column chromatography (silica gel, petroleum ether:ethyl acetate 20:1 to 5:1) to give 300 mg of methyl 2-(4-(4-(cyclopropanecarbonyl) piperazine-1-carbonyl)phenyl)-4-oxo-3-phenyl-1,2,3,4-tetrahydroquinoline-5-carboxylate. LC-MS (ESI) m/z: 538 (M+1)$^+$.

Example 81B 8-(4-(4-(Cyclopropanecarbonyl) piperazine-1-carbonyl)phenyl)-9-phenyl-8,9-dihydro-2H-pyrido[4,3,2-de]phthalazin-3(7H)-one A mixture of methyl 2-(4-(4-(cyclopropanecarbonyl) piperazine-1-carbonyl)phenyl)-4-oxo-3-phenyl-1,2,3,4-tetrahydroquinoline-5-carboxylate (300 mg, 0.55 mmol) and hydrazine monohydrate (3 mL) was stirred room temperature for 3 h. The resulting mixture was evaporated under reduced pressure to 10 mL and then filtered; the filtrate was concentrated to give the crude product. The crude product was purified by pre-HPLC to give 8-(4-(4-(cyclopropanecarbonyl) piperazine-1-carbonyl)phenyl)-9-phenyl-8,9-dihydro-2H-pyrido[4,3,2-de]phthalazin-3(7H)-one as a white solid (4 mg, yield 19%). $^1$H-NMR (400 MHz, DMSO-d6) δ (ppm): □0.71-0.74 (m, 4H), 1.97 (t, 1H), 3.46-3.76 (m, 8H), 4.36 (dd, 1H), 4.83 (dd, 1H), 7.13-7.23 (m, 6H), 7.30 (d, 2H), 7.38 (t, 3H), 7.47 (s, 1H), 7.59 (t, 1H), 12.17 (s, 1H); LC-MS (ESI) m/z: 520 (M+1)$^+$.

Example 82

9-Phenyl-8-(pyridin-4-yl)-8,9-dihydro-2H-pyrido[4,3,2-de]phthalazin-3(7H)-one

Example 82A

Ethyl 4-oxo-3-phenyl-2-(pyridin-4-yl)-1,2,3,4-tetrahydroquinoline-5-carboxylate

A mixture of (E)-4-(pyridin-4-ylmethyleneamino) isobenzofuran-1(3H)-one (1.71 g, 7.18 mmol) and benzaldehyde (837 mg, 7.9 mmol) in ethyl propionate (50 mL) was cooled to 0° C. Then a solution of sodium ethoxide in ethanol [sodium (660 mg, 28.7 mmol) in ethanol (35 mL)] was added drop-wise. After the addition, the mixture was stirred at room temperature for 2 hr. The mixture was quenched with water (20 mL) and solvent was removed in vacuum. The residue was dissolved in water, and then extracted with ethyl acetate (150 mL×4). The combined organic layers were washed with brine, dried over anhydrous sodium sulfate, and concentrated to give crude product. The crude product was purified by chromatography (silica gel, petroleum ether/ethyl acetate=5:1 to 1:1) to give ethyl 4-oxo-3-phenyl-2-(pyridin-4-yl)-1,2,3,4-tetrahydroquinoline-5-carboxylate (340 mg, yield 13%). LC-MS (ESI) m/z: 373 (M+1)$^+$.

Example 82B

9-Phenyl-8-(pyridin-4-yl)-8,9-dihydro-2H-pyrido[4,3,2-de]phthalazin-3(7H)-one

A mixture of ethyl 4-oxo-3-phenyl-2-(pyridin-4-yl)-1,2,3,4-tetrahydroquinoline-5-carboxylate (340 mg) in 85% hydrazine monohydrate (6 mL) and methanol (3 mL) was stirred at room temperature for 2 h. After the evaporation of the solvent, water was added. Filtered and washed the cake by water (5 mL) then ethyl acetate to obtain a white solid. The solid was dried in vacuum at 50° C. to obtain 9-phenyl-8-(pyridin-4-yl)-8,9-dihydro-2H-pyrido[4,3,2-de]phthalazin-3(7H)-one (150 mg, yield: 48%). $^1$H-NMR (400 MHz, DMSO-d6) □ δ (ppm): 4.38-4.40 (d, J=7.6 Hz, 1H), 4.84-7.86 (d, J=8.0 Hz, 1H), 7.15-7.25 (m, 6H), 7.30-7.31 (m, 2H), 7.39-7.41 (d, J=7.6 Hz, 1H), 7.51-7.52 (s, 1H), 7.59-7.62 (t, J=8.0 Hz, 1H), 8.43-8.44 (d, J=6.0 Hz, 2H) 12.19 (s, 1H); LC-MS (ESI) m/z: 341 (M+1)$^+$.

Example 83

9-Phenyl-8-(piperidin-4-yl)-8,9-dihydro-2H-pyrido[4,3,2-de]phthalazin-3(7H)-one

The mixture of 9-phenyl-8-(pyridin-4-yl)-8,9-dihydro-2H-pyrido[4,3,2-de]phthalazin-3(7H)-one (150 mg, 0.4 mmol), con.HCl (0.6 mL) and Platinum (IV) oxide monohydrate (40 mg) in methanol (30 mL) was purged with 50 atm of hydrogen at 50° C. for 18 h. Then the mixture was filtered. The solvent was removed in vacuum to obtain a crude oil which was purified by prep-HPLC to give 9-phenyl-8-(piperidin-4-yl)-8,9-dihydro-2H-pyrido[4,3,2-de]phthalazin-3(7H)-one (95 mg, yield 62%). $^1$H-NMR (400 MHz, DMSO-d6) δ (ppm): 1.24-1.41 (m, 1H), 1.49-1.59 (m, 1H), 1.69-1.78 (m, 2H), 1.98-2.01 (d, J=13.2 Hz, 1H), 2.67-2.86 (m, 2H), 3.22-3.31 (m, 3H), 4.18 (s, 1H), 7.05-7.08 (m, 3H), 7.14-7.21 (m, 2H), 7.24-7.28 (m, 2H), 7.31-7.33 (d, J=7.2 Hz, 1H), 7.52-7.56 (t, J=8.0 Hz, 1H), 8.19-8.24 (m, 1H), 8.54-8.56 (m, 1H), 12.30 (s, 1H); LC-MS (m/z) 347 (M+1)$^+$.

Example 84

9-Phenyl-8-(pyridin-2-yl)-8,9-dihydro-2H-pyrido[4,3,2-de]phthalazin-3(7H)-one

Example 84A

Methyl 4-oxo-3-phenyl-2-(pyridin-2-yl)-1,2,3,4-tetrahydroquinoline-5-carboxylate 4-Aminoisobenzofuran-1(3H)-one (600 mg, 4 mmol), picolinaldehyde (856 mg, 8 mmol) and 1 g of MgSO$_4$ were added into 40 mL of dichloromethane and the mixture was stirred under reflux overnight, then the mixture was evaporated under reduced pressure and the residues was dried in vacuum. 476 mg of (E)-4-(pyridin-2-ylmethyleneamino) isobenzofuran-1(3H)-one was obtained. A mixture of (E)-4-(pyridin-2-ylmethyleneamino) isobenzofuran-1(3H)-one (476 mg, 2 mmol), benzaldehyde (212 mg, 2 mmol), sodium methanolate (432 mg, 8 mmol) and ethyl propionate (40 mL) was stirred at room temperature overnight. Then the resulting mixture was evaporated under reduced pressure and extracted with ethyl acetate (100 mL×4) and concentrated. The crude product was purified by column chromatography (silica gel, petroleum ether:ethyl acetate 20:1 to 5:1) to give 30 mg of methyl 4-oxo-3-phenyl-2-(pyridin-2-yl)-1,2,3,4-tetrahydroquinoline-5-carboxylate; yield 5%. LC-MS (ESI) m/z: 459 (M+1)$^+$.

Example 84B

9-Phenyl-8-(pyridin-2-yl)-8,9-dihydro-2H-pyrido[4,3,2-de]phthalazin-3(7H)-one

A mixture of methyl 4-oxo-3-phenyl-2-(pyridin-2-yl)-1,2,3,4-tetrahydroquinoline-5-carboxylate (30 mg, 0.08 mmol) and hydrazine monohydrate (1 mL) was stirred at room temperature for 3 h. The resulting mixture was evaporated under reduced pressure to 10 mL and then filtered, 10 mg of 9-phenyl-8-(pyridin-2-yl)-8,9-dihydro-2H-pyrido[4,3,2-de]phthalazin-3(7H)-one was obtained, yield 37%. $^1$H-NMR (400 MHz, CDCl$_3$) δ (ppm): 4.60 (d, 1H), 4.86-4.88 (m, 1H), 5.21 (s, 1H), 6.96 (dd, 1H), 7.08-7.17 (m, 4H), 7.22-7.28 (m, 3H), 7.46-7.49 (m, 1H), 7.60 (t, 1H), 7.73 (dd, 1H), 8.59 (d, 1H), 9.77 (s, 1H); LC-MS (ESI) m/z: 341 (M+1)$^+$.

Example 85

8-(4-((4-Methylpiperazin-1-yl)methyl)phenyl)-9-phenyl-8,9-dihydro-2H-pyrido[4,3,2-de]phthalazin-3(7H)-one A mixture of 4-(3-oxo-9-phenyl-3,7,8,9-tetrahydro-2H-pyrido[4,3,2-de]phthalazin-8-yl)benzaldehyde (150 mg, 0.4 mmol), N-methyl-piperazine (123 mg, 1.2 mmol) and acetic acid (120 mg, 1.2 mmol) in methanol (50 mL) was stirred at room temperature for 60 min. Then the mixture was cooled to 0° C. Sodium triacetoxyborohydride (130 mg, 0.6 mmol) was added. After the addition, the mixture was stirred at room temperature for overnight. Methanol was removed under reduced pressure. The crude product was purified by pre-HPLC to give 8-(4-((4-methylpiperazin-1-yl)methyl)phenyl)-9-phenyl-8,9-dihydro-2H-pyrido[4,3,2-de]phthalazin-3(7H)-one (36 mg, yield 19%). $^1$H-NMR (400 MHz, CD$_3$OD) δ (ppm): 2.29 (s, 3H), 2.12-2.73 (br s, 8H), 3.47 (s, 2H), 4.30 (d, J=8.0 Hz, 1H), 4.74 (d, J=8.0 Hz, 1H), 7.08-7.10 (m, 2H), 7.18-7.21 (m, 6H), 7.23-7.25 (m, 2H), 7.55-7.57 (d, J=8.0 Hz, 1H), 7.62-7.64 (m, 1H). LC-MS (ESI) m/z: 452 (M+1)$^+$.

Example 86

8,9-Bis(4-fluorophenyl)-8,9-dihydro-2H-pyrido[4,3,2-de]phthalazin-3(7H)-one

Example 86A

Methyl 2-(4-(dimethoxymethyl)phenyl)-3-(4-fluorophenyl)-4-oxo-1,2,3,4-tetrahydroquinoline-5-carboxylate, ethyl 2-(4-(dimethoxymethyl)phenyl)-3-(4-fluorophenyl)-4-oxo-1,2,3,4-tetrahydroquinoline-5-carboxylate and methyl 2,3-bis-(4-fluorophenyl)-4-oxo-1,2,3,4-tetrahydroquinoline-5-carboxylate A mixture of (E)-4-(4-(diethoxymethyl)benzylideneamino)isobenzofuran-1(3H)-one (1.36 g, 4 mmol), 4-fluorobenzaldehyde (546 mg, 4.4 mmol), sodium methanolate (864 mg, 16 mmol) and ethyl propionate (25 ml) was stirred at room temperature overnight. Then the resulting mixture was evaporated under reduced pressure and extracted with ethyl acetate (100 mL×4) and concentrated. The crude product was purified by column chromatography (silica gel, petroleum ether:ethyl acetate=20:1 to 1:1) to give 440 mg of a mixture of methyl 2-(4-(dimethoxymethyl)phenyl)-3-(4-fluorophenyl)-4-oxo-1,2,3,4-tetrahydroquinoline-5-carboxylate, ethyl 2-(4-(dimethoxymethyl)phenyl)-3-(4-fluorophenyl)-4-oxo-1,2,3,4-tetrahydroquinoline-5-carboxylate and methyl 2,3-bis-(4-fluorophenyl)-4-oxo-1,2,3,4-tetrahydroquinoline-5-carboxylate.

Example 86B

8,9-Bis(4-fluorophenyl)-8,9-dihydro-2H-pyrido[4,3,2-de]phthalazin-3(7H)-one

A mixture of methyl 2-(4-(dimethoxymethyl)phenyl)-3-(4-fluorophenyl)-4-oxo-1,2,3,4-tetrahydroquinoline-5-carboxylate, ethyl 2-(4-(dimethoxymethyl)phenyl)-3-(4-fluorophenyl)-4-oxo-1,2,3,4-tetrahydroquinoline-5-carboxylate and methyl 2,3-bis-(4-fluorophenyl)-4-oxo-1,2,3,4-tetrahydroquinoline-5-carboxylate (440 mg) and hydrazine monohydrate (20 mL) was stirred under room temperature for overnight. The resulting mixture was evaporated under reduced pressure to 10 mL and then filtered, 400 mg of the crude products were obtained. To a solution of this crude products (400 mg) in dichloromethane was added trifluoroacetic acid (1 ml) at 0° C. The mixture was stirred at room temperature for 1 hr. Then the mixture was neutralized with potassium carbonate. The mixture was extracted with ethyl acetate (50 mL×3). The combined organic layers were washed with brine, dried over anhydrous sodium sulfate, and concentrated to give the crude. The crude product was purified by column chromatography (silica gel, petroleum ether:ethyl acetate 10:1 to 1:1) to give 4-(9-(4-fluorophenyl)-3-oxo-3,7,8,9-tetrahydro-2H-pyrido[4,3,2-de]phthalazin-8-yl)benzaldehyde (80 mg) and 8,9-bis(4-fluorophenyl)-8,9-dihydro-2H-pyrido[4,3,2-de]phthalazin-3(7H)-one (36 mg). 4-(9-(4-fluorophenyl)-3-oxo-3,7,8,9-tetrahydro-2H-pyrido[4,3,2-de]phthalazin-8-yl)benzaldehyde: LC-MS (ESI) m/z: 368 (M+1)$^+$. 8,9-bis(4-fluorophenyl)-8,9-dihydro-2H-pyrido[4,3,2-de]phthalazin-3(7H)-one: $^1$H-NMR (400 MHz, CD$_3$OD) δ (ppm): □4.29 (d, J=8.0 Hz, 1H), 4.70 (d, J=8.0 Hz, 1H), 6.92-7.00 (m, 4H), 7.08-7.10 (m, 2H), 7.20-7.20 (m, 1H), 7.28-7.32 (m, 2H), 7.59 (m, 1H), 7.63-7.67 (m, 1H). $^{19}$F-NMR (400 MHz, CD$_3$OD) δ (ppm): −116.77, −118.23; LC-MS (ESI) m/z: 376 (M+1)$^+$. solid.

Example 87

8-(4-((Dimethylamino)methyl)phenyl)-9-(4-fluorophenyl)-8,9-dihydro-2H-pyrido[4,3,2-de]phthalazin-3(7H)-one A mixture of 4-(9-(4-fluorophenyl)-3-oxo-3,7,8,9-tetrahydro-2H-pyrido[4,3,2-de]phthalazin-8-yl)benzaldehyde (80 mg, 0.21 mmol), dimethylamine (47 mg, 1.04 mmol) and acetic acid (62 mg, 1.04 mmol) in methanol (50 mL) was stirred at room temperature for 60 min. Then the mixture was cooled to 0° C. Sodium cyanoborohydride (20 mg, 0.3 mmol) was added. After the addition, the mixture was stirred at room temperature for overnight. Methanol was removed under reduced pressure. The crude product was purified by pre-HPLC to give 8-(4-((dimethylamino)methyl)phenyl)-9-(4-fluorophenyl)-8,9-dihydro-2H-pyrido[4,3,2-de]phthalazin-3(7H)-one (21 mg, yield 24%). $^1$H-NMR (400 MHz, CD$_3$OD) δ (ppm): 2.82 (s, 6H), 4.26 (s, 2H), 4.32 (d, J=8.0 Hz, 1H), 4.77 (d, J=8.0 Hz, 1H), 6.93-6.95 (m, 2H), 7.10-7.11 (m, 2H), 7.23 (m, 1H), 7.40-7.41 (m, 4H), 7.59 (d, J=8.0 Hz, 1H), 7.65 (t, J=8.0 Hz, 1H). $^{19}$F-NMR (400 MHz, CD$_3$OD) δ (ppm): −77.09, −118.00; LC-MS (ESI) m/z: 415 (M+1)$^+$.

Example 88

8-(4-Fluorophenyl)-9-(1-methyl-1H-imidazol-2-yl)-8,9-dihydro-2H-pyrido[4,3,2-de]phthalazin-3(7H)-one

Example 88A

Ethyl 2-(4-fluorophenyl)-3-(1-methyl-1H-imidazol-2-yl)-4-oxo-1,2,3,4-tetrahydroquinoline-5-carboxylate To a stirred mixture of 4-fluorobenzaldehyde (3 g, 20.4 mmol) and anhydrous sodium sulfate (29 g, 20.4 mmol) in anhydrous dichloromethane (200 mL) was added 4-aminoisobenzofuran-1(3H)-one (3.04 g, 24.5 mmol) at 0° C. After the addition, the mixture was stirred at room temperature for 6 days. The mixture was filtered and the cake was washed with dichloromethane (50 mL×3). The filtrate was concentrated to give crude product. The crude product was washed with petroleum ether to give (E)-4-(4-fluorobenzylideneamino)isobenzofuran-1(3H)-one (4.25 g, yield 81%); LC-MS (ESI) m/z: 256 (M+1)$^+$. A mixture of (E)-4-(4-fluorobenzylideneamino)isobenzofuran-1(3H)-one (2.53 g, 10 mmol) and 1-methyl-1H-imidazole-2-carbaldehyde (1.21 g, 11 mmol) in ethyl propionate (50 mL) was cooled to 0° C. Then a solution of sodium ethanoxide in ethanol [sodium (1 g, 44 mmol) in ethanol (30 mL)] was added drop-wise. After the addition, the mixture was stirred at room temperature for 2 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=10:1 to 1:10) to give ethyl 2-(4-fluorophenyl)-

3-(1-methyl-1H-imidazol-2-yl)-4-oxo-1,2,3,4-tetrahydroquinoline-5-carboxylate (210 mg, yield 5%). LC-MS (ESI) m/z: 394 (M+1)+.

Example 88B 8-(4-Fluorophenyl)-9-(1-methyl-1H-imidazol-2-yl)-8,9-dihydro-2H-pyrido[4,3,2-de]phthalazin-3(7H)-one A mixture of ethyl 2-(4-fluorophenyl)-3-(1-methyl-1H-imidazol-2-yl)-4-oxo-1,2,3,4-tetrahydroquinoline-5-carboxylate (210 mg) in 85% hydrazine monohydrate (10 mL) and methanol (10 mL) was stirred at 45° C. for overnight. Methanol was removed under reduced pressure. The mixture was filtered and washed with water to give 8-(4-fluorophenyl)-9-(1-methyl-1H-imidazol-2-yl)-8,9-dihydro-2H-pyrido[4,3,2-de]phthalazin-3(7H)-one 36 mg, yield 19%). $^1$H-NMR (400 MHz, DMSO-d6) □□δ (ppm): 3.42 (s, 3H), 4.66 (d, J=8.0 Hz, 1H), 4.95 (d, J=8.0 Hz, 1H), 6.72 (s, 1H), 6.89 (s, 1H), 7.11-7.17 (m, 3H), 7.30 (s, 1H), 7.40 (d, 1H), 7.43-7.44 (m, 2H), 7.58 (d, 1H), 12.17 (s, 1H); $^{19}$F-NMR (400 MHz, DMSO-d$_6$) δ (ppm): −114.58; LC-MS (ESI) m/z: 362 (M+1)+.

Example 89

8,9-Bis(3-((dimethylamino)methyl)phenyl)-8,9-dihydro-2H-pyrido[4,3,2-de]phthalazin-3(7H)-one

Example 89A 3-(Diethoxymethyl)benzaldehyde

A mixture of isophthalaldehyde (21.44 g, 160 mmol), ammonium chloride (0.34 g, 6.38 mmol) in anhydrous ethanol (23.2 g, 480 mmol) was cooled to 0° C., then triethyl orthoformate was added drop-wise. After the addition, the mixture was warmed to 40° C. and stirred for two days. The mixture was filtered and the filtrate was concentrated to give crude product. The crude product was purified by column chromatography (silica gel, petroleum ether/ethyl acetate=200:1 to 100:1) to give 3-(diethoxymethyl)benzaldehyde (25.4 g, yield 76%) as a colorless oil. $^1$H-NMR (400 MHz, CDCl$_3$) δ (ppm): 1.23-1.27 (m, 6H), 3.53-3.67 (m, 4H), 5.58 (s, 1H), 7.52-7.56 (t, J=7.6 Hz, 1H), 7.74-7.77 (dd, J$_1$=7.6 Hz, J$_{2=3.6}$ Hz, 1H), 8.00 (s, 1H), 10.04 (s, 1H); LC-MS (ESI) m/z: 209 (M+1)+.

Example 89B

Methyl 2,3-bis(3-(diethoxymethyl)phenyl)-4-oxo-1,2,3,4-tetrahydroquinoline-5-carboxylate and ethyl 2,3-bis(3-(diethoxymethyl)phenyl)-4-oxo-1,2,3,4-tetrahydroquinoline-5-carboxylate A mixture of 4-aminoisobenzofuran-1(3H)-one (298 mg, 2 mmol) and 3-(diethoxymethyl)benzaldehyde (0.83 g, 4 mmol) in ethyl propionate (15 mL) was cooled to 0° C. Then a solution of sodium methoxide in methanol [sodium (184 mg, 8 mmol) in methanol (15 mL)] was added drop-wise. After the addition, the mixture was stirred at 25° C. for 18 hr. The mixture was quenched with water (10 mL) and solvent was removed in vacuum. The residue was dissolved in water, and then extracted with ethyl acetate (50 mL×3). The combined organic layers were washed with brine, dried over anhydrous sodium sulfate, and concentrated to give crude product. The crude product was purified by chromatography (silica gel, petroleum ether/ethyl acetate=100:1 to 10:1) to give a mixture of methyl 2,3-bis(3-(diethoxymethyl)phenyl)-4-oxo-1,2,3,4-tetrahydroquinoline-5-carboxylate and ethyl 2,3-bis(3-(diethoxymethyl)phenyl)-4-oxo-1,2,3,4-tetrahydroquinoline-5-carboxylate (370 mg together, yield 33%) as light yellow solid. LC-MS (ESI) m/z: 562 (M+1)+, 576 (M+1)+.

Example 89C 8,9-Bis(3-(diethoxymethyl)phenyl)-8,9-dihydro-2H-pyrido[4,3,2-de]phthalazin-3(7H)-one A mixture of methyl 2,3-bis(3-(diethoxymethyl)phenyl)-4-oxo-1,2,3,4-tetrahydroquinoline-5-carboxylate and ethyl 2,3-bis(3-(diethoxymethyl)phenyl)-4-oxo-1,2,3,4-tetrahydroquinoline-5-carboxylate (370 mg, 0.59 mmol) in hydrazine monohydrate (5 mL) and methanol (5 mL) was stirred at 50° C. for 2 hr. The mixture was cooled to room temperature and filtered to give 8,9-bis(3-(diethoxymethyl)phenyl)-8,9-dihydro-2H-pyrido[4,3,2-de]phthalazin-3(7H)-one (250 mg, yield 77%) as a light yellow solid. $^1$H-NMR (400 MHz, DMSO-d6) δ (ppm): 0.99-1.08 (m, 12H), 3.27-3.33 (m, 8H), 4.28-4.31 (d, J=8.8 Hz, 1H), 4.74-4.76 (d, J=8.4 Hz, 1H), 5.31-5.32 (d, J=6.8 Hz, 2H), 7.04 (s, 1H), 7.12-7.26 (m, 7H), 7.31-7.43 (m, 3H), 7.56-7.60 (t, J=8.0 Hz, 1H); LC-MS (ESI) m/z: 544 (M+1)+.

Example 89D 3,3'-(3-Oxo-3,7,8,9-tetrahydro-2H-pyrido[4,3,2-de]phthalazin-8,8-diyl)dibenzaldehyde A mixture of 8,9-bis(3-(diethoxymethyl)phenyl)-8,9-dihydro-2H-pyrido[4,3,2-de]phthalazin-3(7H)-one (120 mg, 0.46 mmol) in 3N hydrochloric acid (5 mL) was stirred at room temperature for 2 hr. Then the mixture was adjusted to pH=8 with potassium carbonate. The resulting suspension was filtered to give 3,3'-(3-oxo-3,7,8,9-tetrahydro-2H-pyrido[4,3,2-de]phthalazin-8,8-diyl)dibenzaldehyde (160 mg, yield 88%) as a light yellow solid. $^1$H-NMR (400 MHz, DMSO-d6) δ (ppm): 4.57-4.59 (d, J=9.6 Hz, 1H), 4.98-5.00 (d, J=9.2 Hz, 1H), 7.20-7.22 (d, J=7.6 Hz, 1H), 7.42-7.52 (m, 5H), 7.60-7.77 (m, 5H), 7.89 (s, 1H), 9.90 (s, 1H), 9.93 (s, 1H), 12.08 (s, 1H); LC-MS (ESI) m/z: 396 (M+1)+.

Example 89E 8,9-Bis(3-((dimethylamino)methyl)phenyl)-8,9-dihydro-2H-pyrido[4,3,2-de]phthalazin-3(7H)-one A mixture of 3,3'-(3-oxo-3,7,8,9-tetrahydro-2H-pyrido[4,3,2-de]phthalazin-8,8-diyl)dibenzaldehyde (60 mg, 0.16 mmol) and 32% dimethylamine solution (135 mg, 0.96 mmol) in methanol (10 mL) was stirred at room temperature for 40 min. Then the mixture was cooled to 0° C. Sodium borohydride (18.2 mg, 0.48 mmol) was added. After the addition, the mixture was stirred at room temperature for 2 hr. Methanol was removed under reduced pressure. The residue was washed with ethyl acetate and filtered. The filtrate was concentrated to give the crude product. The crude product was purified by prep-HPLC to give 8,9-bis(3-((dimethylamino)methyl)phenyl)-8,9-dihydro-2H-pyrido[4,3,2-de]phthalazin-3(7H)-one (18.6 mg, yield 26%) as a light yellow solid. $^1$H-NMR (400 MHz, CD$_3$OD) δ (ppm): 2.61-2.67 (m, 12H), 4.10-4.15 (m, 4H), 4.25-4.27 (d, J=9.6

Hz, 1H), 4.67-4.69 (d, J=10.0 Hz, 1H), 7.05-7.29 (m, 7H), 7.29-7.39 (m, 2H), 7.49-7.54 (m, 2H); LC-MS (ESI) m/z: 454 (M+1)$^+$.

Example 90

9-(34(Cyclopropylamino)methyl)phenyl)-8-phenyl-8,9-dihydro-2H-pyrido[4,3,2-de]phthalazin-3(7H)-one A mixture of 3-(3-oxo-8-phenyl-3,7,8,9-tetrahydro-2H-pyrido[4,3,2-de]phthalazin-9-yl)benzaldehyde (70 mg, 0.19 mmol) and cyclopropanamine (32.55 mg, 0.57 mmol) in anhydrous methanol (10 mL) was stirred at room temperature for 1.5 h. Then the mixture was cooled to 0° C., sodium borohydride (10.82 mg, 0.286 mmol) was added portionwise. After the addition, the mixture was stirred at this temperature for 2 hr. Methanol was removed under reduced pressure. The residue was dissolved in ethyl acetate (50 mL), extracted with 1N hydrochloric acid (20 mL), the aqueous layer was separated. The organic layer was washed with 1N hydrochloric acid (20 mL). The combined aqueous layers were adjusted to pH=9 with potassium carbonate, extracted with ethyl acetate (25 mL×4). The combined organic layers were dried over anhydrous sodium sulfate, and concentrated to give 9-(3-((cyclopropylamino)methyl)phenyl)-8-phenyl-8,9-dihydro-2H-pyrido[4,3,2-de]phthalazin-3(7H)-one (15 mg, yield 19%) as a light yellow solid. $^1$H-NMR (400 MHz, CD$_3$OD) δ (ppm): 0.19-0.29 (m, 4H), 1.74-1.80 (m, 1H), 3.55 (s, 2H), 4.16-4.19 (d, J=8.8 Hz, 1H), 4.60-4.62 (d, J=8.8 Hz, 1H), 6.88-6.90 (d, J=7.6 Hz, 1H), 6.95 (s, 1H), 7.01-7.10 (m, 6H), 7.13-7.15 (m, 2H), 7.42-7.44 (d, J=7.6 Hz, 1H), 7.48-7.75 (t, J=8.0 Hz, 1H); LC-MS (ESI) m/z: 408 (M+1)$^+$.

Example 91

8-(3-((Dimethylamino)methyl)phenyl)-9-phenyl-8,9-dihydro-2H-pyrido[4,3,2-de]phthalazin-3(7H)-one A mixture of 3-(3-oxo-9-phenyl-3,7,8,9-tetrahydro-2H-pyrido[4,3,2-de]phthalazin-8-yl)benzaldehyde (50 mg, 0.14 mmol) and 1M dimethylamine methanol solution (0.5 ml, 0.41 mmol) in methanol (10 mL) was stirred at room temperature for 40 min. Then the mixture was cooled to 0° C. Sodium cyanoborohydride (13 mg, 0.20 mmol) and acetic acid (40.8 mg, 0.68 mmol) was added. After the addition, the mixture was stirred at 0° C. for 2 hr. Methanol was removed under reduced pressure. The residue was resolved with 1N hydrochloric acid and washed with ethyl acetate. The mother liquor was adjusted to pH=8 and extracted with ethyl acetate. The solvent was removed to give 8-(3-((dimethylamino)methyl)phenyl)-9-phenyl-8,9-dihydro-2H-pyrido[4,3,2-de]phthalazin-3(7H)-one (34 mg, yield 64%) as a light yellow solid. $^1$H-NMR (400 MHz, CD$_3$OD) δ (ppm): 2.17 (s, 6H), 3.17-3.41 (q, 2H), 4.31 (d, J=8.0 Hz, 1H), 4.74 (d, J=8.0 Hz, 1H), 7.08-7.10 (m, 2H), 7.13-7.25 (m, 8H), 7.55-7.57 (d, J=8.0 Hz, 1H), 7.61-7.65 (m, 1H). LC-MS (ESI) m/z: 397 (M+1)$^+$.

Example 92

8-(3-(Morpholinomethyl)phenyl)-9-phenyl-8,9-dihydro-2H-pyrido[4,3,2-de]phthalazin-3(7H)-one A mixture of 3-(3-oxo-9-phenyl-3,7,8,9-tetrahydro-2H-pyrido[4,3,2-de]phthalazin-8-yl)benzaldehyde (40 mg, 0.11 mmol), morpholine (28 mg, 0.33 mmol) and acetic acid (33 mg, 0.55 mmol) in methanol (50 mL) was stirred at room temperature for 40 min. Then the mixture was cooled to 0° C. Sodium triacetoxyborohydride (35 mg, 0.16 mmol) was added. After the addition, the mixture was stirred at 0° C. for 2 hr. Methanol was removed under reduced pressure. The residue was resolved with 1N hydrochloric acid and washed with ethyl acetate. The mother liquor was adjusted to pH=8 and extracted with ethyl acetate. The solvent was removed to give 8-(3-(morpholinomethyl)phenyl)-9-phenyl-8,9-dihydro-2H-pyrido[4,3,2-de]phthalazin-3(7H)-one (31 mg, yield 66%) as a light yellow solid. $^1$H-NMR (400 MHz, CD$_3$OD) δ (ppm): 2.23-2.24 (m, 4H), 3.32-3.43 (q, 2H), 4.30 (d, J=8.0 Hz, 1H), 4.74 (d, J=8.0 Hz, 1H), 7.08-7.10 (m, 2H), 7.13-7.19 (m, 6H), 7.21-7.25 (m, 1H), 7.31-7.33 (m, 1H), 7.55-7.57 (d, J=8.0 Hz, 1H), 7.62-7.64 (m, 1H). LC-MS (ESI) m/z: 439 (M+1)$^+$.

Example 93

8-(4-(Azetidin-1-ylmethyl)phenyl)-9-(4-fluorophenyl)-8,9-dihydro-2H-pyrido[4,3,2-de]phthalazin-3(7H)-one Example 93A Ethyl 2-(4-(diethoxymethyl)phenyl)-3-(4-fluorophenyl)-4-oxo-1,2,3,4-tetrahydroquinoline-5-carboxylate A solution of (E)-4-(4-(diethoxymethyl)benzylideneamino)isobenzofuran-1(3H)-one (10.8 g, 31.9 mmol) and 4-fluorobenzaldehyde (3.95 g, 31.9 mmol) in ethyl propionate (150 mL) was added sodium ethoxide (8.66 g, 127.4 mmol, in ethanol 60 ml) at 0° C. Then the mixture was stirred at room temperature for 5 hr. The resulting mixture was evaporated under reduced pressure and extracted with ethyl acetate (100 mL×4) and concentrated. The crude product was purified by column chromatography (silica gel, petroleum ether:ethyl acetate=20:1 to 1:1) to give the crude product (4.2 g, yield 26%). LC-MS (ESI) m/z: 492 (M+1)$^+$.

Example 93B 8-(4-(Diethoxymethyl)phenyl)-9-(4-fluorophenyl)-8,9-dihydro-2H-pyrido[4,3,2-de]phthalazin-3(7H)-one The crude compound ethyl 2-(4-(diethoxymethyl)phenyl)-3-(4-fluorophenyl)-4-oxo-1,2,3,4-tetrahydroquinoline-5-carboxylate (4.2 g, 8.54 mmol) and hydrazine monohydrate (5 mL) were added in methanol (60 mL) and the mixture was stirred at room temperature for 16 hr. The resulting mixture was concentrated under reduced pressure to a volume of 40 mL and then filtered to obtain the crude title compound (3.0 g, yield 76%). LC-MS (ESI) m/z: 460 (M+1)$^+$.

Example 93C 4-(9-(4-Fluorophenyl)-3-oxo-3,7,8,9-tetrahydro-2H-pyrido[4,3,2-de]phthalazin-8-yl)benzaldehyde To a solution of the crude 8-(4-(diethoxymethyl)phenyl)-9-(4-fluorophenyl)-8,9-dihydro-2H-pyrido[4,3,2-de]phthalazin-3(7H)-one (3.0 g, 6.53 mmol) in water (10 mL) was added hydrochloric hlip://newsearchch.chemexper.com/cheminfo/servlet/org.dbcreator.MainServlet?sort=%3E%7Eentry.intValue&query=structure._ structureID%3D4635571&target=entry&action=
PowerSearch&onclick=1&from=0&history=
off&forGroupNames=&style=&realQuery=
rn.value%3D%22CF3COOH%22+elsor+
entry.catalogID%3D%22CF3COOH%22+elsor+
iupac.value%3D%22CF3COOH%22+elsor+
mf.value%3D%22CF3COOH%22+elsor+
%28iupac.value%3D%7E%22CF3COOH%22+or+
catalog.description%3D%7E%22CF3COOH%22%29-
&format=ccd&searchTemplate=rn.value%3D%3F+elsor+
entry.catalogID%3D%3 acid (1 N, 50 mL) at 0° C. The mixture was stirred at room temperature for 4 hr. Then the mixture was neutralized with potassium carbonate. The mixture was extracted with ethyl acetate (200 mL×3). The combined organic layers were washed with brine, dried over anhydrous sodium sulfate, and concentrated to give the crude title compound (2.5 g, yield 98%). LC-MS (ESI) m/z: 386 (M+1)$^+$.

Example 93D 8-(4-(Azetidin-1-ylmethyl)phenyl)-9-(4-fluorophenyl)-8,9-dihydro-2H-pyrido[4,3,2-de]phthalazin-3(7H)-one To a stirred solution of the crude 4-(9-(4-fluorophenyl)-3-oxo-3,7,8,9-tetrahydro-2H-pyrido[4,3,2-de]phthalazin-8-yl)benzaldehyde (930 mg, 2.42 mmol) in DCM (120 mL) was added acetic acid (0.3 mL) followed by azetidine (670 mg, 11.8 mmol), after the addition, the mixture was stirred at room temperature overnight. Then the mixture was cooled to 0° C. and NaBH(OAc)$_3$(764 mg, 3.62 mmol) was added. After the addition, the mixture was stirred at this temperature for 6 hr. DCM was removed under reduced pressure. The residue was added water followed by hydrochlorichlip://newsearchch.chemexper.com/cheminfo/servlet/
org.dbcreator.MainServlet?sort=%3E                 %
7Eentry.intValue&query=structure._
structureID%3D4635571&target=entry&action=
PowerSearch&onclick=1&from=0&history=
off&forGroupNames=&style=&realQuery=
rn.value%3D%22CF3COOH%22+elsor+
entry.catalogID%3D%22CF3COOH%22+elsor+
iupac.value%3D%22CF3COOH%22+elsor+mf.value%3D
%22CF3COOH%22+elsor+
%28iupac.value%3D%7E%22CF3COOH%22+or+
catalog.description%3D%7E%22CF3COOH%22%29-
&format=ccd&searchTemplate=rn.value%3D%3F+elsor+
entry.catalogID%3D%3 acid (5 mL) at 25° C. The mixture was stirred at room temperature for 0.5 hr. The mixture was extracted with ethyl acetate (100 mL×3). The water layer was neutralized with potassium carbonate and filtered to obtain the title compound as a white solid (500 mg, yield 49%). LC-MS (ESI) m/z: 427 (M+1)$^+$. $^1$H-NMR (400 MHz, DMSO-d6) δ (ppm): 2.24-2.49 (m, 2H), 3.85-4.02 (m, 4H), 4.25 (d, 2H), 4.38 (d, 1H), 4.80 (d, 1H) 7.03 (t, 2H), 7.14-7.20 (m, 3H), 7.36-7.39 (m, 5H), 7.47 (s, 1H), 7.59 (t, 1H) 10.64 (s, 1H), 12.18 (s, 1H).

Example 94

5-fluoro-8-(4-fluorophenyl)-9-(1-methyl-1H-1,2,4-triazol-5-yl)-8,9-dihydro-2H-pyrido[4,3,2-de]phthalazin-3(7H)-one Example 94A Ethyl 7-fluoro-2-(4-fluorophenyl)-3-(1-methyl-1H-1,2,4-triazol-5-yl)-4-oxo-1,2,3,4-tetrahydroquinoline-5-carboxylate To a solution of (E)-6-fluoro-4-(4-fluorobenzylideneamino)isobenzofuran-1(3H)-one (4 g, 14.6 mmol) and 1-methyl-1H-1,2,4-triazole-5-carbaldehyde (4.1 g, 36.9 mmol) in ethyl propionate (220 mL) was added EtONa ((sodium 940 mg, 40.9 mmol), in 70 mL ethanol) at 37° C., then the mixture was stirred at 40° C. for 6 hr. The resulting mixture was evaporated under reduced pressure and extracted with ethyl acetate (100 mL×4).The extract was concentrated to dryness to give a crude product, which was purified by column chromatography (silica gel, dichloromethane:methanol=200:1 to 100:1) to obtain a green solid (1.02 g, yield 14%). LC-MS (ESI) m/z: 413 (M+1)$^+$.

Example 94B

5-Fluoro-8-(4-fluorophenyl)-9-(1-methyl-1H-1,2,4-triazol-5-yl)-8,9-dihydro-2H-pyrido[4,3,2-de]phthalazin-3(7H)-one To a solution of ethyl 7-fluoro-2-(4-fluorophenyl)-3-(1-methyl-1H-1,2,4-triazol-5-yl)-4-oxo-1,2,3,4-tetrahydroquinoline-5-carboxylate (840 mg, 2.04 mmol) in methanol (2 mL) was added hydrazine monohydrate (1 mL), and the mixture was stirred under 25° C. for 10 hr. Then the mixture was filtered to obtain a white solid (650 mg, yield 84%). LC-MS (ESI) m/z: 381 (M+1)$^+$. $^1$H-NMR (400 MHz, DMSO-d$_6$) ☐☐ δ (ppm): 3.66 (s, 3H), 4.97-5.04 (m, 2H), 6.91-6.94 (dd, J$_1$=11.2 Hz, J$_2$=2.4 Hz, 1H), 7.06-7.09 (dd, J$_1$=8.8 Hz, J$_2$=2.4 Hz, 1H), 7.14-7.18 (m, 3H), 7.47-7.51 (m, 2H), 7.72 (s, 1H), 7.80 (s, 1H), 12.35 (s, 1H)

Example 95

9-(1-Methyl-1H-1,2,4-triazol-5-yl)-8-phenyl-8,9-dihydro-2H-pyrido[4,3,2-de]phthalazin-3(7H)-one Example 95A Ethyl 3-(1-methyl-1H-1,2,4-triazol-5-yl)-4-oxo-2-phenyl-1,2,3,4-tetrahydroquinoline-5-carboxylate To a solution of (E)-4-(benzylideneamino)isobenzofuran-1(3H)-one (1.78 g, 7.5 mmol) and 1-methyl-1H-1,2,4-triazole-5-carbaldehyde (1.01 g, 9.16 mmol) in ethyl propionate (110 mL) was added EtONa (sodium (490 mg, 21 mmol) in 35 mL ethanol) at 40° C., then the mixture was stirred at 41° C. for 3 hr. The resulting mixture was evaporated under reduced pressure and extracted with ethyl acetate (150 mL×4) and concentrated. The crude product was purified by column chromatography (silica gel, dichloromethane:

methanol=200:1 to 50:1) to obtain a green solid (400 mg, yield 14%). LC-MS (ESI) m/z: 377 (M+1)$^+$.

Example 95B 9-(1-Methyl-1H-1,2,4-triazol-5-yl)-8-phenyl-8,9-dihydro-2H-pyrido[4,3,2-de]phthalazin-3(7H)-one To a solution of ethyl 3-(1-methyl-1H-1,2,4-triazol-5-yl)-4-oxo-2-phenyl-1,2,3,4-tetrahydroquinoline-5-carboxylate (400 mg, 1.06 mmol) in methanol (8 mL) was added hydrazine monohydrate (0.5 mL), and the mixture was then stirred at 25° C. for 10 hr. The mixture was filtered to obtain a white solid (110 mg, yield 30%). LC-MS (ESI) m/z: 345 (M+1)$^+$. $^1$H-NMR (400 MHz, DMSO-d$_6$) □□δ (ppm): 3.77 (s, 3H), 4.48-4.49 (d, J=6.4 Hz, 1H), 5.16-5.19 (d, J=6.4 Hz, 1H), 7.40-7.42 (m, 2H), 7.54-7.58 (t, 1H), 7.74 (s, 1H), 12.23 (s, 1H).

Example 96

8-(4-((Dimethylamino)methyl)phenyl)-9-(1-methyl-1H-1,2,4-triazol-5-yl)-8,9-dihydro-2H-pyrido[4,3,2-de]phthalazin-3(7H)-one Example 96A Ethyl 2-(4-((dimethylamino)methyl)phenyl)-3-(1-methyl-1H-1,2,4-triazol-5-yl)-4-oxo-1,2,3,4-tetrahydroquinoline-5-carboxylate To a solution of (E)-4-(4-((dimethylamino)methyl)benzylideneamino)isobenzofuran-1(3H)-one (2.21 g, 7.5 mmol) and 1-methyl-1H-1,2,4-triazole-5-carbaldehyde (1.01 g, 9.16 mmol) in ethyl propionate (110 ml) was added rapidly EtONa (sodium (490 mg, 21 mmol) in 35 mL ethanol) at 40° C., then the mixture was stirred at 45° C. for 3 hr. The resulting mixture was evaporated under reduced pressure, extracted with ethyl acetate (200 mL×3), and then concentrated the extract. The crude product was purified by column chromatography (silica gel, dichloromethane:methanol=100:1 to 10:1) to obtain a green solid (510 mg, yield 16%). LC-MS (ESI) m/z: 434 (M+1)$^+$.

Example 96B 8-(4-((Dimethylamino)methyl)phenyl)-9-(1-methyl-1H-1,2,4-triazol-5-yl)-8,9-dihydro-2H-pyrido[4,3,2-de]phthalazin-3(7H)-one To a solution of ethyl 2-(4-((dimethylamino)methyl)phenyl)-3-(1-methyl-1H-1,2,4-triazol-5-yl)-4-oxo-1,2,3,4-tetrahydroquinoline-5-carboxylate (506 mg, 1.17 mmol) in methanol (3 mL) was added hydrazine monohydrate (1 mL), and the mixture was stirred at 25° C. for 10 hrs. The mixture was filtered to obtain a white solid (225 mg, yield 48%). LC-MS (ESI) m/z: 402 (M+1)$^+$. $^1$H-NMR (400 MHz, DMSO-d$_6$) □□δ (ppm): 2.10 (s, 6H), 3.33 (s, 2H), 3.58 (s, 3H), 4.88-4.92 (m, 2H), 7.20-7.22 (m, 3H), 7.34-7.40 (m, 4H), 7.54-7.62 (t, J=8.4 Hz, 1H), 7.79 (s, 1H), 12.20 (s, 1H).

Example 97

8-(4-((Dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one Example 97A Ethyl 2-(4-((dimethylamino)methyl)phenyl)-7-fluoro-3-(1-methyl-1H-1,2,4-triazol-5-yl)-4-oxo-1,2,3,4-tetrahydroquinoline-5-carboxylate To a solution of (E)-4-(4-((dimethylamino)methyl)benzylideneamino)-6-fluoroisobenzofuran-1(3H)-one (2.34 g, 7.5 mmol) and 1-methyl-1H-1,2,4-triazole-5-carbaldehyde (1.01 g, 9.16 mmol) in ethyl propionate (110 mL) was added EtONa (sodium (500 mg, 21 mmol) in 35 mL ethanol) at 40° C., then the mixture was stirred at 48° C. for 3 hr. The resulting mixture was evaporated under reduced pressure, extracted with ethyl acetate (250 mL×3), and concentrated. The crude product was purified by column chromatography (silica gel, dichloromethane:methanol=50:1 to 10:1) to obtain a green solid (160 mg, yield 4.7%). LC-MS (ESI) m/z: 452 (M+1)$^+$.

Example 97B 8-(4-((Dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one To a solution of ethyl 2-(4-((dimethylamino)methyl)phenyl)-7-fluoro-3-(1-methyl-1H-1,2,4-triazol-5-yl)-4-oxo-1,2,3,4-tetrahydroquinoline-5-carboxylate (160 mg, 0.35 mmol) in methanol (2 mL) was added hydrazine monohydrate (0.5 mL), and the mixture was stirred at 25° C. for 10 hr. The mixture was filtered to obtain the title compound as a white solid (45 mg, yield 30%). LC-MS (ESI) m/z: 420 (M+1)$^+$. $^1$H-NMR (400 MHz, DMSO-d$_6$) □□δ (ppm): 2.10 (s, 6H), 3.36 (s, 2H), 3.59 (s, 3H), 4.91-4.99 (m, 2H), 6.91-6.95 (dd, J$_1$=11.2 Hz, J$_2$=2.4 Hz, 1H), 7.05-7.08 (dd, J$_1$=9.2 Hz, J$_2$=2.4 Hz, 1H), 7.20-7.23 (d, J=8.0 Hz, 2H), 7.35-7.37 (d, J=8.0 Hz, 2H), 7.72 (s, 1H), 7.79 (s, 1H), 12.33 (s, 1H).

Example 98

8-(4-Fluorophenyl)-9-methyl-9-(1-methyl-1H-1,2,4-triazol-5-yl)-8,9-dihydro-2H-pyrido[4,3,2-de]phthalazin-3(7H)-one Example 98A Ethyl 2-(4-fluorophenyl)-3-methyl-3-(1-methyl-1H-1,2,4-triazol-5-yl)-4-oxo-1,2,3,4-tetrahydroquinoline-5-carboxylate A solution of ethyl 2-(4-fluorophenyl)-3-(1-methyl-1H-1,2,4-triazol-5-yl)-4-oxo-1,2,3,4-tetrahydroquinoline-5-carboxylate (100 mg, 0.25 mmol) and potassium carbonate (70 mg, 0.51 mmol) in N,N-dimethylformamide (10 mL) was stirred at room temperature for 1 hr. Then the solution was cooled to 0° C. and a solution of iodomethane (0.1 mL) in N,N-dimethylformamide (1 mL) was added dropwise at 0° C. over 1 hr, stirred at room temperature overnight. The mixture was quenched with water (30 mL), extracted with ethyl acetate, washed with brine, and then the extraction was evaporated to get the crude product, which was used in next step without further purification (80 mg, yield 77%). LC-MS (ESI) m/z: 409 (M+1)$^+$.

Example 98B 8-(4-Fluorophenyl)-9-methyl-9-(1-methyl-1H-1,2,4-triazol-5-yl)-8,9-dihydro-2H-pyrido[4,3,2-de]phthalazin-3(7H)-one A mixture of ethyl 2-(4-fluorophenyl)-3-methyl-3-(1-methyl-1H-1,2,4-triazol-5-yl)-4-oxo-1,2,3,4-tetrahydroquinoline-5-carboxylate (80 mg, 0.19 mmol) in 85% hydrazine monohydrate (5 mL) and methanol (1 mL) was stirred under reflux overnight. The resulting solution was cooled and filtered, washed the cake by methanol (2 mL) to obtain a white solid, dried in vacuum at 55° C. to obtain the title compound (40 mg, yield 54%). LC-MS (ESI) m/z: 377 (M+1)$^+$; $^1$H-NMR (400 MHz, DMSO-d6) □δ (ppm): 1.83 (s, 3H), 2.86 (s, 3H), 4.61 (s, 1H), 6.88-6.92 (m, 2H), 7.11-7.169 (t, J=8.8 Hz, 2H), 7.19-7.22 (d, J=8.0 Hz, 1H), 7.41 (s, 1H), 7.47-7.49 (m, 1H), 7.60-7.64 (t, J=8.0 Hz, 1H), 7.72 (s, 1H), 12.40 (s, 1H).

Example 99

8-(4-Fluorophenyl)-9-(1,4,5-trimethyl-1H-imidazol-2-yl)-8,9-dihydro-2H-pyrido[4,3,2-de]phthalazin-3(7H)-one

Example 99A 1,4,5-Trimethyl-1H-imidazole

To a cold suspension of formaldehyde (21 mL, 0.3 mol), methylamine hydrochloride (36.5 g, 540 mmol) and ammonium hydroxide (150 mL) was added butandione (15.8 mL, 180 mmol) and the mixture was then stirred at 100° C. for 30 min. After cooled to room temperature the reaction mixture was extracted with dichloromethane. The organic layers were dried with Na$_2$SO$_4$ and the solvent was removed via rotary evaporation. The crude was purified by chromatography (dichloromethane/methanol=100:1) to give 1,4,5-trimethyl-1H-imidazole. $^1$H-NMR (400 MHz, CDCl$_3$) δ (ppm): 2.11 (s, 3H), 2.15 (s, 3H), 3.49 (s, 3H), 7.28 (s, 1H).

Example 99B 1,4,5-Trimethyl-1H-imidazole-2-carbaldehyde

To a solution of 1,4,5-trimethyl-1H-imidazole (550 mg, 5 mmol) in dry tetrahydrofuran (15 mL) was added dropwise n-BuLi (3 mL, 2.5 M in hexane) at −40° C. After stirring for 2 h at this temperature, to the solution was added dried DMF (840 mg, 11.5 mmol) at −70° C. The resulting yellow suspension was stirred at −70° C. for 1 h, then at 0° C. for 0.5 h and quenched with ice-water. The mixture was extracted with ethyl acetate, and the organic extracts were dried with Na$_2$SO$_4$ before evaporation to afford an oily residue. The residue was purified by silica column (petroleum ether:ethyl acetate=3:1) to obtain 340 mg of white solid, yield: 50%. $^1$H-NMR (400 MHz, CDCl$_3$) δ (ppm): 2.21 (s, 1H), 2.25 (s, 1H), 3.90 (s, 1H), 9.66 (s, 1H). LC-MS (ESI) m/z: 138 (M+1)$^+$.

Example 99C

Ethyl 2-(4-fluorophenyl)-4-oxo-3-(1,4,5-trimethyl-1H-imidazol-2-yl)-1,2,3,4-tetrahydroquinoline-5-carboxylate A mixture of compound (E)-4-(4-fluorobenzylideneamino)isobenzofuran-1(3H)-one (510 mg, 2.0 mmol) and 1,4,5-trimethyl-1H-imidazole-2-carbaldehyde (304 mg, 2.2 mmol) in ethyl propionate (20 mL) was cooled to 0° C. Then a solution of sodium ethoxide in ethanol (sodium (184 mg, 8.0 mmol) in ethanol (10 mL)) was added dropwise. After the addition, the mixture was stirred at room temperature for 2.5 hr. The mixture was quenched with water (20 mL) and solvent was removed under reduced pressure. The residue was dissolved in water and extracted with ethyl acetate (100 mL×3), then the extraction was washed with water, brine and evaporated, the crude product was purified by chromatography to obtain a yellow solid (150 mg, yield: 18%). LC-MS (ESI) m/z: 421 (M+1)$^+$.

Example 99D 8-(4-Fluorophenyl)-9-(1,4,5-trimethyl-1H-imidazol-2-yl)-8,9-dihydro-2H-pyrido[4,3,2-de]phthalazin-3(7H)-one A mixture of ethyl 2-(4-fluorophenyl)-4-oxo-3-(1,4,5-trimethyl-1H-imidazol-2-yl)-1,2,3,4-tetrahydroquinoline-5-carboxylate (150 mg) in 85% hydrazine monohydrate (85%, 3 mL) and methanol (5 mL) was stirred at room temperature for 2 days. The result suspension was filtered and washed the water (20 mL) and methanol (5 ml) to obtain a white solid. The solid was dried in vacuum at 50° C. to afford the title compound (90 mg, yield 65%). $^1$H-NMR (400 MHz, DMSO-d6) δ (ppm): 1.91-1.96 (d, J=18 Hz, 6H), 3.25 (s, 3H), 4.59-4.62 (d, J=10.8 Hz, 1H), 4.92-4.95 (d, J=10.8 Hz, 1H), 7.09-7.15 (m, 3H), 7.22 (s, 1H), 7.36-7.38 (d, J=7.6 Hz, 1H), 7.43-7.46 (m, 2H), 7.54-7.58 (t, J=8 Hz, 1H), 12.13 (s, 1H); LC-MS (ESI) m/z: 390 (M+1)$^+$.

Example 100

8-(4-Fluorophenyl)-9-(1-methyl-1H-1,2,3-triazol-4-yl)-8,9-dihydro-2H-pyrido[4,3,2-de]phthalazin-3(7H)-one

Example 100A (1H-1,2,3-Triazol-4-yl)methanol

TMSN$_3$ (24.8 g, 214 mmol) was added to a solution of CuI (1.4 g, 0.4 mol) and prop-2-yn-1-ol (8.0 g, 142.4 mmol) in DMF (160 mL) and methanol (20 mL) under nitrogen atmosphere. The reaction mixture was stirred at 100° C. for 12 h. Then the mixture was cooled to room temperature and filtered through a short florisil and concentrated. The crude was purified by column chromatography (silica gel, pre-washed with triethylamine, petroleum ether:ethyl acetate 1:3 to 1:5) to give the title compound (12.7 g, 90%) as a yellow oil. $^1$H-NMR (400 MHz, DMSO-d6) □□ δ (ppm): 4.09 (m, 2H), 4.48-4.10 (m, 1H), 5.21-5.24 (m, 1H), 7.62 (s, 1H); LC-MS (ESI) m/z: 100 (M+1)$^+$.

Example 100B (1-Methyl-1H-1,2,3-triazol-4-yl)methanol

To a solution of (1H-1,2,3-triazol-4-yl)methanol (5.0 g, 51.5 mmol) and K$_2$CO$_3$ (8.5 g, 62 mmol) in MeCN (190 mL)

was added methyl iodine (3.8 ml) dropwise at 0° C. Then the reaction was stirred at room temperature overnight, the reaction solution was filtrated, and adjusted to pH=6 with acetic acid, then the solvent was evaporated to obtain the title compound (5.6 g, yield 98%) as yellow oil and used in next step without further purification. LC-MS (ESI) m/z: 114 (M+1)$^+$.

Example 100C

1-Methyl-1H-1,2,3-triazole-4-carbaldehyde (1-Methyl-1H-1,2,3-triazol-4-yl)methanol (5.6 g, 50 mmol) and activated manganese dioxide (55 g, 65 mmol) was dissolved in acetone (130 mL) and the solution was stirred at room temperature for 3 h. Then the reaction mixture was filtered, the solvent was evaporated in vacuum. The residue was purified by flash chromatography (silica gel, petroleum ether:ethyl acetate 5:1 to 2:1) to obtain the title compound (1.1 g, yield 20%). $^1$H-NMR (400 MHz, DMSO-d6) ☐☐ δ (ppm): 4.13 (m, 3H), 8.81 (s, 1H), 10.02 (s, 1H); LC-MS (ESI) m/z: 112 (M+1)$^+$.

Example 100D

Ethyl 2-(4-fluorophenyl)-3-(1-methyl-1H-1,2,3-triazol-4-yl)-4-oxo-1,2,3,4-tetrahydroquinoline-5-carboxylate A mixture of (E)-4-(4-fluorobenzylideneamino)isobenzofuran-1(3H)-one (698 mg, 2.7 mmol) and 1-methyl-1H-1,2,3-triazole-4-carbaldehyde (334 mg, 3 mmol) in ethyl propionate (35 mL) was cooled to 0° C. Then a solution of sodium ethanolate in ethanol (sodium (248 mg, 10.8 mmol) in ethanol (15 mL)) was added dropwise. After the addition, the mixture was stirred at room temperature for 4 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product, which then was purified by chromatography (silica gel, petroleum ether/ethyl acetate=3:1 to 1:1) to give the title compound (426 mg, yield 39%). LC-MS (ESI) m/z: 395 (M+1)$^+$.

Example 100E 8-(4-Fluorophenyl)-9-(1-methyl-1H-1,2,3-triazol-4-yl)-8,9-dihydro-2H-pyrido[4,3,2-de]phthalazin-3 (7H)-one A mixture of ethyl 2-(4-fluorophenyl)-3-(1-methyl-1H-1,2,3-triazol-4-yl)-4-oxo-1,2,3,4-tetrahydroquinoline-5-carboxylate (113 mg, 0.28 mmol) in 85% hydrazine monohydrate (4 mL) stirred for 3 hr at room temperature. The mixture was filtered and washed with water, petroleum ether and ethyl acetate to give the crude product, which was purified by prep-HPLC to give the title compound (41 mg, yield 39%). $^1$H-NMR (400 MHz, DMSO-d6) ☐☐ δ (ppm): 3.93 (s, 3H), 4.50-4.52 (d, J=7.6 Hz, 1H), 4.96-4.98 (d, J=7.6 Hz, 1H), 7.09-7.15 (m, 3H), 7.35-7.42 (m, 4H), 7.55-7.57 (t, J=7.6 Hz, 1H), 7.72 (s, 1H); LC-MS (ESI) m/z: 363 (M+1)$^+$.

Example 101

N,N-Dimethyl-4-(9-(1-methyl-1H-imidazol-2-yl)-3-oxo-3,7,8,9-tetrahydro-2H-pyrido[4,3,2-de]phthalazin-8-yl)benzamide Example 101A 4-Formyl-N,N-dimethylbenzamide To a suspension of 4-formylbenzoic acid (4.00 g, 26.7 mmol) in dry DCM (8 mL) were added thionyl chloride (2.92 g, 40.0 mmol) and DMF (0.6 mL) dropwise at ambient temperature under nitrogen. The reaction mixture was refluxed for 2 h. After cooling, this mixture was added to 33% dimethylamine in water (10.5 mL, 72 mmol) dropwise over 15 min in an ice-water bath, and the reaction mixture stirred for 1 h at the same temperature. The solvent was evaporated in vacuums. The residue was purified by chromatography on silica gel to give the title compound (2.5 g, yield 53%) as a yellow solid. $^1$H-NMR (400 MHz, DMSO-d6) δ (ppm): 2.86 (s, 3H), 3.30 (s, 3H), 7.60 (d, J=7.6 Hz, 2H), 7.95 (d, J=7.6 Hz, 2H), 10.04 (s, 1H); LC-MS (ESI) m/z: 178 (M+1)$^+$.

Example 101B (E)-N,N-dimethyl-4-((1-oxo-1,3-dihydroisobenzofuran-4ylimino)methyl)benzamide 4-Aminoisobenzofuran-1(3H)-one (2.10 g, 14.1 mmol), 4-formyl-N,N-dimethylbenzamide (2.50 g, 14.1 mmol) and dry MgSO$_4$ (9.84 g, 82 mmol) were added to acetonitrile (170 mL) and stirred under reflux overnight. The mixture was filtered, and the solvent was evaporated under reduced pressure and the residue was re-crystallized to obtain 3.5 g of title compound as a pale solid. $^1$H-NMR (400 MHz, CDCl$_3$) δ (ppm): 3.01 (s, 3H), 3.15 (s, 3H), ☐ 5.43 (s, 2H), 7.38-7.40 (d, J=7.6 Hz, 1H), 7.55-7.61 (m, 3H), 7.80-7.82 (d, J=7.6 Hz, 1H), 7.96-7.98 (d, J=8 Hz, 2H), 8.58 (s, 1H); LC-MS (ESI) m/z: 308 (M+1)$^+$.

Example 101C

Ethyl 2-(4-(dimethylcarbamoyl)phenyl)-3-(1-methyl-1H-imidazol-2-yl)-4-oxo-1,2,3,4-tetrahydroquinoline-5-carboxylate (E)-N,N-Dimethyl-4-((1-oxo-1,3-dihydroisobenzofuran-4ylimino)methyl)benzamide (924 mg, 3.0 mmol), 1-methyl-1H-imidazole-2-carbaldehyde (363 mg, 3.3 mmol), sodium (276 mg, 12 mmol) in ethanol (30 mL) and ethyl propionate (45 mL) were added and the mixture was stirred at room temperature overnight. Then the resulting mixture was evaporated under reduced pressure and extracted with ethyl acetate (100 mL×4) and concentrated. The crude product was purified by column chromatography (silica gel, petroleum ether/ethyl acetate=20:1 to 1:2) to afford the title compound as a yellow solid (500 mg, yield 37%). LC-MS (ESI) m/z: 447 (M+1)$^+$.

Example 101D

N,N-dimethyl-4-(9-(1-methyl-1H-imidazol-2-yl)-3-oxo-3,7,8,9-tetrahydro-2H-pyrido[4,3,2-de]phthalazin-8-yl)benzamide Ethyl 2-(4-(dimethylcarbamoyl)phenyl)-3-(1-methyl-1H-imidazol-2-yl)-4-oxo-1,2,3,4-tetrahydroquinoline-5-carboxylate (500 mg, 1.12 mmol) and hydrazine monohydrate (8 mL) were added and the mixture was stirred under 40° C. for 3 h. Then the mixture was cooled to room temperature and filtered to give the title compound (90 mg, yield 19%) as a white solid. ¹H-NMR (400 MHz, DMSO-d6) δ (ppm): 2.86 (s, 3H), 2.96 (s, 3H), 3.42 (s, 3H), □4.66-4.69 (d, J=10.4 Hz, 1H), 4.96-4.99 (d, J=10.4 Hz, 1H), 6.73 (s, 1H), 6.89 (s, 1H), 7.16-7.19 (m, J=7.6 Hz, 1H), 7.29-7.45 (m, 6H), 7.56-7.60 (t, J=7.6 Hz 1H), 12.18 (s, 1H); LC-MS (ESI) m/z: 415 (M+1)⁺.

Example 102

9-(4,5-Dimethyl-4H-1,2,4-triazol-3-yl)-8-phenyl-8,9-dihydro-2H-pyrido[4,3,2-de]phthalazin-3(7H)-one Example 102A Isothiocyanatomethane To a solution of methylamine hydrochloride (61 g, 0.9 mol) in 100 mL of water was added carbon disulfide (68.5 g, 0.9 mol). The mixture was cooled to 10° C., a cold solution of sodium hydroxide (72 g, 1.8 mol) in water (160 mL) was added dropwise over a period of 30 min. After the addition, the internal temperature rise to 85° C. gradually. The solution was kept at this temperature for 1.5 hr. The bright red solution was cooled to 35° C.~40° C., and was added ethyl chlorocarbonate (98 g, 0.9 mol) over a period of 1 hr with stirring. The stirring was continued for 30 min after the addition. The mixture was allowed to stand overnight. The organic layer was separated, dried over Na₂SO₄, and distilled under atmosphere pressure. The fraction, which boils at 115~120° C., was collected as a colorless crystal (40 g, yield 61%). ¹H-NMR (400 MHz, CDCl₃) δ (ppm): □3.29 (s, 3H).

Example 102B

2-Acetyl-N-methylhydrazinecarbothioamide

To a stirred solution of acetohydrazide (3.7 g, 50 mmol) in methanol (30 mL) was added a solution of compound isothiocyanatomethane (3.65 g, 50 mmol) in methanol (50 mL) at 0° C. After the addition, the mixture was stirred at room temperature overnight. The mixture was concentrated to give crude product (7 g) as a white solid which was used in the next step without further purification. LC-MS (ESI) m/z: 148 (M+1)⁺.

Example 102C 3,4-Dimethyl-1H-1,2,4-triazole-5(4H)-thione

To a stirred solution of crude 2-acetyl-N-methylhydrazinecarbothioamide (7 g, 47.6 mmol) in ethanol (100 mL) was added triethylamine (14.4 g, 143 mmol). After the addition, the mixture was heated to reflux overnight and was then concentrated to give the title compound (4.2 g, yield 65% for two steps) as a white solid which was used in the next step without further purification. ¹H-NMR (400 MHz, DMSO-d6) δ (ppm): 2.28 (s, 3H), 3.38 (s, 3H), 13.40 (s, 1H). LC-MS (ESI) m/z: 130 (M+1)⁺.

Example 102D 3,4-Dimethyl-4H-1,2,4-triazole

A suspension of 3,4-dimethyl-1H-1,2,4-triazole-5(4H)-thione (4.2 g, 32.5 mmol) in dichloromethane (72 mL) was cooled to 0° C. A solution of 30% hydrogen peroxide (16.9 mL, 149.5 mmol) in acetic acid (44 mL) was added dropwise. After the addition, the mixture was allowed to stir at room temperature overnight. The solvent was removed under reduced pressure. The residue was dissolved with water (20 mL), treated with aqueous sodium hydroxide to pH=12, extracted with dichloromethane (80 mL×8). The combined organic layers were dried over anhydrous Na₂SO₄, concentrated to give the title compound (2.3 g, yield 73%) as a brown solid. ¹H-NMR (400 MHz, CDCl₃) δ (ppm): □2.47 (s, 3H), 3.63 (s, 3H), 8.09 (s, 1H). LC-MS (ESI) m/z: 98 (M+1)⁺.

Example 102E (4,5-Dimethyl-4H-1,2,4-triazol-3-yl)methanol

A mixture of 3,4-dimethyl-4H-1,2,4-triazole (2.3 g, 23.7 mmol) and formalin (5 mL) was heated to 90° C. overnight. The mixture was concentrated to give crude product. The crude product was purified by silica gel chromatography (dichloromethane/methanol=200:1 to 15:1) to give the title compound (2.48 g, yield 82%) as a white solid. ¹H-NMR (400 MHz, DMSO-d6) δ (ppm): □2.31 (s, 3H), 3.52 (s, 3H), 4.52-4.54 (d, J=5.2 Hz, 2H), 5.49-5.51 (t, J=5.2 Hz, 1H). LC-MS (ESI) m/z: 128 (M+1)⁺.

Example 102F 4,5-Dimethyl-4H-1,2,4-triazole-3-carbaldehyde

A mixture of (4,5-dimethyl-4H-1,2,4-triazol-3-yl)methanol (2.48 g, 19.5 mmol) and manganese (IV) oxide (17.8 g, 204.8 mmol) in dry tetrahydrofuran (72 mL) was stirred at room temperature overnight. The mixture was filtered, and the cake washed with dichloromethane (100 mL×3). The combined filtrate was concentrated to give the title compound (1.6 g, yield 66%) as a white solid. ¹H-NMR (400 MHz, DMSO-d6) δ (ppm): □2.54 (s, 3H), 3.89 (s, 3H), 10.06 (s, 2H). LC-MS (ESI) m/z: 126 (M+1)⁺.

Example 102G

Ethyl 3-(4,5-dimethyl-4H-1,2,4-triazol-3-yl)-4-oxo-2-phenyl-1,2,3,4-tetrahydroquinoline-5-carboxylate A mixture of (E)-4-(benzylideneamino)isobenzofuran-1(3H)-one (237 mg, 1 mmol) and 4,5-dimethyl-4H-1,2,4-triazole-3-carbaldehyde (150 mg, 1.2 mmol) in ethyl propionate (10 mL) was cooled to 0° C. Then a solution of sodium ethoxide in ethanol [sodium (92 mg, 4 mmol) in ethanol (5 mL)] was added dropwise. After the addition, the mixture was stirred at 10° C. for 5 hr, then 30° C. 2.5 hr. The mixture was quenched with water (10 mL) and solvent was removed in vacuum. The residue was dissolved in water, and then extracted with ethyl acetate (30 mL×4). The combined organic layers were washed with brine, dried over anhydrous sodium sulfate, and concentrated to give crude product. The crude product was purified by chromatography (silica gel, petroleum ether/ethyl acetate=5:1 then ethyl acetate/methanol=15:1) to give the title compound (60 mg, yield: 15%). LC-MS (ESI) m/z: 391 (M+1)⁺.

Example 102H 9-(4,5-Dimethyl-4H-1,2,4-triazol-3-yl)-8-phenyl-8,9-dihydro-2H-pyrido[4,3,2-de]phthalazin-3(7H)-one A mixture of ethyl 3-(4,5-dimethyl-4H-1,2,4-triazol-3-yl)-4-oxo-2-phenyl-1,2,3,4-tetrahydroquinoline-5-carboxylate (60 mg) in 85% hydrazine monohydrate (1 mL) and methanol (3 mL) was stirred at 10° C. for 2.5 h. The mixture was purified by prep-HPLC to obtain the title compound as a yellow solid (6 mg, yield: 11%). $^1$H-NMR (400 MHz, CD$_3$OD) δ (ppm): 2.33 (s, 3H), 3.36 (s, 3H), 4.79-4.81 (d, J=11.6 Hz, 1H), 4.99-5.02 (d, J=11.6 Hz, 1H), 7.21-7.23 (m, 2H), 7.31-7.33 (m, 2H), 7.45-7.48 (m, 2H), 7.59-7.67 (m, 2H); LC-MS (ESI) m/z: 359 (M+1)$^+$.

Example 103

9-(4,5-Dimethyl-4H-1,2,4-triazol-3-yl)-8-(4-fluorophenyl)-8,9-dihydro-2H-pyrido[4,3,2-de]phthalazin-3(7H)-one Example 103A Ethyl 3-(4,5-dimethyl-4H-1,2,4-triazol-3-yl)-2-(4-fluorophenyl)-4-oxo-1,2,3,4-tetrahydroquinoline-5-carboxylate A mixture of (E)-4-(4-fluorobenzylideneamino)isobenzofuran-1(3H)-one (510 mg, 2 mmol) and 4,5-dimethyl-4H-1,2,4-triazole-3-carbaldehyde (275 mg, 2.2 mmol) in ethyl propionate (20 mL) was cooled to 0° C. Then a solution of sodium ethoxide in ethanol (sodium (184 mg, 8 mmol) in ethanol (10 mL)) was added dropwise. After the addition, the mixture was stirred at 10° C. for 2 hr, then 30° C. for 4 hr. The mixture was quenched with water (10 ml) and solvent was removed in vacuum. The residue was dissolved in water, and then extracted with ethyl acetate (30 mL×4). The combined organic layers were washed with brine, dried over anhydrous sodium sulfate, and concentrated to give a crude product. The crude product was purified by chromatography (silica gel, petroleum ether/ethyl acetate=3:1 then ethyl acetate/methanol=30:1) to afford the title compound (170 mg, yield: 21%). LC-MS (ESI) m/z: 409 (M+1)$^+$.

Example 103B 9-(4,5-Dimethyl-4H-1,2,4-triazol-3-yl)-8-(4-fluorophenyl)-8,9-dihydro-2H-pyrido[4,3,2-de]phthalazin-3(7H)-one A mixture of ethyl 3-(4,5-dimethyl-4H-1,2,4-triazol-3-yl)-2-(4-fluorophenyl)-4-oxo-1,2,3,4-tetrahydroquinoline-5-carboxylate (170 mg) in 85% hydrazine monohydrate (1 mL) and methanol (3 mL) was stirred at 25° C. for 3 h. The mixture was purified by prep-HPLC to obtain the title compound as a yellow solid (40 mg, yield: 26%). $^1$H-NMR (400 MHz, DMSO-d6) □ δ (ppm): 2.23 (s, 3H), 3.38 (s, 3H), 4.78-4.80 (d, J=11.0 Hz, 1H), 4.99-5.02 (d, J=11.0 Hz, 1H), 7.11-7.18 (m, 3H), 7.35-7.40 (m, 2H), 7.47-7.51 (m, 2H), 7.57-7.61 (t, J=7.6 Hz, 1H), 12.19 (s, 1H); LC-MS (ESI) m/z: 377 (M+1)$^+$.

Example 104

2-Fluoro-N,N-dimethyl-5-(9-(1-methyl-1H-imidazol-2-yl)-3-oxo-3,7,8,9-tetrahydro-2H-pyrido[4,3,2-de]phthalazin-8-yl)benzamide Example 104A 5-(Diethoxymethyl)-2-fluorobenzonitrile To a stirred solution of 2-fluoro-5-formylbenzonitrile (5.96 g, 40 mmol) in ethanol (5.6 g, 120 mmol) was added ammonium chloride (85.6 mg, 1.6 mmol). After the addition, the mixture was cooled to 0° C. and triethyl orthoformate (6.52 g, 44 mmol) was added dropwise. After the addition, the mixture was stirred at room temperature overnight. The mixture was concentrated, then filtered and the cake washed with ethyl acetate (20 mL×2). The filtrate was concentrate to give the title compound (8.8 g, yield 98%) as a colorless oil. $^1$H-NMR (400 MHz, CDCl$_3$) δ (ppm): 1.22-1.29 (m, 6H), 3.50-3.70 (m, 4H), 5.50 (s, 1H), 7.19-7.24 (t, J=8.8 Hz, 1H), 7.70-7.74 (m, 1H), 7.76-7.78 (dd, J$_1$=6.4 Hz, J$_2$=2.4 Hz, 1H). LC-MS (ESI) m/z: 224 (M+1)$^+$.

Example 104B

2-Fluoro-5-formylbenzoic acid

A mixture of 5-(diethoxymethyl)-2-fluorobenzonitrile (8.8 g, 39.5 mmol) in 3N aqueous sodium hydroxide (100 mL) was heated to 90° C. and stirred for 8 hr. Then the mixture was cooled to room temperature and acidified with 3N hydrochloric acid to pH=2, and then extracted with ethyl acetate (200 mL×4). The combined organic layers were dried over anhydrous Na$_2$SO$_4$ and concentrated to give 2-fluoro-5-formylbenzoic acid (6.6 g, yield 99%) as a white solid. $^1$H-NMR (400 MHz, CDCl$_3$) δ (ppm): 7.34-7.39 (dd, J$_1$=10 Hz, J$_2$=8.4 Hz, 1H), 8.14-8.18 (m, 1H), 8.57-8.59 (dd, J$_1$=7.2 Hz, J$_2$=2.4 Hz, 1H), 10.04 (s, 1H). LC-MS (ESI) m/z: 169 (M+1)$^+$.

Example 104C

2-Fluoro-5-formyl-N,N-dimethylbenzamide

The solution of 2-fluoro-5-formylbenzoic acid (3 g, 17.8 mmol) in methylene chloride (10 mL) was added thionyl chloride (2.0 mL, 26.7 mmol) slowly at 0° C. Then the cold reaction mixture was heated to reflux for 3 h. The solution was cooled to 0° C., added dimethylamine (40 wt. % solution in water, 5 mL) slowly, and then stirred at room temperature for 1 h. The solution was washed with water and brine, the organic layer was dried with Na$_2$SO$_4$ and the solvent was removed to get the desired product (2.4 g, yield 76%). LC-MS (ESI) m/z: 196 (M+1)$^+$ Example 104D (E)-2-fluoro-N,N-dimethyl-5-((1-oxo-1,3-dihydroisobenzofuran-4-ylimino)methyl)benzamide A solution of 2-fluoro-5-formyl-N,N-dimethylbenzamide (2.38 g, 12.2 mmol), 4-aminoisobenzofuran-1(3H)-one (1.82 g, 12.2 mmol), anhydrous magnesium sulfate (14.67 g, 122 mmol) in acetonitrile (100 ml) was heated to reflux for 2 days. The solution was filtered and removed in vacuum. The crude product was re-crystal with isopropanol to give the title compound (1.5 g, yield: 37%) $^1$H-NMR (400 MHz, DMSO-d6) δ (ppm): 2.91-2.92 (d, J=0.4 Hz, 3H), 3.07 (s, 3H), 5.55 (s, 2H), 7.52-7.56 (t, J=8.8 Hz, 1H), 7.67-7.70 (m, 2H), 7.76-7.78 (m, 1H), 8.02-8.04 (m, 1H), 8.10-8.14 (m, 1H), 8.83 (s, 1H); LC-MS (ESI) m/z: 327 (M+1)$^+$.

Example 104E

Ethyl 2-(3-(dimethylcarbamoyl)-4-fluorophenyl)-3-(1-methyl-1H-imidazol-2-yl)-4-oxo-1,2,3,4-tetrahydroquinoline-5-carboxylate A mixture of compound 1-methyl-1H-imidazole-2-carbaldehyde (110 mg, 1.0 mmol) and (E)-2-fluoro-N,N-dimethyl-5-((1-oxo-1,3-dihydroisobenzofuran-4-ylimino) methyl)benzamide (300 mg, 0.92 mmol) in ethyl propionate (10 mL) was cooled to 0° C. Then a solution of sodium ethoxide in ethanol (sodium (85 mg, 3.68 mmol) in ethanol (5 mL)) was added dropwise. After the addition, the mixture was stirred at room temperature for 2.5 hr. The mixture was quenched with water (20 mL) and solvent was removed in vacuum. The residue was dissolved in water and extracted with ethyl acetate three times, washed by water, brine then the extraction was evaporated, the crude product was purified by chromatography to obtain a yellow solid. The solid was dried in vacuum at 50° C. to give the title compound (130 mg, yield: 30%). LC-MS (ESI) m/z: 465 (M+1)$^+$.

Example 104F

2-Fluoro-N,N-dimethyl-5-(9-(1-methyl-1H-imidazol-2-yl)-3-oxo-3,7,8,9-tetrahydro-2H-pyrido[4,3,2-de]phthalazin-8-yl)benzamide A mixture of compound ethyl 2-(3-(dimethylcarbamoyl)-4-fluorophenyl)-3-(1-methyl-1H-imidazol-2-yl)-4-oxo-1,2,3,4-tetrahydroquinoline-5-carboxylate (130 mg) in hydrazine monohydrate (85%, 2 mL) and methanol (5 mL) was stirred at room temperature for 4 h. The resulting mixture was filtered and washed with water (20 ml) and methanol (5 ml) to obtain a white solid. The solid was dried in vacuum at 50° C. to obtain the title compound (30.0 mg, yield 30%). $^1$H-NMR (400 MHz, DMSO-d6) □ δ (ppm): 2.72 (s, 3H), 2.97 (s, 3H), 3.43 (s, 3H), 4.67-4.70 (d, J=10.8 Hz, 1H), 4.95-4.97 (d, J=10.8 Hz, 1H), 6.72-6.73 (d, J=1.2 Hz, 1H), 6.89-6.89 (d, J=0.8 Hz, 1H), 7.15-7.23 (m, 2H), 7.34-7.41 (m, 3H), 7.48-7.49 (m, 1H), 7.56-7.60 (t, J=8 Hz, 1H), 12.17 (s, 1H); LC-MS (ESI) m/z: 433 (M+1)$^+$.

Example 105

8-(4-Chlorophenyl)-9-(1-methyl-1H-imidazol-2-yl)-8,9-dihydro-2H-pyrido[4,3,2-de]phthalazin-3(7H)-one Example 105A (E)-4-(4-Chlorobenzylideneamino)isobenzofuran-1(3H)-one To a stirred mixture of 4-chlorobenzaldehyde (2.3 g, 16.1 mmol) and anhydrous magnesium sulfate (16 g, 134 mmol) in anhydrous acetonitrile (200 ml) was added 4-aminoisobenzofuran-1(3H)-one (2 g, 13.4 mmol) at room temperature. After the addition, the mixture was stirred at reflux for overnight. The mixture was filtered and the cake was washed with ethyl acetate (50 mL×3). The filtrate was concentrated to give crude product. The crude product was washed with petroleum ether and re-crystallized from ethyl acetate to give the title compound (2 g, yield: 55%). LC-MS (ESI) m/z: 272 (M+1)$^+$.

Example 105B

Ethyl 2-(4-chlorophenyl)-3-(1-methyl-1H-imidazol-2-yl)-4-oxo-1,2,3,4-tetrahydroquinoline-5-carboxylate A mixture of (E)-4-(4-chlorobenzylideneamino)isobenzofuran-1(3H)-one (500 mg, 1.85 mmol) and N-methyl-2-imidazolecarbaldehyde (222 mg, 2.1 mmol) in ethyl propionate (20 mL) was cooled to 0° C. Then a solution of sodium ethoxide in ethanol (sodium (174 mg, 7.4 mmol) in ethanol (10 mL)) was added dropwise. After the addition, the mixture was stirred at room temperature for 2 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=1:1) to give the title compound (150 mg, yield 20%). LC-MS (ESI) m/z: 410 (M+1)$^+$.

Example 105C 8-(4-Chlorophenyl)-9-(1-methyl-1H-imidazol-2-yl)-8,9-dihydro-2H-pyrido[4,3,2-de]phthalazin-3(7H)-one A mixture of ethyl 2-(4-chlorophenyl)-3-(1-methyl-1H-imidazol-2-yl)-4-oxo-1,2,3,4-tetrahydroquinoline-5-carboxylate (150 mg, 0.37 mmol) in 85% hydrazine monohydrate (4 ml) and methanol (6 ml) was stirred at room temperature for 2h. The mixture was filtered and washed with water to give the title compound (89 mg, yield: 65%). $^1$H-NMR (400 MHz, DMSO-d6) δ (ppm): 3.44 (s, 3H), 4.69 (d, J=10.8 Hz, 1H), 4.96 (d, J=10.8 Hz, 1H), 6.76 (s, 1H), 6.93 (d, 1H), 7.16 (d, J=8 Hz, 1H), 7.33-7.44 (m, 6H), 7.56-7.60 (m, 1H), 12.19 (d, 1H); LC-MS (ESI) m/z: 378 (M+1)$^+$.

Example 106

9-(1-Methyl-1H-imidazol-2-yl)-8-(4-(trifluoromethyl)phenyl)-8,9-dihydro-2H-pyrido[4,3,2-de]phthalazin-3(7H)-one Example 106A (E)-4-(4-(Trifluoromethyl)benzylideneamino)isobenzofuran-1(3H)-one To a stirred mixture of 4-(trifluoromethyl)benzaldehyde (2.8 g, 16.1 mmol) and anhydrous Magnesium sulfate (16 g, 134 mmol) in anhydrous acetonitrile (200 mL) was added 4-aminoisobenzofuran-1(3H)-one (2 g, 13.4 mmol) at room temperature. After the addition, the mixture was stirred at reflux for overnight. The mixture was filtered and the cake was washed with ethyl acetate (50 mL×3). The filtrate was concentrated to give crude product. The crude product was washed with petroleum ether and re-crystallized from ethyl acetate to give the title compound (2.8 g, yield: 68%). LC-MS (ESI) m/z: 306 (M+1)$^+$.

Example 106B

Ethyl 3-(1-methyl-1H-imidazol-2-yl)-4-oxo-2-(4-(trifluoromethyl)phenyl)-1,2,3,4-tetrahydroquinoline-5-carboxylate A mixture of (E)-4-(4-(trifluoromethyl)benzylideneamino)isobenzofuran-1(3H)-one (1 g, 3.28 mmol) and N-methyl-2-imidazolecarbaldehyde (400 mg, 3.61 mmol) in ethyl propionate (40 mL) was cooled to 0° C. Then a solution of sodium ethoxide in ethanol (sodium (31 mg, 13.1 mmol) in ethanol (10 mL)) was added dropwise. After the addition, the mixture was stirred at room temperature for 2 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=1:1) to give the title compound (150 mg, yield 8%). LC-MS (ESI) m/z: 444 (M+1)$^+$.

Example 106C 9-(1-Methyl-1H-imidazol-2-yl)-8-(4-(trifluoromethyl)phenyl)-8,9-dihydro-2H-pyrido[4,3,2-de]phthalazin-3(7H)-one A mixture of ethyl 3-(1-methyl-1H-imidazol-2-yl)-4-oxo-2-(4-(trifluoromethyl)phenyl)-1,2,3,4-tetrahydroquinoline-5-carboxylate (150 mg, 0.34 mmol) in 85% hydrazine monohydrate (4 ml) and methanol (6 mL) was stirred at room temperature for 2h. The mixture was filtered and washed with water to give the title compound (25 mg, yield: 18%). $^1$H-NMR (400 MHz, DMSO-d6) δ (ppm): 3.46 (s, 3H), 4.81 (d, J=10.8 Hz, 1H), 5.07 (d, J=10.8 Hz, 1H), 6.82 (s, 1H), 6.97 (d, 1H), 7.16 (d, J=8 Hz, 1H), 7.41 (d, J=7.6 Hz 2H), 7.58-7.69 (m, 5H), 12.22 (d, 1H); LC-MS (ESI) m/z: 412 (M+1)$^+$.

Example 107

8-(4-Fluorophenyl)-9-(thiazol-2-yl)-8,9-dihydro-2H-pyrido[4,3,2-de]phthalazin-3(7H)-one Example 107A Ethyl 2-(4-fluorophenyl)-4-oxo-3-(thiazol-2-yl)-1,2,3,4-tetrahydroquinoline-5-carboxylate A mixture of (E)-4-(4-fluorobenzylideneamino)isobenzofuran-1(3H)-one (1.88 g, 7.37 mmol) and thiazole-2-carbaldehyde (1 g, 8.8 mmol) in ethyl propionate (50 mL) was cooled to 0° C. Then a solution of sodium ethoxide in ethanol (sodium (678 g, 29 mmol) in ethanol (30 mL)) was added dropwise. After the addition, the mixture was stirred at room temperature for 2 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=10:1 to 1:10) to give the crude compound (180 mg). LC-MS (ESI) m/z: 397 (M+1)$^+$.

Example 107B 8-(4-Fluorophenyl)-9-(thiazol-2-yl)-8,9-dihydro-2H-pyrido[4,3,2-de]phthalazin-3(7H)-one A mixture of ethyl 2-(4-fluorophenyl)-4-oxo-3-(thiazol-2-yl)-1,2,3,4-tetrahydroquinoline-5-carboxylate (180 mg) in 85% hydrazine monohydrate (10 mL) and methanol (10 mL) was stirred at 45° C. for overnight. Methanol was removed under reduced pressure. The mixture was filtered and washed with water to give the title compound (3 mg, yield: 2%). $^1$H-NMR (400 MHz, CD$_3$OD) □□ δ (ppm): 4.88 (d, J=8.0 Hz, 1H), 5.09 (d, J=8.0 Hz, 1H), 7.01 (t, 2H), 7.21 (d, 1H), 7.36-7.40 (m, 2H), 7.47 (d, 1H), 7.59 (d, 1H), 7.65 (t, 1H), 7.74 (d, 1H); $^{19}$F-NMR (400 MHz, CD$_3$OD) δ(ppm): −116.36 (s); LC-MS (ESI) m/z: 365 (M+1)$^+$.

Example 108

9-(1-Ethyl-1H-imidazol-2-yl)-8-(4-fluorophenyl)-8,9-dihydro-2H-pyrido[4,3,2-de]phthalazin-3(7H)-one Example 108A Ethyl 3-(1-ethyl-1H-imidazol-2-yl)-2-(4-fluorophenyl)-4-oxo-1,2,3,4-tetrahydroquinoline-5-carboxylate A mixture of (E)-4-(4-fluorobenzylideneamino)isobenzofuran-1(3H)-one (765 mg, 3 mmol) and N-ethyl-2-imidazolecarbaldehyde (372 mg, 3 mmol) in ethyl propionate (45 mL) was cooled to 0° C. Then a solution of sodium ethoxide (sodium (276 mg, 12 mmol) in ethanol (45 mL)) was added dropwise. After the addition, the mixture was stirred at room temperature for 4 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product. The crude product was purified by chromatography (silica gel, petroleum ether/ethyl acetate=25:1 to 5:1) to give the title compound (90 mg, yield: 7%). LC-MS (ESI) m/z: 408 (M+1)$^+$.

Example 108B

Synthesis of 9-(1-Ethyl-1H-imidazol-2-yl)-8-(4-fluorophenyl)-8,9-dihydro-2H-pyrido[4,3,2-de]phthalazin-3(7H)-one A mixture of ethyl 3-(1-ethyl-1H-imidazol-2-yl)-2-(4-fluorophenyl)-4-oxo-1,2,3,4-tetrahydroquinoline-5-carboxylate (90 mg, 0.22 mmol) in 85% hydrazine monohydrate (4 mL) and methanol (10 mL) was stirred for 4 h at room temperature. Methanol was removed under reduced pressure. The mixture was filtered and washed with water to give the crude product. The crude product was purified by prep-HPLC to give the title compound (38.5 mg, yield: 47%). $^1$H-NMR (400 MHz, MeOD) □□δ(ppm): 1.06-1.09 (t, J=7.2 Hz, 3H), 3.74-3.78 (m, 2H), 4.60-4.62 (d, J=11.6 Hz, 1H), 4.98-5.01 (d, J=11.6 Hz, 1H), 6.91-7.02 (m, 4H), 7.19-7.21 (m, 1H), 7.39-7.43 (m, 2H), 7.56-7.64 (m, 2H); LC-MS (ESI) m/z: 376 (M+1)$^+$.

Example 109

8-(4-((4-Ethyl-3-methylpiperazin-1-yl)methyl)phenyl)-9-phenyl-8,9-dihydro-2H-pyrido[4,3,2-de]phthalazin-3(7H)-one To a stirred solution of 4-(3-oxo-9-phenyl-3,7,8,9-tetrahydro-2H-pyrido[4,3,2-de]phthalazin-8-yl)benzaldehyde (86 mg, 0.23 mmol) in dryness DCM (15 mL) was added HOAc followed by 1-ethyl-2-methylpiperazine (90 mg, 0.7 mmol), after the addition the mixture was stirred at room temperature overnight. Then the mixture was cooled to 0° C. Sodium borohydride (85 mg, 1.4 mmol) was added. After the addition, the mixture was stirred at this temperature for 12 hr. DCM was removed under reduced pressure. The residue was washed with ethyl acetate/methanol (10/1) and filtered. The filtrate was concentrated to give the crude product, which was purified by prep-HPLC to give the title compound as white solid (90 mg, yield 71%). $^1$H-NMR (400 MHz, DMSO-d6) δ (ppm): 1.30 (t, 3H), 1.42 (m, 3H), 3.23 (s, 1H), 3.47-3.56 (m, 6H), 3.80 (t, 2H), 4.46 (m, 3H) 4.91 (m, 10H), 7.20-7.29 (m, 3H), 7.30-7.32 (m, 3H), 7.46-7.48 (m, 3H), 7.59 (m, 1H), 7.69 (t, 1H). LC-MS (ESI) m/z: 552 (M+1)$^+$.

Example 110

8-(4-((4-Ethylpiperazin-1-yl)methyl)phenyl)-9-(4-fluorophenyl)-8,9-dihydro-2H-pyrido[4,3,2-de]phthalazin-3(7H)-one A mixture of 4-(3-oxo-9-phenyl-3,7,8,9-tetrahydro-2H-pyrido[4,3,2-de]phthalazin-8-yl)benzaldehyde (200 mg, 0.52 mmol), N-ethylpiperazine (209 mg, 1.56 mmol) and acetic acid (156 mg, 2.6 mmol) in dichloromethane (30 mL) was stirred at room temperature overnight. Then the mixture was cooled to 0° C. and sodium triacetoxyborohydride (165 mg, 0.78 mmol) was added. After the addition, the mixture was stirred at room temperature for 5 h. Dichloromethane was removed under reduced pressure. The crude product was purified by pre-HPLC to give the title compound (96 mg, yield 33%). $^1$H-NMR (400 MHz, CD$_3$OD) δ (ppm): 1.37-1.41 (t, J=6.8 Hz, 3H), 3.30-3.34 (m, 2H), 3.47-3.86 (m, 8H), 4.36-4.38 (d, J=7.6 Hz, 1H), 4.46 (s, 2H), 4.80-4.82 (d, J=8.4 Hz, 1H), 6.92-6.96 (m, 2H), 7.11-7.15 (m, 2H), 7.21-7.23 (m, 1H), 7.42-7.45 (m, 2H), 7.51-7.56 (m, 3H), 7.63-7.67 (m, 1H). LC-MS (ESI) m/z: 484 (M+H)$^+$.

Example 111

4-(9-(4-Fluorophenyl)-3-oxo-3,7,8,9-tetrahydro-2H-pyrido[4,3,2-de]phthalazin-8-yl)-N,N-dimethylbenzamide Example 111A Ethyl 2-(4-(dimethylcarbamoyl)phenyl)-3-(4-fluorophenyl)-4-oxo-1,2,3,4-tetrahydroquinoline-5-carboxylate Compound (E)-N,N-dimethyl-4-((1-oxo-1,3-dihydroisobenzofuran-4-ylimino)methyl)benzamide (1.36 g, 4.4 mmol), 4-fluorobenzaldehyde (600 mg, 4.84 mmol), sodium (405 mg, 17.6 mmol), ethanol (40 mL) and ethyl propionate (66 mL) were added and the mixture was stirred at room temperature overnight. Then the resulting mixture was evaporated under reduced pressure and extracted with ethyl acetate (100 mL×4) and concentrated. The crude product was purified by column chromatography (silica gel, petroleum ether/ethyl acetate=20:1 to 5:1) to give the title compound as a solid (490 mg, yield 22%). LC-MS (ESI) m/z: 461 (M+1)$^+$.

Example 111B 4-(9-(4-Fluorophenyl)-3-oxo-3,7,8,9-tetrahydro-2H-pyrido[4,3,2-de]phthalazin-8-yl)-N,N-dimethylbenzamide A mixture of ethyl 2-(4-(dimethylcarbamoyl)phenyl)-3-(4-fluorophenyl)-4-oxo-1,2,3,4-tetrahydroquinoline-5-carboxylate (490 mg, 1 mmol) and hydrazine monohydrate (15 mL) was stirred at 40° C. for 3 h. Then the mixture was cooled to room temperature and filtered to give the title compound (110 mg, yield 24%) as a white solid. $^1$H-NMR (400 MHz, DMSO-d6) δ (ppm): 2.82 (s, 1H), 2.93 (s, 1H), ☐4.36-4.38 (d, J=9.2 Hz, 1H), 4.78-4.80 (d, J=9.2 Hz, 1H), 7.01-7.03 (m, 2H), 7.14-7.19 (m, 3H), 7.25-7.28 (m, 2H), 7.32-7.40 (m, 3H), 7.45 (s, 1H), 7.56-7.60 (t, J=8 Hz, 1H), 12.17 (s, 1H); LC-MS (ESI) m/z: 429 (M+1)$^+$.

Example 112

4-(8-(4-((Dimethylamino)methyl)phenyl)-3-oxo-3,7,8,9-tetrahydro-2H-pyrido[4,3,2-de]phthalazin-9-yl)-N,N-dimethylbenzamide Example 112A Ethyl 2-(4-(diethoxymethyl)phenyl)-3-(4-(dimethylcarbamoyl)phenyl)-4-oxo-1,2,3,4-tetrahydroquinoline-5-carboxylate To a mixture of 4-formyl-N,N-dimethylbenzamide (960 mg, 5.42 mmol), (E)-4-(4-(diethoxymethyl)benzylideneamino) isobenzofuran-1(3H)-one (1.84 g, 5.42 mmol) and sodium methoxide (499 mg, 21.7 mmol) was added to ethyl propionate (30 mL) and the mixture was stirred at room temperature overnight. Then the resulting mixture was evaporated under reduced pressure and extracted with EtOAc (100 mL×4) and concentrated. This gave the crude product (250 mg). LC-MS (ESI) m/z: 545 (M+1)$^+$.

Example 112B 4-(8-(4-(Diethoxymethyl)phenyl)-3-oxo-3,7,8,9-tetrahydro-2H-pyrido[4,3,2-de]phthalazin-9-yl)-N,N-dimethylbenzamide Ethyl 2-(4-(diethoxymethyl)phenyl)-3-(4-(dimethylcarbamoyl)phenyl)-4-oxo-1,2,3,4-tetrahydroquinoline-5-carboxylate (250 mg, 0.46 mmol) and hydrazine monohydrate (85%, 5 mL) were added in MeOH (15 mL) and the mixture was stirred room temperature for 5 h. The resulting mixture was concentrated under reduced pressure to a volume of 15 mL and then filtered; the filtrate was evaporated to give the title compound as a white solid (180 mg, yield 76%). LC-MS (ESI) m/z: 513 (M+1)$^+$.

Example 112C 4-(8-(4-Formylphenyl)-3-oxo-3,7,8,9-tetrahydro-2H-pyrido[4,3,2-de]phthalazin-9-yl)-N,N-dimethylbenzamide To a solution of 4-(8-(4-(diethoxymethyl)phenyl)-3-oxo-3,7,8,9-tetrahydro-2H-pyrido[4,3,2-de]phthalazin-9-yl)-N,N-dimethylbenzamide (180 mg, 0.35 mmol) in acetonitrile (10 mL) was added trifluoroacetic acid (5 mL), stirred for 30 min, Then the mixture was evaporated under reduced pressure to get the title compound (140 mg, yield 91%). LC-MS (ESI) m/z: 439 (M+1)$^+$.

Example 112D 4-(8-(4-((Dimethylamino)methyl)phenyl)-3-oxo-3,7,8,9-tetrahydro-2H-pyrido[4,3,2-de]phthalazin-9-yl)-N,N-dimethylbenzamide To a stirred solution of 4-(8-(4-formylphenyl)-3-oxo-3,7,8,9-tetrahydro-2H-pyrido[4,3,2-de]phthalazin-9-yl)-N,N- dimethylbenzamide (140 mg, 0.32 mmol) in dried DCM (20 mL) was added acetic acid followed by dimethylamine (57 mg, 1.3 mmol). After the addition, the mixture was stirred at room temperature overnight. Then the mixture was cooled to 0° C. Sodium borohydride (102 mg, 0.48 mmol) was added. After the addition, the mixture was stirred at this temperature for 12 hr. DCM was removed under reduced pressure. The residue was washed with ethyl acetate/methanol (10/1) and filtered. The filtrate was concentrated to give the crude product, which was purified by prep-HPLC to give the title compound as a white solid (15 mg, yield 10%). $^1$H-NMR (400 MHz, CD$_3$OD) δ (ppm): 2.19 (dd, 6H), 2.93 (s, 3H), 3.06 (s, 3H), 3.40 (dd, 2H), 4.34 (d, 1H), 4.16-7.19 (m, 5H), 7.23-7.26 (m, 4H), 7.54 (d, 1H), 7.61 (t, 1H). LC-MS (ESI) m/z: 468 (M+1)$^+$.

Example 113

9-(4-Fluorophenyl)-8-(4-((4-methylpiperazin-1-yl)methyl)phenyl)-8,9-dihydro-2H-pyrido[4,3,2-de]phthalazin-3(7H)-one A mixture of 4-(9-(4-fluorophenyl)-3-oxo-3,7,8,9-tetrahydro-2H-pyrido[4,3,2-de]phthalazin-8-yl)benzaldehyde (150 mg, 0.39 mmol), N-methylpiperazine (117 mg, 1.17 mmol) and acetic acid (117 mg, 1.95 mmol) in dichloromethane (20 mL) was stirred at room temperature overnight. Then the mixture was cooled to 0° C. and sodium triacetoxyborohydride (124 mg, 0.58 mmol) was added. After the addition, the mixture was stirred at room temperature for 5 h. Dichloromethane was removed under reduced pressure. The crude product was purified by prep-HPLC to give the title compound (48 mg, yield 22%). $^1$H-NMR (400 MHz, CD$_3$OD) δ (ppm): 3.02 (s, 3H), 3.60-3.81 (m, 8H), 4.36-4.38 (d, J=7.6 Hz, 1H), 4.47 (s, 2H), 4.80-4.82 (d, J=7.6 Hz, 1H), 6.93-6.97 (m, 2H), 7.12-7.15 (m, 2H), 7.22-7.24 (m, 1H), 7.43-7.45 (m, 2H), 7.52-7.57 (m, 3H), 7.64-7.68 (m, 1H). LC-MS (ESI) m/z: 470 (M+1)$^+$.

Example 114

9-(4-Fluorophenyl)-8-(4-(piperazin-1-ylmethyl)phenyl)-8,9-dihydro-2H-pyrido[4,3,2-de]phthalazin-3(7H)-one Example 114A tert-Butyl 4-(4-(9-(4-fluorophenyl)-3-oxo-3,7,8,9-tetrahydro-2H-pyrido[4,3,2-de]phthalazin-8-yl)benzyl)piperazine-1-carboxylate A mixture of 4-(9-(4-fluorophenyl)-3-oxo-3,7,8,9-tetrahydro-2H-pyrido[4,3,2-de]phthalazin-8-yl)benzaldehyde (150 mg, 0.39 mmol), tert-butyl piperazine-1-carboxylate (218 mg, 1.17 mmol), and acetic acid (117 mg, 1.95 mmol) in dichloromethane (20 mL) was stirred at room temperature overnight. Then the mixture was cooled to 0° C. and sodium triacetoxyborohydride (124 mg, 0.58 mmol) was added. After the addition, the mixture was stirred at room temperature for 5 h. Dichloromethane was removed under reduced pressure. The crude product was purified by flash chromatography to give the title compound (70 mg, yield 32%). LC-MS (ESI) m/z: 556 (M+1)$^+$.

Example 114B 9-(4-Fluorophenyl)-8-(4-(piperazin-1-ylmethyl)phenyl)-8,9-dihydro-2H-pyrido[4,3,2-de]phthalazin-3(7H)-one The mixture of tert-butyl 4-(4-(9-(4-fluorophenyl)-3-oxo-3,7,8,9-tetrahydro-2H-pyrido[4,3,2-de]phthalazin-8-yl)benzyl)piperazine-1-carboxylate (70 mg, 0.12 mmol) in a solution of HCl(g) in acetonitrile (sat. 10 mL) was stirred for 3 hr at room temperature. Then the mixture was filtered to give the crude product. The crude product was purified by flash chromatography to give the title compound as a hydrochloride salt (35 mg, yield 60%). $^1$H-NMR (400 MHz, CD$_3$OD) δ (ppm): 2.63-2.64 (m, 4H), 3.19-3.21 (m, 4H), 3.54 (s, 2H), 4.29-4.31 (d, J=8.0 Hz, 1H), 4.69-4.71 (d, J=8.4 Hz, 1H), 6.89-6.93 (m, 2H), 7.07-7.10 (m, 2H), 7.19-7.26 (m, 5H), 7.54-7.56 (m, 1H), 7.61-7.65 (m, 1H). LC-MS (ESI) m/z: 456 (M+1)$^+$.

Example 115

9-(4-fluorophenyl)-8-(4-((3-methylpiperazin-1-yl)methyl)phenyl)-8,9-dihydro-2H-pyrido[4,3,2-de]phthalazin-3(7H)-one Example 115A 4-Benzyl 1-tert-butyl 2-methylpiperazine-1,4-dicarboxylate To the solution of 2-methyl-piperazine (2.0 g, 20 mmol) in methylene chloride (15 mL) at 0° C. was added benzylchloroformate (3.0 mL) dropwise. The mixture was stirred at 0° C. for 1 hr and then at room temperature for 2 hr. The mixture was then cooled to 0° C., and diisopropylethylamine (4.5 mL) was added and followed by (Boc)$_2$O (4.8 g, 22 mmol). The mixture was stirred at room temperature overnight, and then the solvent was removed by rotary evaporation. The residue was dissolved in EtOAc, washed with water and brine, dried over Na$_2$SO$_4$, and purified with column chromatograph on silica gel (EtOAc:hexane=1:9) to give an oily intermediate (4.8 g, 72%). LC-MS (ESI) m/z: 357 (M+23)$^+$.

Example 115B tert-Butyl 2-methylpiperazine-1-carboxylate

A solution of 4-benzyl 1-tert-butyl 2-methylpiperazine-1,4-dicarboxylate (4.8 g, 14.4 mmol) in methanol (25 mL) was added 480 mg of 10% Pd/C and stirred at room temperature under hydrogen overnight. Filtered and concentrated to give the title product (2.8 g, yield 97%) as colorless oil. $^1$H-NMR (400 MHz, CDCl$_3$) δ (ppm): 1.21 (d, J=6.8 Hz, 3H), 1.46 (s, 9H), 2.64-2.70 (m, 1H), 2.74-2.78 (m, 1H), 2.88-3.01 (m, 3H), 3.78 (d, J=12.4 Hz, 1H), 4.16 (m, 1H); LC-MS (ESI) m/z: 201 (M+1)$^+$.

Example 115C tert-Butyl 4-(4-(9-(4-fluorophenyl)-3-oxo-3,7,8,9-tetrahydro-2H-pyrido[4,3,2-de]phthalazin-8-yl)benzyl)-2-methylpiperazine-1-carboxylate A mixture of 4-(9-(4-fluorophenyl)-3-oxo-3,7,8,9-tetrahydro-2H-pyrido[4,3,2-de]phthalazin-8-yl)benzaldehyde (200 mg, 0.52 mmol) and tert-butyl 2-methylpiperazine-1-carboxylate (311 mg, 1.56 mmol) in methylene chloride (10 mL) was stirred at room temperature overnight, then NaBH$_3$CN (129 mg, 2.1 mmol) was added and the mixture was stirred for another 5 hours. Concentrated and the residue was purified by chromatography (silica gel, petroleum ether/ethyl acetate=3:1 to 1:1) to give the title compound (70 mg, yield 24%). LC-MS (ESI) m/z: 570 (M+1)$^+$.

Example 115D 9-(4-Fluorophenyl)-8-(4-((3-methylpiperazin-1-yl)methyl)phenyl)-8,9-dihydro-2H-pyrido[4,3,2-de]phthalazin-3(7H)-one A mixture of tert-butyl 4-(4-(9-(4-fluorophenyl)-3-oxo-3,7,8,9-tetrahydro-2H-pyrido[4,3,2-de]phthalazin-8-yl)benzyl)-2-methylpiperazine-1-carboxylate (70 mg, 0.123 mole) in 2 ml of HCl-acetonitrile was stirred for 2 hours. Concentrated and the residue was purified by prep-HPLC to afford the title produce as a white solid (30 mg, yield 52%). $^1$H-NMR (400 MHz, DMSO-d6) □□δ (ppm): 0.87 (d, J=6.4 Hz, 3H), 1.49 (t, J=10 Hz, 1H), 1.83 (t, J=10 Hz, 1H), 2.55 (m, 2H), 2.64 (m, 2H), 2.75 (m, 1H), 3.32 (s, 3H), 4.34 (d, J=9.2 Hz, 1H), 4.72 (d, J=9.2 Hz, 1H), 6.97-7.01 (m, 2H), 7.13-7.24 (m, 7H), 7.37-7.41 (m, 2H), 7.55-7.59 (m, 1H), 12.15 (s, 1H); LC-MS (ESI) m/z: 470 (M+1)$^+$.

Example 116

4-(8-(4-Fluorophenyl)-3-oxo-3,7,8,9-tetrahydro-2H-pyrido[4,3,2-de]phthalazin-9-yl)-N,N-dimethylbenzamide Example 116A Ethyl 3-(4-(dimethylcarbamoyl)phenyl)-2-(4-fluorophenyl)-4-oxo-1,2,3,4-tetrahydroquinoline-5-carboxylate Sodium (115 mg, 5 mmol) was added to EtOH (10 mL) to afford sodium ethoxide. (E)-4-(4-fluorobenzylideneamino)isobenzofuran-1(3H)-one (500 mg, 1.96 mmol) and 4-formyl-N,N-dimethylbenzamide (382 mg, 2.16 mmol) were dissolved in ethyl propionate (10 mL), and the sodium ethoxide solution was added dropwise to the mixture at 0° C., then the mixture were heated to 30° C. for 1 h. To the reaction mixture was added water and EtOAc, the organic phase was separated, washed with water and brine. The organic phase was dried over anhydrous sodium sulfate and then concentrated to afford the crude product. The crude product was purified by flash chromatography (MeOH:DCM 1:25) to give the title compound (400 mg, yield 44%). LC-MS (ESI) m/z: 461 (M+1)$^+$ Example 116B 4-(8-(4-Fluorophenyl)-3-oxo-3,7,8,9-tetrahydro-2H-pyrido[4,3,2-de]phthalazin-9-yl)-N,N-dimethylbenzamide A mixture of ethyl 3-(4-(dimethylcarbamoyl)phenyl)-2-(4-fluorophenyl)-4-oxo-1,2,3,4-tetrahydroquinoline-5-carboxylate (400 mg, 0.87 mmol) and hydrazine monohydrate (85%, 10 mL) were dissolved in MeOH (20 mL), and stirred at 35° C. for 2 h. The mixture was concentrated under reduced pressure. The resulting mixture was filtered, the solid was washed with water and methanol to obtain a white solid, and the solid was dried in vacuum at 40° C. to obtain the title compound (100 mg, yield 54%). $^1$H-NMR (400 MHz, DMSO-d6) □□ δ (ppm): 2.85 (s, 3H), 2.94 (s, 3H), 4.37-4.40 (d, 1H), 4.80-4.82 (d, 1H), 7.17-7.25 (m, 5H), 7.33-7.36 (m, 2H), 7.39-7.41 (d, 1H), 7.45 (s, 1H), 7.57-7.61 (t, 1H), 12.19 (s, 1H); LC-MS (ESI) m/z: 429 (M+1)$^+$.

Example 117

9-(4-Fluorophenyl)-8-(4-(pyrrolidin-1-ylmethyl)phenyl)-8,9-dihydro-2H-pyrido[4,3,2-de]phthalazin-3(7H)-one Example 117A 9-(4-Fluorophenyl)-8-(4-(pyrrolidin-1-ylmethyl)phenyl)-8,9-dihydro-2H-pyrido[4,3,2-de]phthalazin-3(7H)-one To a stirred mixture of 4-(9-(4-fluorophenyl)-3-oxo-3,7,8,9-tetrahydro-2H-pyrido[4,3,2-de]phthalazin-8-yl)benzaldehyde (0.1 g, 0.26 mmol) in anhydrous DCM (4 mL) was added AcOH (94 mg, 1.56 mmol) at 25° C. for 0.5 h, then pyrrolidine (37 mg, 0.52 mmol) was added at 25° C., stirred overnight. NaBH(OAc)$_3$ was added at ice bath, and stirred for 5 h. The mixture was concentrated to give the crude product. The crude product was dissolved in ethyl acetate and to this solution was added 2N HCl (10 mL). The aqueous phase was separated and 20% NaOH (20 ml) was added. The mixture was extracted with ethyl acetate and the organic phase was separated to give the title compound (30 mg, yield 26%). LC-MS (ESI) m/z: 441 (M+1)$^+$.

Example 117B 9-(4-Fluorophenyl)-8-(4-(pyrrolidin-1-ylmethyl)phenyl)-8,9-dihydro-2H-pyrido[4,3,2-de]phthalazin-3(7H)-one A mixture of 9-(4-fluorophenyl)-8-(4-(pyrrolidin-1-ylmethyl)phenyl)-8,9-dihydro-2H-pyrido[4,3,2-de]phthalazin-3(7H)-one (30 mg) in HCl/methanol solution (20 mL) was stirred at 25° C. for 0.5 h. Methanol was removed under reduced pressure. The mixture was filtered and washed with water, dried overnight at 50° C. to give the title compound (24 mg, yield 74%). $^1$H-NMR (400 MHz, CD$_3$OD) δ (ppm): 2.00 (s, 2H), 2.16 (s, 2H), 3.14 (s, 2H), 3.41 (s, 2H), 4.32 (s, 2H), 4.35-4.38 (d, 1H), 4.78-4.80 (d, 1H), 6.91-6.95 (t, 2H), 7.10-7.13 (t, 2H), 7.22-7.24 (d, 1H), 7.42 (m, 4H), 7.56-7.58 (d, 2H), 7.64-7.70 (1H); LC-MS (ESI) m/z: 441 (M+1)$^+$.

Example 118

9-Phenyl-8,9-dihydro-2H-pyrido[4,3,2-de]phthalazin-3(7H)-one

Example 118A

2-Oxo-N-(1-oxo-1,3-dihydroisobenzofuran-4-yl)-2-phenylacetamide

To a solution of 4-aminoisobenzofuran-1(3H)-one (4.0 g, 26.8 mmol), 2-oxo-2-phenylacetic acid (4.1 g, 26.8 mmol), and HBTU (15.2 g, 40.2 mmol) in dichloromethane (240 mL) was added TEA (8 mL). The reaction mixture was stirred at room temperature overnight. The resulting mixture was added water and adjusted to pH=6-7 with 1% aq. HCl, and then was filtered. The filtrate was extracted with ethyl acetate. The ethyl acetate layer was evaporated and the crude product was purified by gradient chromatography (silica gel, petroleum ether/ethyl acetate 6:1 to 3:1) to give the title compound (5.0 g, yield 66%). LC-MS (ESI) m/z: 282 (M+1)$^+$.

Example 118B

N-(4-Methoxybenzyl)-2-oxo-N-(1-oxo-1,3-dihydroisobenzofuran-4-yl)-2-phenylacetamide To a solution of 2-oxo-N-(1-oxo-1,3-dihydroisobenzofuran-4-yl)-2-phenylacetamide (5 g, 11.7 mmol) in DMF (48 mL) was added NaH (0.78 g, 19.5 mmol). The solution was stirring at room temperature for 1.5 hr, followed by the addition of 1-(chloromethyl)-4-methoxy-benzene (2.8 mL). After stirred at 30° C. overnight, the resulting mixture was added water and adjusted to pH=3-4 with 0.5 N aq. HCl. Then ethyl acetate was added, concentrated and filtered, the filtrate was washed by ethyl acetate, the combine ethyl acetate layer was washed with brine, dried over anhydrous sodium sulfate, concentrated, and purified by flash chromatography on silica gel to obtain the desired compound (4.7 g, yield 66%). LC-MS (ESI) m/z: 402 (M+1)$^+$. $^1$H-NMR (400 MHz, DMSO-d6) □□ δ (ppm): 3.73 (s, 3H), 4.83-5.17 (m, 4H), 6.89-6.91 (d, J=8.8 Hz, 2H), 7.18-7.20 (m, 2H), 7.24-7.26 (m, 1H), 7.38-7.42 (t, 1H), 7.52-7.56 (m, 2H), 7.69-7.71 (m, 1H), 7.75-7.81 (m, 3H).

Example 118C

Ethyl 4-hydroxy-1-(4-methoxybenzyl)-2-oxo-3-phenyl-1,2-dihydroquinoline-5-carboxylate A mixture of N-(4-methoxybenzyl)-2-oxo-N-(1-oxo-1,3-dihydroisobenzofuran-4-yl)-2-phenylacetamide (4.7 g, 11.7 mmol) and anhydrous Na$_2$SO$_4$ (16.6 g, 117 mmol) in anhydrous ethyl propionate (120 mL) was cooled to 0° C. Then a solution of sodium ethoxide in ethanol (sodium (673 mg, 29.2 mmol) in anhydrous ethanol (70 mL)) was added dropwise. After the addition, the mixture was stirred at room temperature for 18 hr. The mixture was quenched with water (100 mL) and solvent was removed in vacuum. The residue was dissolved in water, and then extracted with ethyl acetate (250 mL×4). The combined organic layers were washed with brine, dried over anhydrous sodium sulfate, and concentrated to give product (4.02 g, yield 80%). LC-MS (ESI) m/z: 430 (M+1)$^+$. $^1$H-NMR (400 MHz, DMSO-d6) □□δ (ppm): 1.23-1.26 (t, J=6.8 Hz, 3H), 3.69 (s, 3H), 4.21-4.23 (m, 2H), 5.46 (s, 1H), 6.86-6.88 (d, J=7.6 Hz, 2H), 7.11-7.18 (m, 3H), 7.36-7.55 (m, 7H), 10.59 (s, 1H).

Example 118D

Ethyl 4-hydroxy-2-oxo-3-phenyl-1,2-dihydroquinoline-5-carboxylate

A mixture of ethyl 4-hydroxy-1-(4-methoxybenzyl)-2-oxo-3-phenyl-1,2-dihydroquinoline-5-carboxylate (298 mg, 2 mmol) in trifluoroacetic acid was heated to reflux for 48 h. After the removal of the solvents, the residue was washed by ethyl acetate to obtain the title compound as a white solid (250 mg, yield 32%). LC-MS (ESI) m/z: 310 (M+1)$^+$. $^1$H-NMR (400 MHz, DMSO-d6) δ (ppm): 1.25 (t, J=7.2 Hz, 3H), 4.23 (q, J=7.2 Hz, 2H), 7.08 (d, J=7.2 Hz, 1H), 7.31-7.43 (m, 6H), 7.52 (t, J=8 Hz, 1H), 10.39 (s, 1H), 11.64 (s, 1H).

Example 118E

9-Phenyl-2H-pyrido[4,3,2-de]phthalazine-3,8(7H,9H)-dione

Ethyl 4-hydroxy-2-oxo-3-phenyl-1,2-dihydroquinoline-5-carboxylate (330 mg, 1.1 mmol) was added to hydrazine monohydrate (1 mL) and methanol (2 mL), the mixture was stirred at 110° C. for 2.5 h by microwave. Then the mixture was cooled to room temperature, the solvent was evaporated in vacuum. The residue was washed with methanol, and then purified by column chromatography (silica gel, dichloromethane/methanol=300:1 to 50:1) to obtain a pale white solid (148 mg, yield 53%). LC-MS (ESI) m/z: 278 (M+1)$^+$. $^1$H-NMR (400 MHz, DMSO-d6) δ (ppm): 5.09 (s, 1H), 7.17-7.40 (m, 6H), 7.77-7.81 (m, 2H), 11.10 (s, 1H), 12.57 (s, 1H).

Example 118F

9-Phenyl-8,9-dihydro-2H-pyrido[4,3,2-de]phthalazin-3(7H)-one

A mixture of 9-phenyl-2H-pyrido[4,3,2-de]phthalazine-3,8(7H,9H)-dione (80 mg, 2.2 mmol), BH$_3$ (0.7 mL, 1 mol/L in THF), dioxane (4 mL) in sealed tube was stirred for 2 h at 95° C. under nitrogen atmosphere. Then the mixture was treated with MeOH~HCl (g) (0.2 mL), stirred for 20 min at 95° C. Then the mixture was cooled and adjusted to pH=8 with Et$_3$N. The solvent was removed under vacuum and the crude was purified by column chromatography (silica gel, petroleum ether/ethyl acetate=20:1 to 1:1) to obtain the title compound as a yellow solid (18.3 mg, yield 24%). LC-MS (ESI) m/z: 264 (M+1)$^+$. $^1$H-NMR (400 MHz, CD$_3$OD) δ (ppm): 3.60-3.64 (m, 1H), 3.68-3.72 (m, 1H), 4.21 (t, J=5.2 Hz, 1H), □7.09-7.11 (d, J=8 Hz, 1H), 7.16-7.29 (m, 5H), 7.53-7.61 (m, 2H).

Example 119

8-(4-Fluorophenyl)-9-(4-methyl-4H-1,2,4-triazol-3-yl)-8,9-dihydro-2H-pyrido[4,3,2-de]phthalazin-3(7H)-one Example 119A Ethyl 2-(4-fluorophenyl)-3-(4-methyl-4H-1,2,4-triazol-3-yl)-4-oxo-1,2,3,4-tetrahydroquinoline-5-carboxylate A mixture of compound (E)-4-(4-fluorobenzylideneamino)isobenzofuran-1(3H)-one (690 mg, 2.7 mmol) and 4-methyl-4H-1,2,4-triazole-3-carbaldehyde (300 mg, 2.7 mmol) in ethyl propionate (20 mL) was cooled to 0° C. Then a solution of sodium ethoxide in ethanol [sodium (250 mg, 10.8 mmol) in ethanol (10 mL)] was added dropwise. After the addition the mixture was stirred at room temperature for 2.5 hr, then was quenched with water (20 mL) and solvent was removed in vacuum. The residue was dissolved in water and extracted with ethyl acetate three times, washed with water and brine, and then evaporated to give the crude product, which was purified by chromatography to obtain a yellow solid (120 mg, yield 11%). LC-MS (ESI) m/z: 395 (M+1)$^+$.

Example 119B 8-(4-Fluorophenyl)-9-(4-methyl-4H-1,2,4-triazol-3-yl)-8,9-dihydro-2H-pyrido[4,3,2-de]phthalazin-3(7H)-one A mixture of ethyl 2-(4-fluorophenyl)-3-(4-methyl-4H-1,2,4-triazol-3-yl)-4-oxo-1,2,3,4-tetrahydroquinoline-5-carboxylate (120 mg) in 85% hydrazine monohydrate (2 mL) and methanol (5 mL) was stirred at room temperature for 4 h. Then the solution was evaporated, the crude product was purified by prep-HPLC to obtain the title compound as a white solid (20 mg, yield 18%). LC-MS (ESI) m/z: 363 (M+1)$^+$. $^1$H-NMR (400 MHz, DMSO-d6) □ δ (ppm): 3.50 (s, 3H), 4.83-4.86 (d, J=11.6 Hz, 1H), 5.00-5.03 (d, J=11.6 Hz, 1H), 7.12-7.19 (m, 3H), 7.39-7.42 (m, 2H), 7.47-7.51 (m, 2H), 7.60-7.64 (t, J=8 Hz, 1H), 8.31 (s, 1H), 12.24 (s, 1H).

Example 120

8-(4-Fluorophenyl)-9-(1-methyl-1H-1,2,4-triazol-5-yl)-8,9-dihydro-2H-pyrido[4,3,2-de]phthalazin-3(7H)-one

Example 120A

Ethyl 2-(4-fluorophenyl)-3-(1-methyl-1H-1,2,4-triazol-5-yl)-4-oxo-1,2,3,4-tetrahydroquinoline-5-carboxylate To a solution of 4-(4-fluorobenzylideneamino) isobenzofuran-1(3H)-one (5.0 g, 19.6 mmol) and 1-methyl-1H-1,2,4-triazole-5-carbaldehyde (2.8 g, 25.5 mmol) in ethyl propionate (310 mL) was added sodium ethoxide (1.26 g, 54.9 mmol) at room temperature under nitrogen. The mixture was stirred at 55° C. for 2 hr. Then the resulting mixture was evaporated under reduced pressure and extracted with ethyl acetate (150 mL×4) and concentrated the extracts. The crude product was purified by column chromatography (silica gel, petroleum ether:ethyl acetate=20:1 to 1.5:1). A solid product was obtained (2.4 g, yield 31%). LC-MS (ESI) m/z: 395 (M+1)$^+$.

Example 120B 8-(4-Fluorophenyl)-9-(1-methyl-1H-1,2,4-triazol-5-yl)-8,9-dihydro-2H-pyrido[4,3,2-de]phthalazin-3(7H)-one A 100 mL round-bottom flask equipped with a thermometer and magnetic stirrer was charged with ethyl 2-(4-fluorophenyl)-3-(1-methyl-1H-1,2,4-triazol-5-yl)-4-oxo-1,2,3,4-tetrahydroquinoline-5-carboxylate (1.72 g, 4.4 mmol), methanol (15 mL), and NH$_2$NH$_2$ (4 mL, 85%). The mixture was stirred at 25° C. for 5 hr. The reaction was monitored by HPLC for completion. The mixture was evaporated under reduced pressure and methanol was added to make slurry. The suspension was filtered. The obtained solid was washed with 20 mL of methanol, and was dried to afford the title compound (1.4 g, yield 90%). LC-MS (ESI) m/z: 363 (M+1)$^+$. $^1$H-NMR (400 MHz, DMSO-d$_6$) □□ δ (ppm): 3.65 (s, 3H), 4.93-4.97 (m, 2H), 7.12-7.19 (m, 3H), 7.39-7.43 (m, 2H), 7.47-7.50 (m, 2H), 7.58-7.60 (m, 1H), 7.79 (s, 1H), 12.22 (s, 3H).

Example 121

8-(4-Fluorophenyl)-9-(1-methyl-1H-imidazo[4,5-c]pyridin-2-yl)-8,9-dihydro-2H-pyrido[4,3,2-de]phthalazin-3(7H)-one

Example 121A

N-Methyl-3-nitropyridin-4-amine

To a suspension of 4-chloro-3-nitropyridine (2 g, 12.6 mmol) in dichloromethane (15 mL) was cautiously added methyl amine (25% solution in water, 10 mL, 63 mmol). The reaction mixture was heated to 40° C. After stirring for 1 h, the mixture was poured into water (20 mL), and the precipitate was collected by filtration and dried in vacuo to afford the title compound (1.9 g, yield 98%) as a yellow solid. LC-MS (ESI) m/z: 154 (M+1)$^+$.

Example 121B

N-4-methylpyridine-3,4-diamine

The suspension of N-methyl-3-nitropyridin-4-amine (2.5 g, 16.3 mmol) and Pd/C (10%, 500 mg) in methanol (50 mL) was hydrogenated at room temperature overnight. Then the mixture was filtered and the filtrate was evaporated to give the product (1.2 g, yield 60%). LC-MS (ESI) m/z: 124 (M+1)$^+$

Example 121C 1,2-Dimethyl-1H-imidazo[4,5-c]pyridine

The solution of N4-methylpyridine-3,4-diamine (2.5 g, 20.3 mmol) in acetic anhydride (25 mL) was refluxed overnight. Then acetic anhydride was evaporated under reduced pressure and 1 N hydrochloride acid was added. Then the mixture was extracted with dichloromethane (50 mL×3). The aqueous layer was neutralized with sodium bicarbonate, and extracted with dichloromethane (50 mL×3). The organic layers were concentrated to give the title compound (1.9 g, yield 64%). LC-MS (ESI) m/z: 148 (M+1)$^+$. $^1$H-NMR (400 MHz, CDCl$_3$) δ (ppm): 2.64 (s, 3H), 3.74 (s, 3H), 7.23-7.24 (d, J=5.2 Hz, 1H), 8.39-8.41 (d, J=5.2 Hz, 1H), 8.98 (s, 1H).

Example 121D

1-Methyl-1H-imidazo[4,5-c]pyridine-2-carbaldehyde

To a solution of 1,2-dimethyl-1H-imidazo[4,5-c]pyridine (500 mg, 3.40 mmol) in dry 1,4-dioxane (7.5 mL) was addedhttp://newsearchch.chemexper.com/cheminfo/servlet/org.dbcreator.MainServlet?sort=%3E %7Eentry.intValue&query=structure._ structureID%3D4635571&target=entry&action= PowerSearch&onclick=1&from=0&history= off&forGroupNames=&style=&realQuery= rn.value%3D%22CF3COOH%22+elsor+ entry.catalogID%3D%22CF3COOH%22+elsor+ iupac.value%3D%22CF3COOH%22+elsor+ mf.value%3D%22CF3COOH%22+elsor+
%28iupac.value%3D%7E%22CF3COOH%22+or+
catalog.description%3D%7E%22CF3COOH%22%29&-
format=ccd&searchTemplate=rn.value%3D%3F+elsor+
entry.catalogID%3D %3 selenium dioxide (665 mg, 5.10 mmol). The mixture heated by microwave at 130° C. for 5 min. Then the mixture was filtered and concentrated to give the crude product, which was purified by column chromatography (silica gel, petroleum ether:DCM 10:1 to 1:1) to give the title compound (400 mg, yield 28%). LC-MS (ESI) m/z: 162 (M+1)$^+$. $^1$H-NMR (400 MHz, CD$_3$OD) δ (ppm): 3.61 (s, 3H), 5.91 (s, 1H), 7.67-7.70 (d, J=5.6 Hz, 1H), 8.39-8.41 (d, J=5.6 Hz, 1H), 8.93 (s, 1H).

Example 121E

Ethyl 2-(4-fluorophenyl)-3-(1-methyl-1H-imidazo[4, 5-c]pyridin-2-yl)-4-oxo-1,2,3,4-tetrahydroquinoline-5-carboxylate To a solution of 1-methyl-1H-imidazo[4,5-c]pyridine-2-carbaldehyde (400 mg, 2.48 mmol), (E)-4-(4-fluorobenzydeneamino) isobenzofuran-1(3H)-one (634 mg, 2.48 mmol) in ethyl propionate (20 ml) were added a solution of sodium ethanoxide in ethanol [sodium (171 mg, 7.45 mmol) in ethanol (10 mL)] at 0° C. Then the mixture was stirred at room temperature overnight. Then the mixture was quenched with water (10 mL) and solvent was removed in vacuum. The residue was extracted with ethyl acetate (100 mL×4). The combined organic layers were washed with brine, dried over anhydrous sodium sulfate, and concentrated to give crude product, which was purified by chromatography (silica gel, petroleum ether/ethyl acetate=25:1 to 5:1) to give the title compound (150 mg, yield 14%). LC-MS (ESI) m/z: 445 (M+1)$^+$.

Example 121F 8-(4-Fluorophenyl)-9-(1-methyl-1H-imidazo[4,5-c] pyridin-2-yl)-8,9-dihydro-2H-pyrido[4,3,2-de]phthalazin-3(7H)-one The mixture of ethyl 2-(4-fluorophenyl)-3-(1-methyl-1H-imidazo[4,5-c]pyridin-2-yl)-4-oxo-1,2,3,4-tetrahydroquinoline-5-carboxylate (150 mg, 0.34 mmol) and hydrazine monohydrate (2 mL) in methanol (5 mL) was stirred at room temperature for 4 h. Then methanol was evaporated under reduced pressure and the residue was extracted with ethyl acetate (20 mL×4). The combined organic layers were washed with brine, dried over anhydrous sodium sulfate and concentrated to give crude product, which was purified by chromatography (silica gel, DCM/MeOH=25:1 to 1:1) to give the title compound (6.7 mg, yield 5%). LC-MS (ESI) m/z: 413 (M+1)$^+$. $^1$H-NMR (400 MHz, CD$_3$OD) δ (ppm): 3.58 (s, 3H), 4.93-4.95 (d, J=11.6 Hz, 1H), 5.04-5.07 (d, J=11.6 Hz, 1H), 6.85-6.90 (t, J=8.8 Hz, 2H), 7.12-7.14 (d, J=8.0 Hz, 1H), 7.38-7.44 (m, 3H), 7.49-7.57 (m, 2H), 8.19-8.21 (d, J=5.6 Hz, 1H), 8.72 (s, 1H).

Example 122

5-Chloro-9-(1-methyl-1H-imidazol-2-yl)-8-phenyl-8,9-dihydro-2H-pyrido[4,3,2-de]phthalazin-3(7H)-one Example 122A 5-Chloro-2-methyl-3-nitrobenzoic acid To a conc. H$_2$SO$_4$ (90 mL) was added portionwise 5-chloro-2-methylbenzoic acid (13.2 g, 77.6 mmol) at −5~0° C. Then a mixture of conc. HNO$_3$ (10.5 g, 1744 mmol) in conc. H$_2$SO$_4$ (15 mL) was added dropwise at −5~0° C. over a period of about 1.5 hr. After the addition, the mixture was stirred at this temperature for 2 hr. The mixture was poured into crashed ice with vigorous stirring and the precipitate was collected by filtration. The precipitate was dissolved in EtOAc, washed with brine, dried over anhydrous Na$_2$SO$_4$, and concentrated to give a crude title compound (13.2 g), which was used in the next step without further purification.

Example 122B

Methyl 5-chloro-2-methyl-3-nitrobenzoate

A solution of crude 5-chloro-2-methyl-3-nitrobenzoic acid (13.2 g) in dry methanol (100 mL) was cooled to 0° C. (3 mL) was added conc. H$_2$SO$_4$ dropwise. After the addition, the mixture was heated to reflux for 16 hr. After removal of solvents under reduced pressure, the crude product was purified by silica gel chromatography (petroleum ether to petroleum ether/EtOAc=50:1) to give the title compound (6.3 g, yield 35% for two steps) as a white solid. LC-MS (ESI) m/z: 230 (M+1)$^+$, 231 (M+2)$^+$. $^1$H-NMR (400 MHz, CDCl$_3$) □□ δ (ppm): 2.59 (s, 3H), 3.95 (s, 3H), 7.84-7.85 (d, 1H), 7.98-7.99 (d, 1H).

Example 122C

Methyl 2-(bromomethyl)-5-chloro-3-nitrobenzoate

A mixture of methyl 5-chloro-2-methyl-3-nitrobenzoate (6 g, 26.2 mmol), NBS (5.1 g, 28.8 mmol), and BPO (0.63 g, 2.6 mmol) in CCl$_4$ (50 mL) was heated to reflux overnight. Water (200 mL) was added and CCl$_4$ was removed under reduced pressure. The residue was extracted with DCM (200 mL×3). The combined organic layers were washed with brine, dried over Na$_2$SO$_4$, and concentrated to give crude title compound (7 g, yield 87%) as a brown oil which was used in the next step without purification.

Example 122D

6-Chloro-4-nitroisobenzofuran-1(3H)-one

A mixture of methyl 2-(bromomethyl)-5-chloro-3-nitrobenzoate (7 g, 22.8 mmol) in 1, 4-dioxane (50 mL) and water (50 mL) was heated to reflux for 4 days. Dioxane was removed under reduced pressure. The residue was extracted with EtOAc (300 mL×4). The combined organic layers were washed with brine, dried over Na$_2$SO$_4$, and concentrated to give crude product, which was purified by silica gel chromatography (petroleum ether to petroleum ether/EtOAc=5: 1) to give the title compound (4 g, yield 82%) as a white solid.

Example 122E

4-Amino-6-chloroisobenzofuran-1(3H)-one

A suspension of 6-chloro-4-nitroisobenzofuran-1(3H)-one (5 g, 23.5 mmol) and Pd/C (10%, 500 mg) in EtOAc (250 mL) was stirred at 25° C. under 1 atm of hydrogen for 12 hr. The mixture was filtered, and the cake was washed with EtOAc (100 mL×3). The filtrate was concentrated to give the title compound (3.87 g, yield 90%) as a white solid. LC-MS (ESI) m/z: 184 (M+1)$^+$.

Example 122F (E)-4-(Benzylideneamino)-6-chloroisobenzofuran-1 (3H)-one

A mixture of 4-amino-6-chloroisobenzofuran-1(3H)-one (1 g, 5.46 mmol), benzaldehyde (0.72 g, 6.79 mmol) and magnesium sulfate (6 g) in dichloromethane (80 mL) was stirred at reflux overnight. The mixture was evaporated under reduced pressure and the residue was dried in vacuum. A crude product was obtained (740 mg) and used in next step without further purification.

Example 122G

Ethyl 7-chloro-3-(1-methyl-1H-imidazol-2-yl)-4-oxo-2-phenyl-1,2,3,4-tetrahydroquinoline-5-carboxylate To a solution of (E)-4-(benzylideneamino)-6-chloroisobenzofuran-1(3H)-one (720 mg, 2.66 mmol) and 1-methyl-1H-imidazole-2-carbaldehyde (330 mg, 3 mmol) in ethyl propionate (40 mL) was added sodium ethoxide (650 mg, 9.6 mmol). The mixture was stirred at room temperature for 3 hr. Then the resulting mixture was evaporated under reduced pressure and extracted with ethyl acetate (100 mL×4) and concentrated. The crude product was purified by column chromatography (silica gel, petroleum ether:ethyl acetate=20:1 to 1.5:1) to give the title compound as a solid (170 mg, yield 15%).

Example 122H

5-Chloro-9-(1-methyl-1H-imidazol-2-yl)-8-phenyl-8,9-dihydro-2H-pyrido[4,3,2-de]phthalazin-3(7H)-one To a solution of ethyl 7-chloro-3-(1-methyl-1H-imidazol-2-yl)-4-oxo-2-phenyl-1,2,3,4-tetrahydroquinoline-5-carboxylate (429 mg, 1.05 mmol) in methanol (15 mL) was added hydrazine monohydrate (2 mL). The mixture was stirred at 25° C. for 5 hr. The resulting mixture was concentrated under reduced pressure to a volume of 10 ml and then filtered, giving 58 mg of solid (yield 14%). LC-MS (ESI) m/z: 378 (M+1)$^+$; 379 (M+2)$^+$. $^1$H-NMR (400 MHz, DMSO-d$_6$) □□ δ (ppm): 3.42 (s, 3H), 4.69 (d, J=10.0 Hz, 1H), 4.98 (d, J=10.4 Hz, 1H), 5.76 (s, 1H), 6.73 (s, 1H), 6.89 (s, 1H), 7.14 (s, 1H), 7.27 (dd, 4H), 7.38 (d, J=6.4 Hz, 2H), 7.62 (s, 1H), 12.36 (s, 1H).

Example 123

8-(4-((Dimethylamino)methyl)phenyl)-5-fluoro-9-(4-fluorophenyl)-8,9-dihydro-2H-pyrido[4,3,2-de]phthalazin-3(7H)-one

Example 123A (E)-4-(4-((dimethylamino)methyl)benzylideneamino)-6-fluoroisobenzofuran-1(3H)-one To a stirred mixture of 4-((dimethylamino)methyl)benzaldehyde (4 g, 24.5 mmol) and anhydrous magnesium sulfate (15.8 g, 111.5 mmol) in anhydrous acetonitrile (100 mL) was added 4-amino-6-fluoroisobenzofuran-1(3H)-one (4 g, 22.3 mmol) at 0° C. After the addition, the mixture was stirred at reflux for 3 days. The mixture was filtered and the cake was washed with ethyl acetate (50 mL×3). The filtrate was concentrated to give crude product, which was recrystallized with isopropanol to give the title compound (3.7 g, yield 55%). LC-MS (ESI) m/z: 314 (M+1)$^+$.

Example 123B

Ethyl 2-(4-((dimethylamino)methyl)phenyl)-7-fluoro-3-(4-fluorophenyl)-4-oxo-1,2,3,4-tetrahydroquinoline-5-carboxylate A mixture of (E)-4-(4-((dimethylamino)methyl)benzylideneamino)-6-fluoroisobenzofuran-1(3H)-one (500 mg, 1.6 mmol) and 4-fluorobenzaldehyde (218 mg, 1.76 mmol) in ethyl propionate (10 mL) was cooled to 0° C. Then a solution of sodium ethoxide in ethanol (sodium (110 mg, 4.8 mmol) in ethanol (5 mL)) was added dropwise. After the addition the mixture was stirred at room temperature for 3 hr. The mixture was quenched with water (10 mL) and solvent was removed in vacuum. The residue was dissolved in water and then extracted with ethyl acetate (100 mL×4). The combined organic layers were washed with brine, dried over anhydrous sodium sulfate, and concentrated to give crude product, which was purified by chromatography (silica gel, petroleum ether/ethyl acetate=1:1) to give the title compound (100 mg, yield 13%). LC-MS (ESI) m/z: 465 (M+1)$^+$.

Example 123C 8-(4-((Dimethylamino)methyl)phenyl)-5-fluoro-9-(4-fluorophenyl)-8,9-dihydro-2H-pyrido[4,3,2-de]phthalazin-3(7H)-one A mixture of ethyl 2-(4-((dimethylamino)methyl)phenyl)-7-fluoro-3-(4-fluorophenyl)-4-oxo-1,2,3,4-tetrahydroquinoline-5-carboxylate (100 mg) in 85% hydrazine monohydrate (0.5 mL) and methanol (2 mL) was stirred at room temperature overnight. Methanol was removed under reduced pressure. The crude was purified by prep-HPLC to give the title compound (35 mg, yield 37%). LC-MS (ESI) m/z: 433 (M+1)$^+$. $^1$H-NMR (400 MHz, CD$_3$OD) □□ δ (ppm): 2.12 (s, 3H), 3.35 (s, 2H), 4.21 (d, J=8.0 Hz, 1H), 4.64 (d, J=8.0 Hz, 1H), 6.81-6.85 (m, 3H), 6.99-7.01 (m, 2H), 7.13-7.19 (m, 5H); $^{19}$F-NMR (400 MHz, CD$_3$OD) δ (ppm): −105.66 (s), −118.17 (s).

Example 124

8,9-Bis(4-((dimethylamino)methyl)phenyl)-5-fluoro-8,9-dihydro-2H-pyrido[4,3,2-de]phthalazin-3(7H)-one

Example 124A

Ethyl 2,3-bis(4-((dimethylamino)methyl)phenyl)-7-fluoro-4-oxo-1,2,3,4-tetrahydroquinoline-5-carboxylate A mixture of (E)-4-(4-((dimethylamino)methyl)benzylideneamino)-6-fluoroisobenzofuran-1(3H)-one (1 g, 31.9 mmol) and 4-((dimethylamino) methyl) benzaldehyde (0.52 g, 31.9 mmol) in ethyl propionate (50 mL) was cooled to 0° C. Then a solution of sodium ethoxide in ethanol (sodium (220 mg, 95.8 mmol) in ethanol (20 mL)) was added dropwise. After the addition, the mixture was stirred at room temperature for 2 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product, which was purified by chromatography (silica gel, dichloromethane/methanol=10:1 to 20:3) to give the title (520 mg, yield 33%). LC-MS (ESI) m/z: 503.

Example 124B 8,9-Bis(4-((dimethylamino)methyl)phenyl)-5-fluoro-8,9-dihydro-2H-pyrido[4,3,2-de]phthalazin-3(7H)-one A mixture of ethyl 2,3-bis(4-((dimethylamino)methyl)phenyl)-7-fluoro-4-oxo-1,2,3,4-tetrahydroquinoline-5-carboxylate (520 mg) in 85% hydrazine monohydrate (10 mL) and methanol (50 mL) was stirred at 23° C. for overnight. Methanol was removed under reduced pressure. The mixture was filtered and washed with water to give the title compound (11 mg, yield 20%). LC-MS (ESI) m/z: 472 (M+1)$^+$. $^1$H-NMR (400 MHz, CD$_3$OD) □□ δ (ppm): 2.09 (s, 12H), 3.31 (s, 4H), 4.22 (d, J=8.0 Hz, 1H), 4.67 (d, J=8.0 Hz, 1H), 6.80 (dd, 1H), 6.97-6.99 (m, 2H), 7.06-7.11 (m, 5H), 7.14-7.16 (m, 2H); $^{19}$F-NMR (400 MHz, CD$_3$OD) δ (ppm): −105.58 (s).

Example 125

8-(4-((Dimethylamino)methyl)phenyl)-5-fluoro-9-phenyl-8,9-dihydro-2H-pyrido[4,3,2-de]phthalazin-3(7H)-one Example 125A 4-(Diethoxymethyl)benzaldehyde A mixture of terephthalaldehyde (10 g, 74.55 mmol), ammonium chloride (160 mg, 3.0 mmol) in ethanol (10.3 g, 223.6 mmol) was added dropwise triethoxymethane (12.15 g, 82 mmol) at 0° C. After the addition, the mixture was stirred at room temperature overnight. The mixture was concentrated, the residue was purified by silica gel chromatography to give the title compound (7.0 g, yield 50%) as a white solid. LC-MS (ESI) m/z: 209 (M+1)$^+$.

Example 125B 1-(4-(Diethoxymethyl)phenyl)-N,N-dimethylmethanamine

A solution of 4-(diethoxymethyl)benzaldehyde (6.8 g, 32.69 mmol) and dimethylamine 33 wt. % solution in water (9.25 g, 98 mmol) in methanol (200 mL) was stirred at room temperature for overnight. Sodium borohydride (1.85 g, 49 mmol) was added by portions with ice cooling. After the addition, the mixture was stirred at room temperature for 4 hr. The mixture was quenched with water (100 mL) and extracted with ethyl acetate (100 ml×3). The extract was dried over anhydrous sodium sulfate and concentrated to give crude title compound (7.0 g, yield 90%), which was used in the next step without further purification. LC-MS (ESI) m/z: 238 (M+1)$^+$.

Example 125C 4-((Dimethylamino)methyl)benzaldehyde

To the mixture of 1-(4-(diethoxymethyl)phenyl)-N,N-dimethylmethanamine (7.0 g, 29.5 mmol) in hydrogen chloride (3M in water 30 mL) was stirred at room temperature for 5 hr. Then the mixture was extracted with ethyl acetate (50 ml×3).The aqueous layer was basified with sodium carbonate to pH=10, extracted with ethyl acetate (50 ml×3), dried with anhydrous sodium sulfate, and concentrated to give crude product (3.95 g, yield 82%). LC-MS (ESI) m/z: 164 (M+1)$^+$.

Example 125D (E)-4-(4-((Dimethylamino)methyl)benzylideneamino)-6-fluoroisobenzofuran-1(3H)-one A solution of 4-((dimethylamino)methyl)benzaldehyde (1.0 g, 6.13 mmol), 4-amino-6-fluoroisobenzofuran-1(3H)-one (1.024 g, 6.13 mmol) and anhydrous magnesium sulfate (7.356 g, 61.3 mmol) in acetonitrile (50 ml) was heated at reflux for 2 days. The solution was filtered and concentrated in vacuum. The crude product was re-crystallized with isopropanol to obtain the title compound (1.15 g, yield 60%). LC-MS (ESI) m/z: 313 (M+1)$^+$. $^1$H-NMR (400 MHz, CDCl$_3$) δ (ppm): 2.28 (s, 6H), 3.52 (s, 2H), 5.38-5.38 (m, 2H), 7.09-7.12 (m, 1H), 7.42-7.44 (m, 1H), 7.46-7.48 (d, J=8 Hz, 2H), 7.87-7.89 (d, J=8 Hz, 2H), 8.51 (s, 1H).

Example 125E

Ethyl 2-(4-((dimethylamino)methyl)phenyl)-7-fluoro-4-oxo-3-phenyl-1,2,3,4-tetrahydroquinoline-5-carboxylate A mixture of compound benzaldehyde (75 mg, 0.705 mmol) and (E)-4-(4-((dimethylamino)methyl)benzylideneamino)-6-fluoroisobenzofuran-1(3H)-one (220 mg, 0.705 mmol) in ethyl propionate (5 mL) was cooled to 0° C. Then a solution of sodium ethoxide in ethanol (sodium (65 mg, 2.82 mmol) in ethanol (3 mL)) was added dropwise. After the addition, the mixture was stirred at room temperature for 2.5 hr. The mixture was quenched with water (20 mL) and solvent was removed in vacuum. The residue was dissolved in water and extracted with ethyl acetate for three times. The extract was washed with water and brine and then the solvent was evaporated. The crude product was purified by chromatography to obtain the title compound as a yellow solid (80 mg, yield 25%). LC-MS (ESI) m/z: 447 (M+1)$^+$.

Example 125F 8-(4-((Dimethylamino)methyl)phenyl)-5-fluoro-9-phenyl-8,9-dihydro-2H-pyrido[4,3,2-de]phthalazin-3(7H)-one A mixture of compound ethyl 2-(4-((dimethylamino)methyl)phenyl)-7-fluoro-4-oxo-3-phenyl-1,2,3,4-tetrahydroquinoline-5-carboxylate (80 mg, 0.18 mmol) in 85% hydrazine monohydrate (1 mL) and methanol (5 mL) was stirred at room temperature for 4 h. The solvent was removed in vacuum; the crude product was purified by chromatography to obtain the title compound as a yellow solid (22 mg, yield 30%). LC-MS (ESI) m/z: 415 (M+1)$^+$. 1H-NMR (400 MHz, DMSO-d6) □ δ (ppm): 2.14 (s, 6H), 3.36 (s, 2H), 4.18-4.21 (d, J=8.8 Hz, 1H), 4.67-4.69 (d, J=9.2 Hz, 1H), 6.81-6.84 (m, 1H), 6.99-7.01 (m, 2H), 7.08-7.19 (m, 8H).

Example 126

8-(4-((3,4-Dimethylpiperazin-1-yl)methyl)phenyl)-9-(4-fluorophenyl)-8,9-dihydro-2H-pyrido[4,3,2-de]phthalazin-3(7H)-one Example 126A tert-Butyl 3-methylpiperazine-1-carboxylate To a solution of 2-methyl-piperazine (2.0 g, 0.02 mol) and triethylamine (6 mL) in methylene chloride (15 mL) at 0° C. was added (Boc)$_2$O (4.14 g, 0.019 mol) dropwise. The mixture was stirred at room temperature for 1 hour, and then the solvent was removed by rotary evaporation. The residue was dissolved in methylene chloride, washed with saturated sodium bicarbonate and brine, dried over Na$_2$SO$_4$, and purified by column chromatography on silica gel (DCM: MeOH:Et$_3$N=75:1:0.2) to give an white solid (1.65 g, 42%). LC-MS (ESI) m/z: 201 (M+1)$^+$.

Example 126B tert-Butyl 3,4-dimethylpiperazine-1-carboxylate tert-Butyl-3-methylpiperazine carboxylate (1.49 g, 7.45 mmol) and paraformaldehyde (1.12 g, 37.2 mmol) were dissolved in a mixture of MeOH and acetic acid (5:1) on molecular sieves. NaBCNH$_3$ (1.88 g, 29.8 mmol) was added to the suspension at 25° C. The slurry was subsequently heated to 80° C. for 10 hr. Then the mixture was cooled, filtered, and concentrated. The residue was dissolved in dichloromethane and washed with saturated sodium bicarbonate. The organic solution was dried over Na$_2$SO$_4$, and concentrated to give a white oily (1.2 g, 90%). LC-MS (ESI) m/z: 215 (M+1)$^+$.

Example 126C 1,2-Dimethylpiperazine

Trifluoroacetic acid (7 mL) was added to a solution of tert-butyl-3,4-dimethylpiperazine-1-carboxylate (1.7 g, 7.94 mmol) in methylene chloride (15 mL) at room temperature, followed by stirring for 1 hour. The residue obtained by removal of solvents by rotary evaporation under reduced pressure to give the title compound. LC-MS (ESI) m/z: 201 (M+1)$^+$. $^1$H-NMR (400 MHz, CDCl$_3$) □□δ (ppm): 1.21 (d, J=6.8 Hz, 3H), 1.46 (s, 9H), 2.64-2.70 (m, 1H), 2.74-2.78 (m, 1H), 2.88-3.01 (m, 3H), 3.78 (d, J=12.4 Hz, 1H), 4.16 (m, 1H).

Example 126D 8-(4-((3,4-Dimethylpiperazin-1-yl)methyl)phenyl)-9-(4-fluorophenyl)-8,9-dihydro-2H-pyrido[4,3,2-de]phthalazin-3(7H)-one A mixture of 4-(9-(4-fluorophenyl)-3-oxo-3,7,8,9-tetrahydro-2H-pyrido[4,3,2-de]phthalazin-8-yl)benzaldehyde (200 mg, 0.52 mmol), 1,2-dimethylpiperazine (311 mg, 1.56 mmol) in methylene chloride (10 mL) was stirred at room temperature overnight, then NaBCNH$_3$ (129 mg, 2.08 mmole) was added and the mixture was stirred for another 5 hours. After removal of solvents, the residue was purified by column chromatography (silica gel, petroleum ether/ethyl acetate=3:1 to 1:1) to give the title compound (70 mg, 26%). LC-MS (ESI) m/z: 484 (M+1)$^+$. $^1$H-NMR (400 MHz, CDCl$_3$) □□δ (ppm): 1.43 (d, J=5.2 Hz, 3H), 2.84 (s, 3H), 3.29 (m, 1H), 3.33-3.44 (m, 6H), 4.03 (s, 2H), 4.22 (m, 1H), 4.65 (m, 1H), 6.91 (m, 1H), 6.97 (m, 1H), 7.00 (d, J=8 Hz, 2H), 7.23-7.37 (m, 4H), 7.65 (m, 1H), 7.77 (d, J=7.2 Hz, 1H), 9.92 (s, 1H).

Example 127

8-(4-((3,5-Dimethylpiperazin-1-yl)methyl)phenyl)-9-(4-fluorophenyl)-8,9-dihydro-2H-pyrido[4,3,2-de]phthalazin-3(7H)-one Example 127A 4-Benzyl 1-tert-butyl 2,6-dimethylpiperazine-1,4-dicarboxylate To a solution of 2,6-dimethylpiperazine (2.28 g, 20 mmol) in methylene chloride (15 mL) at 0° C. was added benzyl-chloroformate (3.0 mL) dropwise. The mixture was stirred at 0° C. for one hour then at room temperature for 2 hours. The mixture was cooled to 0° C., Diisopropylethylamine (4.5 mL) was added and followed by (Boc)$_2$O (4.8 g, 22 mmol). The mixture was stirred at room temperature overnight and then the solvent was removed by rotary evaporation. The residue was dissolved in EtOAc, washed with water and brine, dried over Na$_2$SO$_4$, and purified by column chromatography on silica gel (EtOAc:hexane=1:9) to give an oily intermediate (4.8 g, 72%). LC-MS (ESI) m/z: 361 (M+23)$^+$.

Example 127B tert-Butyl 2,6-dimethylpiperazine-1-carboxylate

A solution of 4-benzyl 1-tert-butyl 2,6-dimethylpiperazine-1,4-dicarboxylate (4.8 g, 0.0144 mol) in methanol (25 mL) was added 480 mg of 10% Pd/C and stirred at room temperature under H$_2$ overnight. The resulting mixture was filtered and concentrated to give the title product (2.8 g, 97%) as colorless oil. LC-MS (ESI) m/z: 215 (M+1)$^+$. $^1$H-NMR (400 MHz, CDCl$_3$) □□ δ (ppm): 1.25 (d, J=6.8 Hz, 3H), 1.46 (s, 9H), 1.64 (s, 1H), 2.78-2.87 (m, 4H), 3.99-4.05 (m, 2H).

Example 127C (2R,6R)-tert-Butyl 4-(4-(9-(4-fluorophenyl)-3-oxo-3,7,8,9-tetrahydro-2H-pyrido[4,3,2-de]phthalazin-8-yl)benzyl)-2,6-dimethylpiperazine-1-carboxylate A mixture of 4-(9-(4-fluorophenyl)-3-oxo-3,7,8,9-tetrahydro-2H-pyrido[4,3,2-de]phthalazin-8-yl)benzaldehyde (200 mg, 520 mmol), tert-butyl 2,6-dimethylpiperazine-1-carboxylate (335 mg, 1.56 mmol) in methylene chloride (10 mL) was stirred at room temperature overnight, then NaBCNH$_3$ (129 mg, 2.08 mmol) was added and the mixture was stirred for another 5 hours. After removal of solvents, the residue was purified by column chromatography (silica gel, petroleum ether/ethyl acetate=3:1 to 1:1) to give the title compound (72 mg, 24%). LC-MS (ESI) m/z: 584 (M+1)$^+$.

Example 127D 8-(4-((3,5-Dimethylpiperazin-1-yl)methyl)phenyl)-9-(4-fluorophenyl)-8,9-dihydro-2H-pyrido[4,3,2-de]phthalazin-3(7H)-one A mixture of (2R,6R)-tert-butyl 4-(4-(9-(4-fluorophenyl)-3-oxo-3,7,8,9-tetrahydro-2H-pyrido[4,3,2-de]phthalazin-8-yl)benzyl)-2,6-dimethylpiperazine-1-carboxylate (72 mg, 0.12 mmol) in HCl—CH$_3$CN (2 mL) was stirred for 2 hours. After removal of solvents, the residue was purified by prep-HPLC to afford the title product as a white solid (33 mg, 53%). LC-MS (ESI) m/z: 497 (M+1)$^+$. $^1$H-NMR (400 MHz, DMSO) δ (ppm): 1.02-1.03 (d, J=6.4 Hz, 6H), 1.58 (t, J=10 Hz, 1H), 2.66 (d, J=10 Hz, 1H), 2.91 (t, J=6.8 Hz, 2H), 3.41 (s, 2H), 4.20 (d, J=10 Hz, 1H), 4.58 (d, J=10 Hz, 1H), 4.98 (s, 1H), 6.97 (t, J=2.4 Hz, 2H), 7.04 (d, J=8.0 Hz, 1H), 7.09 (d, J=2.4 Hz, 2H), 7.16 (d, J=2.4 Hz, 2H), 7.58 (t, J=7.6 Hz, 1H), 7.73 (d, J=7.6 Hz, 1H), 10.34 (s, 1H).

Example 128

9-Phenyl-8-(4-(pyrrolidin-1-ylmethyl)phenyl)-8,9-dihydro-2H-pyrido[4,3,2-de]phthalazin-3(7H)-one To a stirred solution of 4-(3-oxo-9-phenyl-3,7,8,9-tetrahydro-2H-pyrido[4,3,2-de]phthalazin-8-yl)benzaldehyde (367 mg, 1 mmol) in dry DCM (15 mL) was added acetic acid (0.2 mL) followed by pyrrolidine (213 mg, 3 mmol). After the addition, the mixture was stirred at room temperature overnight. Then sodium borohydride (318 mg, 1.5 mmol) was added at 0° C. After the addition, the mixture was stirred at this temperature for 12 hr. DCM was removed under reduced pressure. The residue was washed with ethyl acetate/methanol (10/1) and filtered. The filtrate was concentrated to give the crude product, which was purified by prep-HPLC to give the title compound (62 mg, yield 14%) as white solid. LC-MS (ESI) m/z: 423 (M+1)$^+$. $^1$H-NMR (400 MHz, DMSO-d6) δ (ppm): 1.82-1.85 (m, 2H), 1.97 (s, 2H), 3.01-3.05 (m, 2H), 3.26 (d, 2H), 4.27 (d, 2H), 4.36 (d, 1H), 4.84 (d, 1H), 7.13-7.23 (m, 6H), 7.36-7.40 (m, 5H), 7.48 (s, 1H), 7.57-7.61 (t, 1H), 12.18 (s, 1H).

Example 129

8-(4-(azetidin-1-ylmethyl)phenyl)-9-phenyl-8,9-dihydro-2H-pyrido[4,3,2-de]phthalazin-3(7H)-one To a stirred solution of 4-(3-oxo-9-phenyl-3,7,8,9-tetrahydro-2H-pyrido[4,3,2-de]phthalazin-8-yl)benzaldehyde (150 mg, 0.41 mmol) in dry dichloromethane (20 mL) and MeOH (2 mL) was added acetic acid (120 mg) followed by azetidine (70 mg, 1.23 mmol). After the addition, the mixture was stirred at room temperature overnight. Then sodium triacetoxyborohydride (131 mg, 0.62 mmol) was added at 0° C. After the addition, the mixture was stirred at this temperature for 5 hr. DCM was removed under reduced pressure. The residue was washed with ethyl acetate/methanol (10/1) and filtered. The filtrate was concentrated to give the crude product, which was purified by column chromatography (silica gel, dichloromethane/methanol=100:1 to 15:1) to give the title compound (84 mg, yield 51%) as yellow solid. LC-MS (ESI) m/z: 409 (M+1)$^+$. $^1$H-NMR (400 MHz, CD$_3$OD) δ (ppm): 2.38-2.43 (m, 2H), 3.98 (t, J=8 Hz, 4H), 4.20 (s, 2H), 4.27 (d, J=8 Hz, 1H), 4.77 (d, J=8 Hz, 1H), 7.03-7.05 (m, 2H), 7.10-7.17 (m, 4H), 7.27-7.35 (m, 4H), 7.50-7.52 (m, 1H), 7.57-7.62 (m, 1H).

Example 130

9-(1-Methyl-1H-imidazol-2-yl)-8-(4-(pyrrolidin-1-ylmethyl)phenyl)-8,9-dihydro-2H-pyrido[4,3,2-de]phthalazin-3(7H)-one A mixture of 4-(9-(1-methyl-1H-imidazol-2-yl)-3-oxo-3,7,8,9-tetrahydro-2H-pyrido[4,3,2-de]phthalazin-8-yl)benzaldehyde (80 mg, 0.22 mmol), acetic acid (60 uL) and pyrrolidine (1.05 g, 15 mmol) in acetonitrile (7 mL) was stirred at room temperature for 4 hr. To this mixture was added NaCNBH$_3$(36 mg, 0.67 mmol) at 0° C. After the addition, the mixture was stirred at room temperature for 4 hr. Upon removal of solvents under reduced pressure, the residue was washed with ethyl acetate and filtered. The filtrate was concentrated to give the title compound as a white solid (21 mg, yield 22%). LC-MS (ESI) m/z: 427 (M+1)$^+$. $^1$H-NMR: (400 MHz, DMSO-d$_6$ & D$_2$O) δ (ppm): 1.66 (d, J=2.8 Hz, 4H), 2.37 (s, 4H), 3.38 (s, 3H), 3.50 (s, 2H), 4.62 (d, J=10 Hz, 1H), 4.90 (d, J=10.4 Hz, 1H), 6.72 (s, 1H), 6.87 (s, 1H), 7.15-7.20 (m, 3H), 7.29-7.32 (m, 3H), 7.36-7.38 (m, 1H), 7.54-7.58 (m, 1H), 12.15 (s, 1H).

Example 131

9-(4-Fluorophenyl)-8-(1-methyl-1H-imidazol-2-yl)-8,9-dihydro-2H-pyrido[4,3,2-de]phthalazin-3(7H)-one

Example 131A (E)-4-((1-methyl-1H-imidazol-2-yl)methyleneamino) isobenzofuran-1(3H)-one A solution of 1-methyl-1H-imidazole-2-carbaldehyde (680 mg, 6.18 mmol), 4-aminoisobenzofuran-1(3H)-one (920.8 mg, 6.18 mmol) and anhydrous magnesium sulfate (7.41 g, 61.8 mmol) in acetonitrile (100 ml) was heated to reflux for two days. The mixture was filtered and the solvents were removed in vacuum. The crude product was re-crystallized from isopropanol to get the title compound (1.49 g, yield 68%). LC-MS (ESI) m/z: 242 (M+1)$^+$. $^1$H-NMR (400 MHz, DMSO-d6) □; 4.06 (s, 3H), 5.52 (s, 2H), 7.22 (s, 1H), 7.52 (s, 1H), 7.65-7.67 (m, 1H), 7.72-7.74 (m, 2H), 8.66 (s, 1H).

Example 131B

Ethyl 3-(4-fluorophenyl)-2-(1-methyl-1H-imidazol-2-yl)-4-oxo-1,2,3,4-tetrahydroquinoline-5-carboxylate A mixture of compound 4-fluorobenzaldehyde (248 mg, 2 mmol) and (E)-4-((1-methyl-1H-imidazol-2-yl)methyleneamino)isobenzofuran-1(3H)-one (482 mg, 2 mmol) in ethyl propionate (10 mL) was cooled to 0° C. Then a solution of sodium ethoxide in ethanol (sodium (184 mg, 8 mmol) in ethanol (5 mL)) was added dropwise. After the addition, the mixture was stirred at room temperature for 0.5 hr. The mixture was quenched with water (20 mL) and solvent was removed in vacuum. The residue was dissolved in water and extracted with ethyl acetate three times, washed with water and brine, and then concentrated to give the crude product, which was purified by column chromatography to obtain a yellow solid (200 mg, yield 25%). LC-MS (ESI) m/z: 394 (M+1)$^+$ Example 131C 9-(4-Fluorophenyl)-8-(1-methyl-1H-imidazol-2-yl)-8,9-dihydro-2H-pyrido[4,3,2-de]phthalazin-3(7H)-one A mixture of ethyl 3-(4-fluorophenyl)-2-(1-methyl-1H-imidazol-2-yl)-4-oxo-1,2,3,4-tetrahydroquinoline-5-carboxylate (200 mg, 0.5 mmol) in 85% hydrazine monohydrate (1 mL) and methanol (5 mL) was stirred at room temperature for 4 h. The resulting mixture was filtered and washed by water (20 mL) and methanol (5 mL) to obtain a white solid, which was dried in vacuum at 50° C. to obtain the title compound (25 mg, yield 14%). LC-MS (ESI) m/z: 362 (M+1)$^+$. $^1$H-NMR (400 MHz, DMSO-d6) □δ (ppm): 3.58 (s, 3H), 4.52-4.54 (d, J=7.2 Hz, 1H), 4.94-4.97 (m, 1H), 6.69-6.70 (m, 1H), 6.96-6.97 (m, 1H), 7.04-7.08 (m, 3H), 7.18-7.22 (m, 2H), 7.36-7.38 (m, 2H), 7.51-7.55 (t, J=8.0 Hz, 1H), 12.2 (s, 1H).

Example 132

9-(4-Fluorophenyl)-8-(quinolin-6-yl)-8,9-dihydro-2H-pyrido[4,3,2-de]phthalazin-3(7H)-one Example 132A Quinoline-6-carbaldehyde A mixture of SeO$_2$ (10.89 g, 99 mmol) and 6-methylquinoline (12.87 g, 90 mmol) was heated to 150° C. and stirred for 16 h. Then it was cooled to room temperature and EtOAc (400 ml) was added. After filtration, the filtrate was concentrated to obtain the crude compound, which was purified by chromatography (silica gel, petroleum ether/EtOAc 5:1 to 2:1) to afford the title compound (2.87 g, yield 20%). LC-MS (ESI) m/z: 158 (M+1)$^+$.

Example 132B (E)-4-(quinolin-6-ylmethyleneamino)isobenzofuran-1(3H)-one

A solution of quinoline-6-carbaldehyde (786 mg, 5.0 mmol), 4-aminoisobenzofuran-1(3H)-one (745 mg, 5.0 mmol) and anhydrous magnesium sulfate (6.0 g, 50.0 mmol) in acetonitrile (100 ml) was heated at reflux for two days. The solution was filtered and removed in vacuum. The crude product was re-crystallized from isopropanol to give the title compound (1.348 g, yield 93%) LC-MS (ESI) m/z: 289 (M+1)$^+$. $^1$H-NMR (400 MHz, DMSO-d6) □ δ (ppm): 5.57 (s, 2H), 7.63-7.77 (m, 4H), 8.14-8.16 (d, J=8.8 Hz, 1H), 8.39-8.42 (m, 1H), 8.53-8.56 (m, 2H), 8.99-9.01 (m, 2H).

Example 132C

Ethyl 3-(4-fluorophenyl)-2-(1-methyl-1H-imidazol-2-yl)-4-oxo-1,2,3,4-tetrahydroquinoline-5-carboxylate A mixture of compound 4-fluorobenzaldehyde (248 mg, 2 mmol) and (E)-4-(quinolin-6-ylmethyleneamino)isobenzofuran-1(3H)-one (576 mg, 2 mmol) in ethyl propionate (10 mL) was cooled to 0° C. Then a solution of sodium ethoxide in ethanol (sodium (184 mg, 8 mmol) in ethanol (5 mL)) was added dropwise. After the addition, the mixture was stirred at room temperature for 0.5 hr. The mixture was quenched with water (20 mL) and solvent was removed in vacuum. The residue was dissolved in water and extracted with ethyl acetate three times. After washed with water and brine, the solvents were removed by rotary evaporation. The crude product was purified by chromatography to obtain a yellow solid. The solid was dried in vacuum at 50° C. to give the title compound (260 mg, yield 29%). LC-MS (ESI) m/z: 441 (M+1)$^+$.

Example 132D 9-(4-Fluorophenyl)-8-(quinolin-6-yl)-8,9-dihydro-2H-pyrido[4,3,2-de]phthalazin-3(7H)-one A mixture of ethyl 3-(4-fluorophenyl)-2-(1-methyl-1H-imidazol-2-yl)-4-oxo-1,2,3,4-tetrahydroquinoline-5-carboxylate (260 mg, 0.59 mmol) in 85% hydrazine monohydrate (1 mL) and methanol (5 mL) was stirred at room temperature for 4 h. The resulting mixture was filtered and washed by water (20 mL) and methanol (5 mL) to obtain the title compound as a white solid (61 mg, yield 25%). LC-MS (ESI) m/z: 409 (M+1)$^+$. 1H-NMR (400 MHz, DMSO-d6) δ (ppm): 4.52-4.55 (d, J=9.6 Hz, 1H), 4.98-5.01 (d, J=9.6 Hz, 1H), 6.97-7.01 (m, 2H), 7.19-7.22 (m, 3H), 7.41-7.43 (d, J=7.6 Hz, 1H), 7.46-7.50 (m, 1H), 7.54 (s, 1H), 7.59-7.63 (t, J=7.6 Hz, 1H), 7.77-7.79 (m, 1H), 7.84 (s, 1H), 7.91-7.93 (m, 1H), 8.24-8.26 (d, J=7.6 Hz, 1H), 8.85-8.86 (m, 1H), 12.20 (s, 1H).

Example 133

8-(4-((Dimethylamino)methyl)phenyl)-9-p-tolyl-8,9-dihydro-2H-pyrido[4,3,2-de]phthalazin-3(7H)-one Example 133A Ethyl 2-(4-((dimethylamino)methyl)phenyl)-4-oxo-3-p-tolyl-1,2,3,4-tetrahydroquinoline-5-carboxylate A mixture of (E)-4-(4-((dimethylamino)methyl)benzylideneamino)isobenzofuran-1(3H)-one (500 mg, 1.7 mmol) and 4-methylbenzaldehyde (204 mg, 1.7 mmol) in ethyl propionate (30 mL) was cooled to 0° C. Then a solution of sodium ethoxide in ethanol (sodium (156 mg, 6.8 mmol) in ethanol (30 mL)) was added dropwise. After the addition, the mixture was stirred at 10° C. for 1 hr, then at 30° C. for 3 hr. The mixture was quenched with water (30 mL) and solvent was removed in vacuum. The residue was dissolved in water, and then extracted with ethyl acetate (30 mL×4). The combined organic layers were washed with brine, dried over anhydrous sodium sulfate, and concentrated to give crude product, which was purified by chromatography (silica gel, dichloromethane/methanol=100:1 to 10:1) to give the title compound (110 mg, yield: 15%). LC-MS (ESI) m/z: 443 (M+1)$^+$.

Example 133B 8-(4-((Dimethylamino)methyl)phenyl)-9-p-tolyl-8,9-dihydro-2H-pyrido[4,3,2-de]phthalazin-3(7H)-one A mixture of ethyl 2-(4-((dimethylamino)methyl)phenyl)-4-oxo-3-p-tolyl-1,2,3,4-tetrahydroquinoline-5-carboxylate (120 mg) in 85% hydrazine monohydrate (1 mL) and methanol (3 mL) was stirred at 10° C. for 2.5 h. The mixture was purified by prep-HPLC to obtain the title compound as a white solid (14 mg, yield 11%). LC-MS (ESI) m/z: 411 (M+1)$^+$; $^1$H-NMR (400 MHz, CD$_3$OD) □ δ (ppm): 2.18 (s, 3H), 2.31 (s, 6H), 3.57 (s, 2H), 4.25-4.27 (d, J=8.4 Hz, 1H), 4.72-4.74 (d, J=8.4 Hz, 1H), 6.95-7.02 (m, 4H), 7.19-7.29 (m, 5H), 7.55-7.57 (m, 1H), 7.62-7.64 (t, J=8 Hz, 1H).

Example 134

9-(4-Chlorophenyl)-8-(4-((dimethylamino)methyl) phenyl)-8,9-dihydro-2H-pyrido[4,3,2-de]phthalazin-3(7H)-one Example 134A Ethyl 3-(4-chlorophenyl)-2-(4-((dimethylamino) methyl)phenyl)-4-oxo-1,2,3,4-tetrahydroquinoline-5-carboxylate A mixture of (E)-4-(4-((dimethylamino)methyl)benzylideneamino)isobenzofuran-1(3H)-one (588 mg, 2 mmol) and 4-chlorobenzaldehyde (281 mg, 2 mmol) in anhydrous ethyl propionate (25 mL) was cooled to 0° C. The sodium methoxide in methanol solution (sodium (115 mg, 5 mmol) in anhydrous ethanol (10 mL)) was added dropwise and the mixture was stirred at 25° C. for 3 hr. The resulting mixture was quenched with water (5 mL), and then evaporated under reduced pressure. The residue was extracted with ethyl acetate (100 mL×3) and the combined organic layers were dried over anhydrous sodium sulfate and concentrated to give crude product, which was purified by column chromatography (silica gel, dichloromethane to dichloromethane/methanol=30:1) to give the title compound (260 mg, yield 28%) as a yellow solid. LC-MS (ESI) m/z: 463 (M+1)$^+$.

Example 134B 9-(4-Chlorophenyl)-8-(4-((dimethylamino)methyl) phenyl)-8,9-dihydro-2H-pyrido[4,3,2-de]phthalazin-3(7H)-one A mixture of ethyl 3-(4-chlorophenyl)-2-(4-((dimethylamino)methyl)phenyl)-4-oxo-1,2,3,4-tetrahydroquinoline-5-carboxylate (260 mg, 0.56 mmol) and hydrazine monohydrate (3 mL) in methanol (20 mL) was stirred at 30° C. for 4 hr. The mixture was concentrated to give crude product, which was purified by prep-HPLC to give the title compound (34 mg, yield 14%) as a white solid of formic acid salt. LC-MS (ESI) m/z: 431 (M+1)$^+$. $^1$H-NMR (400 MHz, DMSO-d6) δ (ppm): □2.66 (s, 6H), 4.20-4.21 (d, J=4.8 Hz, 2H), 4.39-4.42 (d, J=8.8 Hz, 1H), 4.82-4.84 (d, J=8.8 Hz, 1H), 7.15-7.20 (m, 4H), 7.25-7.27 (d, 2H), 7.35-7.42 (m, 5H), 7.46 (s, 1H), 7.58-7.62 (t, J=8.0 Hz, 1H), 9.74 (br s, 1H), 12.18 (s, 1H).

Example 135

8-(4-((Dimethylamino)methyl)phenyl)-9-(4-methoxyphenyl)-8,9-dihydro-2H-pyrido[4,3,2-de] phthalazin-3(7H)-one Example 135A Ethyl 2-(4-((dimethylamino)methyl)phenyl)-3-(4-methoxyphenyl)-4-oxo-1,2,3,4-tetrahydroquinoline-5-carboxylate To a solution of 4-methoxybenzaldehyde (231 mg, 1.7 mmol) and (E)-4-(4-((dimethylamino)methyl)benzylideneamino)isobenzofuran-1(3H)-one (500 mg, 1.7 mmol) in ethyl propionate (30 mL) was added sodium methanolate (120 mg, 5.2 mmol) and the mixture was stirred at 25° C. for 4 h. Then the resulting mixture was added water (10 mL) and evaporated under reduced pressure, extracted with EtOAc (4×100 ml), and concentrated to dryness. A crude product was obtained (250 mg) and was used for next step reaction without further purification. LC-MS (ESI) m/z: 459 (M+1)$^+$.

Example 135B 8-(4-((Dimethylamino)methyl)phenyl)-9-(4-methoxyphenyl)-8,9-dihydro-2H-pyrido[4,3,2-de] phthalazin-3(7H)-one A mixture of ethyl 2-(4-((dimethylamino)methyl)phenyl)-3-(4-methoxyphenyl)-4-oxo-1,2,3,4-tetrahydroquinoline-5-carboxylate (70 mg, 0.15 mmol) and hydrazine monohydrate (1 mL) in methanol (5 mL) was stirred at room temperature for 5 hr. The resulting mixture was evaporated under reduced pressure to a volume of 1 mL and then filtered. The filtrate was concentrated to give the title compound as a white solid (26.5 mg). LC-MS (ESI) m/z: 427 (M+1)$^+$. $^1$H-NMR (400 MHz, CD$_3$OD) δ (ppm): 2.79 (s, 6H), 3.71 (s, 3H), 4.24 (s, 2H), 4.26 (d, 1H), 4.77 (d, 1H), 6.74 (d, 2H), 6.99 (d, 2H), 7.18-7.21 (m, 1H), 7.35-7.43 (m, 4H), 7.55-7.57 (m, 1H), 7.65 (t, 3H).

Example 136

8-(4-((Diethylamino)methyl)phenyl)-9-phenyl-8,9-dihydro-2H-pyrido[4,3,2-de]phthalazin-3(7H)-one A mixture of 4-(3-oxo-9-phenyl-3,7,8,9-tetrahydro-2H-pyrido[4,3,2-de]phthalazin-8-yl)benzaldehyde (80 mg, 0.22 mmol), diethylamine (47 mg, 0.65 mmol) and acetic acid (39 mg, 0.65 mmol) in dichloromethane (50 mL) was stirred at room temperature for 60 min. Upon cooling the mixture to 0° C., sodium triacetoxyborohydride (69.3 mg, 0.33 mmol) was added. After the addition, the mixture was stirred at room temperature overnight. Dichloromethane was removed under reduced pressure. The crude product was purified by chromatography (silica gel, dichloromethane/Methanol=50:1) to give the title compound (34 mg, yield 36%). LC-MS (ESI) m/z: 425 (M+H)$^+$. $^1$H-NMR (400 MHz, CD$_3$OD) δ (ppm): 1.10 (t, 6H), 2.64 (q, 4H), 3.70 (s, 2H), 4.30 (d, J=8.0 Hz, 1H), 4.75 (d, J=8.0 Hz, 1H), 7.06-7.09 (m, 2H), 7.13-7.20 (m, 4H), 7.22-7.29 (m, 4H), 7.54-7.56 (dd, J=8.0 Hz, 1H), 7.62-7.64 (m, 1H).

Example 137

8-(4-((Diethylamino)methyl)phenyl)-9-(4-fluorophenyl)-8,9-dihydro-2H-pyrido[4,3,2-de]phthalazin-3 (7H)-one To a stirred solution of 4-(9-(4-fluorophenyl)-3-oxo-3,7,8,9-tetrahydro-2H-pyrido[4,3,2-de]phthalazin-8-yl)benzaldehyde (260 mg, 0.68 mmol) in dryness DCM (15 mL) was added acetic acid (0.2 mL) followed by diethylamine (148 mg, 2.03 mmol). After the addition, the mixture was stirred at room temperature overnight. Then sodium borohydride (212 mg, 1.01 mmol) was added to the mixture at 0° C. The mixture was stirred at this temperature for 12 hr. DCM was removed under reduced pressure. The residue was washed with ethyl acetate/methanol (10/1) and filtered. The filtrate was concentrated to give the crude product, which was purified by flash chromatography to give the title compound as white solid (27.3 mg, yield 9%). LC-MS (ESI) m/z: 442 (M+1)+. 1H-NMR (400 MHz, CD3OD) δ (ppm): 3.12-3.17 (m, 4H), 4.27 (s, 2H), 4.34 (d, 1H), 4.78 (d, 1H), 6.91 (t, 2H), 7.09-7.12 (m, 1H), 7.38-7.45 (m, 4H), 7.56-7.58 (m, 1H), 7.64 (t, 1H).

Example 138

9-(4-Chlorophenyl)-8-(4-((diethylamino)methyl) phenyl)-8,9-dihydro-2H-pyrido[4,3,2-de]phthalazin-3(7H)-one Example 138A (E)-4-(4-((diethylamino)methyl)benzylideneamino) isobenzofuran-1(3H)-one To a stirred mixture of 4-((diethylamino)methyl)benzaldehyde (3.7 g, 19.4 mmol) and anhydrous magnesium sulfate (11.6 g, 96.8 mmol) in anhydrous acetonitrile (100 mL) was added 4-aminoisobenzofuran-1(3H)-one (2.89 g, 19.4 mmol) at 0° C. After the addition the mixture was stirred refluxed for 3 days. The mixture was filtered and the cake was washed with ethyl acetate (50 mL×3). The filtrate was concentrated to give crude product, which was re-crystallized from isopropanol to give the title compound (2.1 g, yield: 32%). LC-MS (ESI) m/z: 323 (M+1)+.

Example 138B

Ethyl 3-(4-chlorophenyl)-2-(4-((diethylamino) methyl)phenyl)-4-oxo-1,2,3,4-tetrahydroquinoline-5-carboxylate A mixture of (E)-4-(4-((diethylamino)methyl)benzylideneamino)isobenzofuran-1(3H)-one (500 mg, 1.55 mmol) and 4-chlorobenzaldehyde (218 mg, 1.55 mmol) in ethyl propionate (10 mL) was cooled to 0° C. Then a solution of sodium ethoxide in ethanol (sodium (107 mg, 4.66 mmol) in ethanol (5 mL)) was added dropwise. After the addition, the mixture was stirred at room temperature for 3 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product, which was purified by chromatography (silica gel, petroleum ether/ethyl acetate=1:1) to give the crude of the title compound (268 mg, yield 35%). LC-MS (ESI) m/z: 491 (M+1)+.

Example 138C 9-(4-Chlorophenyl)-8-(4-((diethylamino)methyl) phenyl)-8,9-dihydro-2H-pyrido[4,3,2-de]phthalazin-3(7H)-one A mixture of ethyl 3-(4-chlorophenyl)-2-(4-((diethylamino)methyl)phenyl)-4-oxo-1,2,3,4-tetrahydroquinoline-5-carboxylate (268 mg) in 85% hydrazine monohydrate (0.5 mL) and methanol (2 mL) was stirred at 23° C. for overnight. Methanol was removed under reduced pressure. The crude was purified by prep-HPLC to give the title compound (93 mg, yield 37%). LC-MS (ESI) m/z: 459 (M+1)+. 1H-NMR (400 MHz, DMSO-d6) δ (ppm): 0.93 (t, 6H), 2.38 (q, 4H), 3.44 (s, 2H), 4.35 (d, 1H), 4.73 (d, 1H), 7.13-7.19 (m, 5H), 7.22-7.25 (m, 4H), 7.38 (d, 2H), 7.41 (s, 1H), 7.56-7.59 (m, 1H).

Example 139

5-Fluoro-8-(1-methyl-1H-imidazol-2-yl)-9-phenyl-8, 9-dihydro-2H-pyrido[4,3,2-de]phthalazin-3(7H)-one Example 139A (E)-6-Fluoro-4-((l-methyl-1H-imidazol-2-yl)methyleneamino)isobenzofuran-1(3H)-one A solution of 1-methyl-1H-imidazole-2-carbaldehyde (659 mg, 6.0 mmol), 4-amino-6-fluoroisobenzofuran-1(3H)-one (1.0 g, 6.0 mmol), and anhydrous magnesium sulfate (7.2 g, 60.0 mmol) in acetonitrile (100 mL) was heated to reflux for 2 days. The solution was filtered and the solvents were removed in vacuum. The crude product was re-crystallized from isopropanol to afford the title compound (1.068 g, yield 68%) LC-MS (ESI) m/z: 260 (M+1)+. 1H-NMR (400 MHz, DMSO-d6) δ (ppm): 4.04 (s, 3H), 5.49 (s, 2H), 7.24 (s, 1H), 7.54-7.58 (m, 2H), 7.73-7.76 (m, 1H), 8.70 (s, 1H).

Example 139B

Ethyl 7-fluoro-2-(1-methyl-1H-imidazol-2-yl)-4-oxo-3-phenyl-1,2,3,4-tetrahydroquinoline-5-carboxylate A mixture of benzaldehyde (212 mg, 2 mmol) and (E)-6-fluoro-4-((1-methyl-1H-imidazol-2-yl)methyleneamino) isobenzofuran-1(3H)-one (518 mg, 2 mmol) in ethyl propionate (10 mL) was cooled to 0° C. Then a solution of sodium ethoxide in ethanol (sodium (184 mg, 8 mmol) in ethanol (5 mL)) was added dropwise. After the addition, the mixture was stirred at room temperature for 0.5 hr. The mixture was quenched with water (20 mL) and solvent was removed in vacuum. The residue was dissolved in water and extracted with ethyl acetate three times. The combined organic layers were washed by water and brine, and then evaporated to dryness, the crude product was purified by chromatography to obtain a yellow solid. The solid was dried in vacuum at 50° C. to give the title compound (250 mg, yield 32%). LC-MS (ESI) m/z: 394 (M+1)+.

Example 139C

5-Fluoro-8-(1-methyl-1H-imidazol-2-yl)-9-phenyl-8, 9-dihydro-2H-pyrido[4,3,2-de]phthalazin-3(7H)-one A mixture of ethyl 7-fluoro-2-(1-methyl-1H-imidazol-2-yl)-4-oxo-3-phenyl-1,2,3,4-tetrahydroquinoline-5-carboxylate (250 mg, 0.636 mmol) in 85% hydrazine monohydrate (1 mL) and methanol (5 mL) was stirred at room temperature for 4 h. The resulting mixture wax filtered and washed water (20 mL) and methanol (5 mL) to obtain a white solid, which after dried in vacuum at 50° C. afforded the title compound (34.6 mg, yield 15%). LC-MS (ESI) m/z: 362 (M+1)+; 1H-NMR (400 MHz, DMSO-d6) □ δ (ppm): 3.56 (s, 3H), 4.48-4.49 (d, J=6.0 Hz, 1H), 5.01-5.03 (m, 1H), 6.70-6.71 (m, 1H), 6.81-6.84 (m, 1H), 6.98-7.02 (m, 2H), 7.14-7.26 (m, 5H), 7.66-7.67 (m, 1H), 12.33 (s, 1H).

Example 140

5-Fluoro-9-(4-fluorophenyl)-8-(1-methyl-1H-imidazol-2-yl)-8,9-dihydro-2H-pyrido[4,3,2-de]phthalazin-3(7H)-one

Example 140A

Ethyl 7-fluoro-3-(4-fluorophenyl)-2-(1-methyl-1H-imidazol-2-yl)-4-oxo-1,2,3,4-tetrahydroquinoline-5-carboxylate A mixture of 4-fluorobenzaldehyde (248 mg, 2 mmol) and (E)-6-fluoro-4-((1-methyl-1H-imidazol-2-yl)methyleneamino)isobenzofuran-1(3H)-one (518 mg, 2 mmol) in ethyl propionate (10 mL) was cooled to 0° C. Then a solution of sodium ethoxide in ethanol (sodium (184 mg, 8 mmol) in ethanol (5 mL)) was added dropwise. After the addition, the mixture was stirred at room temperature for 0.5 hr. The mixture was quenched with water (20 mL) and solvents were removed in vacuum. The residues were dissolved in water and extracted with ethyl acetate three times. The combined organic layers were washed with water and brine. After the removal of solvents, the crude product was purified by flash column chromatography to obtain a yellow solid, which was dried in vacuum at 50° C. to give the title compound (200 mg, yield: 24%). LC-MS (ESI) m/z: 412 (M+1)$^+$.

Example 140B

5-Fluoro-9-(4-fluorophenyl)-8-(1-methyl-1H-imidazol-2-yl)-8,9-dihydro-2H-pyrido[4,3,2-de]phthalazin-3(7H)-one A mixture of ethyl 7-fluoro-3-(4-fluorophenyl)-2-(1-methyl-1H-imidazol-2-yl)-4-oxo-1,2,3,4-tetrahydroquinoline-5-carboxylate (200 mg, 0.486 mmol) in 85% hydrazine monohydrate (1 mL) and methanol (5 mL) was stirred at room temperature for 4 h. The resulting mixture was filtered and washed by water (20 mL) and methanol (5 mL) to obtain a white solid, which was then dried in vacuum at 50° C. to obtain the title compound (25.4 mg, yield 14%). LC-MS (ESI) m/z: 380 (M+1)$^+$; 1H-NMR (400 MHz, DMSO-d6) □ δ (ppm): 3.56 (s, 3H), 4.52-4.53 (d, J=6.8 Hz, 1H), 5.02-5.04 (m, 1H), 6.73 (s, 1H), 6.82-6.85 (m, 1H), 6.99-7.09 (m, 4H), 7.18-7.22 (m, 2H), 7.69 (s, 1H), 12.34 (s, 1H).

Example 141

8-(4-((Dimethylamino)methyl)phenyl)-9-(4-ethylphenyl)-8,9-dihydro-2H-pyrido[4,3,2-de]phthalazin-3(7H)-one

Example 141A

Ethyl 2-(4-((dimethylamino)methyl)phenyl)-3-(4-ethylphenyl)-4-oxo-1,2,3,4-tetrahydroquinoline-5-carboxylate A mixture of (E)-4-(4-((dimethylamino)methyl)benzylideneamino)isobenzofuran-1(3H)-one (588 mg, 2 mmol) and 4-ethylbenzaldehyde (268 mg, 2 mmol) in ethyl propionate (15 mL) was cooled to 0° C. Then a solution of sodium ethoxide in ethanol (sodium (138 mg, 6 mmol) in ethanol (5 mL)) was added dropwise. After the addition, the mixture was stirred at room temperature for 3 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product, which was purified by chromatography (silica gel, petroleum ether/ethyl acetate=1:1) to give the crude title compound (290 mg, yield 32%). LC-MS (ESI) m/z: 457 (M+1)$^+$.

Example 141B 8-(4-((Dimethylamino)methyl)phenyl)-9-(4-ethylphenyl)-8,9-dihydro-2H-pyrido[4,3,2-de]phthalazin-3(7H)-one A mixture of ethyl 2-(4-((dimethylamino)methyl)phenyl)-3-(4-ethylphenyl)-4-oxo-1,2,3,4-tetrahydroquinoline-5-carboxylate (290 mg) in 85% hydrazine monohydrate (1 mL) and methanol (10 mL) was stirred at 30° C. for overnight. Methanol was removed under reduced pressure. The crude product was purified by chromatography (silica gel, Petroleum ether/ethyl acetate=1:1) to give the title compound (112 mg, yield 42%). LC-MS (ESI) m/z: 425 (M+1)$^+$. $^1$H-NMR (400 MHz, CD$_3$OD) δ (ppm): 1.12 (t, 3H), 2.10 (s, 6H), 2.52 (q, 2H), 3.34 (s, 2H), 4.31 (d, J=8.0 Hz, 1H), 4.76 (d, J=8.0 Hz, 1H), 7.04 (m, 4H), 7.15-7.20 (m, 3H), 7.25-7.27 (m, 2H), 7.38-7.41 (m, 3H), 7.59-7.61 (m, 1H).

Example 142

8-(4-((Dimethylamino)methyl)phenyl)-9-(4-isopropylphenyl)-8,9-dihydro-2H-pyrido[4,3,2-de]phthalazin-3(7H)-one

Example 142A

Ethyl 2-(4-((dimethylamino)methyl)phenyl)-3-(4-isopropylphenyl)-4-oxo-1,2,3,4-tetrahydroquinoline-5-carboxylate A mixture of (E)-4-(4-((dimethylamino)methyl)benzylideneamino)isobenzofuran-1(3H)-one (588 mg, 2 mmol) and 4-isopropylbenzaldehyde (296 mg, 2 mmol) in ethyl propionate (15 mL) was cooled to 0° C. Then a solution of sodium ethoxide in ethanol (sodium (138 mg, 6 mmol) in ethanol (5 mL)) was added dropwise. After the addition, the mixture was stirred at room temperature for 3 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product, which was then purified by column chromatography (silica gel, petroleum ether/ethyl acetate=1:1) to give the title compound (210 mg, yield 22%). LC-MS (ESI) m/z: 471 (M+1)$^+$.

Example 142B 8-(4-((Dimethylamino)methyl)phenyl)-9-(4-isopropylphenyl)-8,9-dihydro-2H-pyrido[4,3,2-de]phthalazin-3(7H)-one A mixture of ethyl 2-(4-((dimethylamino)methyl)phenyl)-3-(4-isopropylphenyl)-4-oxo-1,2,3,4-tetrahydroquinoline-5-carboxylate (210 mg) in 85% hydrazine monohydrate (1 mL) and methanol (10 mL) was stirred at 23° C. for overnight. Methanol was removed under reduced pressure. The crude was purified by flash chromatography to give the title compound (72 mg, yield 37%). LC-MS (ESI) m/z: 439 (M+1)+. $^1$H-NMR (400 MHz, CD$_3$OD) δ (ppm): 1.18 (d, 3H), 1.19 (d, 3H), 2.26 (s, 6H), 2.79-2.83 (m, 1H), 3.51 (d, 2H), 4.27 (d, J=8.0 Hz, 1H), 4.73 (d, J=8.0 Hz, 1H), 6.98-7.00 (m, 2H), 7.05-7.07 (m, 2H), 7.18-7.22 (m, 3H), 7.25-7.27 (m, 2H), 7.54-7.56 (m, 1H), 7.56-7.59 (m, 1H).

Example 143

8-(4-((Dimethylamino)methyl)phenyl)-9-(4-(trifluoromethyl)phenyl)-8,9-dihydro-2H-pyrido[4,3,2-de]phthalazin-3(7H)-one

Example 143A

Ethyl 2-(4-((dimethylamino)methyl)phenyl)-4-oxo-3-(4-(trifluoromethyl)phenyl)-1,2,3,4-tetrahydroquinoline-5-carboxylate A mixture of (E)-4-(4-((dimethylamino)methyl)benzylideneamino)isobenzofuran-1(3H)-one (541 mg, 1.84 mmol) and 4-(trifluoromethyl)benzaldehyde (320 mg, 1.84 mmol) in anhydrous ethyl propionate (25 mL) was cooled to 0° C. Then sodium ethoxide in methanol solution (sodium (127 mg, 5.51 mmol) in anhydrous ethanol (10 mL)) was added dropwise and the mixture was stirred at 25° C. for 4 hr. The resulting mixture was quenched with water (5 mL), and then evaporated the solvents off under reduced pressure. The residue was extracted with ethyl acetate (100 mL×3) and the combined organic layers were dried over anhydrous sodium sulfate and concentrated to give crude product, which was purified by column chromatography (silica gel, dichloromethane to dichloromethane/methanol=30:1) to give the title compound (150 mg, yield 16%) as a yellow solid. LC-MS (ESI) m/z: 497 (M+1)+.

Example 143B 8-(4-((Dimethylamino)methyl)phenyl)-9-(4-(trifluoromethyl)phenyl)-8,9-dihydro-2H-pyrido[4,3,2-de]phthalazin-3(7H)-one A mixture of ethyl 2-(4-((dimethylamino)methyl)phenyl)-4-oxo-3-(4-(trifluoromethyl)phenyl)-1,2,3,4-tetrahydroquinoline-5-carboxylate (150 mg, 0.30 mmol) and hydrazine monohydrate (0.5 mL) in methanol (10 mL) was stirred at 30° C. overnight. The mixture was concentrated under reduced pressure to give crude product, which was purified by flash chromatography to give the title compound (60 mg, yield 34.5%) as a white solid. LC-MS (ESI) m/z: 465 (M+1)+. $^1$H-NMR (400 MHz, DMSO-d6) δ (ppm) □: 2.64 (s, 3H), 2.65 (s, 3H), 4.19-4.20 (d, J=4.0 Hz, 2H), 4.53-4.55 (d, J=9.2 Hz, 1H), 4.88-4.90 (d, J=9.2 Hz, 1H), 7.20-7.22 (d, J=7.6 Hz, 1H), 7.35-7.46 (m, 7H), 7.50 (s, 1H), 7.56-7.63 (m, 3H), 9.69-9.71 (br s, 1H), 12.20 (s, 1H).

Example 144

8-(4-((Diethylamino)methyl)phenyl)-9-p-tolyl-8,9-dihydro-2H-pyrido[4,3,2-de]phthalazin-3(7H)-one

Example 144A

Ethyl 2-(4-((diethylamino)methyl)phenyl)-4-oxo-3-p-tolyl-1,2,3,4-tetrahydroquinoline-5-carboxylate A mixture of (E)-4-(4-((diethylamino)methyl)benzylideneamino)isobenzofuran-1(3H)-one (644 mg, 2 mmol) and 4-methylbenzaldehyde (240 mg, 2 mmol) in ethyl propionate (15 mL) was cooled to 0° C. Then a solution of sodium ethoxide in ethanol (sodium (138 mg, 6 mmol) in ethanol (5 mL)) was added dropwise. After the addition, the mixture was stirred at room temperature for 3 hr. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give crude product, which was purified by column chromatography (silica gel, petroleum ether/ethyl acetate=1:1) to give the title compound (320 mg, yield 34%). LC-MS (ESI) m/z: 471 (M+1)+.

Example 144B 8-(4-((Diethylamino)methyl)phenyl)-9-p-tolyl-8,9-dihydro-2H-pyrido[4,3,2-de]phthalazin-3(7H)-one A mixture of ethyl 2-(4-((diethylamino)methyl)phenyl)-4-oxo-3-p-tolyl-1,2,3,4-tetrahydroquinoline-5-carboxylate (320 mg) in hydrazine monohydrate (2 mL, 85%) and methanol (10 mL) was stirred at 30° C. for overnight. Methanol was removed under reduced pressure. The crude product was purified by chromatography (silica gel, petroleum ether/ethyl acetate=1:1) to give the title compound (85 mg, yield 29%). LC-MS (ESI) m/z: 439 (M+1)+. $^1$H-NMR (400 MHz, DMSO-d6) δ (ppm): 0.93 (t, 6H), 2.20 (s, 3H), 2.39 (q, 4H), 3.42 (d, 2H), 4.27 (d, J=8.0 Hz, 1H), 4.73 (d, J=8.0 Hz, 1H), 6.98-7.00 (m, 4H), 7.15-7.17 (m, 3H), 7.22-7.24 (m, 2H), 7.35-7.38 (m, 2H), 7.54-7.56 (m, 1H), 12.12 (s, 1H).

Example 145

9-(4-Fluorophenyl)-8-(4-(1-methylpyrrolidin-2-yl)phenyl)-8,9-dihydro-2H-pyrido[4,3,2-de]phthalazin-3(7H)-one

Example 145A tert-Butyl 2-oxopyrrolidine-1-carboxylate

To a solution of 2-pyrrolidinone (10.82 g, 127 mmol) in acetonitrile (400 mL) was added DMAP (1.53 g, 12.6 mmol), followed by a solution of di-tert-butyldicarbonate (33.6 g, 77.1 mmol) in acetonitrile (20 mL). The reaction mixture was stirred at room temperature for 1 h. The resulting mixture was concentrated in vacuo and the resulting oil was taken up in diethyl ether. The mixture was washed consecutively with 1 N HCl and brine. The organic phase was dried over sodium sulfate, and concentrated in vacuo to afford the title compound as a yellow oil (15 g, 64%) which was used directly in the next step.

Example 145B tert-Butyl 4-(4-bromophenyl)-4-oxobutylcarbamate

A thoroughly dried three-necked round-bottom flask was equipped with reflux condenser, addition funnel and argon inlet. Then magnesium powder (7.5 g, 311 mmol, activated by iodine) and dry THF (300 mL) were placed into this apparatus. A solution of 1, 4-dibromobenzene (73.5 g, 311 mmol) in dry THF (200 mL) was slowly added at such a rate that the mixture maintained at reflux. When the addition was completed the mixture was refluxed for additional 2 hrs.

After cooling to room temperature, the solution was added into a solution of tert-butyl 2-oxopyrrolidine-1-carboxylate (48 g, 260 mmol) in THF (320 mL) at −78° C. and the mixture was stirred at −78° C. for 2 hrs. The solution was warmed to ambient temperature and stirred for another 10 hrs before quenching with water. Hydrochloric acid (1 N, 100 mL) was added and the mixture was stirred at ambient temperature for 10 minutes. The mixture was concentrated and the residue was partitioned between ethyl acetate and brine. The organic phase was dried over magnesium sulfate and concentrated in vacuo to afforded the crude product, which was purified by column chromatography (EtOAc:DCM:hexane=1:1:15) to give the title compound as a white solid (53 g, yield 60%). LC-MS (ESI) m/z: 342 (M+1)$^+$.

Example 145C 5-(4-Bromophenyl)-3,4-dihydro-2H-pyrrole tert-Butyl 4-(4-bromophenyl)-4-oxobutylcarbamate (3.42 g, 10 mmol) was stirred in TFA (10 mL) for 6 hrs. Then 50% NaOH solution was added to the mixture to make pH=13-14, the white precipitate was filtered, washed with water and dried to give the title compound as a white solid (1.8 g, yield 80%). LC-MS (ESI) m/z: 224 (M+1)$^+$.

Example 145D 2-(4-Bromophenyl)pyrrolidine

NaBH$_4$ (1.52 g, 40 mmol) was added to a solution of 5-(4-bromophenyl)-3,4-dihydro-2H-pyrrole (4.48 g, 20 mmol) in H$_2$O/MeOH (30 mL, v/v 1:4) at −41° C. After stirred for 4 hrs, the solution was allowed to warm to room temperature. Once the reaction was deemed complete by TLC, the unreacted NaBH$_4$ was quenched by the addition of 2 N HCl. The solution was then diluted with water and ether, and separated two layers. The aqueous layer was washed with an additional portion of ether, basified with 4 M NaOH (pH 12-13) and washed with ethyl acetate. The combined organic extracts were washed with brine, and then dried over Na$_2$SO$_4$. Evaporation of the solvent afforded the title crude product as a yellow oil (3.8 g, yield 84%), which was used directly in the next step. LC-MS (ESI) m/z: 226 (M+1)$^+$.

Example 145E 2-(4-Bromophenyl)-1-methylpyrrolidine

A mixture of 2-(4-bromophenyl)pyrrolidine (0.5 g, 2.2 mmol), formic acid (0.11 mL, 2.42 mmol), formaldehyde (0.2 mL, 2.42 mmol, 37% in water), water (4 mL) in a sealed tube was heated to 150° C. under microwave for 5 minutes. After cooling to room temperature the reaction mixture was extracted with EtOAc (3×15 mL), the combined organic phase was washed consecutively with saturated NaHCO$_3$(5 mL) and brine (5 mL), dried over Na$_2$SO$_4$ and concentrated in vacuo to give the crude product (0.48 g, 91%), which was used directly in the next step. LC-MS (ESI) m/z: 240 (M+1)$^+$.

Example 145F 4-(1-Methylpyrrolidin-2-yl)benzaldehyde

To a solution of 2-(4-bromophenyl)-1-methylpyrrolidine (0.45 g, 2 mmol) in dry THF (10 mL) was added dropwise n-BuLi (0.88 mL, 2.2 mmol, 2.5 mol/L in hexane) at −78° C., after the addition was completed the mixture was stirred for 1 h, then dry DMF (0.18 mL, 2.4 mmol) was added to the reaction system and stirring was continued for another 1 hr. Then the reaction mixture was partitioned between EtOAc and 1 N HCl, the aqueous solution was extracted with EtOAc (3×15 mL). The combined organic phase was washed with brine, dried over Na$_2$SO$_4$, and concentrated in vacuo to give crude product (0.28 g, yield 74%) as a yellow oil. The product was used directly in the next step without further purification. LC-MS (ESI) m/z: 189 (M+1)$^+$.

Example 145G (E)-4-(4-(1-methylpyrrolidin-2-yl)benzylideneamino)isobenzofuran-1(3H)-one A mixture of 4-(1-methylpyrrolidin-2-yl)benzaldehyde (1.89 g, 10 mmol), 4-aminoisobenzofuran-1(3H)-one (1.49 g, 10 mmol) and MgSO$_4$(12 g, 100 mmol) in CH$_3$CN (60 mL) was refluxed at 120° C. for 4 days. After a hot filtration, CH$_3$CN was partially removed under reduced pressure and a white precipitate was appeared, the title compound was obtained by a direct filtration (1.3 g, yield 41%) as a white solid. LC-MS (ESI) m/z: 440 (M+1)$^+$.

Example 145H

Ethyl 3-(4-fluorophenyl)-2-(4-(1-methylpyrrolidin-2-yl)phenyl)-4-oxo-1,2,3,4-tetrahydroquinoline-5-carboxylate A mixture of (E)-4-(4-(1-methylpyrrolidin-2-yl)benzylideneamino)isobenzofuran-1(3H)-one (0.32 g, 1 mmol), 4-flourobenzenaldehyde (0.248 g, 2 mmol) was dissolved in dry ethyl propionate (5 mL), EtONa (0.136 g, 2 mmol) in EtOH (5 mL) was added to this solution and the mixture was stirred at room temperature until the starting material was disappeared as monitored by TLC. The reaction was quenched with 0.5 mL of water, the resulting mixture was concentrated in vacuo, and the residue was purified by column chromatography (MeOH:DCM=1:20) to give the title compound (200 mg, yield 42%) as a pale yellow solid. LC-MS (ESI) m/z: 472 (M+1)$^+$.

Example 145I 9-(4-Fluorophenyl)-8-(4-(1-methylpyrrolidin-2-yl)phenyl)-8,9-dihydro-2H-pyrido[4,3,2-de]phthalazin-3(7H)-one To a stirred solution of ethyl 3-(4-fluorophenyl)-2-(4-(1-methylpyrrolidin-2-yl)phenyl)-4-oxo-1,2,3,4-tetrahydroquinoline-5-carboxylate (200 mg, 0.42 mmol) in MeOH (20 ml) was added N$_2$H$_4$.H$_2$O (2 mL), the mixture was stirred for 4 hrs, and then concentrated in vacuo and the residue was purified by chromatography (MeOH:DCM=1:20) to give the title compound as a white solid (45 mg, yield 24%). LC-MS (ESI) m/z: 440 (M+1)$^+$; $^1$H-NMR (400 MHz, CDCl$_3$) □ δ (ppm): 1.67-1.97 (m, 3H), 2.11 (s, 3H), 2.25 (m, 1H), 2.17-2.30 (m, 1H), 2.97-2.99 (m, 1H), 3.21-3.25 (m, 1H), 4.19-4.22 (d, J=10.4 Hz, 1H), 4.57-4.59 (d, J=10.4 Hz, 1H), 4.90 (s, 1H), 6.86-6.91 (m, 2H), 6.95-6.97 (m, 2H), 7.03-7.05 (d, J=7.6 Hz, 1H), 7.10-7.12 (d, J=8 Hz, 2H), 7.20-7.22 (d, J=8 Hz, 2H), 7.57-7.61 (t, J=7.6 Hz, 1H), 7.74-7.76 (d, J=7.6 Hz, 1H), 9.94 (s, 1H).

Example 146

9-(4-Fluorophenyl)-8-(4-(pyrrolidin-2-yl)phenyl)-8,9-dihydro-2H-pyrido[4,3,2-de]phthalazin-3(7H)-one

Example 146A

Benzyl 2-(4-bromophenyl)pyrrolidine-1-carboxylate

A solution of 2-(4-bromophenyl)pyrrolidine (2.26 g, 10 mmol) in dioxane (18 mL) and water (12 mL) was added potassium carbonate (5.52 g, 40 mol) and benzyl chloroformate (1.88 g, 11 mmol) at ambient temperature and stirred overnight. Then the mixture was partitioned between ethyl acetate and brine. The organic phase was concentrated in vacuo and the residue was purified by column chromatography (silica gel, EtOAc:hexane=1:10) to give the title compound (2.95 g, 82%) as a colorless oil. LC-MS (ESI) m/z: 360 (M+1)$^+$.

Example 146B

Benzyl 2-(4-formylphenyl)pyrrolidine-1-carboxylate

To a 50 mL round-bottomed flask were placed Pd (PPh$_3$)$_2$Cl$_2$ (70 mg, 0.1 mmol), and sodium formate (510 mg, 7.5 mmol) and purged with carbon monoxide. DMF (7 mL) and benzyl 2-(4-bromophenyl)pyrrolidine-1-carboxylate (1.8 g, 5 mmol) were added via syringes. The mixture was vigorously stirred at 100° C. under carbon monoxide atmosphere for 8 hrs. Then the reaction mixture was cooled to room temperature and partitioned between ether (100 mL) and water (15 mL). The organic phase was washed with water (3×15 mL), dried over Na$_2$SO$_4$, and concentrated in vacuo. The residue was purified by column chromatography (silica gel, EtOAc:hexane=1:10) to give the title compound (0.31 g, yield 20%) as a colorless oil. LC-MS (ESI) m/z: 309 (M+1)$^+$; $^1$H-NMR (400 MHz, DMSO-d6) δ (ppm): 1.73-1.88 (m, 3H), 2.31-2.41 (m, 1H), 3.57-3.67 (m, 2H), 4.84-5.06 (m, 3H), 6.84-6.86 (m, 1H), 7.12-7.34 (m, 4H), 7.41-7.43 (d, J=8.0 Hz, 2H), 7.85-7.87 (d, J=8.0 Hz, 2H), 9.98-9.99 (d, J=6.0 Hz, 1H).

Example 146C (E)-benzyl 2-(4-((1-oxo-1,3-dihydroisobenzofuran-4-ylimino)methyl)phenyl)pyrrolidine-1-carboxylate A mixture of benzyl 2-(4-formylphenyl)pyrrolidine-1-carboxylate (0.62 g, 2 mmol), 4-aminoisobenzofuran-1(3H)-one (0.298 g, 2 mmol), MgSO$_4$ (2.4 g, 20 mmol) in CH$_3$CN (20 mL) was refluxed at 120° C. for 4 days. After a hot filtration, the filtrate was concentrated in vacuo and the residue was purified by column chromatography (EtOAc:DCM:hexane=1:1:6) to give the title compound (0.35 g, yield 30%) as a white solid. LC-MS (ESI) m/z: 440 (M+1)$^+$.

Example 146D

Ethyl 2-(4-(1-(benzyloxycarbonyl)pyrrolidin-2-yl)phenyl)-3-(4-fluorophenyl)-4-oxo-1,2,3,4-tetrahydroquinoline-5-carboxylate A solution of (E)-benzyl 2-(4-((1-oxo-1,3-dihydroisobenzofuran-4-ylimino)methyl)phenyl)pyrrolidine-1-carboxylate (0.5 g, 1.14 mmol) and 4-flourobenzaldehyde (0.284 g, 2.28 mmol) in dry ethyl propionate (5 mL) was added EtONa (0.155 g, 2.28 mmol) in EtOH (6 mL), and the mixture was stirred at room temperature until the starting material was disappeared as monitored by TLC. Then the reaction mixture was quenched with 0.5 mL of water, the resulting mixture was concentrated in vacuo, and the residue was purified by column chromatography to give the title compound (130 mg, yield 20%) as a yellow solid. LC-MS (ESI) m/z: 592 (M+1)$^+$.

Example 146E

Benzyl 2-(4-(9-(4-fluorophenyl)-3-oxo-3,7,8,9-tetrahydro-2H-pyrido[4,3,2-de]phthalazin-8-yl)phenyl)pyrrolidine-1-carboxylate To a stirred solution of ethyl 2-(4-(1-(benzyloxycarbonyl)pyrrolidin-2-yl)phenyl)-3-(4-fluorophenyl)-4-oxo-1,2,3,4-tetrahydroquinoline-5-carboxylate (130 mg, 0.22 mmol) in MeOH (20 mL) was added N$_2$H$_4$.H$_2$O (2 mL), the reaction was continued for 4 hrs, then mixture was concentrated in vacuo and the residue was purified by chromatography (EtOAc:hexane=1:2) to give the title compound (100 mg, yield 81%) as a white solid. LC-MS (ESI) m/z: 560 (M+1)$^+$ $^1$H-NMR (400 MHz, CDCl$_3$) δ (ppm): 1.77-1.90 (m, 3H), 2.25 (m, 1H), 3.65-3.68 (m, 2H), 4.10-4.23 (m, 2H), 4.59-4.61 (d, J=10.0 Hz, 1H), 4.90-5.14 (m, 2H), 6.82-7.09 (m, 10H), 7.27-7.32 (m, 2H), 7.37 (s, 2H), 7.60-7.64 (m, 1H), 7.77-7.79 (m, 1H), 9.61 (s, 1H).

Example 146F 9-(4-Fluorophenyl)-8-(4-(pyrrolidin-2-yl)phenyl)-8,9-dihydro-2H-pyrido[4,3,2-de]phthalazin-3(7H)-one Benzyl 2-(4-(9-(4-fluorophenyl)-3-oxo-3,7,8,9-tetrahydro-2H-pyrido[4,3,2-de]phthalazin-8-yl)phenyl)pyrrolidine-1-carboxylate (60 mg, 0.107 mmol) was dissolved in distilled methanol (15 mL), and the reaction mixture was stirred at room temperature under an atmosphere of hydrogen in the presence of a catalytic amount of palladium on carbon (11 mg, 0.01 mmol) for 2 hrs. After the reaction was completed, the catalyst was removed by filtration through a pad of Celite, and the solvent was removed under reduced pressure. The residue was purified by preparative TLC (MeOH:DCM=1:10) to give the title compound (5 mg, yield 11%) as a white foam. LC-MS (ESI) m/z: 426 (M+1)$^{+1}$H-NMR (400 MHz, CD$_3$OD) □ δ (ppm): 1.78-1.88 (m, 1H), 1.95-2.08 (m, 2H), 2.24-2.32 (m, 1H), 3.05-3.12 (m, 1H), 3.21-3.27 (m, 1H), 4.17-4.21 (m, 1H), 4.34-4.36 (d, J=8.0 Hz, 1H), 4.75-4.77 (d, J=8.0 Hz, 1H), 6.91-6.95 (m, 2H), 7.09-7.15 (m, 2H), 7.17-7.25 (m, 1H), 7.22-7.25 (m, 1H), 7.29-7.34 (m, 4H), 7.55-7.57 (m, 1H), 7.63-7.67 (m, 1H).

Example 147

8-(4-Fluorophenyl)-9-methyl-9-(1-methyl-1H-imidazol-2-yl)-8,9-dihydro-2H-pyrido[4,3,2-de]phthalazin-3(7H)-one

Example 147A

Ethyl 2-(4-fluorophenyl)-3-methyl-3-(1-methyl-1H-imidazol-2-yl)-4-oxo-1,2,3,4-tetrahydroquinoline-5-carboxylate To a solution of ethyl 2-(4-fluorophenyl)-3-(1-methyl-1H-imidazol-2-yl)-4-oxo-1,2,3,4-tetrahydroquinoline-5-carboxylate (150 mg, 0.38 mmol) and cesium carbonate (268 mg, 0.76 mmol) in DMF (10 mL) was added iodomethane (0.2 mL, 2.28 mmol) at 0° C. under N2. The reaction mixture was stirred at 0° C. for 4 h and then at room temperature overnight. The resulting solution was added 50 mL of water, and then extracted with ethyl acetate (100 mL×3). The extracts were concentrated to give the crude product as a yellow solid (145 mg, yield 90%), which was used in the next step without further purification. LC-MS (ESI) m/z: 408 (M+1)$^+$.

Example 147B 8-(4-Fluorophenyl)-9-methyl-9-(1-methyl-1H-imidazol-2-yl)-8,9-dihydro-2H-pyrido[4,3,2-de]phthalazin-3(7H)-one Ethyl 2-(4-fluorophenyl)-3-methyl-3-(1-methyl-1H-imidazol-2-yl)-4-oxo-1,2,3,4-tetrahydroquinoline-5-carboxylate (70 mg, 0.18 mmol) was added to hydrazine monohydrate (5 mL) and the mixture was stirred at 67° C. for 10 hr. The resulting mixture was concentrated and purified by prep-HPLC to obtain the title compound as a white solid (9 mg, yield 14%). LC-MS (ESI) m/z: 376 (M+1)$^+$. $^1$H-NMR (400 MHz, DMSO-d$_6$) □□ δ (ppm): 1.79 (s, 3H), 2.57 (s, 3H), 4.50 (s, 1H), 6.68-6.69 (d, J=0.9 Hz, 1H), 6.78-6.82 (m, 2H), 6.84-6.85 (d, J=0.9 Hz, 1H), 7.05-7.09 (m, 2H), 7.16-7.18 (dd, J$_1$=8.0 Hz, J$_2$=0.8 Hz, 1H), 7.34 (s, 1H), 7.43-7.45 (dd, J$_1$=8.0 Hz, J$_2$=0.8 Hz, 1H), 7.57-7.61 (t, J=7.6 Hz, 1H), 12.30 (s, 1H).

Example 148

9-(4-Fluorophenyl)-8-(1H-imidazol-2-yl)-8,9-dihydro-2H-pyrido[4,3,2-de]phthalazin-3(7H)-one Example 148A 1-Benzyl-1H-imidazole-2-carbaldehyde To a solution of 1H-imidazole-2-carbaldehyde (240 mg, 2.4 mmol) and potassium carbonate (662 mg, 4.8 mmol) in acetonitrile (5 mL) at 0° C. was added dropwise (bromomethyl)benzene (493 mg, 2.88 mmol). The mixture was stirred at 40° C. for 4 hr. Then the mixture was filtrated, evaporated to remove the acetonitrile from the filtrate, added EtOAc to extract the residues, and washed the extract with brine and water. The organic layer was dried with anhydrous Na$_2$SO$_4$, concentrated, and chromatographed on a silica gel column (EtOAc:hexane=1:9) to obtain the title compound (430 mg, yield 95%). LC-MS (ESI) m/z: 187 (M+1)$^+$.

Example 148B (E)-4-((1-Benzyl-1H-imidazol-2-yl)methyleneamino)isobenzofuran-1(3H)-one The mixture of 1-benzyl-1H-imidazole-2-carbaldehyde (430 mg, 1.48 mmol), 4-aminoisobenzofuran-1(3H)-one (221 mg, 1.48 mmol) and magnesium sulfate (4.3 g) in acetonitrile was heated to reflux for 48 hr. Then the mixture was filtrated off and evaporated to remove the solvent. The crude was re-crystallized from isopropanol to obtain the title compound (470 mg, 65%). LC-MS (ESI) m/z: 318 (M+1)$^+$.

Example 148C

Ethyl 2-(1-benzyl-1H-imidazol-2-yl)-3-(4-fluorophenyl)-4-oxo-1,2,3,4-tetrahydroquinoline-5-carboxylate A solution of (E)-4-((1-benzyl-1H-imidazol-2-yl)methyleneamino)isobenzofuran-1(3H)-one (470 mg, 1.48 mmol) in ethyl propanate (5 mL) was added EtONa/EtOH (136 mg of sodium in 5 mL of ethanol) and stirred at room temperature under N$_2$ for 30 min. Then the mixture was partitioned between water and ethyl acetate. The organic layer was separated, washed with water and brine, dried with anhydrous Na$_2$SO$_4$, and chromatographed on a silica gel column (EtOAc:hexane=1:9 to 1:1) to obtain the title compound (280 mg, yield 40%). LC-MS (ESI) m/z: 470 (M+1)$^+$.

Example 148D 8-(1-Benzyl-1H-imidazol-2-yl)-9-(4-fluorophenyl)-8,9-dihydro-2H-pyrido[4,3,2-de]phthalazin-3(7H)-one A mixture of ethyl 2-(1-benzyl-1H-imidazol-2-yl)-3-(4-fluorophenyl)-4-oxo-1,2,3,4-tetrahydroquinoline-5-carboxylate (280 mg, 0.59 mmol) and hydrazine monohydrate (2 mL, 85%) in methanol (4 mL) was stirred at 40° C. for 2 hr, and then evaporated to half of the original volume. The mixture was filtered and washed the solid with ethyl acetate to obtain the title compound (200 mg, yield 96%). LC-MS (ESI) m/z: 437 (M+1)$^+$.

Example 148E 9-(4-Fluorophenyl)-8-(1H-imidazol-2-yl)-8,9-dihydro-2H-pyrido[4,3,2-de]phthalazin-3(7H)-one A mixture of 8-(1-benzyl-1H-imidazol-2-yl)-9-(4-fluorophenyl)-8,9-dihydro-2H-pyrido[4,3,2-de]phthalazin-3(7H)-one (200 mg, 0.46 mmol) and palladium hydroxide (200 mg) in methanol (4 mL) was purged with hydrogen and stirred at 60° C. for 18 hr. Then the mixture was filtered, evaporated to remove the solvent, and washed the solid with ethyl acetate to obtain the title compound (150 mg, yield 94%). LC-MS (ESI) m/z: 348 (M+1)$^+$. $^1$H-NMR (400 MHz, DMSO-d6) □□ δ (ppm): 4.93 (d, J=8.4 Hz, 1H), 5.21 (d, J=8.4 Hz, 1H), 7.10 (t, J=8.4 Hz, 2H), 7.21-7.30 (m, 3H), 7.37 (s, 1H), 7.45-7.49 (m, 3H), 4.58 (d, J=10 Hz, 1H), 7.62-7.67 (m, 1H), 7.87 (s, 1H).

Example 149

5-Fluoro-9-(1-methyl-1H-1,2,4-triazol-5-yl)-8-phenyl-8,9-dihydro-2H-pyrido[4,3,2-de]phthalazin-3(7H)-one Example 149A Ethyl 7-fluoro-3-(1-methyl-1H-1,2,4-triazol-5-yl)-4-oxo-2-phenyl-1,2,3,4-tetrahydroquinoline-5-carboxylate To a solution of (E)-4-(benzylideneamino)-6-fluoroisobenzofuran-1(3H)-one (1.25 g, 4.9 mmol), anhydrous Na$_2$SO$_3$ (1.24 g, 9.82 mmol), anhydrous Na$_2$SO$_4$ (2 g, 14.7 mmol) and 1-methyl-1H-1,2,4-triazole-5-carbaldehyde (900 mg, 8.1 mmol) in ethyl propanate (50 mL) was added EtONa [(sodium 316 mg, 13.8 mmol) in 25 mL ethanol] at 40° C., then the mixture was stirred at 40° C. for 3 hr. The resulting mixture was evaporated under reduced pressure, extracted with ethyl acetate (100 mL×4) and concentrated to dryness. The crude product was purified by column chromatography (silica gel, dichloromethane:methanol=200:1 to 50:1) to obtain the title compound as a green solid (190 mg, yield 10%). LC-MS (ESI) m/z: 395 (M+1)$^+$.

Example 149B

5-Fluoro-9-(1-methyl-1H-1,2,4-triazol-5-yl)-8-phenyl-8,9-dihydro-2H-pyrido[4,3,2-de]phthalazin-3(7H)-one To a solution of ethyl 7-fluoro-3-(1-methyl-1H-1,2,4-triazol-5-yl)-4-oxo-2-phenyl-1,2,3,4-tetrahydroquinoline-5-carboxylate (186 mg, 0.47 mmol) in methanol (1 mL) was added hydrazine monohydrate (0.5 mL), and the mixture was stirred at 25° C. for 15 hr. Then the mixture was filtered to obtain a white solid (40 mg, yield 24%). LC-MS (ESI) m/z: 363 (M+1)$^+$. $^1$H-NMR (400 MHz, DMSO-d$_6$) □□ δ (ppm): 3.63 (s, 3H), 4.94-5.03 (m, 2H), 6.91-6.94 (dd, J$_1$=11.6 Hz, J$_2$=2.4 Hz, 1H), 7.05-7.08 (dd, J$_1$=9.6 Hz, J$_2$=2.4 Hz, 1H), 7.29-7.35 (m, 3H), 7.42-7.48 (m, 2H), 7.74 (s, 1H), 7.79 (s, 1H), 12.34 (s, 1H).

Example 150

9-(4-Fluorophenyl)-9-hydroxy-8-(1-methyl-1H-imidazol-2-yl)-8,9-dihydro-2H-pyrido[4,3,2-de]phthalazin-3(7H)-one Example 150A Ethyl 3-(4-fluorophenyl)-3-hydroxy-2-(1-methyl-1H-imidazol-2-yl)-4-oxo-1,2,3,4-tetrahydroquinoline-5-carboxylate To a mixture of (E)-4-((l-methyl-1H-imidazol-2-yl)methyleneamino)isobenzofuran-1(3H)-one (590 mg, 2.4 mmol) and 4-fluorobenzaldehyde (300 mg, 2.4 mmol) in ethyl propionate (20 mL) was added a solution of sodium ethoxide in ethanol [sodium (220 mg, 9.6 mmol) in ethanol (10 mL)]. After the addition, the mixture was stirred at room temperature overnight. The mixture was quenched with water (10 mL) and solvent was removed in vacuum. The residue was dissolved in water, and then extracted with ethyl acetate (100 mL×4). The combined organic layers were washed with brine, dried over anhydrous sodium sulfate, and concentrated to give a crude product, which was purified by flash chromatography to give the title compound (100 mg, yield 10%). LC-MS (ESI) m/z: 410 (M+1)$^+$.

Example 150B 9-(4-Fluorophenyl)-9-hydroxy-8-(1-methyl-1H-imidazol-2-yl)-8,9-dihydro-2H-pyrido[4,3,2-de]phthalazin-3(7H)-one A mixture of ethyl 3-(4-fluorophenyl)-3-hydroxy-2-(1-methyl-1H-imidazol-2-yl)-4-oxo-1,2,3,4-tetrahydroquinoline-5-carboxylate (60 mg) in 85% hydrazine monohydrate (0.2 mL) and methanol (2 mL) was stirred at room temperature for 1 hr. Then the solvent was removed under reduced pressure. The residue was purified by prep-TLC (methanol:dichloromethane=1:20) to give the title compound (50 mg, yield 80%). LC-MS (ESI) m/z: 378 (M+1)$^+$; $^1$H-NMR (400 MHz, DMSO-d6) □; 3.44 (s, 3H), 5.24 (s, 1H), 6.84 (s, 1H), 6.98-7.06 (m, 4H), 7.11-7.13 (d, J=8.0 Hz, 1H), 7.38-7.42 (m, 3H), 7.46 (s, 1H), 7.56-7.60 (t, J=8.0 Hz, 1H).

Example 151

8-(4-Fluorophenyl)-8-methyl-9-(1-methyl-1H-imidazol-2-yl)-8,9-dihydro-2H-pyrido[4,3,2-de]phthalazin-3(7H)-one Example 151A (E)-4-(1-(4-Fluorophenyl)ethylideneamino)isobenzofuran-1(3H)-one To a solution of 4-aminoisobenzofuran-1(3H)-one (1 g, 6.7 mmol) and 1-(4-fluorophenyl)ethanone (1.4 g, 10.1 mmol) in toluene (35 mL) was added anhydrous magnesium sulfate (8.8 g, 73.7 mmol) and acetic acid (0.2 mL) at room temperature under N$_2$. The reaction mixture was then stirred at 120° C. for 36 hr. The reaction mixture was cooled to 90° C. and filtered. After filter cake was washed with acetonitrile, the filtrates were combined and evaporated to dryness to obtain yellow solid, which was washed by petroleum ether to obtain the title compound as a white solid (1.58 g, yield 88%). LC-MS (ESI) m/z: 270 (M+1)$^+$ $^1$H-NMR (400 MHz, CDCl$_3$) □□ δ (ppm): 2.30 (s, 3H), 5.16 (s, 2H), 7.00-7.02 (d, J=7.6 Hz, 1H), 7.13-7.18 (m, 2H), 7.51-7.56 (t, J=7.6 Hz, 1H), 7.66-7.69 (d, J=7.6 Hz, 1H), 7.99-8.03 (m, 2H).

Example 151B

Ethyl 2-(4-fluorophenyl)-2-methyl-3-(1-methyl-1H-imidazol-2-yl)-4-oxo-1,2,3,4-tetrahydroquinoline-5-carboxylate To a solution of 1-methyl-1H-imidazole-2-carbaldehyde (580 mg, 5.2 mmol), and (E)-4-(1-(4-fluorophenyl)ethylideneamino)isobenzofuran-1(3H)-one (1 g, 3.7 mmol) in ethyl propionate (20 ml) was added rapidly EtONa [sodium (340 mg, 14.8 mmol) in 8 mL ethanol] at 0° C., then the mixture was stirred at 30° C. for 3 hr. The resulting mixture was added ethyl acetate (150 mL) and washed with water (25 mL×3), the organic layers were combined and evaporated to dryness to give the crude product, which was purified by column chromatography (silica gel, dichloromethane:methanol=200:1 to 50:1) to afford the title compound as a red solid (120 mg, yield 8%). LC-MS (ESI) m/z: 408 (M+1)$^+$ Example 151C 8-(4-Fluorophenyl)-8-methyl-9-(1-methyl-1H-imidazol-2-yl)-8,9-dihydro-2H-pyrido[4,3,2-de]phthalazin-3(7H)-one To a solution of ethyl 2-(4-fluorophenyl)-2-methyl-3-(1-methyl-1H-imidazol-2-yl)-4-oxo-1,2,3,4-tetrahydroquinoline-5-carboxylate (120 mg, 0.30 mmol) in methanol (4 mL) was added hydrazine monohydrate (0.7 mL) at room temperature, the mixture was stirred under 30° C. for 10 hr. The solvent was evaporated to obtain crude solid, which was washed by 14 mL of mixture of ethyl acetate and methanol (13:1) to obtain the title compound as a green solid (40 mg, yield 36%). LC-MS (ESI) m/z: 376 (M+1)$^+$. $^1$H-NMR (400

MHz, DMSO-d$_6$) □□ δ (ppm): 1.39 (s, 3H), 3.71 (s, 3H), 4.74 (s, 1H), 6.72 (s, 1H), 7.03 (s, 1H), 7.06-7.11 (m, 2H), 7.16-7.19 (d, J=8 Hz, 1H), 7.25-7.28 (d, J=8 Hz, 1H), 7.49 (s, 1H), 7.54-7.58 (m, 3H), 12.05 (s, 1H).

Example 152

Racemate of (8R,9R)-8-(4-((dimethylamino)methyl) phenyl)-5-fluoro-9-(1-methyl-1H-1,2,4-triazol-5-yl)-8,9-dihydro-2H-pyrido[4,3,2-de]phthalazin-3(7H)-one and (8S,9S)-8-(4-((dimethylamino)methyl) phenyl)-5-fluoro-9-(1-methyl-1H-1,2,4-triazol-5-yl)-8,9-dihydro-2H-pyrido[4,3,2-de]phthalazin-3(7H)-one; and racemate of (8S,9R)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one and (8R,9S)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one Example 152A Ethyl 2-(4-((dimethylamino)methyl)phenyl)-7-fluoro-3-(1-methyl-1H-1,2,4-triazol-5-yl)-4-oxo-1,2,3,4-tetrahydroquinoline-5-carboxylate To a solution of (E)-4-(4-((dimethylamino)methyl)benzylideneamino)-6-fluoroisobenzofuran-1(3H)-one (4.2 g, 13.5 mmol) and compound 1-methyl-1H-1,2,4-triazole-5-carbaldehyde (3.0 g, 27 mmol) in ethyl propionate (150 mL) was added rapidly NaOEt [sodium (870 mg, 37.8 mmol) in 70 mL ethanol] at 40° C., then the mixture was stirred at 48° C. for 3 hr. The resulting mixture was concentrated under reduced pressure and extracted with ethyl acetate (250 mL×3). The extract was evaporated to give a crude product, which was purified by column chromatography (silica gel, dichloromethane:methanol=50:1 to 10:1) to obtain the title compound (560 mg, yield 9%) (a mixture of cis and trans isomers). LC-MS (ESI) m/z: 452 (M+1)$^+$.

Example 152B

Racemate of (8R,9R)-8-(4-((dimethylamino)methyl) phenyl)-5-fluoro-9-(1-methyl-1H-1,2,4-triazol-5-yl)-8,9-dihydro-2H-pyrido[4,3,2-de]phthalazin-3(7H)-one and (8S,9S)-8-(4-((dimethylamino)methyl) phenyl)-5-fluoro-9-(1-methyl-1H-1,2,4-triazol-5-yl)-8,9-dihydro-2H-pyrido[4,3,2-de]phthalazin-3(7H)-one; and racemate of (8S,9R)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one and (8R,9S)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one To a solution of ethyl 2-(4-((dimethylamino)methyl)phenyl)-7-fluoro-3-(1-methyl-1H-1,2,4-triazol-5-yl)-4-oxo-1,2,3,4-tetrahydroquinoline-5-carboxylate (560 mg, 1.24 mmol, a mixture of cis and trans isomers) in methanol (2 mL) was added hydrazine monohydrate (0.5 mL) and the mixture was stirred under 25° C. for 10 hr. The mixture was concentrated in vacuum and the residue was purified by prep-TLC then prep-HPLC to obtain the two pairs of diastereomers as white solids (racemate of (8R,9R)-8-(4-((dimethylamino)methyl) phenyl)-5-fluoro-9-(1-methyl-1H-1,2,4-triazol-5-yl)-8,9-dihydro-2H-pyrido[4,3,2-de]phthalazin-3(7H)-one and (8S,9S)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one: 20 mg, yield 4%). LC-MS (ESI) m/z: 420 (M+1)$^+$; $^1$H-NMR (400 MHz, DMSO-d$_6$) □□ δ (ppm): 2.16 (s, 6H), 2.88 (s, 3H), 3.34 (s, 2H), 4.73-4.74 (d, J$_2$=4.0 Hz, 1H), 5.02-5.03 (d, J$_2$=4.0 Hz, 1H), 6.92-6.95 (dd, J$_1$=10.8 Hz, J$_2$=2.4 Hz, 1H), 7.07-7.09 (dd, J$_1$=10.8 Hz, J$_2$=2.4 Hz, 1H), 7.04-7.06 (d, J=7.6 Hz, 2H), 7.23-7.25 (d, J=7.6 Hz, 2H), 7.56 (s, 1H), 7.69 (s, 1H), 12.45 (s, 1H). Racemate of (8S,9R)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one and (8R,9S)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one: 140 mg, yield 27%). LC-MS (ESI) m/z: 420 (M+1)$^+$; $^1$H-NMR (400 MHz, DMSO-d$_6$) □□ δ (ppm): 2.10 (s, 6H), 3.36 (s, 2H), 3.59 (s, 3H), 4.91-4.99 (m, 2H), 6.91-6.95 (dd, J$_2$=11.2 Hz, 1H), 7.05-7.08 (dd, J$_2$=9.2 Hz, 1H), 7.20-7.23 (d, J=8.0 Hz, 2H), 7.35-7.37 (d, J=8.0 Hz, 2H), 7.72 (s, 1H), 7.79 (s, 1H), 12.33 (s, 1H).

Example 153

Racemate of (8S,9S)-8-(4-fluorophenyl)-9-(1-methyl-1H-imidazol-2-yl)-8,9-dihydro-2H-pyrido[4,3,2-de]phthalazin-3(7H)-one and (8R,9R)-8-(4-fluorophenyl)-9-(1-methyl-1H-imidazol-2-yl)-8,9-dihydro-2H-pyrido[4,3,2-de]phthalazin-3(7H)-one A racemate of (8R,9S)-8-(4-fluorophenyl)-9-(1-methyl-1H-imidazol-2-yl)-8,9-dihydro-2H-pyrido[4,3,2-de]phthalazin-3(7H)-one and (8S,9R)-8-(4-fluorophenyl)-9-(1-methyl-1H-imidazol-2-yl)-8,9-dihydro-2H-pyrido[4,3,2-de]phthalazin-3(7H)-one (600 mg, 1.67 mmol) was added to 30% NaOH (32 mL) at room temperature, the mixture was stirred at 85° C. for 3 hr. Then the solution was cooled to 5° C. and filtered to obtain 555 mg of white solid, which was purified by prep-HPLC to obtain the title compound as white solid (40 mg, yield 7%). LC-MS (ESI) m/z: 362 (M+1)$^+$. $^1$H-NMR (400 MHz, DMSO-d$_6$) □□ δ (ppm): 2.74 (s, 3H), 4.47 (d, J=4 Hz, 1H), 4.90 (d, J=4 Hz, 1H), 6.65 (s, 1H), 6.81 (s, 1H), 7.07-7.17 (m, 6H), 7.40-7.42 (d, J=8 Hz, 1H), 7.55-7.59 (t, J=8 Hz, 1H), 12.23 (s, 1H).

Examples on Chiral Resolution

Example 154

Enantiomers of (8R,9S)-8-(4-fluorophenyl)-9-(1-methyl-1H-imidazol-2-yl)-8,9-dihydro-2H-pyrido[4,3,2-de]phthalazin-3(7H)-one and (8S,9R)-8-(4-fluorophenyl)-9-(1-methyl-1H-imidazol-2-yl)-8,9-dihydro-2H-pyrido[4,3,2-de]phthalazin-3(7H)-one 8-(4-Fluorophenyl)-9-(1-methyl-1H-imidazol-2-yl)-8,9-dihydro-2H-pyrido[4,3,2-de]phthalazin-3(7H)-one was dissolved in DMF and chiral resolution was performed using super-fluid chromatography (SFC) with IA chiral column and methanol (30%) and CO$_2$ (70%) as the eluents.

Example 155

Enantiomers of (8R,9S)-5-fluoro-8-(4-fluorophenyl)-9-(1-methyl-1H-1,2,4-triazol-5-yl)-8,9-dihydro-2H-pyrido[4,3,2-de]phthalazin-3(7H)-one and (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one 5-Fluoro-8-(4-fluorophenyl)-9-(1-methyl-1H-1,2,4-triazol-5-yl)-8,9-dihydro-2H-pyrido[4,3,2-de]phthalazin-3(7H)-one was dissolved in DMF and chiral resolution was performed using super-fluid chromatography (SFC) with IA chiral column and methanol (20%) and $CO_2$ (80%) as the eluents.

Example 156

(8R,9S)-5-Fluoro-8-(4-fluorophenyl)-9-(1-methyl-1H-imidazol-2-yl)-8,9-dihydro-2H-pyrido[4,3,2-de]phthalazin-3(7H)-one and (8S,9R)-5-fluoro-8-(4-fluorophenyl)-9-(1-methyl-1H-imidazol-2-yl)-8,9-dihydro-2H-pyrido[4,3,2-de]phthalazin-3(7H)-one 5-Fluoro-8-(4-fluorophenyl)-9-(1-methyl-1H-imidazol-2-yl)-8,9-dihydro-2H-pyrido[4,3,2-de]phthalazin-3(7H)-one was dissolved in DMF and chiral resolution was performed using super-fluid chromatography (SFC) with IA chiral column and methanol (30%) and $CO_2$ (70%) as the eluents.

Example 157

(8R,9S)-8-(4-Fluorophenyl)-9-(1-methyl-1H-1,2,4-triazol-5-yl)-8,9-dihydro-2H-pyrido[4,3,2-de]phthalazin-3(7H)-one and (8S,9R)-8-(4-fluorophenyl)-9-(1-methyl-1H-1,2,4-triazol-5-yl)-8,9-dihydro-2H-pyrido[4,3,2-de]phthalazin-3(7H)-one 8-(4-Fluorophenyl)-9-(1-methyl-1H-1,2,4-triazol-5-yl)-8,9-dihydro-2H-pyrido[4,3,2-de]phthalazin-3(7H)-one was dissolved in DMF and chiral resolution was performed using super-fluid chromatography (SFC) with IA chiral column and methanol (30%) and $CO_2$ (70%) as the eluents.

Example 158

(8R,9S)-8-(4-(Azetidin-1-ylmethyl)phenyl)-9-(4-fluorophenyl)-8,9-dihydro-2H-pyrido[4,3,2-de]phthalazin-3(7H)-one and (8S,9R)-8-(4-(azetidin-1-ylmethyl)phenyl)-9-(4-fluorophenyl)-8,9-dihydro-2H-pyrido[4,3,2-de]phthalazin-3(7H)-one 8-(4-(Azetidin-1-ylmethyl)phenyl)-9-(4-fluorophenyl)-8,9-dihydro-2H-pyrido[4,3,2-de]phthalazin-3(7H)-one was dissolved in methanol and chiral resolution was performed using super-fluid chromatography (SFC) with OJ-H chiral column and methanol (40%) and $CO_2$ (60%) as the eluents

Example 159

(8R,9S)-8-(4-((Dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one and (8S,9R)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one 8-(4-((Dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one was dissolved in methanol and chiral resolution was performed using super-fluid chromatography (SFC) with AS-H chiral column and methanol (20%) and $CO_2$ (80%) as the eluents.

Biological Studies

Inhibitory effects of test compounds against human PARP 1 enzyme was assessed using Trevigen's Universal Chemiluminescent PARP Assay Kit (Trevigen CAT #4676-096-K) following the manufacturer's recommended protocol.

Immediately prior to performing the assay, the following reagents were prepared: A) 20×PARP Assay Buffer was diluted to 1× with $dH_2O$; B) 10×PARP Cocktail, which contains a mixture of NAD and biotinylated NAD, was diluted by the addition of 10× Activated DNA and 1×PARP Assay Buffer. Both the PARP Cocktail and Activated DNA are 1× after the dilution; C) all test compounds were initially dissolved in DMSO, and subsequently serial diluted with 1×PARP Assay Buffer; D) recombinant human PARP 1 enzyme was diluted with 1×PARP Assay Buffer to generate 0.5 unit/15 µl; E) 10× Strep-Diluent was diluted to 1× with 1×PBS/0.1% Triton X-100; F) Just before use, dilute Strep-HRP 500-fold with 1× Strep-Diluent.

The chemiluminescent assays for PARP activity were performed in white 96-well plates that are pre-coated with histones. Briefly, strip wells were removed from the wrapper, 50 µl/well of 1×PARP Buffer was added to rehydrate the histones and incubation was allowed for 30 minutes at room temperature. Removal of the 1×PARP Buffer from the wells was accomplished by tapping the strip wells on paper towel. Serial dilutions of the test compounds were added to duplicate wells in 10 µl/well volume. Final assay concentrations of test compounds were typically between 1 and 0.0001 µM. Subsequently, recombinant human PARP 1 enzyme was added to 0.5 unit of PARP 1 enzyme/well in 15 µl/well volume. Combined volume of enzyme and inhibitor was 25 µl. Incubate the enzyme/inhibitor mixtures for 10 minutes at room temperature. To start the reaction, 25 µl/well of the 1×PARP Cocktail was added to all the wells. Controls included background wells with 1× Assay Buffer alone (no PARP) and wells with no inhibitor for determining the maximum or 100% PARP activity value. In all cases the final reaction volume was 50 µl.

The reactions were allowed to proceed for 1 hour at room temperature. The plate was then washed 4 times with 200 µl/well 1×PBS/0.1% Triton X-100, using ELx50 Automated Strip Washer (BIO-TEK). After washing, all wells were incubated for 60 minutes with 50 µl/well Strep-HRP, diluted 1:500 with 1× Strep-Diluent. The plate was washed 4 times with 200 µl/well 1×PBS/0.1% Triton X-100 using ELx50 Automated Strip Washer (BIO-TEK). After washing, dry the wells by tapping plate onto paper towels. Mix equal volumes of PeroxyGlow™ A and B together and add 100 µl per well. The light output was immediately determined in a plate reader (EnVision, by Perkin Elmer) set up for measuring chemiluminescence.

The % enzyme activity for each compound is then calculated using the following equation:

$$\% \text{ Inhibition} = \frac{\text{Activity Ctrl} - X}{\text{Activity Ctrl} - \text{Negative Ctrl}} \times 100\%$$

$IC_{50}$ values (the concentration at which 50% of the enzyme activity is inhibited) of each test compound were calculated using GraphPad Prism5 software.

All of the compounds tested had or were expected to have enzymatic PARP inhibitory activity. Of the compounds tested, over 100 compounds had a PARP inhibitory activity in the enzymatic assay of less than 50 nM, with approximately 60 of these compounds having an inhibitory activity of less than 5 nM.

Chemosensitization assay determines the extent by which a PARP inhibitor enhances the tumor cell-killing effect of cytotoxic drugs expressed as $PF_{50}$ (potentiation factor at $GI_{50}$)]. 8000 LoVo cells were seeded into each well of a flat-bottomed 96-well microtiter plate in a volume of 50 µl and incubated in F12K containing 10% (v/v) FBS (medium) overnight at 37° C. Cells were added with 50 µl medium alone, medium containing 2 µM PARP inhibitor, medium containing increasing concentration of Temozolomide (0-2000 µM), and medium containing 2 µM PARP inhibitor and increasing concentration of Temozolomide (0-2000 µM). Final concentration range for Temozolomide was 0-1000 µM where applicable, final concentration of PARP inhibitor was 1 µM where applicable. Final concentration of DMSO was 1% in each well. Cells were allowed to grow for 5 days before cell survival was determined by CellTiter Glo staining (Promega, Madison, Wis., USA). Cell growth, determined after subtraction of time 0 values, was expressed as a percentage of the control well that contained medium with 1% DMSO. $GI_{50}$ (concentration of drug that inhibited growth by 50%) values were calculated from the computer generated curves (GraphPad Software, Inc. San Diego Calif.). The potentiation factor [$PF_{50}$ (potentiation factor at $GI_{50}$)] was calculated as $GI_{50}$ of Temozolomide alone/$GI_{50}$ of Temozolomide+PARP inhibitor. Reference: Thomas H. D. et al. (2007). Preclinical selection of a novel poly(ADP-ribose) polymerase inhibitor for clinical trial. *Molecular Cancer Therapy* 6, 945-956.

Most of the compounds tested had a PF50 of more than 2×.

Xenograft Studies
Antitumor In Vivo Animal Efficacy Study

Female athymic nu/nu mice (8-10 weeks old) were used for all in vivo xenograft studies. Mice were quarantined for at least 1 week before experimental manipulation. Exponentially growing cells or in vivo passaged tumor fragments were implanted subcutaneously at the right flank of nude mice. Tumor-bearing mice were randomized according to tumor size into 6-8 mice/group in each study (average tumor size ~150 mm³). Mice were observed daily for survival and tumors were measured twice weekly by caliper in two dimensions and converted to tumor mass using the formula for a prolate ellipsoid (V=0.5 a×b²), where a and b are the long and short diameters of the tumor, respectively, and assuming unit density (1 mm³=1 mg).

Single agent activity: PARP inhibitors were evaluated in Capan-1 and MX-1 xenografts for single agent activities. Compounds were dosed orally (p.o.), once daily for 28 days in vehicle 10% DMAc/6% Solutal/84% PBS, and the same vehicle was used as control. Mice were continuously monitored for 10 more days after the last day of dosing.

Combination study: PARP inhibitory compounds described herein in vehicle 10% DMAc/6% Solutal/84% PBS, were either administered orally, once daily for 5 days with Temozolomide (17 mg/kg or 34 mg/kg, p.o., qdx5, 30 min after each dose of compounds) in SW620 xenograft model or dosed orally, once daily for 8 days with 6 mg/kg Cisplatin (once by ip on day 3, 30 min after first dose of PARP inhibitors) in MX-1 xenograft model. Mice were observed and individual tumor was measured for 30 more days after the last dosing of PARP inhibitory compounds.

In vivo animal study on a few potent PARP inhibitory compounds described in the Examples section have demonstrated single agent activities in reducing both MX-1 and Capan-1 tumor growth by themselves when administered orally for 28 days. A few compounds when combined with DNA damaging agent Temozolomide significantly slowed tumor progression in SW620 model. In the MX-1 breast xenograft model, these compounds potentiated the platinum drug Cisplatin causing regression of established tumors, whereas with comparable doses of cisplatin or PARP inhibitor alone, only small to modest tumor inhibition was exhibited.

BRCA2-Deficient V-$C_8$ or BRCA2-Complimented V-$C_8$+ B2 Cells

BRCA2-deficient V-$C_8$ or BRCA2-complimented V-$C_8$+ B2 cells are implanted intramuscularly into the thigh of 40 CD-1 nude mice. Treatments are initiated when tumors are of measurable size (approximate leg diameter of 11 mm). Animals receive either a compound of Formula (I), (IA) or (II) (two doses of 25 or 50 mg/kg in saline) or saline (10 mg/ml) intraperitoneallly administered on days 1-5, and are monitored on a daily basis during treatment (tumor measurements, body weights and clinical evidence are recorded); and as required after the last treatment.

ES-Cell-Derived Tumors

ES-cell-derived tumors (teratomas) are produced by subcutaneous injection of 2×10⁶ ES cells into 6-8 week athymic BALB/c-nude (nu/nu) mice. 40 mice are injected with BRCA2-deficient ES cells or isogenic wild-type cells. Two days after cell injection, treatment with a compound of Formula (I), (IA) or (II) is initiated. For three consecutive days, two intraperitoneal doses of a compound of Formula (I), (IA) or (II) or vehicle is administered, 6 h apart, each at a dosage of 15 mg/kg per animal. This treatment is stopped for 5 days and then re-initiated for another three consecutive days. Growth of tumors is monitored from a minimum volume of 0.2 cm³.

The in vitro assays disclosed herein, along with other known in vitro assays (Farmer et al., Nature 2005; 434:913-7: clonogenic survival assay finding that a BRCA2-deficient cell line V-$C_8$, compared with the BRCA2 wild type control exhibited sensitivity to AG14361, a PARP-1 inhibitor, (Ki=5 nM) and NU1025, a moderately potent PARP-1 inhibitor (Ki=50 nM); & Mcabe et al., Cancer Biology & Therapy 2005; 4:9, 934-36; clonogenic survival assay using CAPAN-1 cells maintained in DMEM supplemented with FCS (20% v/v), glutamine and antibiotics showing sensitivity to PARP inhibition using KU0058684) demonstrates the activity of PARP-inhibitors in a static test situation. Additionally, animal models have been used to analyze the relationship between in vitro tests and parameters of in vivo efficacy. By way of example only, Farmer et al., has shown in vivo efficacy in blocking the growth of BRCA2-deficient tumors using KU0058684, a PARP-1 inhibitor. Nature 2005; 434:913-7. This indicates that PARP-1 inhibition is a viable cancer treatment for BRCA1/2 mutation carriers. Furthermore, KU0059436, a PARP-1 inhibitor is currently in Phase I clinical trials for patients with advanced solid tumors. Given this information, compounds of Formula (I), (IA) or (II) which have shown in vitro inhibitory action are likely to show analogous in vivo (mouse and human) efficacy.

Phase II Clinical Trial of the Safety and Efficacy of Compounds of Formula (I), (IA) or (II)

The purpose of this phase II trial is to study the side effects and best dose of a compound of Formula (I), (IA) or (II) and to determine how well it works in treating patients with locally advanced or metastatic breast cancer or advanced ovarian cancer.

Objectives:
  Primary:
    A. To determine the response rate to a compound of Formula (I), (IA) or (II) in patients with locally advanced or metastatic breast or advanced ovarian cancer shown to express the BRCA 1 or 2 mutations
    B. To evaluate the toxicity of a compound of Formula (I), (IA) or (II) in these patients
  Secondary:
    A. To evaluate the time to progression and overall survival in patients treated with a compound of Formula (I), (IA) or (II)
    B. To study pharmacokinetics of a compound of Formula (I), (IA) or (II) in these patients
    C. To evaluate the Poly(ADP-ribose) polymerase (PARP) activity in peripheral blood lymphocytes from BRCA 1 and 2 heterozygotic patients
  Tertiary:
    A. To evaluate PARP expression using quantitative western blotting immuno-assays
    B. To investigate pharmacogenomics, including CYP2D6 and CYP3A5, drug transport proteins, as well as polymorphisms in the genes coding for the PARP enzymes themselves
    C. To analyze tumor biopsy samples (when possible) for BRCA mutation status, PARP activity, and PARP expression
    D. To analyze paraffin sections from original diagnostic biopsies/operative procedures (when available) for DNA repair enzyme status using immunohistochemical techniques
    E. To analyze cells obtained from ascitic or pleural fluid (where available) for primary cell culture for DNA double strand break repair pathway function Patients: Eligible subjects will be men and women 18 years and older Criteria:
  Disease Characteristics:
    Histologically confirmed locally advanced or metastatic breast cancer or advanced ovarian cancer
    Must meet 1 of the following criteria:
      Proven a carrier of a known mutation of BRCA 1 or BRCA 2
      Considered highly likely a carrier of BRCA 1 or 2 mutation (score of ≥20 per Manchester criteria)
    No more than 3 prior chemotherapy regimens for patients with breast or ovarian cancer
      More than 2 months since prior carboplatin- or cisplatin-containing chemotherapy for ovarian cancer
    Measurable disease, as defined by RECIST criteria and measured by x-ray, CT scan, or MRI
      Patients with bone disease must have other measurable disease for evaluation
      Previously irradiated lesions cannot be used for measurable disease
    No known brain metastases
    Hormone receptor status not specified
  Patient Characteristics:
    WHO performance status 0-1
    Life expectancy ≥12 weeks
    Menopausal status not specified
    Hemoglobin ≥9.0 g/dL
    Absolute neutrophils ≥1,500/mm$^3$
    Platelets ≥100,000/mm$^3$
    Serum bilirubin ≤1.5 times upper limit of normal (ULN)
    ALT or AST ≤2.5 times ULN (≤5 times ULN if due to tumor)
    Glomerular filtration rate (GFR) ≥50 mL/min
    Not pregnant or nursing
    Negative pregnancy test
    Fertile patients must use two highly effective forms of contraception (i.e., oral, injected, or implanted hormonal contraception, intrauterine device, barrier method of condom plus spermicide, or are surgically sterile) 4 weeks prior to (females), during, and for 6 months after (males and females) completion of study therapy
    Able to cooperate with treatment and follow-up
    No non-malignant systemic disease, including active uncontrolled infection
    No other concurrent malignancy, except adequately treated cone-biopsied carcinoma in situ of the uterine cervix, basal cell or squamous cell carcinoma of the skin, or breast and ovarian carcinoma
      Cancer survivors who have undergone potentially curative therapy for a prior malignancy, have no evidence of that disease for 5 years, and are deemed at low risk for recurrence are eligible
    No active or unstable cardiac disease or history of myocardial infarction within the past 6 months
      Patients with cardiovascular signs or symptoms should have a MUGA scan or echocardiogram, and those with a left ventricular ejection fraction (LVEF) below the institutional limit of normal should be excluded
    No other condition which, in the investigator's opinion, would not make the patient a good candidate for this study
  Prior Concurrent Therapy:
    At least 4 weeks since prior radiotherapy (except for palliative reasons), endocrine therapy, immunotherapy or chemotherapy (6 weeks for nitrosoureas and mitomycin C)
    At least 4 weeks since prior major thoracic and/or abdominal surgery and recovered
    Concurrent radiotherapy for the control of bone pain or skin lesions allowed, but not within 5 days of the last dose of study drug
    Concurrent bisphosphonates allowed provided the dose is stable and treatment was started at least 2 weeks prior to recruitment
    No unresolved toxicities (CTCAE ≥grade 1) from prior treatments (except for alopecia)
    No concurrent anticancer therapy or investigational drugs
    No concurrent tetracycline antibiotic therapy for prolonged periods (short courses [5-7 days] for treatment of infection are allowed)

Study Design: This is a dose-escalation study followed by an open label multicenter study. Patients will be stratified according to tumor type (breast vs ovarian) and mutation status (BRCA 1 vs BRCA 2). Patients will receive a compound of Formula (I), (IA) or (II) (at one of several possible dosages) over 30 minutes once daily on days 1-5. Treatment repeats every 21 days for 12 courses in the absence of disease progression or unacceptable toxicity. Patients who achieve stable or responding disease may receive additional courses of treatment at the discretion of the chief investigator or Drug Development Office (DDO). Patients will undergo blood sample collection periodically for pharmacokinetic and pharmacodynamic studies. Samples will be analyzed for tumor marker (CA 125 or CA 15.3) measurements, plasma levels of a compound of Formula (I), (IA) or (II) via liquid chromatography/mass spectrometry/mass spectrometry, PARP activity, and PARP protein expression via western blotting immunoassays. Paraffin embedded sections from original diagnostic biopsy are also collected and analyzed for PARP protein expression via immunohistochemical technique. Pleural and ascitic fluid may be collected and analyzed for DNA DS break repair proficiency via immunohistochemical technique. Some patients will also undergo biopsy of tumors and samples will be analyzed for BRCA 2 mutation as well as PARP activity via validated PARP immunoblotting assay. After completion of the study treatment, patients will be followed for 28 days.

Primary Outcome Measures:
Assessment of antitumor activity according to RECIST using tumor size measured clinically or radiologically with CT scan, MRI, plain x-ray, or other imaging techniques
Safety profile Secondary Outcome Measures:
Time to progression and overall survival
Plasma levels by Liquid Chromatography/Mass Spectrometry/Mass Spectrometry
Poly(ADP-ribose) polymerase (PARP) activity measured ex vivo using validated assays
PARP expression using quantitative Western blotting immuno-assays
Pharmacogenomics including CYP2D6 and CYP3A5, drug transport proteins, as well as polymorphisms in the genes coding for the PARP enzymes themselves
BRCA mutation status, PARP activity, and PARP expression in tumor biopsy samples (when possible)
DNA repair enzyme status using immunohistochemical techniques in paraffin sections from original diagnostic biopsies/operative procedures (where available)
DNA double strand break repair pathway function in cells obtained from ascitic or pleural fluid (where available) for primary cell culture

What is claimed is:

1. A method of treating lung cancer in a subject, comprising administering to the subject a therapeutically effective amount of 5-fluoro-8-(4-fluorophenyl)-9-(1-methyl-1H-1,2,4-triazol-5-yl)-8,9-dihydro-2H-pyrido[4,3,2-de]phthalazin-3(7H)-one, or a pharmaceutically acceptable salt or solvate thereof.

2. The method of claim 1, wherein said administration is in combination with ionizing radiation, one or more chemotherapeutic agents, or a combination thereof.

3. The method of claim 2, wherein the compound is used in combination with one or more chemotherapeutic agents, wherein each chemotherapeutic agent is independently methyl methanesulfonate, temozolomide, dacarbazine (DTIC), a topoisomerase-1 inhibitor, Topotecan, Irinotecan, Rubitecan, Exatecan, Lurtotecan, Gimetecan, Diflomotecan, a homocamptothecin, Doxorubicin, a platinum based antineoplastic agent, a 7-substituted non-silatecan, a 7-silyl camptothecin, paclitaxel, cetuximab, daunorubicin, methotrexate, a hormone, an antiestrogen, an antiandrogen, a gonadotropin releasing hormone analog, an interferon, alpha interferon, a tyrosine kinase inhibitor, gefitinib, imatinib, gemtuzumab, or BNP 1350.

4. The method of claim 2, wherein the compound is used in combination with one or more chemotherapeutic agents, wherein each chemotherapeutic agent is independently irinotecan, cisplatin, carboplatin, paclitaxel, or temozolomide.

5. The method of claim 1, wherein the subject is a human.
6. The method of claim 2, wherein the subject is a human.
7. The method of claim 3, wherein the subject is a human.
8. The method of claim 4, wherein the subject is a human.

9. A method of treating lung cancer in a subject, comprising administering to the subject a therapeutically effective amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one, or a pharmaceutically acceptable salt or solvate thereof.

10. The method of claim 9, wherein said administration is in combination with ionizing radiation, one or more chemotherapeutic agents, or a combination thereof.

11. The method of claim 10, wherein the compound is used in combination with one or more chemotherapeutic agents, wherein each chemotherapeutic agent is independently methyl methanesulfonate, temozolomide, dacarbazine (DTIC), a topoisomerase-1 inhibitor, Topotecan, Irinotecan, Rubitecan, Exatecan, Lurtotecan, Gimetecan, Diflomotecan, a homocamptothecin, Doxorubicin, a platinum based antineoplastic agent, a 7-substituted non-silatecan, a 7-silyl camptothecin, paclitaxel, cetuximab, daunorubicin, methotrexate, a hormone, an antiestrogen, an antiandrogen, a gonadotropin releasing hormone analog, an interferon, alpha interferon, a tyrosine kinase inhibitor, gefitinib, imatinib, gemtuzumab, or BNP 1350.

12. The method of claim 10, wherein the compound is used in combination with one or more chemotherapeutic agents, wherein each chemotherapeutic agent is independently irinotecan, cisplatin, carboplatin, paclitaxel, or temozolomide.

13. The method of claim 9, wherein the subject is a human.
14. The method of claim 10, wherein the subject is a human.
15. The method of claim 11, wherein the subject is a human.
16. The method of claim 12, wherein the subject is a human.

* * * * *